(12) United States Patent
Butora et al.

(10) Patent No.: US 7,247,725 B2
(45) Date of Patent: Jul. 24, 2007

(54) GAMMA-AMINOAMIDE MODULATORS OF CHEMOKINE RECEPTOR ACTIVITY

(75) Inventors: Gabor Butora, Martinsville, NJ (US); Alexander Pasternak, Princeton, NJ (US); Lihu Yang, Edison, NJ (US); Changyou Zhou, Plainsboro, NJ (US)

(73) Assignee: Merck & Co., Inc., Rahway, NJ (US)

( * ) Notice: Subject to any disclaimer, the term of this patent is extended or adjusted under 35 U.S.C. 154(b) by 38 days.

(21) Appl. No.: 10/528,329

(22) PCT Filed: Oct. 24, 2003

(86) PCT No.: PCT/US03/34009

§ 371 (c)(1), (2), (4) Date: Mar. 18, 2005

(87) PCT Pub. No.: WO2004/041279

PCT Pub. Date: May 21, 2004

(65) Prior Publication Data

US 2005/0261325 A1    Nov. 24, 2005

Related U.S. Application Data

(60) Provisional application No. 60/422,268, filed on Oct. 30, 2002.

(51) Int. Cl.
*C07D 221/20*    (2006.01)
*A61K 31/438*    (2006.01)

(52) U.S. Cl. .......................................... 546/17; 514/17

(58) Field of Classification Search ................ 546/17; 514/278
See application file for complete search history.

(56) References Cited

U.S. PATENT DOCUMENTS

| | | | |
|---|---|---|---|
| 4,166,119 A * | 8/1979 | Effland et al. .............. 514/278 |
| 5,403,842 A | 4/1995 | Leonardi et al. |
| 6,117,880 A | 9/2000 | Guo et al. |
| 2002/0169181 A1* | 11/2002 | Pairet et al. .............. 514/291 |

FOREIGN PATENT DOCUMENTS

| | | |
|---|---|---|
| EP | 518805 A1 * | 12/1992 |
| EP | 630887 A1 * | 12/1994 |
| WO | WO 9417045 A1 * | 8/1994 |
| WO | WO 9429309 A1 * | 12/1994 |
| WO | WO 0248117 A1 * | 6/2002 |
| WO | WO 03000677 A1 * | 1/2003 |
| WO | WO 2004004714 A1 * | 1/2004 |

OTHER PUBLICATIONS v. Braun, J. Ber. (1909), 42, 2035-57. CAS Abstract attached.*
CAS Abstracts are provided for each reference.*

* cited by examiner

*Primary Examiner*—Joseph K. McKane
*Assistant Examiner*—Jason M. Nolan
(74) *Attorney, Agent, or Firm*—David Rubin; William Krovatin

(57) ABSTRACT

The present invention is directed to compounds of the formula (I), wherein $R^1$, $R^2$, $R^3$, $R^4$, $R^5$, $R^6$, $R^7$, $R^8$, $R^{11}$, $R^{12}$, W, X, and n are defined herein, which are useful as modulators of chemokine receptor activity. In particular, these compounds are useful as modulators of the chemokine receptor CCR-2.

3 Claims, No Drawings

GAMMA-AMINOAMIDE MODULATORS OF CHEMOKINE RECEPTOR ACTIVITY

RELATED APPLICATION DATA

This is a National filing under 35 USC 371 of PCT/US2003/034009, filed Oct. 24, 2003, which claims priority from U.S. Ser. No. 60/422,648, filed Oct. 30, 2002.

BACKGROUND OF THE INVENTION

The chemokines are a family of small (70–120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The chemokines are secreted by a wide variety of cell types and bind to specific G-protein coupled receptors (GPCRs) (reviewed in Horuk, *Trends Pharm. Sci.*, 15, 159–165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/ "CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood*, 90, 908–928 (1997)); CCR-4 (or "CKR-4" or "CC-CKR-4") [MIP-1α, RANTES, MCP-1] (Rollins, et al., *Blood* 90, 908–928 (1997)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989–992 (1999)). A review of the role of eosinophils in allergic inflammation is provided by Kita, H., et al., *J. Exp. Med.* 183, 2421–2426 (1996). A general review of the role of chemokines in allergic inflammation is provided by Lustger, A. D., *New England J. Med.*, 338(7), 426–445 (1998). A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.*, 187, 601–608 (1998); Kurihara et al. *J. Exp. Med.*, 186, 1757–1762 (1997); Boring et al. *J. Clin. Invest.*, 100, 2552–2561 (1997); Kuziel et al. *Proc. Natl. Acad. Sci.*, 94, 12053–12058 (1997)). Furthermore, these animals show reduced monocyte infiltration into granulomatous lesions induced by the injection of schistosomal or mycobacterial antigens (Boring et al. *J. Clin. Invest.*, 100, 2552–2561 (1997); Warmington et al. *Am J. Path.*, 154, 1407–1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases. Accordingly, agents which modulate chemokine receptors such as the CCR-2 receptor would be useful in such disorders and diseases. In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 -/- or CCR2 -/- mice backcrossed to APO-E -/-, LDL-R -/- or Apo B transgenic mice maintained on high fat diets (Boring et al. *Nature*, 394, 894–897 (1998); Gosling et al. *J. Clin. Invest.*, 103, 773–778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

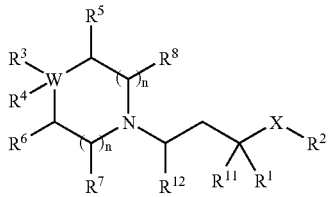

wherein:
W is selected from the group consisting of:
C, N, and —O—, wherein when W is N, then $R^4$ is absent, and when W is —O—, then both $R^3$ and $R^4$ are absent;
X is selected from the group consisting of:
—$NR^{10}$—, —O—, —$CH_2O$—, —$CONR^{10}$—, —$NR^{10}CO$—, —$CO_2$—, —OCO—, —$CH_2(NR^{10})$CO—, —$N(COR^{10})$—, and —$CH_2N(COR^{10})$—,
and where $R^{10}$ is independently selected from: hydrogen, $C_{1-6}$ alkyl, benzyl, phenyl,
and $C_{1-6}$ alkyl-$C_{3-6}$ cycloalkyl,
which is unsubstituted or substituted with 1–3 substituents where the substituents
are independently selected from: halo, $C_{1-3}$alkyl, $C_{1-3}$alkoxy and trifluoromethyl;
or where $R^{10}$ and $R^2$ may be joined together to form a 5- or 6-membered ring,
$R^1$ is selected from:
hydrogen, —$C_{0-6}$alkyl-Y-phenyl-, —$CO_0$alkyl-Y-heterocycle-,
—$C_{0-6}$alkyl-Y—($C_{1-6}$alkyl)-, and
—($C_{0-6}$alkyl)-Y—($C_{0-6}$alkyl)-($C_{3-7}$cycloalkyl)-($C_{0-6}$alkyl),
where Y is selected from:
a single bond, —O—, —S—, —SO—, —$SO_2$—, and —$NR^{10}$—,
and where the phenyl, heterocycle, alkyl and the cycloalkyl are unsubstituted or substituted with 1-7 substituents where the substituents are independently selected from:
(a) halo,
(b) hydroxy,
(c) —O—$C_{1-3}$alkyl,
(d) trifluoromethyl,
(e) $C_{1-3}$alkyl,
(f) —$C_{3-6}$cycloalkyl
(g) —$CO_2R^9$, wherein $R^9$ is independently selected from: hydrogen, $C_{1-6}$ alkyl, $C_{5-6}$ cycloalkyl, benzyl or phenyl, which is unsubstituted or substituted with 1-3 substituents where the substituents are independently selected from: halo, $C_{1-3}$alkyl, $C_{1-3}$alkoxy and trifluoromethyl,
(h) —CN,
(i) —$NR^9R^{10}$,
(j) —$NR^9COR^{10}$,
(k) —$NR^9SO_2R^{10}$,
(l) —$NR^9CO_2R^{10}$,
(m) —$NR^9CONR^9R^{10}$,
(n) —$CONR^9R^{10}$,
(o) heterocycle,
(p) phenyl;
$R^2$ is selected from:
($C_{0-6}$alkyl)-phenyl and ($C_{0-6}$alkyl)-heterocycle,
where the alkyl is unsubstituted or substituted with 1-7 substituents where the substituents are independently selected from:
(a) halo,
(b) hydroxy,
(c) —O—$C_{1-3}$alkyl,
(d) trifluoromethyl,
(e) —$C_{1-3}$alkyl,
(f) —$CO_2R^9$, and
(g) oxo;
and where the phenyl and the heterocycle may be unsubstituted or substituted with 1-5 substituents where the substituents are independently selected from:
(a) halo,
(b) trifluoromethyl,
(c) trifluoromethoxy,
(d) hydroxy,
(e) $C_{1-6}$alkyl,
(f) $C_{3-7}$cycloalkyl,
(g) —O—$C_{1-6}$alkyl,
(h) —O—$C_{3-7}$cycloalkyl,
(i) —$SCF_3$,
(j) —S—$C_{1-6}$alkyl,
(k) —$SO_2$—$C_{1-6}$alkyl,
(l) phenyl,
(m) heterocycle,
(n) —$CO_2R^9$,
(o) —CN,
(p) —$NR^9R^{10}$,
(q) —$NR^9$—$SO_2$—$R^{10}$,
(r) —$SO_2$—$NR^9R^{10}$,
(s) —$CONR^9R^{10}$, and
(t) —O-phenyl;
$R^3$ is selected from:
hydrogen, ($C_{0-6}$alkyl)-phenyl, ($C_{0-6}$alkyl)-heterocycle, $C_{1-6}$alkyl, $CF_3$, $C_{3-7}$cycloalkyl, —$NR^9R^{10}$, —$CO_2R^9$, —$NR^9$—$SO_2$—$R^{10}$, —$NR^9CONR^9R^{10}$, and —$CONR^9R^{10}$,
where the alkyl is unsubstituted or substituted with 1-5 substituents where the substituents are independently selected from:
(a) halo,
(b) hydroxy,
(c) —O—$C_{1-3}$alkyl, and
(d) trifluoromethyl,
and where the phenyl, heterocycle, and cycloalkyl are unsubstituted or substituted with 1-5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$
(j) $NR^9SO_2R^{10}$,
(k) $SO_2NR^9R^{10}$
(l) phenyl,
(m) heterocycle;

and where the phenyl, heterocycle, and cycloalkyl may or may not be fused to another phenyl or heterocycle;

$R^4$ is selected from:
(a) hydrogen,
(b) hydroxy,
(c) $C_{1-6}$alkyl,
(d) $C_{1-6}$alkyl-hydroxy,
(e) —O—$C_{1-13}$alkyl,
(f) $C_{0-6}CO_2R^9$,
(g) —$CONR^9R^{10}$, and
(h) —CN;

or $R^3$ and $R^4$ may be joined together to form a ring which is selected from:
(a) 1H-indene,
(b) 2,3-dihydro-1H-indene,
(c) 2,3-dihydro-benzofuran,
(d) 1,3-dihydro-isobenzofuran,
(e) 2,3-dihydro-benzothiofuran, and
(f) 1,3-dihydro-isobenzothiofuran,
where the 1H-indene, 2,3-dihydro-1H-indene, 2,3-dihydro-benzofuran, 1,3-dihydro-isobenzofuran, 2,3-dihydrobenzothiofuran, and 1,3-dihydro-isobenzothiofuran may be unsubstituted or substituted with 1-5 substituents where the substituents are independently selected from:
(i) halo,
(ii) trifluoromethyl,
(iii) hydroxy,
(iv) $C_{1-3}$alkyl,
(v) —O—$C_{1-3}$alkyl,
(vi) $C_{0-4}CO_2R^9$,
(vii) —CN,
(viii) —$NR^9R^{10}$, and
(ix) —$CONR^9R^{10}$
(x) $NR^9SO_2R^{10}$,
(xi) $SO_2NR^9R^{10}$
(xii) phenyl,
(xiii) heterocycle;

$R^5$, $R^6$, $R^7$ and $R^8$ are independently selected from:
(a) hydrogen,
(b) hydroxy,
(c) $C_{1-6}$alkyl,
(d) $C_{1-6}$alkyl-hydroxy,
(e) —O—$C_{1-3}$alkyl,
(f) oxo, and
(g) halo,
(h) $C_{0-4}CO_2R^9$, and
(i) $CF_3$,
or where $R^5$ and $R^6$, or $R^7$ and $R^8$ may be joined together via a $C_{2-3}$alkyl chain to form a ring, or where $R^3$ and $R^5$, or $R^4$ and $R^6$ may be joined together to form a ring which is phenyl, heterocycle, or cycloalkyl, wherein the ring is unsubstituted or substituted with 1-7 substituents where the substituents are independently selected from:
(i) halo,
(ii) trifluoromethyl,
(iii) hydroxy,
(iv) $C_{1-3}$alkyl,
(V) —O—$C_{1-3}$alkyl,
(vi) —$CO_2R^9$,
(vii) —CN,
(viii) —$NR^9R^{10}$,
(ix) —$CONR^9R^{10}$, and
(x) phenyl;

$R^{11}$ is selected from:
(a) hydrogen,
(b) halo
(c) $C_{1-6}$alkyl,
(d) hydroxy,
(e) $CO_2R^9$,
(f) —O—$C_{1-3}$alkyl, and
(g) —$NR^9R^{10}$;

$R^{12}$ is selected from:
(a) hydrogen,
(b) $C_{1-6}$alkyl, and
(c) $CO_2R^9$;

n is an integer selected from 0, 1, 2 and 3;

and pharmaceutically acceptable salts thereof and individual diastereomers thereof.

More preferred compounds of the present invention include those of formula Ib:

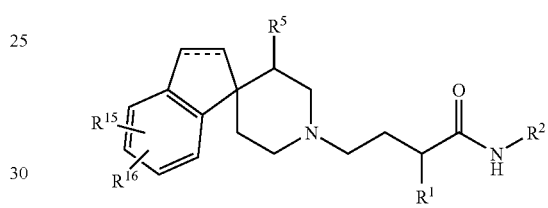

Ib wherein the dashed line represents a single or a double bond and $R^1$, $R^2$, and $R^5$ are defined herein, and wherein $R^{15}$ and $R^{16}$ are independently selected from:
(a) hydrogen,
(b) halo,
(c) trifluoromethyl,
(d) hydroxy,
(e) $C_{1-3}$alkyl,
(f) —O—$C_{1-3}$alkyl,
(g) —$CO_2H$,
(h) —$CO_2C_{1-3}$alkyl,
(i) —CN, and
(j) heterocycle;

and pharmaceutically acceptable salts and individual diastereomers thereof.

More preferred compounds of the present invention also include those of formula Ic:

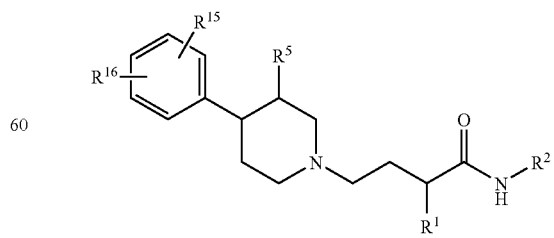

Ic wherein $R^1$, $R^2$, $R^5$, $R^{15}$, and $R^{16}$ are defined herein.

More preferred compounds of the present invention include those of formula Id:

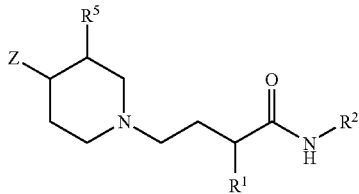

wherein $R^1$, $R^2$, and $R^5$ are defined herein, and
where Z is a heterocycle selected from the group consisting of:
benzoimidazolyl, benzofuranyl, benzofurazanyl, benzopyrazolyl, benzotriazolyl,
benzothiophenyl, benzoxazolyl, carbazolyl, carbolinyl, cinnolinyl, furanyl, imidazolyl,
indolinyl, indolyl, indolazinyl, indazolyl, isobenzofuranyl, isoindolyl, isoquinolyl,
isothiazolyl, isoxazolyl, naphthpyridinyl, oxadiazolyl, oxazolyl, oxetanyl, pyranyl,
pyrazinyl, pyrazolyl, pyridazinyl, pyridopyridinyl, pyridazinyl, pyridyl, pyrimidyl,
pyrrolyl, quinazolinyl, quinolyl, quinoxalinyl, tetrahydropyranyl, tetrazolyl,
tetrazolopyridyl, thiadiazolyl, thiazolyl, thienyl, triazolyl, azetidinyl, 1,4-dioxanyl,
hexahydroazepinyl, piperazinyl, piperidinyl, pyrrolidinyl, morpholinyl, thiomorpholinyl,
dihydrobenzoimidazolyl, dihydrobenzofuranyl, dihydrobenzothiophenyl,
dihydrobenzoxazolyl, dihydrofuranyl, dihydroimidazolyl, dihydroindolyl,
dihydroisooxazolyl, dihydroisothiazolyl, dihydrooxadiazolyl, dihydrooxazolyl,
dihydropyrazinyl, dihydropyrazolyl, dihydropyridinyl, dihydropyrimidinyl,
dihydropyrrolyl, dihydroquinolinyl, dihydrotetrazolyl, dihydrothiadiazolyl,
dihydrothiazolyl, dihydrothienyl, dihydrotriazolyl, dihydroazetidinyl,
methylenedioxybenzoyl, tetrahydrofuranyl, and tetrahydrothienyl, and N-oxides thereof,
and where the heterocycle may be unsubstituted or substituted with 1-3 substituents, where the substituents are selected from:
(a) hydrogen,
(b) halo,
(c) trifluoromethyl,
(d) hydroxy,
(e) $C_{1-3}$alkyl,
(f) —O—$C_{1-3}$alkyl,
(g) —$CO_2H$,
(h) —$CO_2C_{1-13}$alkyl, and
(i) —CN,
and where the heterocycle may be fused to a phenyl or another heterocycle, and pharmaceutically acceptable salts and individual diastereomers thereof.
In the present invention it is preferred that X is —CONH—.

In the present invention it is preferred that $R^1$ is selected from:
—$C_{0-6}$alkyl-phenyl, $C_{0-6}$alkyl-heterocycle, —$C_{1-6}$alkyl, —$C_{0-6}$alkyl-O—$C_{1-6}$alkyl-, —$C_{0-6}$alkyl-S—$C_{1-6}$alkyl-, and —($C_{0-6}$alkyl)-($C_{3-7}$cycloalkyl)-($C_{0-6}$alkyl), where the phenyl, heterocycle, alkyl and the cycloalkyl are unsubstituted or substituted with 1-7 substituents where the substituents are independently selected from:
(a) halo,
(b) hydroxy,
(c) —O—$C_{1-3}$alkyl,
(d) trifluoromethyl,
(e) $C_{1-3}$alkyl,
(f) —$C_{3-6}$cycloalkyl
(g) —$CO_2R^9$, wherein $R^9$ is independently selected from: hydrogen, $C_{1-6}$ alkyl, $C_{5-6}$ cycloalkyl, benzyl or phenyl, which is unsubstituted or substituted with 1-3 substituents where the substituents are independently selected from: halo, $C_{1-3}$alkyl, $C_{1-3}$alkoxy and trifluoromethyl,
(h) —CN,
(i) —$NR^9R^{10}$,
(j) —$NR^9COR^{10}$,
(k) —$NR^9SO_2R^{10}$,
(l) —$NR^9CO_2R^{10}$,
(m) —$NR^9CONR^9R^{10}$,
(n) —$CONR^9R^{10}$,
(o) heterocycle, and
(p) phenyl.
In the present invention it is more preferred that $R^1$ is selected from:
(1) —$C_{1-6}$alkyl, which is unsubstituted or substituted with 1-6 substituents where the substituents are independently selected from:
(a) halo,
(b) hydroxy,
(c) —O—$C_{1-3}$alkyl,
(d) trifluoromethyl,
(e) —CN,
(f) —$NR^9SO_2R^{10}$,
(g) —$NR^9CO_2R^{10}$,
(h) —$NR^9CONR^9R^{10}$,
(i) heterocycle,
(j) —$CO_2R^9$, and
(k) —$CONR^9R^{10}$,
(2) —$C_{0-6}$alkyl-O—$C_{1-6}$alkyl-, which is unsubstituted or substituted with 1-6 substituents where the substituents are independently selected from:
(a) halo, and
(b) trifluoromethyl,
(3) —$C_{0-6}$alkyl-S—$C_{1-6}$alkyl-, which is unsubstituted or substituted with 1-6 substituents where the substituents are independently selected from:
(a) halo, and
(b) trifluoromethyl,
(4) —($C_{3-5}$cycloalkyl)-($C_{0-6}$alkyl), which is unsubstituted or substituted with 1-7 substituents where the substituents are independently selected from:
(a) halo,
(b) hydroxy,
(c) —O—$C_{1-3}$alkyl,
(d) trifluoromethyl,
(e) —CN,
(f) —$NR^9SO_2R^{10}$,
(g) —$NR^9CO_2R^{10}$,
(h) —$NR^9CONR^9R^{10}$,
(i) heterocycle, (j) —CO$_2$R$^9$, and
k) —CONR$^9$R$^{10}$,
(5) phenyl, which is unsubstituted or substituted with 1-5 substituents where the substituents are independently selected from:
   (a) halo,
   (b) hydroxy,
   (c) —O—C$_{1-3}$alkyl,
   (d) trifluoromethyl,
   (e) —CN,
   (f) —NR$^9$SO$_2$R$^{10}$,
   (g) —NR$^9$CO$_2$R$^{10}$,
   (h) —NR$^9$CONR$^9$R$^{10}$,
   (i) heterocycle,
   (j) —CO$_2$R$^9$, and
   (k) —CONR$^9$R$^{10}$,
   or where the phenyl may be fused to another phenyl or heterocycle,
(6) heterocycle, which is unsubstituted or substituted with 1-5 substituents where the substituents are independently selected from:
   (a) halo,
   (b) hydroxy,
   (c) —O—C$_{1-3}$alkyl,
   (d) trifluoromethyl,
   (e) —CN,
   (f) —NR$^9$SO$_2$R$^{10}$,
   (g) —NR$^9$CO$_2$R$^{10}$,
   (h) —NR$^9$CONR$^9$R$^{10}$,
   (i) heterocycle,
   (j) —CO$_2$R$^9$, and
   (k) —CONR$^9$R$^{10}$,
   or where the heterocycle is fused to another heterocycle or a phenyl.

In the present invention it is even more preferred that R$^1$ is selected from:

(1) —CH(CH$_3$)$_2$,
(2) —CH$_2$CH$_2$CH$_3$,
(3) —CH$_2$CH(CH$_3$)$_2$,
(4) —cyclopropyl,
(5) —cyclobutyl,
(6) —cyclopentyl,
(7) —CH$_2$—cyclopropyl,
(8) —CH$_2$—cyclobutyl,
(9) —C(CH$_3$)$_2$(OH),
(10) —(OH)cyclobutyl,
(11) —(OH)cyclopentyl,
(12) —C(CH$_3$)$_2$(NHCOCH$_3$),
(13) —O—CH$_3$,
(14) —O—CH(CH$_3$)$_2$,
(15) —S—CH$_3$,
(16) —S—CF$_3$,
(17) —SO$_2$—CH$_3$,
(18) —S—CH(CH$_3$)$_2$,
(19) —SO$_2$—CH(CH$_3$)$_2$,
(20) —NH—SO$_2$—CH$_3$,
(21) —phenyl,

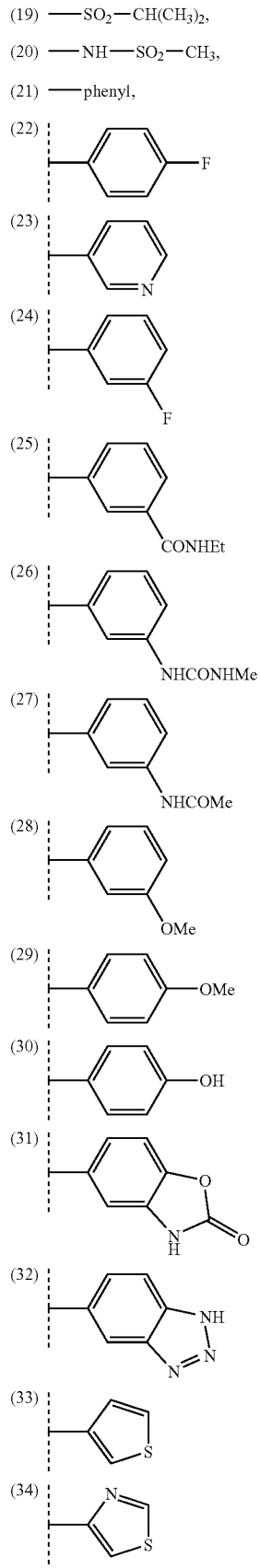

(22) 4-F-phenyl
(23) pyridyl
(24) 3-F-phenyl
(25) 3-CONHEt-phenyl
(26) 3-NHCONHMe-phenyl
(27) 3-NHCOMe-phenyl
(28) 3-OMe-phenyl
(29) 4-OMe-phenyl
(30) 4-OH-phenyl
(31) benzoxazol-2(3H)-one
(32) benzotriazole
(33) thiophene
(34) thiazole

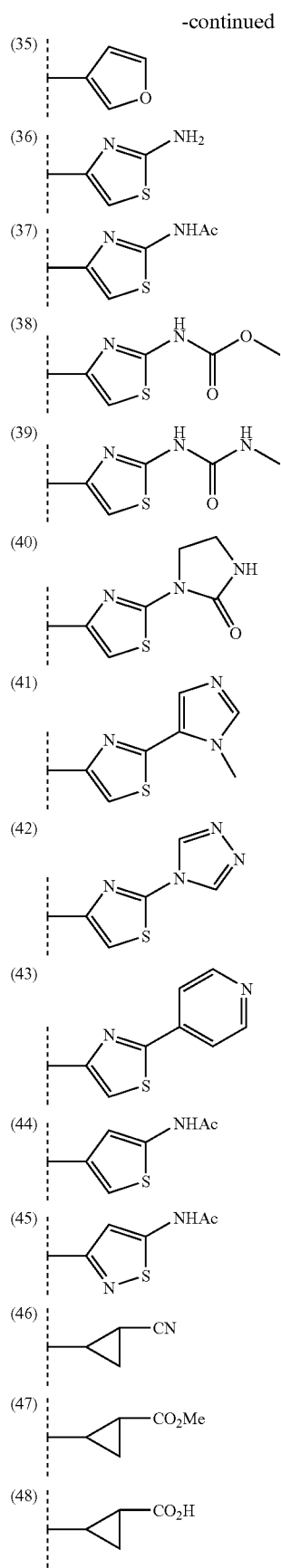
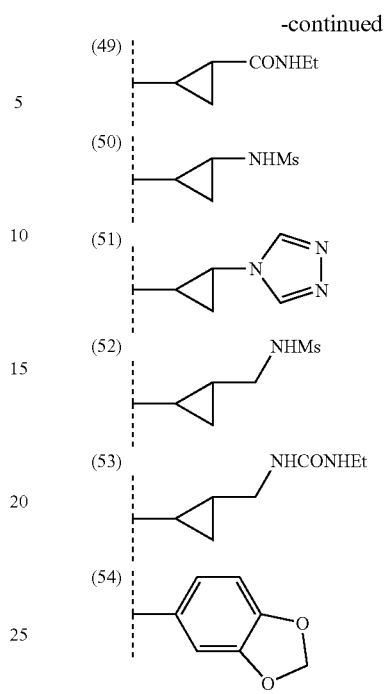

and positional and stereo isomers thereof.

In the present invention it is preferred that $R^2$ is selected from:

—($C_{0-4}$alkyl)-phenyl and —($C_{0-4}$alkyl)-heterocycle, where heterocycle is selected from:
furanyl, imidazolyl, oxadiazolyl, oxazolyl, pyrazolyl, pyrazinyl, pyridyl,
pyridazinyl, pyrimidyl, pyrrolyl, thiadiazolyl, thiazolyl, thienyl, and triazolyl, and
N-oxides thereof, where the alkyl is unsubstituted or substituted with 1-7 substituents where the substituents are independently selected from:
(a) halo,
(b) hydroxy,
(c) —O—$C_{1-3}$alkyl,
(d) trifluoromethyl,
(e) —$CO_2R^9$ and where the phenyl or heterocycle is unsubstituted or substituted with 1-5 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2R^9$,
(h) —S—$C_{1-3}$alkyl,
(i) —$SO_2$—$C_{1-3}$alkyl,
(j) —$SCF_3$,
(k) —OPh,
(l) —$NR^9R^{10}$,
(m) —$NR^9$—$SO_2$—$R^{10}$,
(n) —$SO_2$—$NR^9R^{10}$,
(o) —$CONR^9R^{10}$, and
(p) heterocycle.

In the present invention it is more preferred that $R^2$ is selected from:

—$CH_2$-phenyl and —$CH_2$-heterocycle, where the heterocycle is selected from: pyridyl, pyridazinyl, pyrimidyl, and N-oxides thereof, and where the phenyl or heterocycle is unsubstituted or substituted with 1-3 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2$—$C_3$alkyl,
(h) —$CO_2H$,
(i) —S—$C_{1-3}$alkyl,
(j) —$SO_2$—$C_{1-3}$alkyl,
(k) —$SCF_3$,
(l) —$NH_2$,
(m) —NH—$SO_2$—$C_{1-3}$alkyl,
(n) —$SO_2$—$NH_2$, and
(o) heterocycle.

In the present invention it is still more preferred that $R^2$ is selected from:
(1) —$CH_2$-(phenyl),
(2) —$CH_2$-(4-bromophenyl),
(3) —$CH_2$-(3-chlorophenyl),
(4) —$CH_2$-(3,5-difluorophenyl),
(5) —$CH_2$-((2-trifluoromethyl)phenyl),
(6) —$CH_2$-((3-trifluoromethyl)phenyl),
(7) —$CH_2$-((4-trifluoromethyl)phenyl),
(8) —$CH_2$-((3-trifluoromethoxy)phenyl),
(9) —$CH_2$-((3-trifluoromethylthio)phenyl),
(10) —$CH_2$-((3-trifluoromethoxy-5-thiomethyl)phenyl),
(11) —$CH_2$-((3-trifluoromethoxy-5-methoxy)phenyl),
(12) —$CH_2$-((3-trifluoromethoxy-5-methanesulfonyl)phenyl),
(13) —$CH_2$-((3-trifluoromethoxy-5-amino)phenyl),
(14) —$CH_2$-((3-trifluoromethoxy-5-aminomethanesulfonyl)phenyl),
(15) —$CH_2$-((3-trifluoromethoxy-5-sulfonylamino)phenyl),
(16) —$CH_2$-((3,5-bis-trifluoromethyl)phenyl),
(17) —$CH_2$-((3-fluoro-5-trifluoromethyl)phenyl),
(18) —$CH(CH_3)$-((3,5-bis-trifluoromethyl)phenyl),
(19) —$C(CH_3)_2$-((3,5-bis-trifluoromethyl)phenyl),
(20) —$CH_2$-(4-(2-trifluoromethyl)pyridyl),
(21) —$CH_2$-(5-(3-trifluoromethyl)pyridyl),
(22) —$CH_2$-(5-(3-trifluoromethyl)pyridazinyl),
(23) —$CH_2$-(4-(2-trifluoromethyl)pyridyl-N-oxide), and
(24) —$CH_2$-(5-(3-trifluoromethyl)pyridyl-N-oxide).

In the present invention it is preferred that $R^3$ is phenyl or heterocycle, where the phenyl or heterocycle is unsubstituted or substituted with 1–5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$.

In the present invention it is more preferred that $R^3$ is phenyl or heterocycle, where the phenyl or heterocycle is unsubstituted or substituted with 1–3 substituents where the substituents are independently selected from:
(a) halo,
(c) hydroxy,
(d) $C_{1-3}$alkyl,
(e) —O—$C_{1-3}$alkyl, and
(f) —$CO_2R^9$.

In the present invention it is still more preferred that $R^3$ is phenyl, para-fluorophenyl, 3-carboxyphenyl, 3-pyridyl, 3,5-pyrimidyl, 1-benzimidazole, 3-indole, 1-indazole, 1-pyrrole, imidazoyl, diazoyl, triazoyl or tetrazoyl.

In the present invention it is more preferred that $R^4$ is selected from:
(a) hydrogen,
(b) hydroxy,
(c) —$CO_2C_{1-6}$alkyl,
(d) —CN,
(e) fluoro, and
(f) methyl.

In the present invention it is more preferred that $R^5$ and $R^6$ are independently selected from:
(a) hydrogen,
(b) hydroxy,
(c) —$CH_3$,
(d) —O—$CH_3$,
(e) oxo, and
(f)-fluoro.

In the present invention it is preferred that $R^{11}$ is hydrogen.

In the present invention it is preferred that $R^{12}$ is hydrogen.

Especially preferred compounds of the present invention include those of the formula:

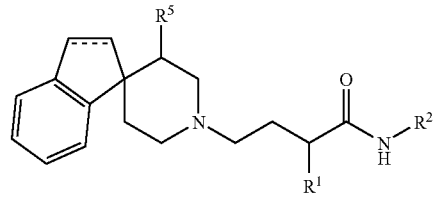

wherein the dashed line represents a single or a double bond, $R^5$ is hydrogen or methyl, and $R^1$ and $R^2$ are defined herein;

and pharmaceutically acceptable salts and individual diastereomers thereof.

Especially preferred compounds of the present invention include those of the formula:

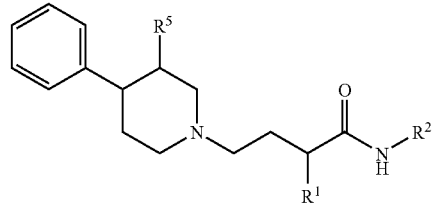

-continued
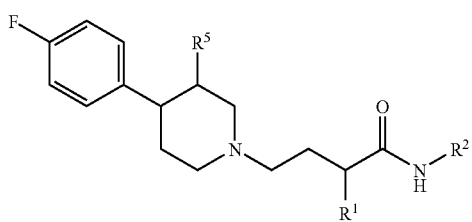
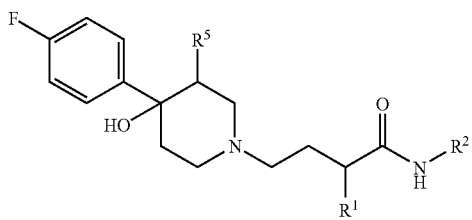
wherein R¹ and R² are defined herein;
and pharmaceutically acceptable salts and individual diastereomers thereof.
Especially preferred compounds of the present invention include those of the formula:
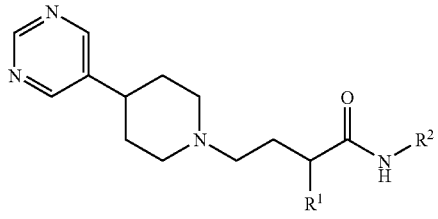
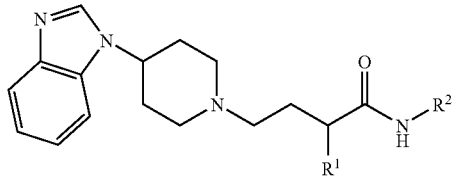
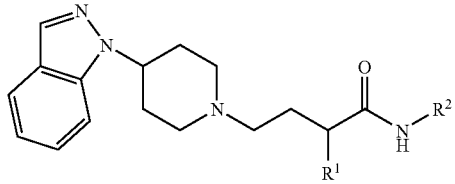
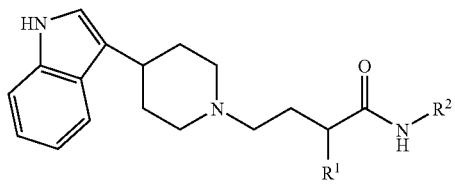
-continued
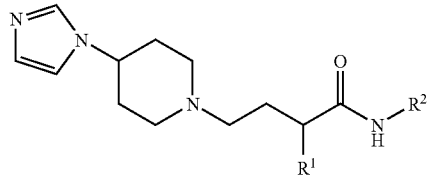
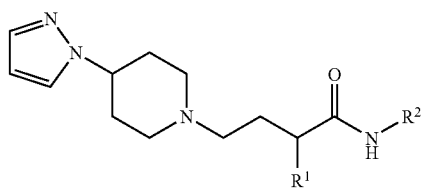
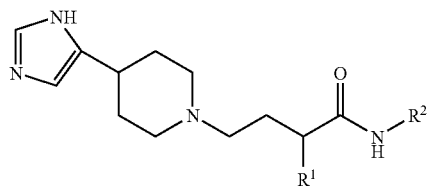
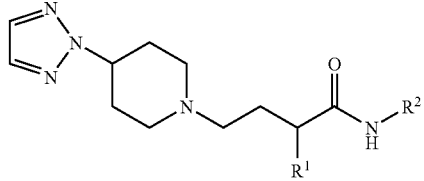
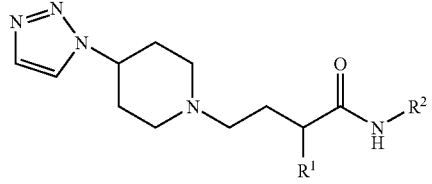
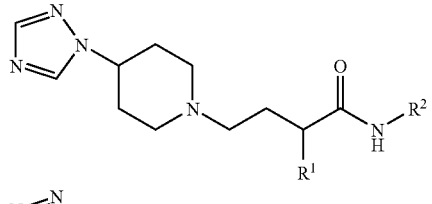
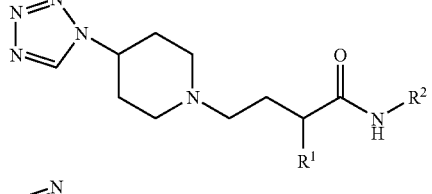
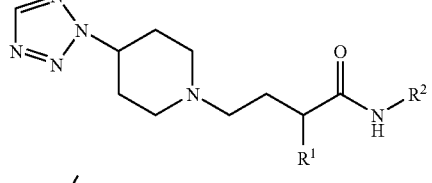
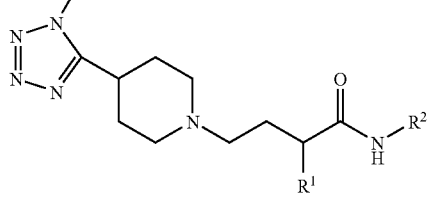

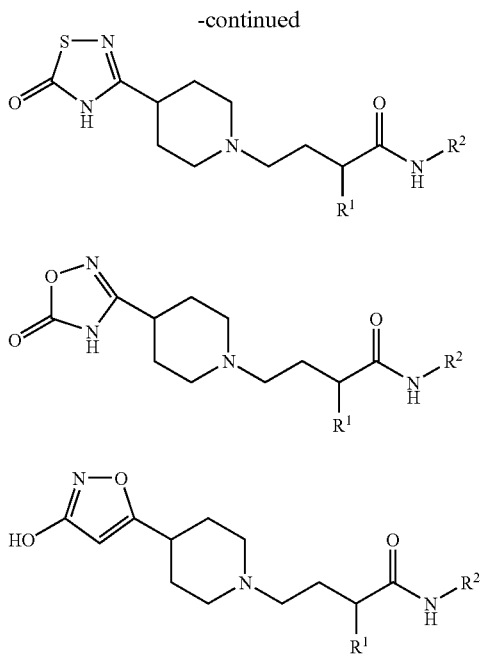

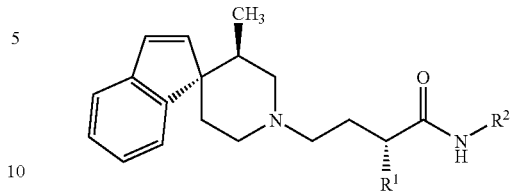

wherein R¹ and R² are defined herein;

and pharmaceutically acceptable salts and individual diastereomers thereof. Representative compounds of the present invention include those presented in the Examples and pharmaceutically acceptable salts and individual diastereomers thereof.

The compounds of the instant invention have at least one asymmetric center at the position α-to the amide carbonyl. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of the more preferred compounds of this invention are of the configuration shown below, where the position α-to the amide carbonyl

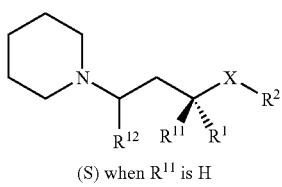

(S) when R¹¹ is H is designated as being of the "S" absolute configuration (when R¹¹ is H, although the designation at this position may be specified as "R" if the priority for assignment of the groups at that position differs).

The absolute configurations of the more preferred compounds of this invention having the structure below are as shown, where the position α-to the amide carbonyl is designated as being of the "S" absolute configuration, and where the piperidine 3 and 4-positions have the 3-(R) and 4-(R) configurations.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, $C_{1-3}$alkyl is defined to identify the group as having 1, 2 or 3 carbons in a linear or branched arrangement, such that $C_{1-3}$alkyl specifically includes methyl, ethyl, n-propyl, and iso-propyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound. The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuramimidase-treated sheep erythrocytes. Once isolated, the cells were washed with HBSS containing 0.1 mg/ml BSA and suspended at $1 \times 10^7$ cells/ml. Cells were fluorescently labeled in the dark with 2 µM Calcien-AM (Molecular Probes), for 30 min at 37° C. Labeled cells were washed twice and suspended at $5 \times 10^6$ cells/m in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant.

In particular, the compounds of the following examples had activity in binding to the CCR-2 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a preferred embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (*Trichuriasis, Enterobiasis, Ascariasis, Hookworm, Strongyloidiasis, Trichinosis, filariasis*), trematodes (flukes) (*Schistosomiasis, Clonorchiasis*), cestodes (tape worms) (*Echinococcosis, Taeniasis saginata, Cysticercosis*), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof. The terms "administration of," and or "administering a" compound should be understood to mean providing a compound of the invention to the individual in need of treatment. As used herein, the term "treatment" refers both to the treatment and to the prevention or prophylactic therapy of the aforementioned conditions.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; ( ) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin. Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents. Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of these pathological conditions. In treating, preventing, ameliorating, controlling or reducing the risk of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, preferably 2.0 to 500, more preferably 3.0 to 200, particularly 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made by known procedures or as illustrated.

Alternatively, an ester may be used as the starting material 1—1 (where $R^{17}$ can be methyl, ethyl, benzyl, or t-butyl). In this case deprotonation with one equivalent of base, such as LDA, KHMDS, LHMDS, NaH, and the like, followed by treatment with allyl bromide furnishes 1-2 (where $R^{17}$ is an alkyl group). Conversion of ester 1-2 to the carboxylic acid 1-2a can be achieved by a number of conditions depending on the nature of the ester. For example, methyl or ethyl esters can be readily saponified with sodium hydroxide, or lithium hydroxide; tert-butyl ester can be removed by treatment with TFA. Coupling of the acid 1-2a with amine 1-3 to give amide 1-4 can be accomplished by the standard amide bond formation conditions using a coupling reagent such as DCC, EDC and a catalyst such as DMAP, HOBT or HOAT. Oxidation of the olefin 1-4 to the aldehyde 1-5 can be carried out under numerous conditions, such as with ozone followed by treatment with methyl sulfide or triphenylphosphine, or with osmium tetroxide and sodium periodate (see March J. "Advanced Organic Chemistry", 4th ed., John Wiley & Sons, New York, pp. 1167–1171 (1992)). Reductive amination with amine 1-6 in the presence of a borohydride such as

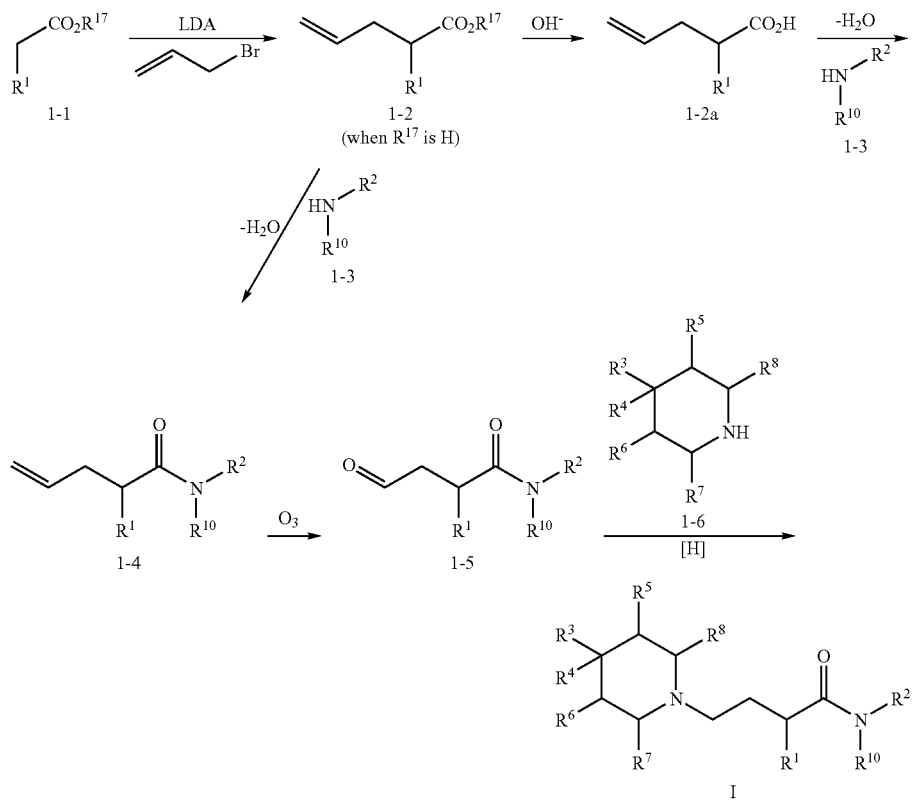

The preparation of compounds within the scope of the instant invention is detailed in Scheme 1, starting from commercially available or known 1—1, where $R^{17}$ is hydrogen or an alkyl protecting group (Greene, T; Wuts, P. G. M. *Protective Groups in Organic Synthesis*, John Wiley & Sons, Inc., New York, N.Y. 1991). Formation of the dianion of carboxylic acid 1—1, where $R^{17}$ is a hydrogen atom, with 2 equivalents of a base such as LDA or LHMDS, followed by treatment with allyl bromide gives 1-2a (where $R^{17}$ is H).

sodium triacetoxyborohydride or sodium cyanoborohydride then provides the compound of formula I. Alternatively, compounds of formula I may be prepared in one pot by reductive amination of the ozonide without converting it to the ketone. When $R^1$ is not hydrogen, a chiral center is generated by alkylation with allyl bromide. The resulting acid 1-2a can be resolved in a variety of ways, including by crystallization with optically pure amines such as α-methylbenzylamine. The resolved acid can then be used to prepare I as a single enantiomer, or as a single diastereomer when other chiral centers are present.

SCHEME 1A

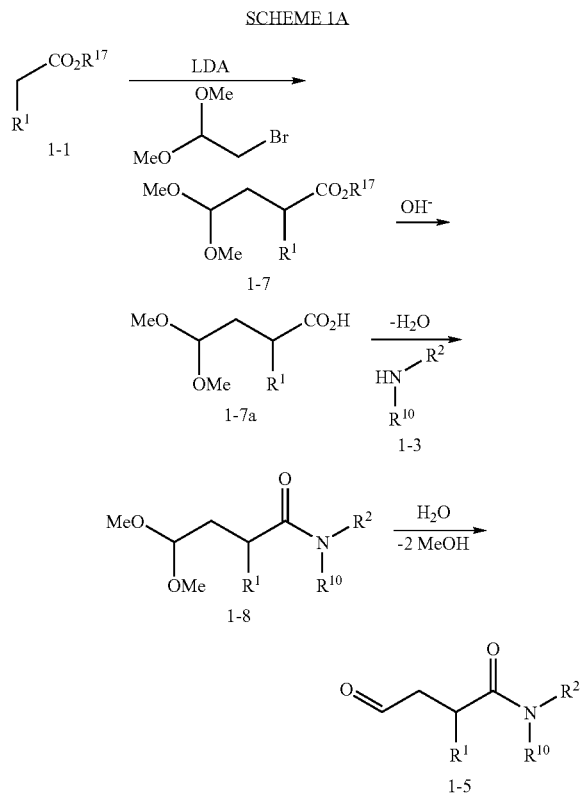

The preparation of aldehydes 1-5 as intermediates can also be achieved as depicted in Scheme 1A. Alkylation of 1—1 with commercially available bromoacetaldehyde dimethyl acetal can be achieved with a strong base such as sodium, lithium or potassium hexamethyldisilazide, lithium diisopropylamide, and the like, to give 1-7. Conversion of ester 1-7 to the carboxylic acid 1-7a can be achieved by a number of conditions depending on the nature of the ester. For example, methyl or ethyl esters can be readily saponified with potassium hydroxide, sodium hydroxide, or lithium hydroxide. Coupling of the acid 1-7a with amine 1-3 to give amide 1-8 can be accomplished by the standard amide bond formation conditions using a coupling reagent such as DCC, EDC and a catalyst such as DMAP, HOBT or HOAT. These compounds can be then converted to the compound of formula I according to Scheme 1.

SCHEME 1B

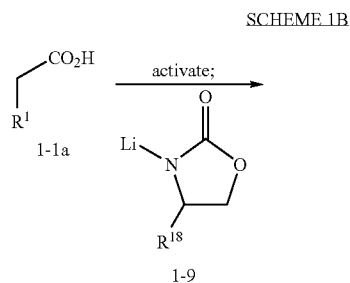

-continued

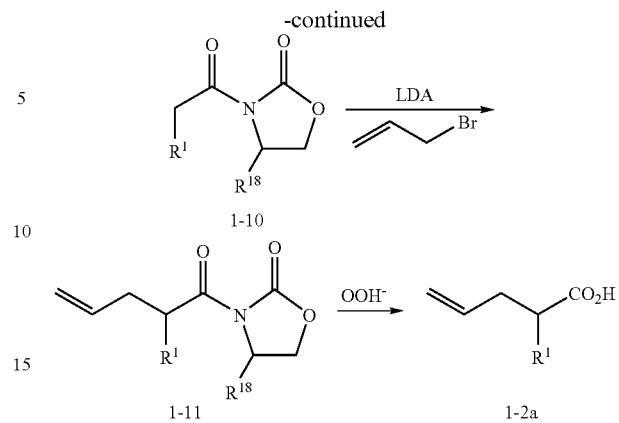

The preparation of carboxylic acids 1-2a as intermediates can also be achieved as depicted in Scheme 1B. Activation of acid 1-1a by formation of an acid chloride or mixed anhydride under standard conditions, followed by treatment with an optically pure lithium oxazolidinone 1-9 (R can be isopropyl or benzyl; other related oxazolidinones may be used), furnishes the N-acyloxazolidinone 1-10, according to precedents by Evans et al Evans, D. A., Ennis, M. D., Mathre, D. J., *J. Am. Chem. Soc.* 1982, 104, 1737). Deprotonation of 1-10 with one equivalent of strong base, such as LDA, ADS, LHMDS, and the like, followed by treatment with allyl bromide furnishes 1-11 as a single isomer after purification, again according to the precedents of Evans et al. Conversion of N-acyloxazolidinone 1-11 to the optically pure carboxylic acid 1-2a can be achieved by a number of conditions including treatment with lithium hydroperoxide, or bases such as potassium hydroxide, sodium hydroxide, or lithium hydroxide. Scalemic 1-2a can be then converted to isomerically pure compounds of formula I according to Scheme 1.

SCHEME 1C

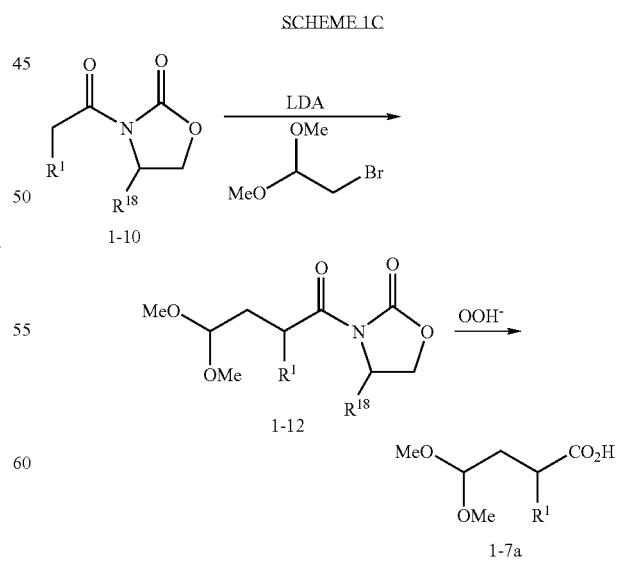

The preparation of carboxylic acids 1-7a as intermediates can also be achieved as depicted in Scheme 1C. Deprotonation of 1-10 (Scheme 1B) with one equivalent of strong base, such as LDA, KHMDS, LHMDS, and the like, followed by treatment with bromoacetaldehyde dimethyl acetal furnishes 1-12 as a single isomer after purification. Conversion of N-acyloxazolidinone 1-12 to the optically pure carboxylic acid 1-7a can be achieved by a number of conditions including treatment with lithium hydroperoxide, or bases such as potassium hydroxide, sodium hydroxide, or lithium hydroxide. Scalemic 1-7a can be then converted to isomerically pure compounds of formula I according to Scheme 1.

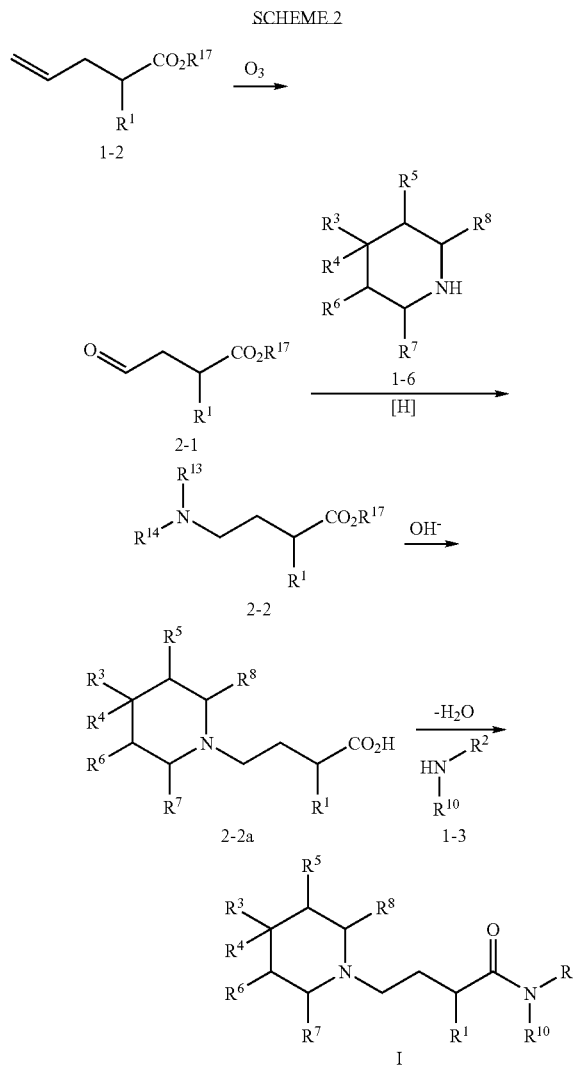

Compounds within the scope of the instant invention can alternatively be prepared as detailed in Scheme 2, starting from 1-2 (see Scheme 1), where $R^{17}$ is an alkyl protecting group such as methyl, ethyl, benzyl or t-butyl (Greene, T; Wuts, P. G. M. *Protective Groups in: Organic Synthesis*, John Wiley & Sons, Inc., New York, N.Y. 1991). Oxidation of the olefin 1-2 to the aldehyde 2-1 can be carried out under numerous conditions, such as with ozone followed by treatment with methyl sulfide or triphenylphosphine, or with osmium tetroxide and sodium periodate (see March J. "Advanced Organic Chemistry", 4th ed., John Wiley & Sons, New York, pp. 1167–1171 (1992)). Reductive amination with amine 1-6 in the presence of a borohydride such as sodium triacetoxyborohydride or sodium cyanoborohydride then provides the compound 2-2. Hydrolysis of 2-2 can be achieved by a number of conditions depending on the nature of the ester. For example, methyl or ethyl esters can be readily saponified with sodium hydroxide, or lithium hydroxide; tert-butyl ester can be removed by treatment with TFA. Coupling of the acid 2-2a with amine 1-3 to give the compound of the formula I can be accomplished by the standard amide bond formation conditions using a coupling reagent such as DCC, EDC and a catalyst such as DMAP, HOBT or HOAT.

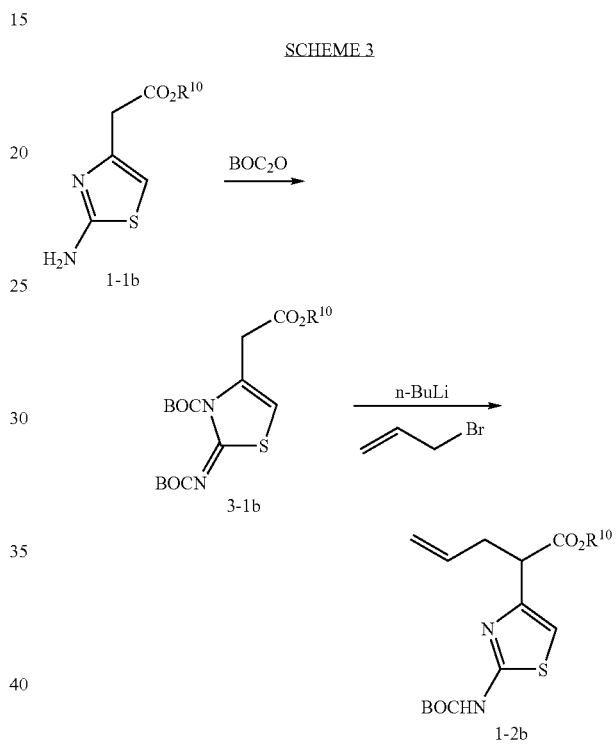

In certain cases, it may be necessary to protect $R^1$, for example in the cases of certain aminoheterocycles, in order to proceed with the syntheses in Schemes 1 and 2. Scheme 3 shows one general example involving 1-1b, where $R^1$ is 4-(2-aminothiazole). Compound 1-1b is commercially available, where $R^{10}$ is ethyl. Protection of 1-1b with a t-butoxycarbonyl group can be accomplished with $BOC_2O$ to give 3-1b. Deprotonation with a strong base such as n-butyl lithium, followed by treatment with allyl bromide provides 1-2b, which can be carried to compounds of formula I in the usual way as described in Scheme 2. The approach shown in Scheme 2b can be applied to a variety of closely related aminoheterocycles, for example 3-(5-aminoisothiazole) and 5-(2-aminothiazole).

SCHEME 4

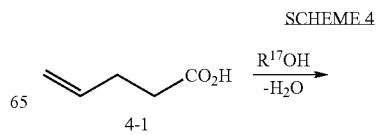

-continued

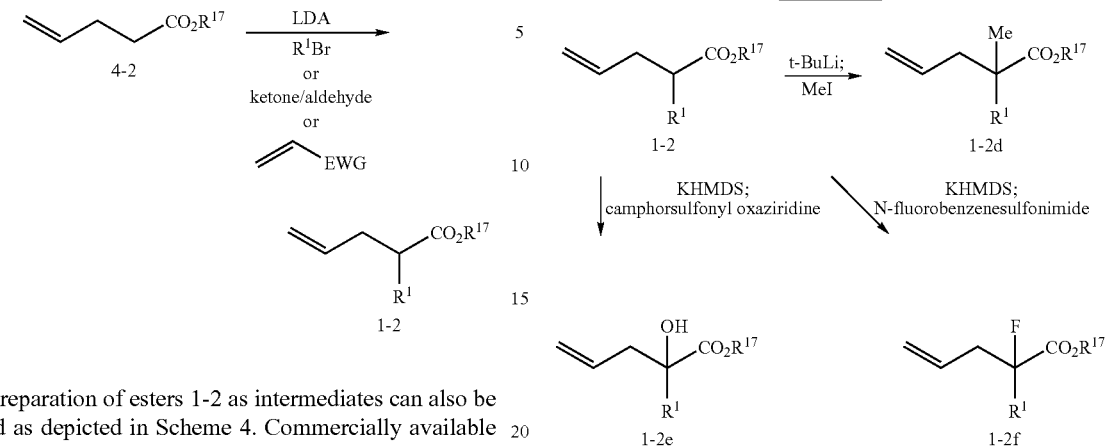

The preparation of esters 1-2 as intermediates can also be achieved as depicted in Scheme 4. Commercially available acid 4-1 can be protected as an ester by various means, depending upon the nature of $R^{17}$ (i.e., methyl, ethyl, benzyl, t-butyl). For example, the t-butyl ester can be prepared using t-butanol, magnesium sulfate, and sulfuric acid according to the method of Wright, et al (Wright, S. W., Hageman, D. L., Wright, A. S., McClure, L. D. *Tetrahedron Lett.* 1997, 38(42), 7345). Deprotonation of 4-2 with a strong base such as LDA, followed by treatment with an electrophile such as an alkyl halide, a ketone, an aldehyde, an epoxide, or an α, β-unsaturated ester, nitrile or nitro compound can provide 1-2, which in turn may be used to prepare compounds of the formula I as described in Schemes 1 and 2.

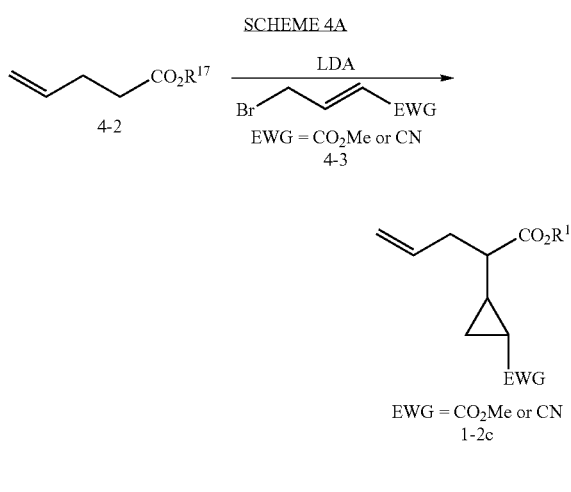

In an extension of the strategy shown in Scheme 4, compounds 1-2c can be prepared by alkylation of the enolate of 4-2 with γ-bromo-α, β-unsaturated ester or nitrile 4-3. The trans cyclopropanes are obtained and the diastereoselectivity of this reaction to give erythro or threo products can be controlled by solvent choice according to the work of Prempree, et al. (*J. Org. Chem.* 1983, 48, 3553, and *Tetrahedron Lett.* 1985, 26, 1723). Compounds 1-2c may be used to prepare compounds of the formula I as described in Schemes 1 and 2.

Compounds 1-2 can be modified as shown in Scheme 4B so that $R^{11}$ is something other than hydrogen, for example methyl, hydroxy, and fluoro. Treatment of 1-2 with a strong base such as t-butyl lithium, followed by methyl iodide, gives 1-2d. Similarly, deprotonation of 1-2 with a strong base such as potassium hexamethylsilazide, followed by treatment with camphorsulfonyl oxaziridine or N-fluorobenzenesulfonamide provides hydroxy and fluoro compounds 1-2e and 1-2f, respectively. Intermediates 1-2d, 1-2e, and 1-2f can be carried on to compounds of the formula I (except where the hydrogen α-to the amide carbonyl is replaced by methyl, hydroxy and fluoro) using the methods outlined in Schemes 2.

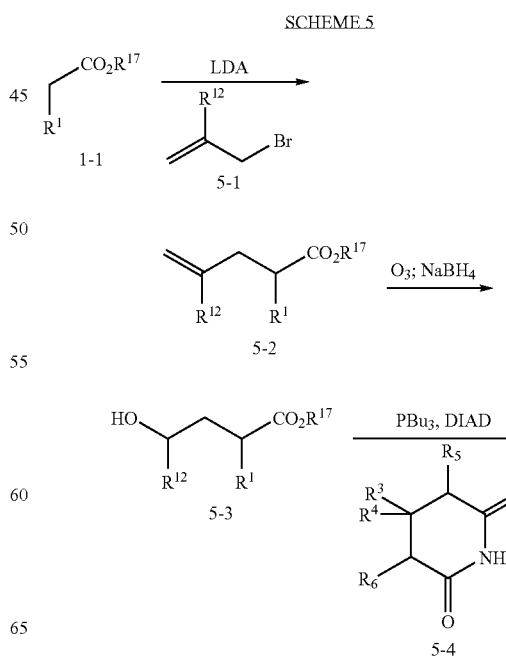

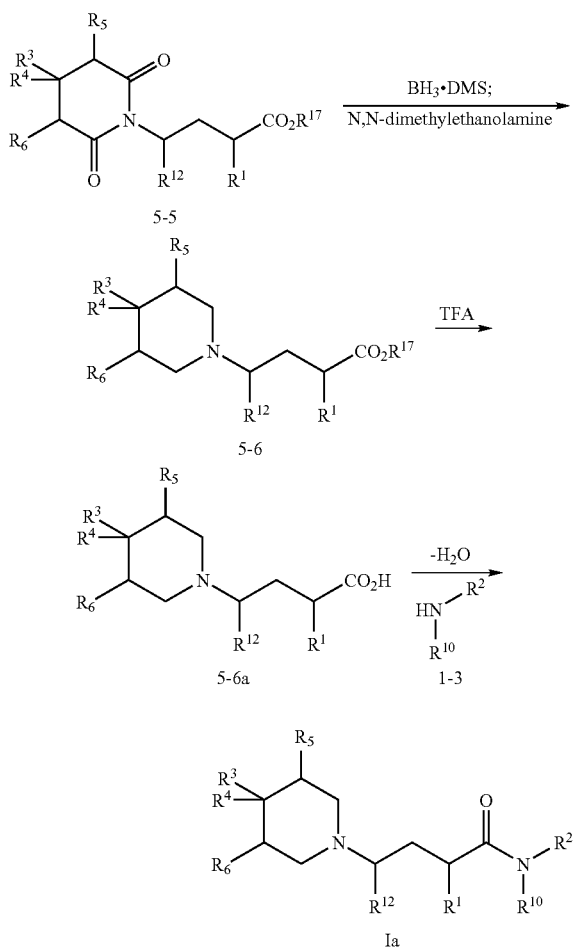

Compounds within the scope of the instant invention can alternatively be prepared as detailed in Scheme 5, starting from 1-1 (see Scheme 1), where $R^{17}$ is an alkyl protecting group such as t-butyl (Greene, T; Wuts, P. G. M. *Protective Groups in Organic Synthesis*, John Wiley & Sons, Inc., New York, N.Y. 1991). Deprotonation of 1—1 with one equivalent of strong base, such as LDA, KHMDS, LHMDS, and the like, followed by treatment with bromides 5-1 (for example commercially available 3-bromo-2-methylpropene) furnishes 5-2. Oxidation of the olefin 5-2 to the ketone followed by reduction to the alcohol 5-3 can be carried out under numerous conditions, such as with ozone followed by treatment with sodium borohydride, or with osmium tetroxide and sodium periodate (see March J. "Advanced Organic Chemistry", 4th ed., John Wiley & Sons, New York, pp. 1167–1171 (1992)), again followed by sodium borohydride. Mitsunobo reaction (Mitsunobu, O. *Synthesis* 1981, 1) of 5-3 with glutarimides 5-4 (glutarimide is commercially available, substituted analogs are known from the literature) gives intermediates 5—5. Reduction of the imide 5—5 can be accomplished with $BH_3.DMS$ to provide 5-6. Hydrolysis of the ester 5-6 can be achieved by a number of conditions depending on the nature of the ester. For example, methyl or ethyl esters can be readily saponified with sodium hydroxide, or lithium hydroxide; tert-butyl ester can be removed by treatment with TFA. Coupling of the acid 5-6a with amine 1-3 to give the compound of the formula Ia can be accomplished by the standard amide bond formation conditions using a coupling reagent such as DCC, EDC and a catalyst such as DMAP, HOBT or HOAT.

SCHEME 6

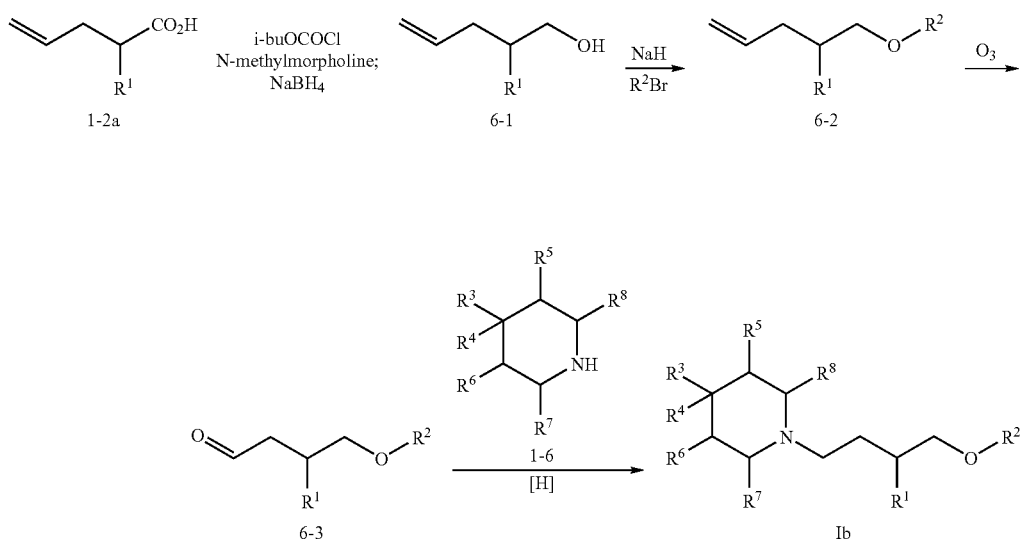

Compounds within the scope of the instant invention can alternatively be prepared as detailed in Scheme 6, starting from 1-2a (see Scheme 1). Reduction of the acid to the corresponding alcohol 6-1 can be accomplished by forming the mixed anhydride with isobutylchloroformate and a base such as N-methylmorpholine, followed by reduction with NaBH$_4$. The intermediate 6-1 can be converted to ethers 6-2 in a variety of ways, for example, by treatment with NaH and an alkyl halide. Oxidation of the olefin 6-2 to the aldehyde 6-3 can be carried out under numerous conditions, such as with ozone followed by treatment with methyl sulfide or triphenylphosphine, or with osmium tetroxide and sodium periodate (see March J. "Advanced Organic Chemistry", 4th ed., John Wiley & Sons, New York, pp. 1167–1171 (1992)). Reductive amination with amine 1–6 in the presence of a borohydride such as sodium triacetoxyborohydride or sodium cyanoborohydride then provides the compound of formula Ib.

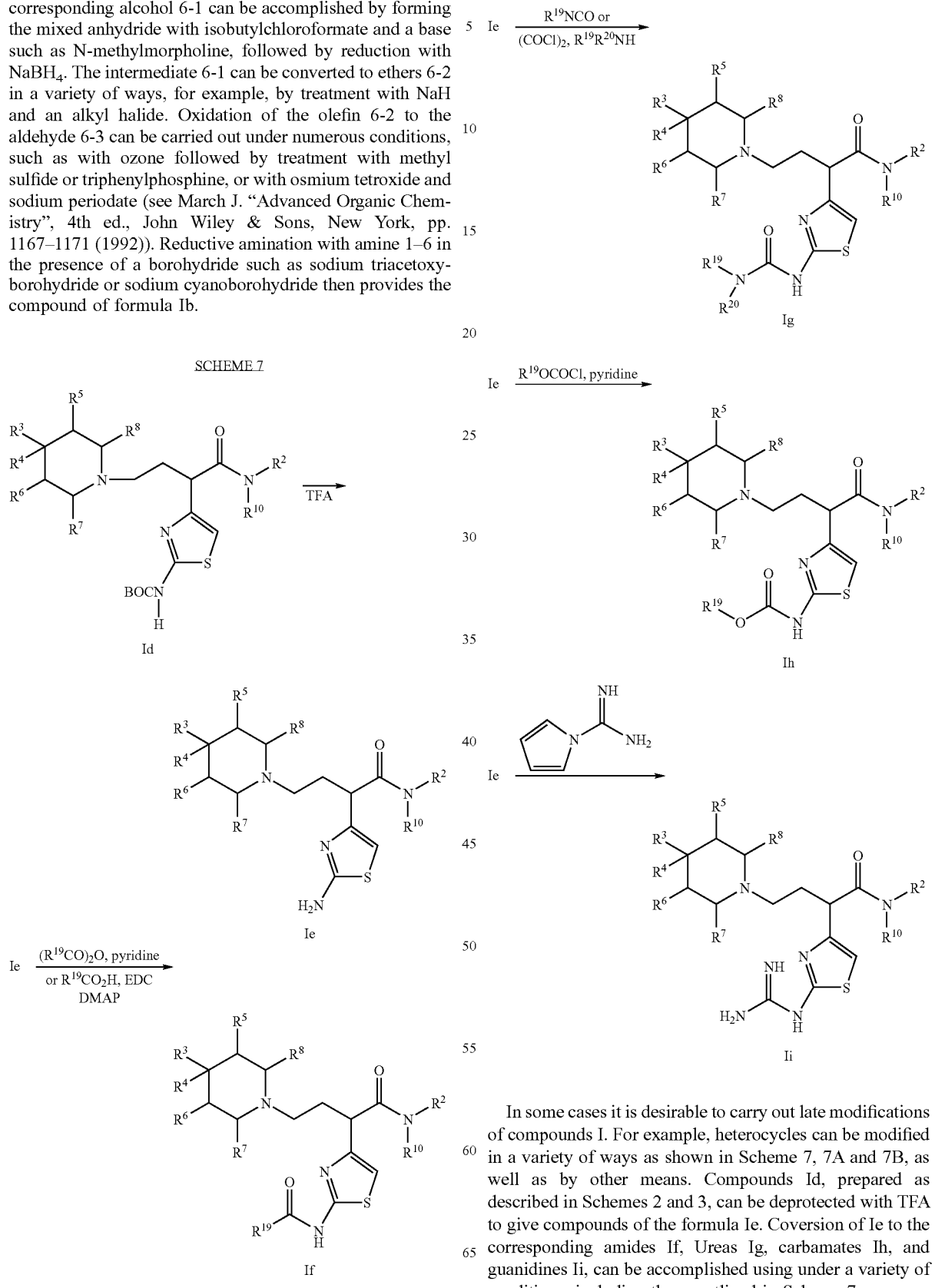

In some cases it is desirable to carry out late modifications of compounds I. For example, heterocycles can be modified in a variety of ways as shown in Scheme 7, 7A and 7B, as well as by other means. Compounds Id, prepared as described in Schemes 2 and 3, can be deprotected with TFA to give compounds of the formula Ie. Coversion of Ie to the corresponding amides If, Ureas Ig, carbamates Ih, and guanidines Ii, can be accomplished using under a variety of conditions, including those outlined in Scheme 7.

SCHEME 7A

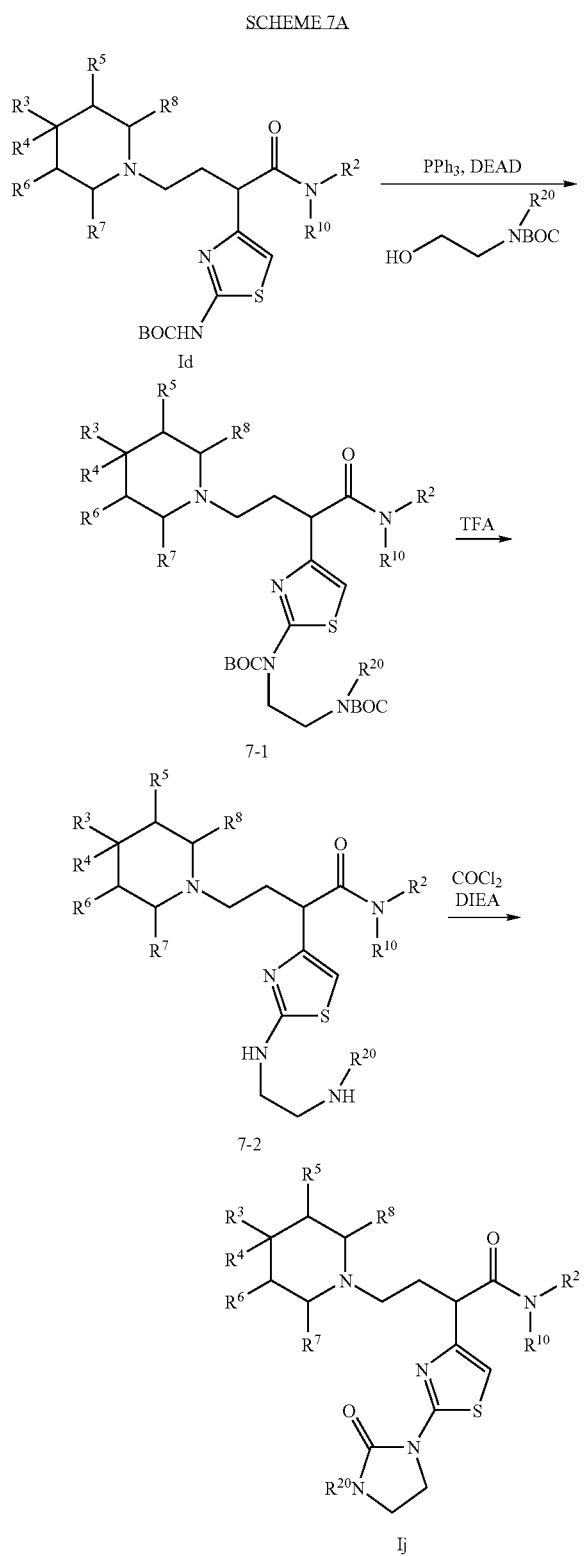

triphenylphosphine and diethylazodicarboxylate to give adducts 7-1. Deprotection with, for example, TFA gives diamines 7-2, which in turn can be cyclized in a number of different ways, including by treatment with phosgene in the presence of a base such as diisopropylethylamine to provide compounds of the formula Ij. Related compounds of the formula Ik can be prepared starting from compounds Ie. Amide coupling under a variety of conditions (such as with EDC and catalytic DMAP) affords 7-3. Rearrangement is accomplished by treatment with NaH and DMF to provide 7-4. Cyclization can be achieved by standard amide coupling with, for example, EDC and catalytic DMAP, to give the target compounds of the formula Ik.

SCHEME 7B

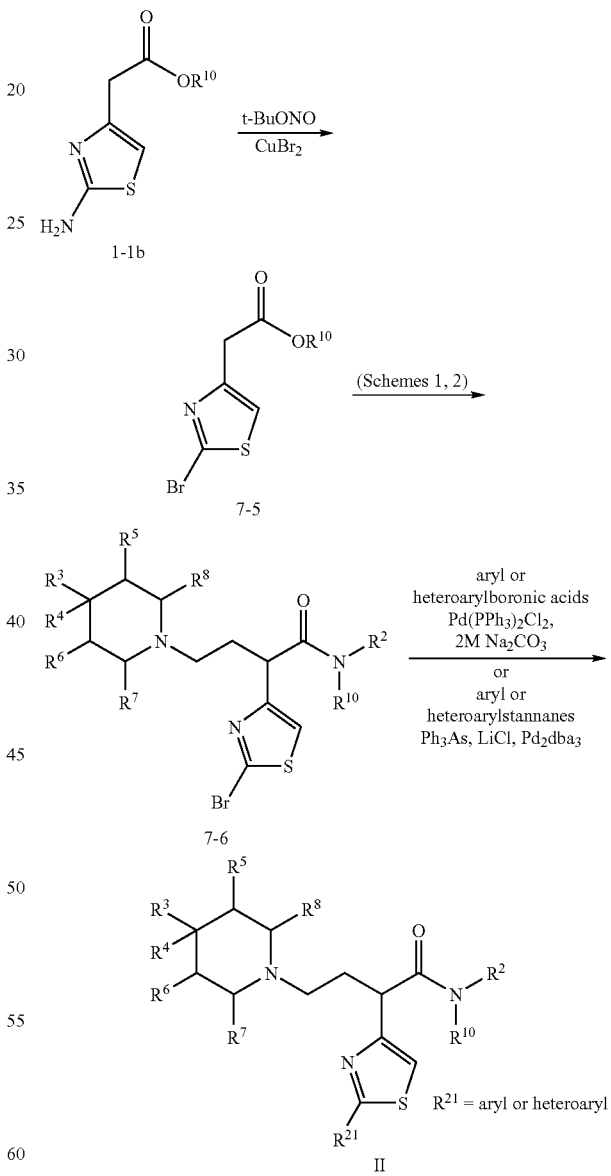

As an extension to the examples in Scheme 7, one can construct a variety of rings off of the aminothiazole core. Scheme 7a gives two examples. Compounds Id, prepared as described in Schemes 2 and 3, can be reacted with Boc-ethanolamines ($R^{20}$=H, or alkyl groups) in the presence of Scheme 7b shows how the thiazole core may be linked to various aryl and heteroaryl groups. Intermediate 1–1b can be converted to the corresponding 2-halothiazole 7-5 by, for example, treatment with t-butylONO and $CuBr_2$. Elaboration to compounds of the formula 7-6 is accomplished using protocols described in Schemes 1 and 2. Compounds 7-6 can readily be coupled to aryl and heteroarylboronic acids and stannanes under palladium catalyzed conditions, to give compounds of the formula II.

Substituted cyclopropyl compounds may be modified in a variety of ways as shown in part in Scheme 8. Compounds 1–2c (prepared as described in Scheme 4A) can be elaborated to compounds 8-1 using the methods shown in

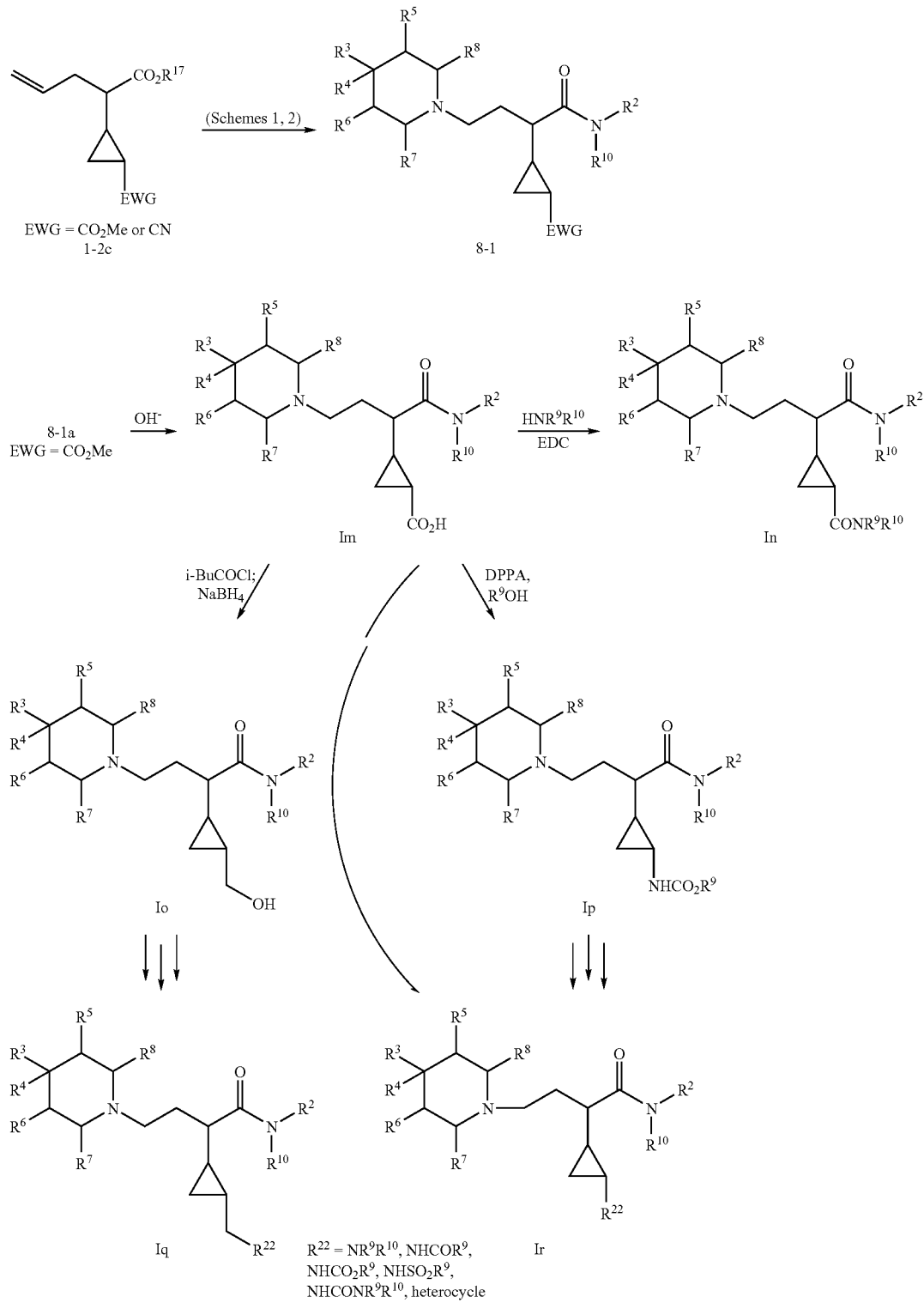

Schemes 1 or 2. These, in turn can be hydrolyzed to the corresponding carboxylic acids Im. The acids can be converted to carbamates by a Curtius rearrangement and then further converted to amines, amides, ureas, sulfonamides, heterocycles, etc., using standard techniques known to those skilled in the art. Alternatively, the acids can be reduced to the corresponding primary alcohols which, themselves may be carried on to amines, amides, carbamates, ureas, sulfonamides, and heterocycles, using standard techniques known to those skilled in the art. Additionally, the carboxylic acids and nitriles 8-1 can themselves be converted to heterocycles. Substituted cyclopropyl compounds of the formulas 8-1, and Im-r have at least three stereocenters, allowing for 8 possible isomers. These can be separated a various stages of the syntheses by a number of means including, preparative thin layer chromatography, flash chromatography, HPLC, and HPLC using columns with chiral packing components.

The subject compounds may be prepared by modification of the procedures disclosed in the Examples as appropriate. Starting materials are made by known procedures or as illustrated. The following examples are provided for the purpose of further illustration only and are not intended to be limitations on the disclosed invention. The following are representative procedures for the preparation of the compounds used in the following Examples or which can be substituted for the compounds used in the following Examples which may not be commercially available.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230–400 mesh). NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative Procedures for the preparation of the compounds used in the following Examples or which can be substituted for the compounds used in the following Examples which may not be commercially available.

Intermediate 1

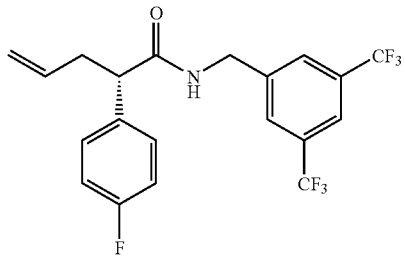

Step A:

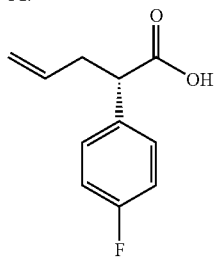

To a mechanically stirred solution of 4-fluorophenylacetic acid (50.0 g, 0.324 mol) in 800 mL THF at about −15° C. (ice salt bath) was added dropwise LHMDS in THF (1.0 M, 811 mL, 0.811 mol) over 2.25 h. Initially during the addition, the mixture was a slurry, then at the end the mixture cleared. After an additional 0.5 h, allyl bromide (30.9 mL, 43.2 g, 0.357 mol) was added neat, dropwise over 3 minutes. The reaction mixture was stirred for 15 minutes, then warmed to rt, stirred another 0.5 h and quenched by pouring into 1N HCl solution (1L). The resulting mixture was extracted three times with ethyl acetate (400 mL). The combined organic layers were washed with brine (800 mL), dried over anhydrous MgSO$_4$, filtered, and concentrated to afford 63 g of crude product.

To the crude acid in ethyl acetate (~1L) was added (S)-(−)-α-methylbenzylamine (23.6 g, 0.194 mol). The mixture was warmed to ~60° C. until most of the solids had dissolved (more ethyl acetate was added), then cooled to rt while stirring. The solids were collected by filtration and recrystallized twice from hot ethyl acetate to give 23.2 g of salt. The free acid was obtained by partitioning between 1N HCl and ethyl acetate. The organic phase was washed again with 1N HCl, then with brine, dried over anhydrous MgSO$_4$, and concentrated to give 15.5 g of acid (49% yield) as a clear oil which solidified on standing. $^1$H NMR (CDCl$_3$, 400 MHz): δ 7.26 (m, 2H), 7.00 (m, 2H), 5.68 (m, 1H), 4.98–5.08 (m, 2H), 3.61 (t, J=7.6 Hz, 1H), 2.78 (m, 1H), 2.49 (m, 1H).

The enantiomeric purity of the acid prepared above was determined by derivatization with L-Trp-OMe (amide formation). The methyl ester signal for the resolved acid (one singlet, 3.59 ppm)) was compared with that of the racemic acid (two singlets, 3.59 and 3.66 ppm) and determined to be >95% de, hence the acid is >95% ee. The procedure for derivatization is as follows:

4-fluorophenylpentenoic acid (21 mg, 0.11 mmol), L-Trp-OMe.HCl (41 mg, 0.16 mmol), EDC (31 mg, 0.16 mmol), HOBt (22 mg, 0.16 mmol), and DIEA (37 μL, 0.22 mmol) were combined in DCM and stirred overnight. The reaction mixture was diluted with more DCM, and washed with water, then brine. The organic layer was dried over MgSO$_4$, filtered and concentrated.

Step B:

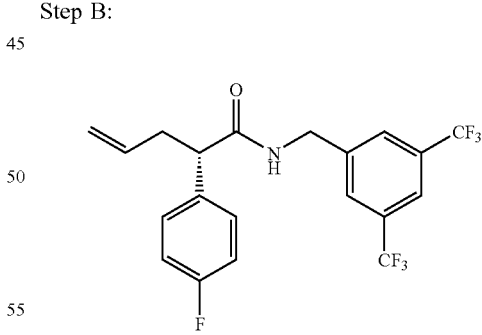

(S)-2-(4-fluorophenyl)-pentenoic acid (4.93 g, 25.4 mmol), 3,5-Bis(trifluoromethyl) benzylamine (6.48 g, 26.7 mmol), EDC (5.85 g, 30.5 mmol) and HOBt (4.12 g, 30.5 mmol) were combined in DCM and stirred overnight. The reaction mixture was diluted with more DCM and washed twice with water and once with brine. The organic layer was dried over anhydrous MgSO$_4$, filtered, and concentrated. The crude product was purified by flash chromatography (5% MeOH/DCM) to afford 9.41 g (88%) of a white solid. H NMR (CDCl$_3$, 500 MHz): δ 7.76 (s, 1H), 7.58 (s, 2H), 7.28 (m, 2H), 7.05 (m, 2H), 5.96 (br s, 1H), 5.74 (m, 1H), 5.02–5.11 (m, 2H), 4.53 (d, J=6 Hz, 2H), 3.49 (t, J=7.50 Hz, 1H), 2.92 (m, 1H), 2.52 (m, 1H). ESI-MS calc. for C20H16F7NO: 419; Found: 420 (M+H).

Intermediate 2

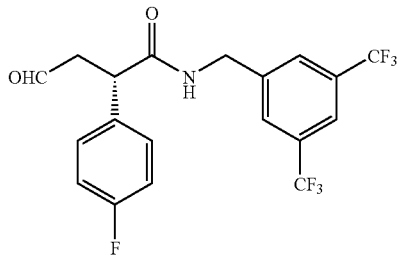

Intermediate 1 (5.05 g, 12.0 mmol), prepared in step B above, was dissolved in acetone (30 mL) and cooled to −78° C. O3 was bubbled through this solution for 15 min, at which point the solution had changed from colorless to blue. Nitrogen gas was passed through the solution until the blue color had disappeared and then dimethylsulfide (8.84 mL, 7.48 g, 120 mmol) was added and the reaction mixture allowed to warm to rt. After 1 h at rt, the reaction mixture was concentrated and the crude product was used as is in subsequent reactions. TLC and HNMR indicated that the product was a mixture, probably the result of intramolecular cyclization of the aldehyde and amide groups. The presence of aldehyde in the mixture was verified by HNMR which showed a peak at 9.81 ppm. This crude material was used as is in reductive amination reactions.

Intermediate 3

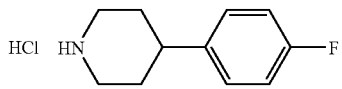

4-(4-Fluorophenyl)piperidine hydrochloride is now commercially available from Arch Corporation (catalog # AR01507). It can also be prepared in quantitative yield from commercially available 4-(4-fluorophenyl)-1,2,3,6-tetrahydropyridine hydrochloride (20 g. 94 mmol) by hydrogenation using Pd/C catalyst (2 g) in 200 mL of ethanol at 40 psi H2 pressure for 2 days using a Parr aparatus.

Intermediate 4

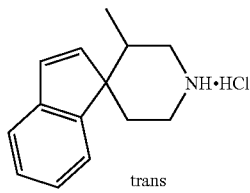

Step A:

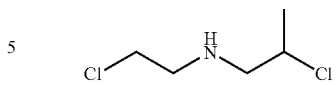

To a solution of thionyl chloride (6.58 mL, 10.7 g, 90.2 mmol) in CHCl3 (10 mL) was added dropwise commercially available 1-(2-hydroxyethylamino)-2-propanol (5.0 g, 42 mmol) in CHCl3 (5 mL). The resulting reaction was exothermic. The reaction mixture was brought to reflux whereupon it became a thick slurry. An additional 5 mL of CHCl3 was added. The reaction mixture was stirred at reflux for 2.5 h, then concentrated under vacuum to afford 7.97 g (99%) of crude salt. ESI-MS calc. for C5H11Cl2N: 155; Found: 156 (M+H).

Step B:

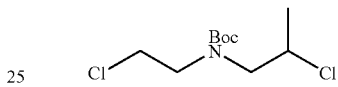

The hydrochloride salt prepared as described in Step A above (7.89 g, 41.0 mmol) and Boc2O (8.94 g, 41.0 mmol) were combined in DCM (75 mL). Triethylamine (8.6 mL, 6.2 g, 62 mmol) was then added and an ice water bath was used to control the exotherm. The reaction was then allowed to stir at rt for 6 h. The mixture was then diluted with DCM and washed three times with 1 N HCl, once with saturated NaHCO3 solution, and once with brine. The organic layer was dried over MgSO4, filtered, and concentrated in vacuo. The resulting crude product was purified by MPLC, eluting with a 10–15% gradient of ethyl acetate/hexane, to give 4.45 g (42%) of pure product. H NMR (CDCl3, 400 M): δ 4.30, 4.17 (m, 1H, rotamers), 3.50–3.72 (m, 5H), 3.37 (dd, J=14.8, 7.6 Hz, 0.5 H, rotamer), 3.21 (dd, J=14.4, 8.4 Hz, 0.5 H, rotamer), 1.46 (app d, J=6.8 Hz, 3H), 1.45 (s, 9H).

Step C:

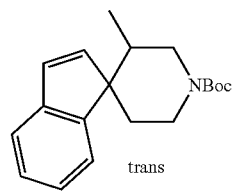

To a THF solution of LHMDS (1.0 M, 36.5 mL, 36.5 mmol) at 0° C. was added indene (2.02 g, 17.4 mmol) in THF (10 mL), dropwise. The reaction mixture was stirred at 0° C. for 50 min., then the dichloride prepared as described in Step B above (4.45 g, 17.4 mmol) was added in THF (15 mL), dropwise over 5–6 min. The resulting purple solution was stirred at 0° C. for 45 min., then warmed to rt and stirred for 48 h. The reaction mixture was diluted with ethyl acetate and washed with brine. The organic layer was dried over MgSO4, filtered, and concentrated. Purification by MPLC, eluting with 20% ethyl acetate/hexane, afforded 3.71 g (71%) of clear oil. ESI-MS calc. for C19H25NO2: 299; Found: 300 (M+H).

Step D:

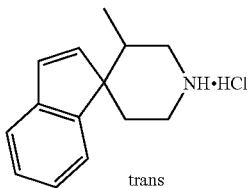

trans

The Bocpiperidine prepared in Step C (3.66 g, 12.2 mmol) was dissolved in anhydrous 4 N HCl (30 mL, 120 mmol) and stirred at rt for 45 min. The reaction mixture was concentrated to give 2.93 g crude product. $^1$H NMR analysis indicated that the product was a 93:7 ratio of trans to cis isomers.

H NMR trans (CD$_3$OD, 400 MHz): δ 7.20–7.37 (m, 4H), 6.95 (d, J=5.6 Hz, 1H), 6.80 (d, J=6.0 Hz, 1H), 3.52 (m, 1H), 3.42 (ddd, J=12.8, 4.0, 1.2 Hz, 1H), 3.29 (m, 1H), 3.07 (t, J=12.8 Hz, 1H), 2.48 (m, 1H), 2.37 (dt, J=4.4, 14.4 Hz, 1H), 1.45 (dt, J=14.4, 2.4 Hz, 1H), 0.40 (d, J=6.8 Hz, 3H).

Intermediate 5

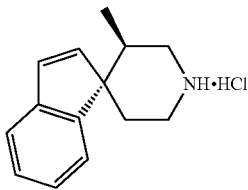

Step A:

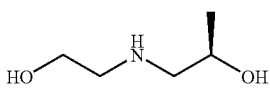

To a cooled (0° C.) solution of ethanolamine (41.8 g, 0.685 mol) in water (90 mL) was added neat (R)-propylene oxide (4.97 g, 85.6 mmol), dropwise. After 1 h at 0° C. the reaction was allowed to warm to rt and was stirred overnight. The reaction mixture was concentrated at ~80° C. in vacuo to remove the water and most of the ethanolamine, to give 11.79 g of crude product, containing some residual ethanolamine. This material was used without further purification in Step B.

Step B:

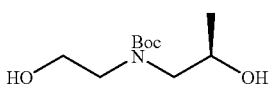

The diol prepared in Step A (11.8 g crude [~86% pure], ca. 83 mmol) was dissolved in DCM (150 mL) and treated with Boc$_2$O (23.4 g, 107 mmol) in DCM (75 mL) over 15 min. The reaction mixture was stirred over the weekend, concentrated, and purified by MPLC, eluting with 5% MeOH/EtOAc to provide 14.8 g (81%) of product.

Step C:

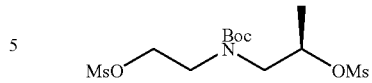

To a solution of the Boc-protected diol prepared in Step B (13.2 g, 60.3 mmol) and triethylamine (21.0 mL, 15.3 g, 151 mmol) in DCM (150 mL) at 0° C. was added dropwise methanesulfonyl chloride (9.56 mL, 14.1 g, 125 mmol). The reaction mixture was then stirred for 1.5 h, diluted with more DCM (100 mL) and washed with 3N HCl (250 mL). The aqueous layer was extracted again with DCM (200 mL), and the organic layers were combined and washed with 1N HCl (250 mL), saturated NaHCO$_3$ solution (250 mL), and brine (250 mL). The organic layer was dried over MgSO$_4$, filtered, and concentrated to give 22.8 g of crude bis-mesylate, which was used immediately. If not used immediately the bis-mesylate underwent decomposition.

Step D:

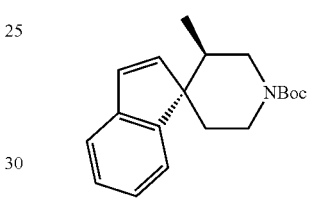

Indene (7.03 mL, 7.00 g, 60.3 mmol) was added dropwise over 4 min to a 1.0 M THF solution of LHMDS (127 mL, 127 mmol) at 0° C. After stirring for an additional 30 min., this solution was transferred via cannula to a solution of bis-mesylate (22.6 g, 60.3 mmol), prepared as described in Step C above, in THF (75 mL) at 0° C. The mixture was stirred for 2 h, warmed to rt and stirred overnight. The reaction mixture was partially concentrated and then partitioned between ethyl acetate and water. The organic layer was extracted again with ethyl acetate and the organic layers were combined. The organic phase was then washed with brine, dried over MgSO$_4$, filtered and concentrated to give 17.3 g of crude product. Purification by MPLC, eluting with 15% ethyl acetate/hexane, afforded 9.51 g (53%) of piperidine as a ~3:1 mixture of trans to cis (determined by H NMR). The mixture was crystallized from hot hexane to give 6 g (33%) of pure trans isomer (>20:1 by H NMR).

H NMR (CDCl$_3$, 400 MHz): δ 7.29 (dt, J=6.4, 1.6 Hz, 1H), 7.20 (m, 3H), 6.83 (d, J=6.0 Hz, 1H), 6.67 (d, J=5.6 Hz, 1H), 4.20 (br s, 2H), 2.97 (br t, J=3.2 Hz, 1H), 2.69 (br t, J=2.4 Hz, 1H), 2.16 (m, 1H), 2.07 (dt, J=4.4, 13.2 Hz, 1H), 1.49 (s, 9H), 1.25 (m, 1H), 0.31 (d, J=6.8 Hz, 3H).

Step E:

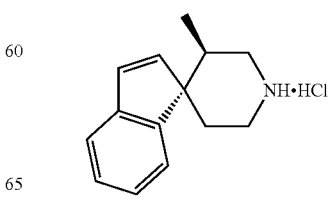

The Boc-piperidine prepared in Step D (4.35 g, 14.5 mmol) was dissolved in an anhydrous 4 N HCl solution in THF and stirred at rt for 1 h. The reaction mixture was then concentrated to afford 3.81 g of product.

EI-MS calc. for C14H17N: 199; Found: 200 (M)+.

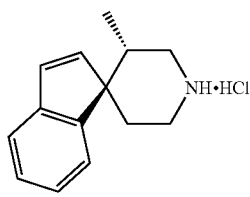

Intermediate 6 was prepared in exactly the same way as intermediate 5 except the starting epxide was (S)-(−)-propylene oxide.

H NMR (CD₃OD, 400 MHz): δ 7.22–7.36 (m, 4H), 6.95 (d, J=5.6 Hz, 1H), 6.80 (d, J=6.0 Hz, 1H), 3.53 (m, 1H), 3.42 (m, 1H), 3.29 (m, 1H), 3.06 (t, J=12.8 Hz, 1H), 2.48 (m, 1H), 2.37 (dt, J=4.4 Hz, 14.4 Hz, 1H), 1.45 (dt, J=14.8, 2.4 Hz, 1H), 0.40 (d, J=6.8 Hz, 3H).

Intermediate 7

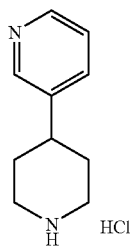

Step A

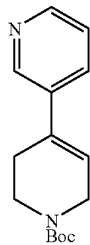

A mixture of 1-t-butoxycarbonyl-4-trifluoromethanesulfonate-1,2,3,6-tetrahydropyridine (known: Wustrow, D. J., Wise, L. D. *Synthesis* (1991), 993., 2.50 g, 7.53 mmol), triphenylarsine (184 mg, 0.602 mmol), lithium chloride (958 mg, 22.6 mmol) and Tris(dibenzylideneacetone)-dipalladium(0) (138 mg, 0.151 mmol) in anhydrous 1-methylpyrrolidin-2-one (50 mL) was stirred for 5 min, whereupon the reaction color changed from brown/purple to yellow. Then commercially available 3-(tributylstannyl)pyridine (3.27 g, 8.89 mmol) was added in anhydrous 1-methylpyrrolidin-2-one (7 mL). The reaction mixture was purged with argon, stirred at rt for 30 min, at 80° C. for 2.5 h, and at 65° C. for overnight. To the reaction mixture was added 1 M KF solution (15 mL) and the resulting mixture was stirred for 1 h. The reaction mixture was diluted with ethyl acetate and filtered through celite. More 1 M KF solution and ethyl acetate was added to the filtrate. The layers were separated and the aqueous layer was extracted with more ethyl acetate. The combined organic layers were washed six times with water, and once with brine, then were dried over anhydrous MgSO₄, filtered, and concentrated. Purification by MPLC (silica, 3% methanol/ethyl acetate) provided 1.09 g (56%) of coupled product. ¹H NMR (400 MHz, CDCl₃): δ 8.63 (d, J=1.6 Hz, 1H), 8.48 (dd, J=4.8, 1.6 Hz, 1H), 7.64 (dt, J=8.0, 2.0 Hz, 1H), 7.25 (obsc m, 1H), 6.08 (br s, 1H), 4.09 (m, 2H), 3.64 (t, J=5.6 Hz, 2H), 2.50 (br s, 2H), 1.47 (s, 9H).

Step B

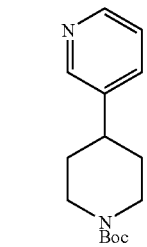

A mixture of 1-t-butoxycarbonyl-4-(3-pyridyl)-1,2,3,6-tetrahydropyridine (1.09 g, 4.19 mmol) and Pd(OH)₂ (20% Pd on Carbon, 220 mg) in ethanol (20 mL) was stirred under a hydrogen atmosphere (balloon) for 5 h. The reaction mixture was filtered and concentrated, but was found to be incomplete, so was resubmitted to the reaction, this time with 300 mg Pd(OH)₂ and under a hydrogen pressure of 50 psi for 7.5 h. The reaction mixture was filtered and concentrated to give 1.12 g of the desired piperidine product. ESI-MS calc. for C15H22N2O2: 262; Found: 263 (M+H).

Step C

The Boc-piperidine from Step B (1.11 g, 4.23 mmol) was dissolved in 4 N HCl in dioxane (20 mL) and stirred at rt for 1 h. The reaction mixture was concentrated, redissolved in methanol, filtered through a 0.45 μm PTFE filter, and concentrated again to give 950 mg of piperidine hydrochloride. ¹H NMR (400 MHz, CD₃OD): δ 8.90 (d, J=1.6 Hz, 1H), 8.80 (d, J=6.0 Hz, 1H), 8.66 (dt, J=8.4, 2.0 Hz, 1H), 8.11 (dd, J=8.0, 6.0 Hz, 1H), 3.57 (m, 2H), 3.28 (obsc m, 1H), 3.20 (br t, J=13.2 Hz, 2H), 2.21 (m, 2H), 2.05 (m, 2H).

Intermediate 8

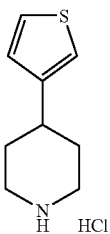

Step A

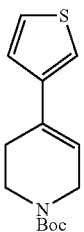

According to literature procedures (Wustrow, D. J., Wise, L. D. *Synthesis* (1991), 9932), N Na$_2$CO$_3$ (7 mL) was combined with 3-thiophene boronic acid (862 mg, 6.73 mmol), lithium chloride (606 mg, 14.4 mmol), 1-t-butoxycarbonyl-4-trifluoromethanesulfonate-1,2,3,6-tetrahydropyridine (1.60 g, 4.81 mmol), and tetrakis(triphenylphosphine)-palladium(0) (555 mg, 0.481 mmol) in DME (17 mL) under a nitrogen atmosphere. The reaction mixture was warmed to reflux and stirred for 2 h. The reaction mixture was concentrated, redissolved in DCM, and washed with 2N Na$_2$CO$_3$ solution, concentrated NH$_4$OH solution, and brine. The organic layer was dried over anhydrous MgSO$_4$, filtered, and concentrated. Purification by flash chromatography (silica, 10% ethyl acetate/hexane) gave 694 mg (55%) of coupled product. $^1$H NMR (500 MHz, CDCl$_3$): δ 7.22 (d, 1H), 7.19 (d, 1H), 7.07 (s, 1H), 6.00 (br s, 1H), 4.03 (br s, 2H), 3.60 (br s, 2H), 2.45 (br s, 2H), 1.47 (s, 9H).

Step B

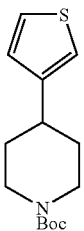

Hydrogenation to the piperidine was accomplished in a similar fashion to that shown in Step B of the synthesis of Intermediate 7 starting from 1-t-butoxycarbonyl-4-(3-thiophene)-1,2,3,6-tetrahydropyridine (694 mg, 2.62 mmol) and providing 540 mg of desired product. ESI-MS calc. for C14H21NO2S: 267; Found: 268 (M+H).

Step C

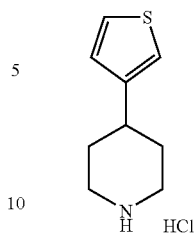

Deprotection was accomplished in a similar fashion to that shown in Step C of the synthesis of Intermediate 7 starting from 1-t-butoxycarbonyl-4-(3-thiophene)-piperidine (540 mg, 2.02 mmol) and providing 408 mg of desired product. ESI-MS calc. for C9H13NS: 167; Found: 168 (M+H).

A variety of substituted 4-phenyl piperidines as well 4-heterocycle piperidines were prepared in the same fashion as described in the synthesis of Intermediate 8. Some examples are listed in the Table below:

| Intermediate | Piperidine | Calc. MW | Found ESI-MS (M + H)+ |
|---|---|---|---|
| 8-1 | furan-3-yl piperidine·HCl | 151 | 152 |
| 8-2 | thiophen-2-yl piperidine·HCl | 167 | 168 |
| 8-3 | 3-chlorophenyl piperidine·HCl | 195 | 196 |
| 8-4 | 3-methoxyphenyl piperidine·HCl | 191 | 192 |

-continued

| Intermediate | Piperidine | Calc. MW | Found ESI-MS (M + H)+ |
|---|---|---|---|
| 8-5 | 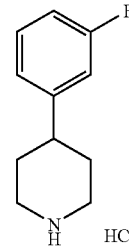 | 179 | 180 |
| 8-6 | 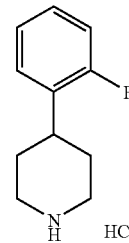 | 179 | 180 |
| 8-7 | 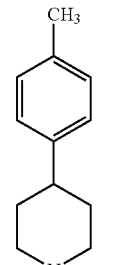 | 175 | 176 |

Intermediate 9

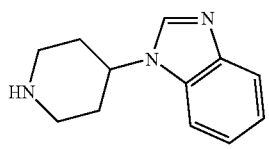

Formic acid (568 mg, 12.3 mmol) was added to Ac₂O (1.05 g, 10.3 mmol) at 0° C. and the resulting mixture was warmed to 60° C., stirred for 2.75 h and cooled to room temperature. THF (5 mL) was then added, the solution was cooled to −15° C., and the 2-(1-t-butoxycarbonylpiperidin-4-ylamino)aniline (2.00 g, 6.86 mmol) was added in THF (5 mL). After 0.5 h the reaction mixture was concentrated (with warming at 40° C.) and the resulting crude product was purified by MPLC (silica, 90% ethyl acetate/hexane, then 100% ethyl acetate, then 4% methanol/ethyl acetate) to give 1.25 g of the benzimidazole. The BOC group was removed by dissolving the intermediate (1.21 g, 4.00 mmol) in ethyl acetate and bubbling HCl (g) through this solution for 10 min. The solvent was removed to afford 962 mg of crude Intermediate 10 as its hydrochloride salt.

BOC intermediate: ESI-MS calculated for C17H23N3O2: 301; Found: 302 (M+H).

Intermediate 10

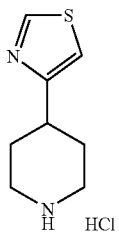

Step A

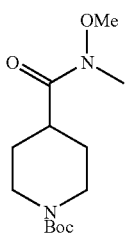

N-Boc-isonipecotic acid (8.04 g, 35.1 mmol) was combined with N,O-dimethylhydroxylamine hydrochloride (5.13 g, 52.6 mmol), EDC (10.1 g, 52.6 mmol) and DIEA (9.2 mL, 53 mmol) in DCM (100 mL). Then N,N-dimethylaminopyridine (~200 mg) was added and the reaction mixture was permitted to stir at rt for 2 h. The reaction mixture was diluted with more DCM and washed with 2 N HCl solution, saturated NaHCO₃ solution, and brine. The organic layer was dried over anhydous MgSO₄, filtered, and concentrated to give 8.43 g of crude product which was used without further purification. ESI-MS calc. for C13H24N2O4: 272; Found: 273 (M+H).

Step B

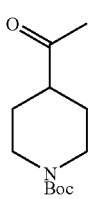

A cooled (−78° C.) solution of the amide prepared as described in Step A (8.35 g, 30.7 mmol) in 100 mL ether was treated dropwise with 3.0 M methylmagnesium chloride in THF (20.4 mL, 61.3 mmol) over a period of five min. The resulting thick slurry was warmed to 0° C. and stirred for 0.5 h. The reaction mixture was poured into 1 N HCl solution and extracted with ether. The ethereal layer was washed with brine, dried over anhydrous MgSO₄, filtered, and concentrated to give 5.81 g of crude product which did not require further purification.

Step C

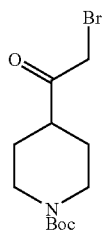

To a cooled (−78° C.) solution of 2.0 M LDA (in heptane/THF/benzene, 13.7 mL, 27.3 mmol) in 100 mL THF was added dropwise over 40 min a solution of the methyl ketone prepared as described in Step B (5.17 g, 22.8 mmol) in 40 mL THF. After an additional 25 min, chlorotrimethylsilane (5.79 mL, 45.6 mmol) was added dropwise over 10 minutes. After stirring the for 1 h, the reaction mixture was poured into 300 mL of saturated NaHCO$_3$ solution and the resulting mixture was extracted twice with 200 mL of ether. The combined ethereal layers were washed with brine, dried over anhydrous MgSO$_4$, filtered, and concentrated to give 7.35 g of TMS-enol ether, which was then redissolved in 120 mL THF, cooled to 0° C., and treated with sodium bicarbonate (2.87 g, 34.2 mmol), followed by N-bromosuccinimide (4.06 g, 22.8 mmol). The reaction mixture was warmed to rt and stirred for 1 h and 10 min, at which point, it was poured into 200 mL of saturated NaHCO$_3$ solution. The resulting mixture was extracted twice with 200 mL of ether and the combined ethereal layers were washed with saturated NaHCO$_3$ solution and brine, dried over anhydrous MgSO$_4$, filtered, and concentrated to give 7.62 g of crude product which was used without further purification.

Step D

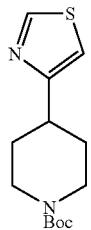

The bromomethylketone prepared as described in Step C (1.48 g, 4.83 mmol) was combined with thioformamide (295 mg, 4.83 mmol) in 10 mL of THF. The reaction mixture was warmed to 60° C. and stirred for 4 days. The reaction mixture was then diluted with ethyl acetate and washed with water, then brine, dried over anhydrous MgSO$_4$, filtered, and concentrated. Purification by MPLC (silica, 60% ethyl acetate/hexane) afforded 627 mg of thiazole product. $^1$H NMR (400 MHz, CDCl$_3$): δ 8.75 (d, J=2.0 Hz, 1H), 6.93 (d, J=2.4 Hz, 1H), 4.19 (br s, 2H), 2.96 (m, 1H), 2.84 (br m, 2H), 2.03 (m, 2H), 1.62 (m, 2H), 1.44 (s, 9H).

Step E

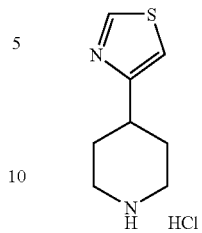

The thiazole prepared as described in Step D (588 mg, 2.19 mmol) was treated with 4 N HCl in dioxane (15 mL). Since the mixture was heterogeneous, 1 mL of water was added to solubilize the starting material and the mixture was stirred for 1.5 h. The reaction mixture was then concentrated to give 526 mg of piperidine hydrochloride. $^1$H NMR (400 MHz, CD$_3$OD): δ 9.60 (d, J=2.4 Hz, 1H), 7.72 (d, J=2.80 Hz, 1H), 3.52 (m, 2H), 3.31 (m, 1H), 3.19 (m, 2H), 2.29 (m, 2H), 1.99 (m, 2H). ESI-MS calc. for C8H12N2S: 168; Found: 169 (M+H).

Intermediate 11

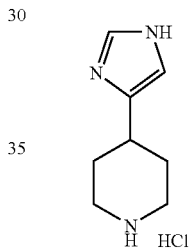

Step A

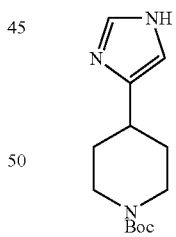

The bromomethylketone prepared as described in Steps A–C of the synthesis of Intermediate 10 (2.02 g, 6.60 mmol) was combined with formamidine acetate (1.37 g, 13.2 mmol) in ~130 mL of NH$_3$ (1) and heated in an autoclave at 40° C. and 194 psi for 20 h. The NH$_3$ was allowed to evaporate, the residue was dissolved in DCM and filtered. The filtrate was concentrated. Purification by flash chromatography (silica, 10% of 1:9 NH$_4$OH/methanol in DCM) afforded 649 mg of the imidazole product.

$^1$H NMR (400 MD, CD$_3$OD): δ 7.56 (d, J=1.2 Hz, 1H), 6.74 (d, J=1.2 Hz, 1H), 4.13 (br s, 2H), 2.82 (m, 2H), 2.74 (m, 1), 1.97 (m, 2H), 1.54 (m, 2H), 1.44 (s, 9).

Step B

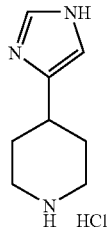

The intermediate from Step A (402 mg, 1.60 mmol) was dissolved in 4N HCl in dioxane (5 mL) and stirred at rt for 1.5 h. The reaction mixture was concentrated to afford 384 mg of piperidine hydrochloride. ESI-MS calc. for C8H13N3: 151; Found: 151 (M+).

EXAMPLE 1

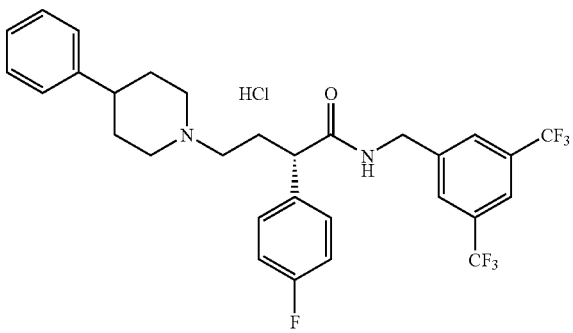

The crude aldehyde intermediate 1 (107 mg, 0.255 mmol), prepared as described above, was combined with 4-phenylpiperidine (49.3 mg, 0.306 mmol), NaB(OAc)$_3$H (108 mg, 0.510 mmol) and 4° A molecular sieves (250 mg) in DCE (5 mL) and stirred overnight. The reaction mixture was filtered through celite, diluted with ethyl acetate, and washed with saturated, NaHCO$_3$ solution, followed by brine. The organic layer was dried over MgSO$_4$, filtered, and concentrated. The crude product was purified by preparative TLC, eluting with 0.75/6.75/92.5 NH$_4$OH/MeOH/DCM, providing the product as a free base. H NMR (CDCl$_3$, 400 MHz): δ 7.71 (s, 1H), 7.64 (s, 2H), 7.28–7.37 (m, 4H), 7.21 (m, 3H), 7.01 (m, 2H), 4.51 (m, 2H), 4.15 (br s, 1H), 3.20–3.33 (m, 2H), 2.32–2.75 (m, 6H), 2.21 (br m, 2H), 2.05 (m, 1H), 1.93 (m, 2H). The free base was converted to its HCl salt by dissolving it in DCM (2 mL) and adding anhydrous 4 N HCl in dioxane (70 µL, 0.3 mmol), then concentrated off the solvents to give 50.2 mg (33%) of a white solid. ESI-MS calc. for C30H29F7N2O: 566; Found: 567 (M+H).

EXAMPLE 2

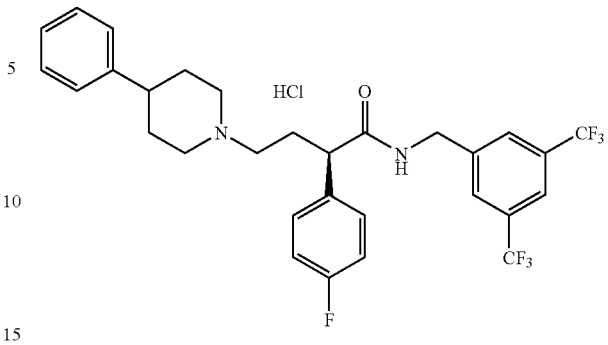

The enantiomer of the compound prepared as described in EXAMPLE 1 was prepared in exactly the same way except that in the preparation of the corresponding enantiomer of Intermediate 1, (R)-(+)-α-methylbenzylamine was used instead of (S)-(−)-α-methylbenzylamine in the resolution of the racemic carboxylic acid. ESI-MS calc. for C30H29F7N2O: 566; Found: 567 (M+H).

Additional compounds were prepared essentially using the same experimental protocols as described in EXAMPLE 1 are displayed in Tables 1 and 2. Requisite amines incorporated via the reductive amination step are either commercially available, known from the chemical literature, or were prepared as described above.

TABLE 1

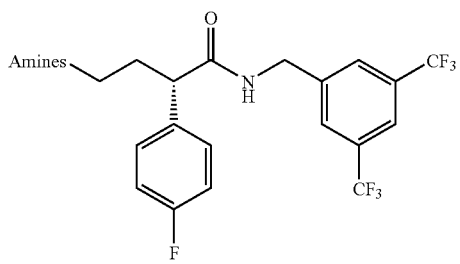

| Entry | Amine | calc. MW | ESI-MS Found (M + H)+ |
|---|---|---|---|
| 1-1 |  | 490 | 491 |
| 1-2 | 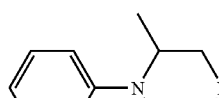 | 581 | 582 |
| 1-3 | 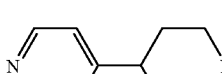 | 567 | 568 |
| 1-4 | 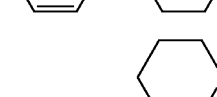 | 580 | 581 |

TABLE 1-continued

[Structure: Amines-CH2CH2-CH(4-fluorophenyl)-C(=O)-NH-CH2-(3,5-bis(trifluoromethyl)phenyl)]

| Entry | Amine | calc. MW | ESI-MS Found (M + H)+ |
|---|---|---|---|
| 1-5 | 4-(4-fluorophenyl)piperidine | 584 | 585 |
| 1-6 | 4-(4-fluorophenyl)-1,2,3,6-tetrahydropyridine | 582 | 583 |
| 1-7 | 4-propylpiperidine | 532 | 533 |
| 1-8 | 1,2,3,4-tetrahydro-β-carboline | 577 | 578 |
| 1-9 | 4-hydroxy-4-phenylpiperidine | 582 | 583 |
| 1-10 | 4-(ethoxycarbonyl)-4-phenylpiperidine | 638 | 639 |
| 1-11 | 4-cyano-4-phenylpiperidine | 591 | 592 |
| 1-12 | 3-phenylpyrrolidine | 552 | 553 |
| 1-13 | 4-(2-methylphenyl)piperidine | 580 | 581 |
| 1-14 | 4-(ethoxycarbonyl)piperidine | 562 | 563 |

TABLE 1-continued

[Structure: Amines-CH2CH2-CH(4-fluorophenyl)-C(=O)-NH-CH2-(3,5-bis(trifluoromethyl)phenyl)]

| Entry | Amine | calc. MW | ESI-MS Found (M + H)+ |
|---|---|---|---|
| 1-15 | 1-(piperidin-4-yl)benzimidazole | 597 | 598 |
| 1-16 | 3-(piperidin-4-yl)-1H-indole | 605 | 606 |
| 1-17 | 4-(2-fluorophenyl)piperidine | 584 | 585 |
| 1-18 | 4-(3-fluorophenyl)piperidine | 584 | 585 |
| 1-19 | 4-(2-methoxyphenyl)piperidine | 596 | 597 |
| 1-20 | 4-(3-methoxyphenyl)piperidine | 596 | 597 |
| 1-21' | 4-(4-methylphenyl)piperidine | 580 | 581 |
| 1-22 | 4-phenyl-azabicyclic amine | 592 | 593 |
| 1-23 | 4-(thiophen-2-yl)piperidine | 572 | 573 |

TABLE 1-continued

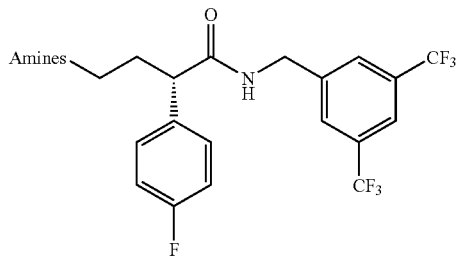

| Entry | Amine | calc. MW | ESI-MS Found (M + H)+ |
|---|---|---|---|
| 1-24 | 3-thienyl-piperidine | 572 | 573 |
| 1-25 | 3-furyl-piperidine | 556 | 557 |
| 1-26 | thiazolyl-piperidine | 573 | 574 |
| 1-27 | imidazolyl-piperidine | 556 | 557 |
| 1-28 | 2-pyridyl-piperidine | 567 | 568 |
| 1-29 | 3-pyridyl-piperidine | 567 | 568 |
| 1-30 | 4-phenyl-4-methyl-piperidine | 580 | 581 |
| 1-31 | 3-methyl-4-phenyl-piperidine | 580 | 581 |
| 1-32 | 3-methyl-4-phenyl-piperidine | 580 | 581 |
| 1-33 | 3-chlorophenyl-piperidine | 601 | 602 |

TABLE 1-continued

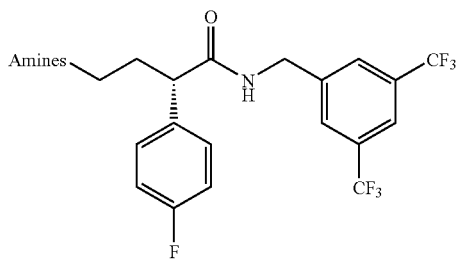

| Entry | Amine | calc. MW | ESI-MS Found (M + H)+ |
|---|---|---|---|
| 1-34 | 1-phenyl-3-aminopiperidine | 581 | 582 |
| 1-35 | tryptamine | 565 | 566 |

TABLE 2

Spiropiperidines

| Entry | Amine | calc. MW | ESI-MS Found (M + H)+ |
|---|---|---|---|
| 1-36 | indene-spiropiperidine | 590 | 591 |
| 1-37 | indane-spiropiperidine | 592 | 593 |
| 1-38 | methyl-indene-spiropiperidine (trans) | 604 | 605 |

TABLE 2-continued
Spiropiperidines
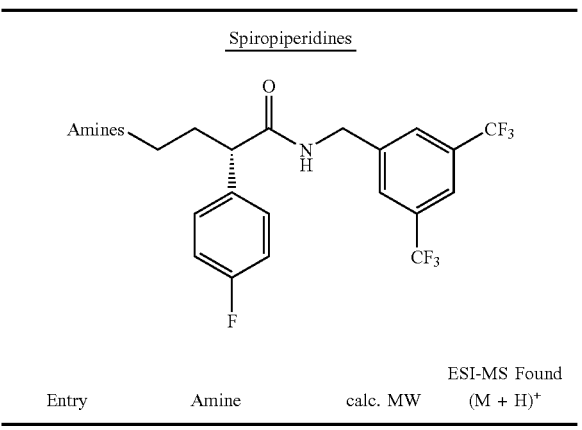
| Entry | Amine | calc. MW | ESI-MS Found (M + H)+ |
|---|---|---|---|
| 1-39 | | 594 | 595 |
| 1-40 | | 696 | 697 |
| 1-41 | | 610 | 611 |
| 1-42 | | 635 | 636 |
| 1-43 | | 570 | 571 |
| 1-44 | | 618 | 619 |
TABLE 2-continued
Spiropiperidines
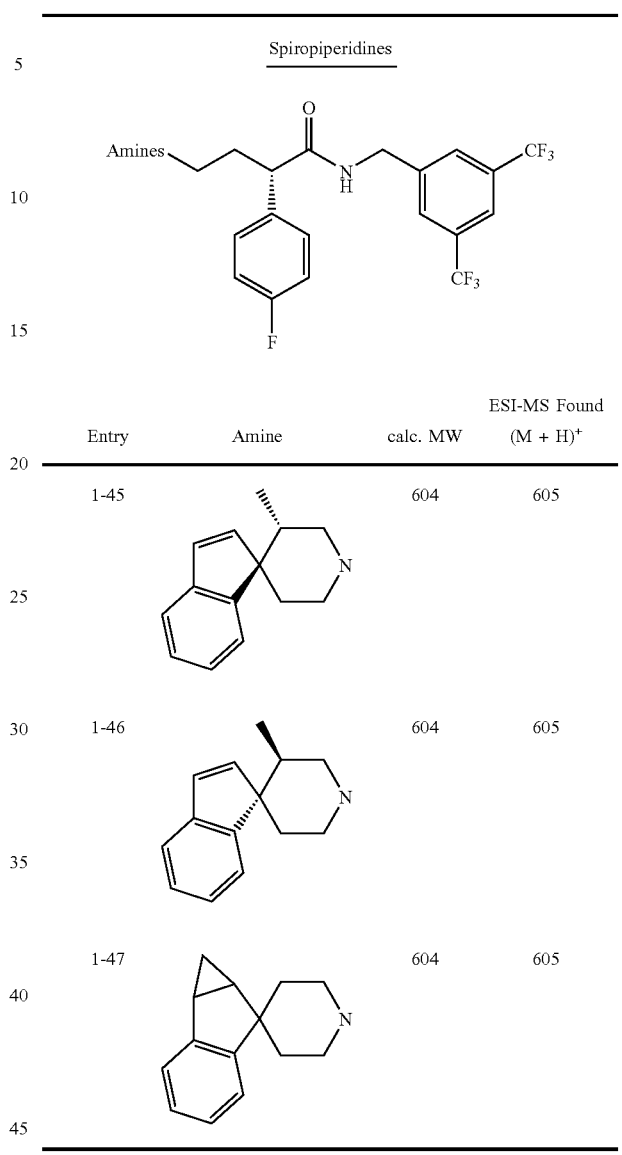
| Entry | Amine | calc. MW | ESI-MS Found (M + H)+ |
|---|---|---|---|
| 1-45 | | 604 | 605 |
| 1-46 | | 604 | 605 |
| 1-47 | | 604 | 605 |
EXAMPLE 3
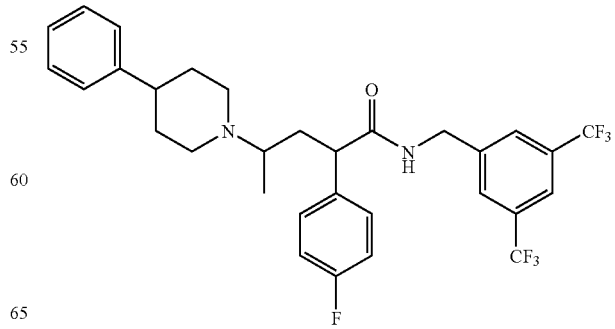

Step A:

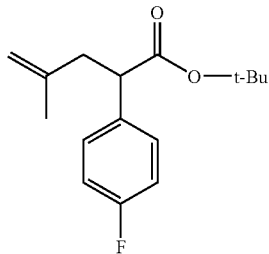

Sulfuric acid (7.28 mL, 137 mmol) was added to a suspension of MgSO₄ (65.6 g, 547 mmol) in DCM (~500 mL). After stirring for 30 min, 4-fluorophenylacetic acid (18.6 g, 137 mmol) was added, followed by t-butanol (65.3 mL, 683 mmol). The reaction mixture was stirred vigorously for 23 h, then was quenched with saturated NaHCO₃ solution (until MgSO₄ had dissolved). The mixture was extracted with DCM, then the organic layer was washed with brine, dried over anhydrous MgSO₄, filtered, and concentrated to give 22.4 g of crude ester. A cooled (−78° C.) solution of the resulting t-butyl ester (10.0 g, 47.6 mmol) in THF (~75 mL) was treated dropwise with 1M lithium hexamethyldisilazide solution in THF (143 mL, 143 mmol), stirred for an additional 30 min, then treated dropwise with 3-bromo-2-methylpropene. The reaction mixture was allowed to slowly warm to rt over a period of 1.5 h. The reaction mixture was quenched with water and concentrated. The residue was redissolved in ethyl acetate and washed with 1N HCl solution, then brine. The organic layer was dried over anhydrous MgSO₄, filtered, and concentrated to give 12.3 g of desired title compound, which did not require further purification.

H NMR (CDCl₃, 500 MHz): δ 7.31 (m, 2H), 7.01 (m, 2H), 4.79 (s, 1H), 4.73 (s, 1H), 3.68 (m, 1H), 2.79 (m, 1), 2.38 (m, 1H), 1.74 (s, 3H), 1.40 (s, 9H).

Step B:

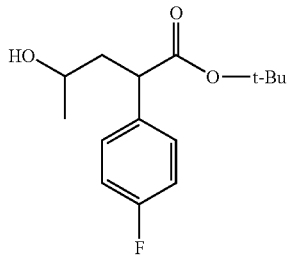

Ozone was bubbled through a cooled (−78° C.) solution of the olefin from Step B (4.0 g, 15 mmol) in methanol until a green/blue color persisted. Nitrogen was bubbled through the solution until the blue color has disappeared. Then sodium borohydride (576 mg, 15.2 mmol) was added and the mixture was stirred for 1.5 h. The reaction mixture was quenched with water and concentrated to remove the methanol. The resulting aqueous mixture was extracted with ethyl acetate and the organic layer was washed with 1 N HCl solution and brine, dried over anhydrous MgSO₄, filtered, and concentrated to give 2.37 g of product which was not further purified (~6:4 ratio of diastereomers). H NMR (CDCl₃, 500 MHz): δ 7.32 (m, 2H), 7.02 (m, 2H), 3.70 (m, 1.4H), 3.47 (m, 0.6 H), 2.15 (m, 1H), 2.07 (m, 1H), 1.80 (m, H1H), 1.63 (m, 1H), 1.38 (s, 9H), 1.18 (d, 1.2H), 1.15 (d, 1.8H).

Step C:

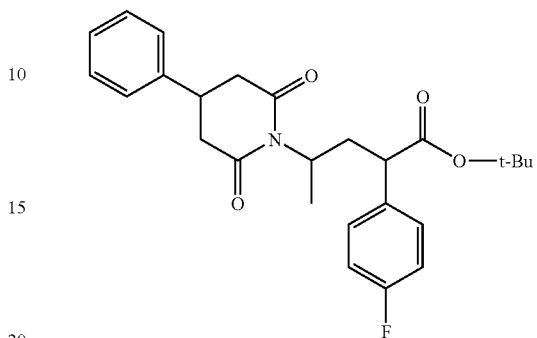

To a cooled (0° C.) solution of the alcohol prepared as described in Step B (1.19 g, 4.46 mmol), 4-phenyl glutarimide (1.04 g, 5.35 mmol), and triphenylphosphine (1.40 g, 5.35 mmol) in THF (20 mL) was added a solution of diisopropyl azodicarboxylate (1.05 mL, 5.35 mmol). The reaction mixture was permitted to warm to rt and stir for 3 h. The reaction mixture was concentrated, redissolved in ethyl acetate, and washed with saturated NaHCO₃ solution, then brine, dried over anhydrous MgSO₄, filtered, and concentrated. Purification by flash chromatography (silica, 50% ethyl acetate/hexane), followed by MPLC (silica, 75% ethyl acetate/hexane) gave 968 mg of the desired product.

Step D:

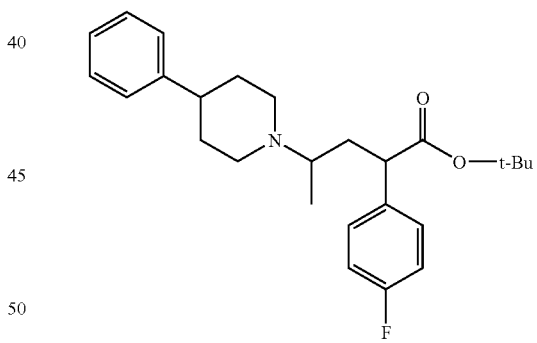

To a cooled solution (0° C.) solution of the glutarimidoester prepared as described in Step C (544 mg, 1.24 mmol) in THF (5 mL) under an N₂ atmosphere was added borane dimethylsulfide complex (0.372 mL, 3.72 mmol). The resulting mixture was warmed to rt and stirred for 3 h. The reaction mixture was concentrated and N,N-dimethylethanolamine (3.73 mL, 37.2 mmol) was added. The resulting mixture was stirred at reflux for 2 h, then concentrated. Purification by preparative TLC (silica, 1% of 1:9 NH₄OH/methanol in DCM) furnished 275 mg of piperidine product (54%).

ESI-MS calc. for C26H34FNO2: 411; Found: 412 (M+H).

Step E:

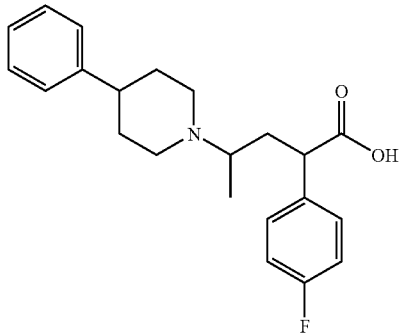

A solution of the piperidine ester prepared as described in Step D (30 mg, 0.073 mmol) in 4 N HCl in dioxane (~3 ml) was stirred overnight at rt., then concentrated to give 25 mg of acid which required no further purification (96%). ESI-MS calc. for C22H26FNO2: 355; Found: 356 (M+H).

Step F:

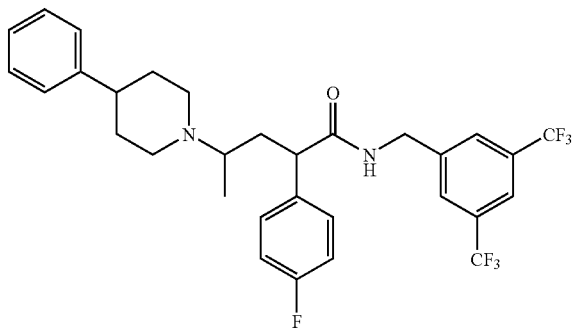

The acid from Step E (21 mg, 0.059 mmol) was combined with 3,5-Bis(trifluoromethyl)benzylamine hydrochloride (17 rag, 0.071 mmol), EDC (14 mg, 0.071 mmol), and triethylamine (20 µL, 0.15 mmol) in DCM (2 mL). After 30 min, HOAt (10 mg, 0.071 mmol) was added and the reaction mixture was stirred for 72 h. The reaction mixture was diluted with DCM and washed with saturated NaHCO3 solution and brine. The aqueous layer was back-washed with more DCM and the combined organic layers were dried over anhydrous MgSO4, filtered, and concentrated. Purification by preparative TLC (silica, 2% of 1:9 NH4OH/methanol in DCM) furnished 18 mg of amide product ESI-MS calc. for C31H31F7N2O: 580; Found: 581 (M+H).

Intermediate 12

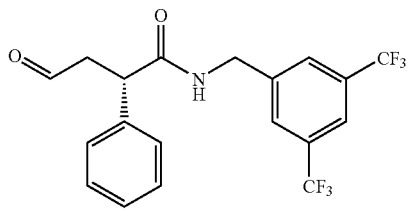

Step A

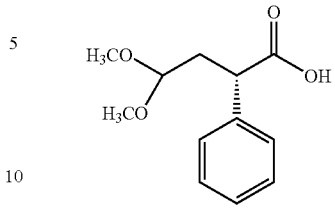

To a solution of lithium bis(trimethylsilyl)amide, LHMDS, (11.38 g, 68.0 mmol) in THF (100 ml) cooled to −78° C. by dry ice/acetone bath was added phenyl acetic acid (8.05 g, 59.16 mmol) in 40 ml THF via syringe and the resulting mixture stirred for one hour. The mixture was treated with 2,2-dimethyoxy-1-bromoethane (10 g, 59.16 mmol) and stirred overnight allowing to warm to room temperature. The reaction was quenched with a saturated solution of ammonium chloride (100 ml) and the resulting mixture was poured into a separatory funnel. The organic layer was separated, washed with brine (1×50 mL), dried with anhydrous sodium sulfate and the solvent was evaporated in vacuo to yield 11.50 g (87%) of the crude product. The crude residue was purified by flash column (gradient eluant 20% ethyl acetate/hexane to 60%.ethyl acetate/hexane) to yield 9.0 g (68%) of the racemic desired product. The desired S isomer was obtained through crystallization with (R) (+)-alpha methyl benzylamine (2.55-ml, 20.11 mmol, 0.5 eq) in ether (80 ml) cooled by refrigeration overnight. The solid white precipitate was filtered and washed with cold ether, then dissolved in ethyl acetate (200 ml) and washed with 0.5N HCl (2×50 ml). The organic layer was dried over anhydrous sodium sulfate and the solvent was evaporated in vacuo to yield 3.47 g (26%) of the title compound. $^1$H NMR (500 MHz, CDCl$_3$): 4.28 (dd, J=6.4, 8.0 Hz, 1H), 3.75 (dd, J=7.1, 8.0, 1H), 3.26 (s, 3H), 3.24 (s, 3H), 3.24 (s, 3H), 2.50–2.43 (m, 1H), 2.07–2.00 (m, 1H).

Step B

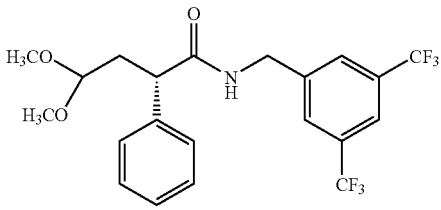

A mixture of the acid (described in step A, 1.0 g, 4.46 mmol), 3,5-bis(trifluoromethyl)benzylamine hydrochloride (1.25 g, 4.46 mmol), HOBt (602 mg, 4.46 mmol), N,N-diisopropyl ethylamine (776 µl, 4.46 mmol) in dichloromethane (20 mL) was treated with 1-[3-(dimethylamino) propyl]-3-ethylcarbodiimide hydrochloride (EDC, 1.71 g, 8.92 mmol) and stirred at room temperature overnight. The reaction mixture was diluted with dichloromethane (30 mL), washed with water (2×20 mL), brine (1×30 mL), dried over anhydrous sodium sulfate and the solvent was evaporated. The pure compound was obtained by MPLC purification (eluant 20% ethyl acetate/hexane), 1.62 g (81%). LC-MS: for C$_{21}$H$_{21}$NO$_3$F$_6$ [M+H] calculated 449.14 found 450.

Step C

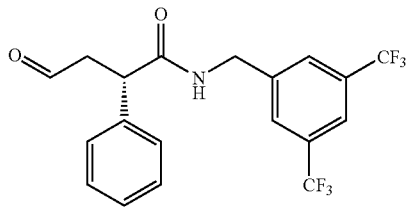

The intermediate in Step B (1.0 g, 2.23 mmol) was treated with solution of 90% trifluoroacetic acid/water (20 ml) for 10 minutes. The reaction mixture was diluted with water (30 mL) and extracted with ether (3×40 ml). The organic layer was washed with saturated sodium bicarbonate (3×50 mL), brine (1×50 mL), dried over anhydrous sodium sulfate and the solvent was evaporated in vacuo to yield 512 mg (57%) of the crude product. No further purification was done and the material was stored under a blanket of nitrogen in the freezer (−16° C.).

EXAMPLE 4

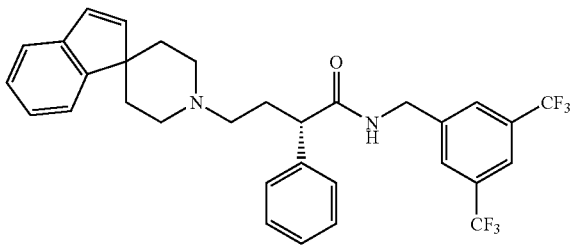

A solution of Intermediate 12 (Intermediate 12, 100.0 mg, 0.256 mmol) spiroindenylpiperidine hydrochloride (70.0 mg, 0.315 mmol), diisopropylethylamine (55 µL, 0.315 mmol) and crushed molecular sieves (4A, 50 mg) in dichloroethane (5 mL) was treated with sodium triacetoxyborohydride (378 mg, 1.783 mmol) and stirred at room temperature overnight. The sieves were filtered off (plug of Celite), washed with dichloromethane and the combined organic washings were extracted with a saturated solution of sodium bicarbonate (1×10 mL), water (2×10 mL), brine (1×10 mL) and dried over anhydrous sodium sulfate. The solvent was evaporated to dryness to yield 133 mg (91%) of the crude product. The residue was purified by preparative TLC (eluent: 100% ethyl acetate) to yield 105.2 mg (72%) of the final pure desired product. LC-MS for $C_{32}H_{30}N2OF_6$ [M+H]$^+$ calculated 572.24, found 573.

Additional compounds were prepared in a similar fashion as Example 4 above, with the modification of replacing phenylacetic acid with variably substituted phenylacetic acids, as appropriate.

TABLE 4

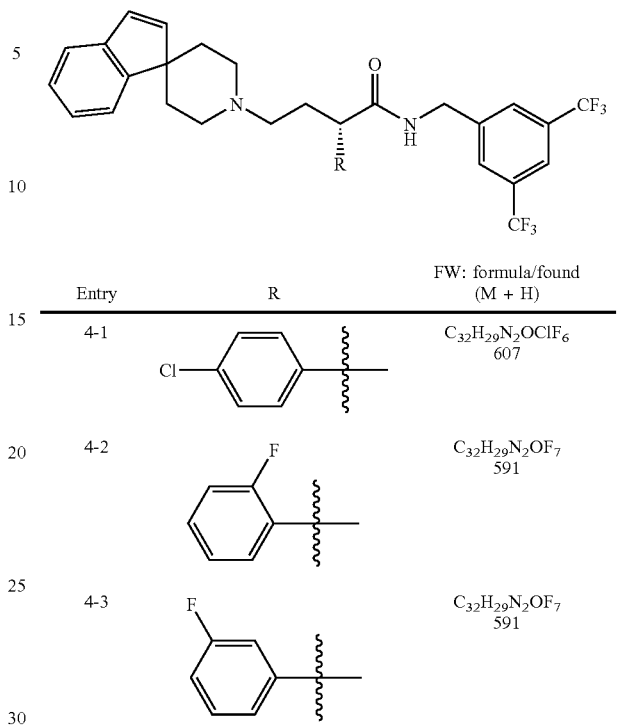

| Entry | R | FW: formula/found (M + H) |
|---|---|---|
| 4-1 | Cl—⌬— | $C_{32}H_{29}N_2OClF_6$ 607 |
| 4-2 | 2-F-⌬— | $C_{32}H_{29}N_2OF_7$ 591 |
| 4-3 | 3-F-⌬— | $C_{32}H_{29}N_2OF_7$ 591 |

EXAMPLE 5

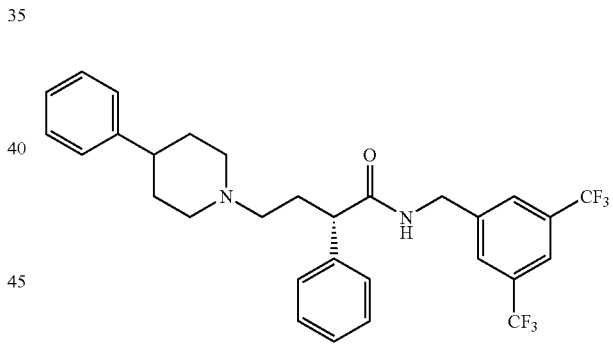

A solution of Intermediate 12 (intermediate 12, 100.0 mg, 0.256 mmol) 4-phenylpiperidine hydrochloride (70.0 mg, 0.354 mmol), diisopropylethylamine (62 µL, 0.354 mmol) and crushed molecular sieves (4A, 50 mg) in dichloroethane (5 mL) was treated with sodium triacetoxyborohydride (378 mg, 1.78 mmol) and stirred at room temperature overnight. The sieves were filtered off (plug of Celite), washed with dichloromethane and the combined organic washings were extracted with a saturated solution of sodium bicarbonate (1×10 mL), water (2×10 mL), brine (1×10 mL) and dried over anhydrous sodium sulfate. Solvent was evaporated to dryness to yield 120 mg (86%) of the crude product. The residue was purified by preparative TLC (eluent: 5% methanol/95% ethyl acetate) to yield 84.6 mg (60%) of the final pure desired product.

LC-MS for $C_{32}H_{30}N_{20}F_6$ [M+H]$^+$ calculated 548.23, found 549.

Additional compounds were prepared in a similar fashion as Example 5 above, with the modification of replacing phenylacetic acid with variably substituted phenylacetic acids, as appropriate.

TABLE 5

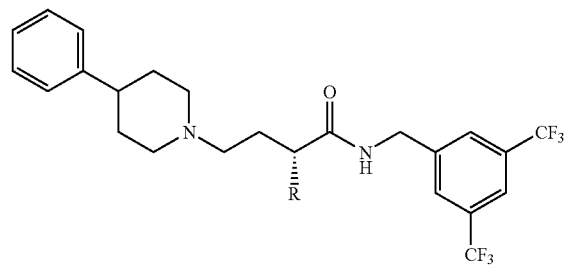

| Entry | R | FW: formula/found (M + H) |
|---|---|---|
| 5-1 | 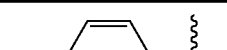 | C$_{30}$H$_{29}$N$_{2}$OClF$_{6}$ 583 |
| 5-2 | 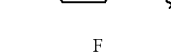 | C$_{30}$H$_{29}$N$_{2}$OF$_{7}$ 567 |

Intermediate 13

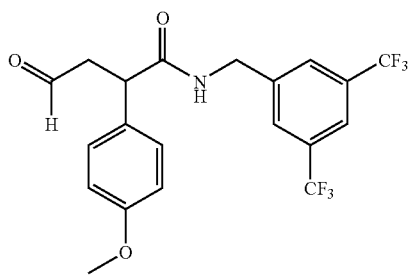

Step A

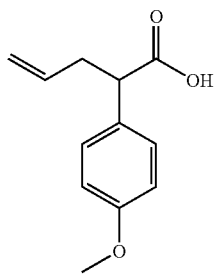

A solution of 4-methoxyphenylacetic acid (5.0 g, 30.088 mmol) in tetrahydrofuran (50 mL) was added drop-wise onto a suspension of sodium hydride (1.60 g, 40.20 mmol, 60%) in THF (50 mL), and then heated to reflux for 2 hrs. The suspension of the salt was cooled to 10° C. and a solution of lithium diisopropylamid (generated from 4.64 mL, 33.09 mmol) of diisopropylamine and 21.0 mL of nBuLi (1.6 M, hexanes)) in 50 mL of tetrahydrofuran was added via canula. The reaction mixture was allowed to warm up to room temperature and stirring was continued for another 2 hrs. To this slurry was added neat allyl bromide (2.86 mL, 33.09 mmol) via syringe. The temperature rose spontaneously to app. 45° C., and was stirred at room temperature overnight. The reaction mixture was diluted with diethyl ether (100 mL), and extracted with water (1×50 mL). The aqueous layer was washed with diethyl ether two more times. The combined organic extracts were dried (anhydrous magnesium sulfate) to yield after evaporation 5.74 g (93%) of the crude acid. This was used without any additional purification in the subsequent step.

Step B

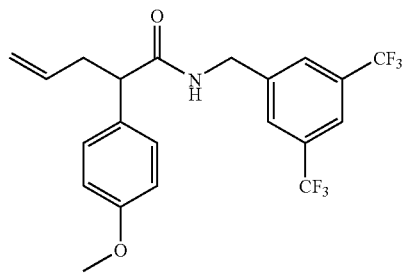

Starting with the acid from Step A and 3,5-bistrifluoromethylbenzylamine, this amide was synthesized in an analogous fashion to the procedure described in Step B, synthesis of Intermediate 1, except that HOAt was used in place of HOBt. MS: for C$_{21}$H$_{19}$NO$_{2}$F$_{6}$ [M+H]$^{+}$ calculated: 432.13, found 432.4.

Step C

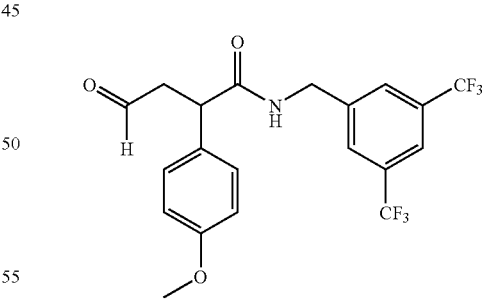

The olefin (980 mg, 2.27 mmol) was ozonized at −78° C. in dichloromethane until permanent blue color indicated complete consumption of the olefin. The excess ozone was purged with a stream of nitrogen, and the ozonide was reduced with dimethylsulfide (1.6 mL, 122.7 mmol). The cooling bath was removed, and the reaction mixture was gradually warmed up to room temperature. The solvent and excess of DMS was concentrated, and the resulting residue was used in the next reaction without purification.

EXAMPLE 6

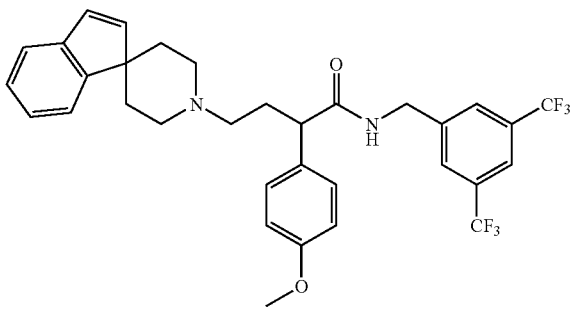

Example 6 was synthesized starting from aldehyde Intermediate 13 and 4-spiroindenylpiperidine hydrochloride according to a procedure described for preparation of Example 1, except that 1.2 equivalents of DIEA was added and the solvent was DCM instead of DCE. MS: for $C_{33}H_{32}N_2O_2F_6$ [M+H]$^+$ calculated: 603.24, found 603.20.

EXAMPLE 7

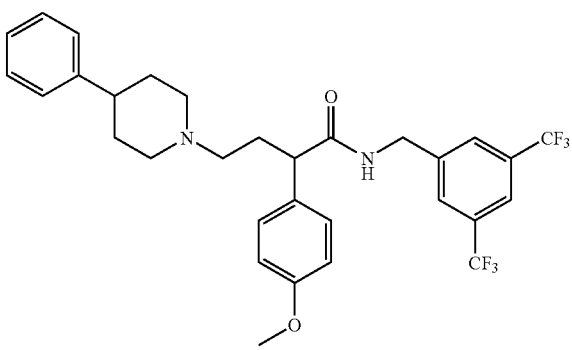

Example 7 was synthesized starting from acid Intermediate 13 and 4-phenylpiperidine hydrochloride according to the procedure described for preparation of Example 6. MS: for $C_{31}H_{32}N_2O_2F_6$ [M+H]$^+$ calculated: 579.24, found 579.00.

EXAMPLE 8

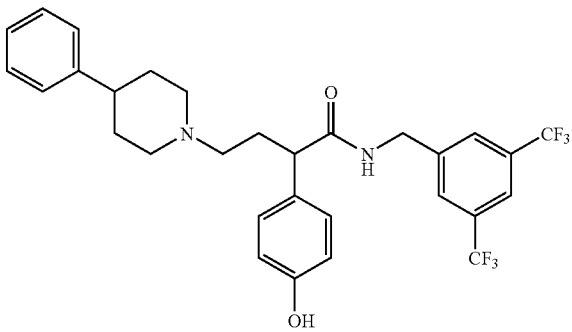

A solution of Example 7 (100 mg, as hydrochloride, 0.163 mmol) was dissolved in dry dichloromethane (10 mL), and treated at 0° C. with neat boron tribromide (980 μL, 0.975 mmol). After stirring at 0° C. for 30 minutes the temperature was allowed warm up to ambient, and stirring was continued for another 3 hrs. The reaction mixture was cooled again to 0° C. and quenched with ammonium hydroxide (4.0 mL, 30% aq. Solution). After 30 minutes of stirring the product was extracted with dichloromethane (3×20 mL). After drying (anhydrous sodium sulfate) the solvent was removed in vacuo to leave 93 mg (100%) of the desired phenol. MS: for $C_{30}H_{30}N_2O_2F_6$ [M+H]$^+$ calculated: 565.22, found 565.00.

EXAMPLE 9

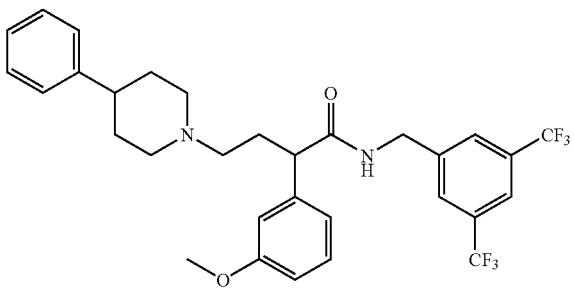

Example 9 was prepared using the synthetic sequence described for preparation of Example 7 except that 3-methoxyphenylacetic acid was used instead of 4-methoxyphenylacetic acid. MS: for $C_{31}H_{32}N_2O_2F_6$ [M+H]$^+$ calculated: 579.24, found 579.2.

EXAMPLE 10

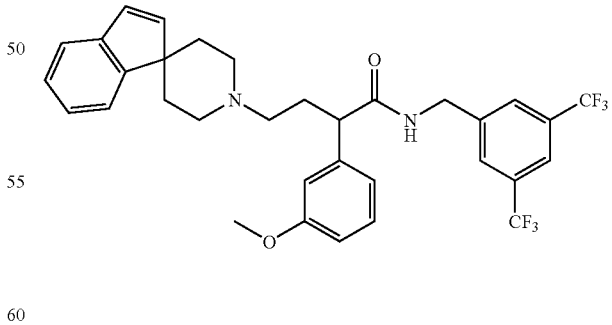

Example 10 was prepared using the synthetic sequence described for preparation of Example 6 except that 3-methoxyphenylacetic acid was used instead of 4-methoxyphenylacetic acid. MS: for $C_{33}H_{32}N_2O_2F_6$ [M+H]$^+$ calculated: 603.24, found 646.5.

EXAMPLE 11

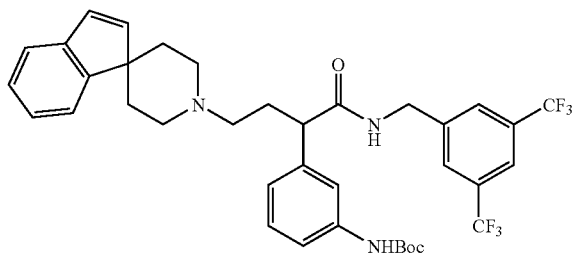

Step A

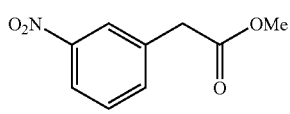

11-A

Thionyl Chloride (1.61 mL, 22.1 mmol) was pipetted dropwise into methanol (75 mL) in a 250 mL round-bottomed flask. Then a solution of 3-nitrophenylacetic acid (2 g, 11.0 mmol) in methanol (10 mL) was added. The mixture was refluxed for 1 hour and concentrated in vacuo to yield 11-A (2.12 g, 98.6%). The crude product was used on the next step.

Step B

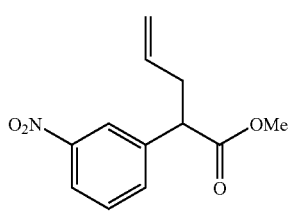

11-B

To a 250 mL round-bottomed flask equipped with a stir bar, septum, and an argon baloon, was suspended sodium hydride 60% (490 mg, 11.8 mmol) in anhydrous DMF (40 mL). A solution of 11-A (2.10 g, 10.8 mmol) in anhydrous DMF (10 mL) was added via syringe. The mixture was cooled to 0° C. before allyl bromide (1.22 mL, 14.1 mmol) was added. The reaction was slowly warmed up to room temperature and stirred overnight. The mixture was diluted with ether, washed with water and brine, dried over anhydrous magnesium sulfate, and concentrated in vacuo. The crude product was purified by MPLC (20/80: ethyl acetate/hexanes) to yield 11-B (2.32 g, 91.3%).

Step C

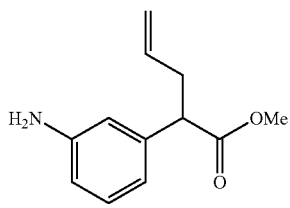

11-C

To a solution of 11-B (2.32 g, 9.86 mmol) in MeOH (25 mL) was added concentrated HCl (25 mL) followed by Zn dust (12.9 g, 197 mmol) in several portions. The reaction mixture was allowed to stir at room temperature for 1 hr before filtered through celite to remove the excess zinc. The filtrate was diluted with ethyl acetate and extracted with saturated NaHCO$_3$ solution. The organic layer was dried over MgSO$_4$ and concentrated in vacuo to yield 11-C (2.62 g, 99+%). The crude product was used in the next step.

Step D

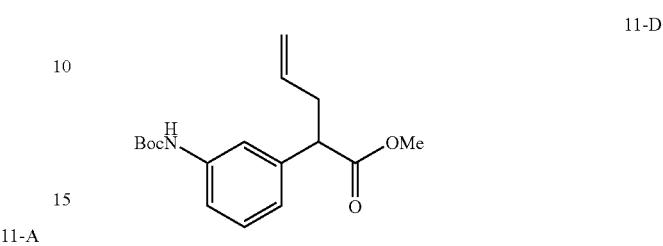

11-D

To a solution of 11-C (2.39 g, 9.86 mmol) in CH$_2$Cl$_2$ (50 mL) was added DMAP (tare). The mixture was cooled to 0° C. in an ice bath before di-tert-butyl dicarbonate (3.24 g, 14.8 mmol) was added slowly. The mixture was stirred at room temperature overnight before concentrated in vacuo. The resulting oil was redissolved in ethyl acetate, extracted with saturated NaHCO$_3$ solution, washed with brine, dried over MgSO$_4$, and concentrated in vacuo. The crude product was further purified by a flash column (10/90 ethyl acetate/hexanes) to yield 11-D (1.12 g, 37.1% for last two steps).

Step E

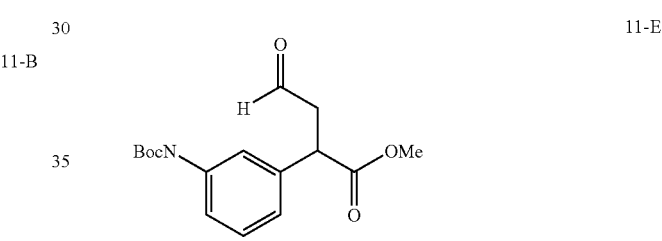

11-E

A solution of 11-D (1.12 g, 3.67 mmol) in CH$_2$Cl$_2$ (25 mL) was cooled to −78° C. in a dry ice/acetone bath before ozone was bubbled in from an ozonator. After the mixture turned a gray-blueish color, nitrogen gas was bubbled in until the solution was colorless. Methyl sulfide (2.70 mL, 36.7 mmol) was added and the solution was allowed to stir at −78° C. for an additional 30 minutes. The reaction mixture was warmed up to room temperature and concentrated in vacuo. The concentrate was diluted with water and extracted with ether (5×), dried over MgSO$_4$, and concentrated in vacuo to yield a crude product of 11-E (1.13 g) which was immediately used on next step.

Step F

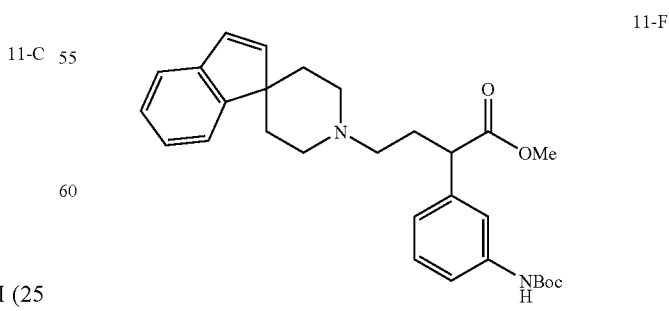

11-F

11-E (1.13 g, 3.67 mmol), spiralenedine (813 mg, 2.67 mmol), DIEA (639 µL, 3.67 mmol) were dissolved in Dichloro methane. Molecular sieves were added to eliminate water, and sodium triacetoxy-borohydride (3.9 g, 18.4 mmol) was added. The mixture was stirred overnight, then was quenched with a saturate NaHCO₃ solution, washed with brine, dried over MgSO₄, and concentrated in vacuo. Purification with a flash column (20/80 ethyl acetate/hexane) yielded 11-F (1.32 g, 75.4% over two steps).

Step G

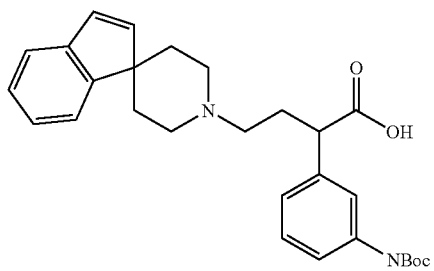

11-F (1.32 g, 2.77 mmol) was dissolved in THF (5 mL), MeOH (5 mL), and H₂O (5 mL). Lithium hydroxide (232 mg, 5.54 mmol) was added. The reaction mixture was stirred and monitored by TLC. After completion of reaction, the mixture was concentrated in vacuo and redissolved in H₂O. pH of the solution was adjusted to 7.0 by 2N HCl and extracted with CH₂Cl₂ (5×). The combined organic layer was dried over MgSO₄ and concentrated in vacuo to yield 11-G (890 mg, 69.5%). The crude product was used in the next step.

Step H

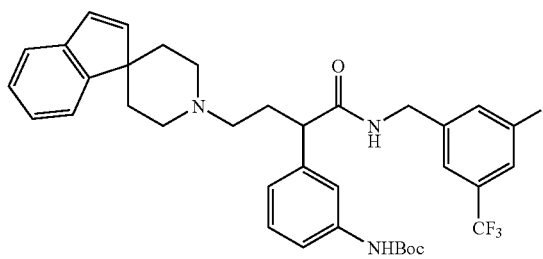

EXAMPLE 11

The acid 11-G (890 mg, 1.92 mmol), 3,5-bistrifluoromethylbenzylamine hydrochloride (538 mg, 1.92 mmol), Hunnig's base (1.34 mL, 7.68 mmol), HOAt (261 mg, 1.92 mmol), EDC (552 mg, 2.88 mmol), and DCM were stirred overnight before washing with 1N NaOH solution and brine. The organic layer was dried over MgSO₄ and concentrated in vacuo. The crude product was purified by a flash column (100% ethyl acetate) to yield Example 11 (747 mg, 53.7%). LC-MS.: MW calculated 687.71, found 688.3.

EXAMPLE 12

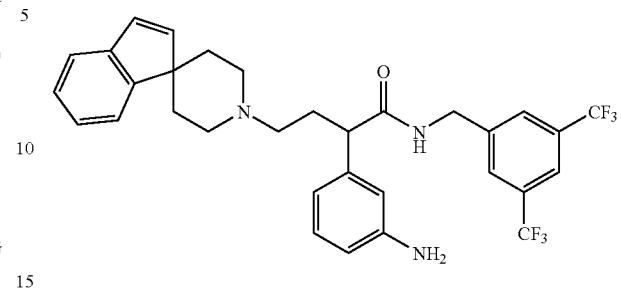

Example 11 (640 mg, 0.93 mmol) and TFA (7 mL) were combined and stirred for half hour before concentrating in vacuo. The crude product was redissolved in DCM and salted out with 4N HCl in dioxane to yield Example 12 (600 mg, 99⁺%). LC-MS: MW calculated 587.6, found 588.4.

A variety of N-substituted derivatives of Example 12 were synthesized. These compounds were made by simple coupling reactions known to those skilled in the art. Table 6 below summarizes these compounds.

TABLE 6

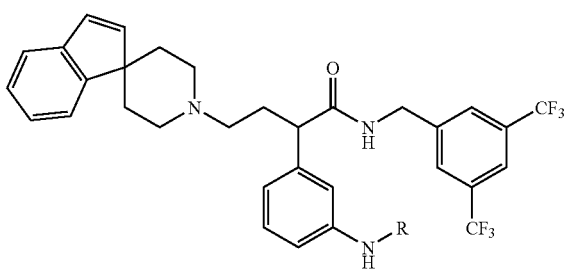

| Example | R | MF | Calc'd MW | ESI-MS found (M + H)⁺ |
|---|---|---|---|---|
| 12-1 | COCH₃ | C₃₄H₃₃F₆N₃O₂ | 629 | 630 |
| 12-2 | CO₂CH₃ | C₃₄H₃₃F₆N₃O₃ | 645 | 646 |
| 12-3 | SO₂CH₃ | C₃₄H₃₃F₆N₃O₃S | 665 | 666 |
| 12-4 | CONHCH₃ | C₃₄H₃₄F₆N₄O₂ | 644 | 645 |
| 12-5 | CONHCH₂CH₃ | C₃₅H₃₆F₆N₄O₂ | 658 | 659 |
| 12-6 | CONH₂ | C₃₃H₃₂F₆N₄O₂ | 630 | 631 |

EXAMPLE 13

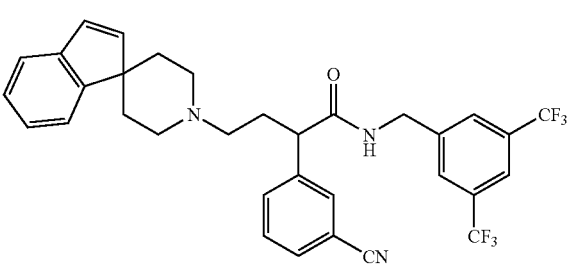

Step A

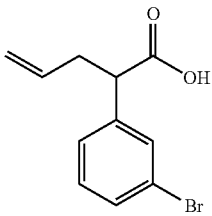

13-A

Potassium bis(trimethylsilyl)amide (7.17 g, 35.9 mmol) was dissolved in anhydrous THF (55 in L) under argon. The mixture was cooled to −78° C. before a solution of 3-bromophenylacetic acid (3.09 g, 14.4 mmol) in THF (15 mL) was added dropwise via an addition funnel. The mixture was stirred for another 30 minutes before allyl bromide (1.87 mL, 21.6 mmol) was added. The reaction was monitored by TLC. After the completion of the reaction, the mixture was concentrated in vacuo and redissolved in water. The aqueous layer was washed with ether, acidified by citric acid, and extracted by ethyl acetate. The organic layer was dried over MgSO$_4$ and concentrated in vacuo. The crude product was purified by MPLC (50/50 ethyl acetate/hexanes) to yield 13-A (3.18 g, 86.9%).

Step B

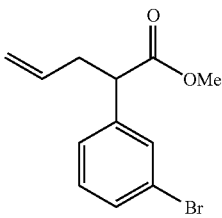

13-B

Thionyl chloride (1.8 mL, 24.4 mmol) was pipetted dropwise into methanol (60 mL) in a 250 mL round-bottomed flask. Then a solution of 13-A (3.10 g, 12.2 mmol) in methanol (10 mL) was added. The mixture was stirred at reflux for 30 minutes and concentrated in vacuo to yield 13-B (3.21 g, 98.2%). The crude product was used on the next step.

Step C

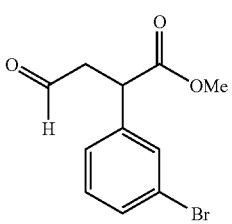

13-C

A solution of 13-B (3.0 g, 11.1 mmol) in CH$_2$Cl$_2$ (50 mL) was cooled to −78° C. before ozone was bubbled in from an ozonator. After the mixture turned gray-blue in color, nitrogen gas was bubbled in until the solution was colorless. Methyl sulfoxide (8.15 mL, 11.1 mmol) was added and the solution was allowed to stir at −78° C. for an additional 30 minutes. The reaction mixture was warmed up to room temperature and concentrated in vacuo. The concentrate was diluted with water and extracted with ether (5×), dried over MgSO$_4$, and concentrated in vacuo to yield a crude product of 13-C (3.0 g, 100%) which was immediately used in the next step.

Step D

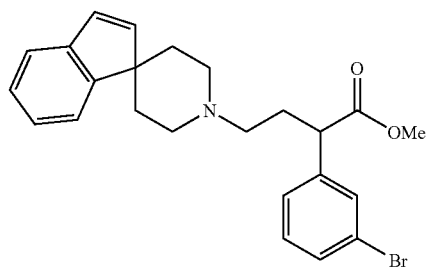

13-D

13-C (100 mg, 0.369 mmol), spiralenedine (81.8 mg, 0.369 mmol), and DIEA (64.3 μL, 0.369 mmol) were dissolved in DCE. Molecular sieves were added to eliminate water and sodium triacetoxyborohydride (392 mg, 1.85 mmol) was added last. The mixture was stirred overnight, then quenched with a saturate NaHCO$_3$ solution, washed with brine, dried over MgSO$_4$, and concentrated in vacuo. Purification by preparative TLC (40/60 ethyl acetate/hexane) yielded 13-D (133 mg, 82.1%).

Step E

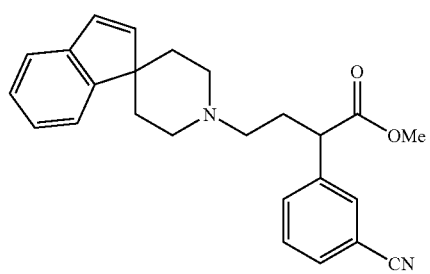

13-E

DMF (2 mL) was deoxygenated by bubbling with nitrogen for 30 minutes before a solution of 13-D (125 mg, 0.284 mmol) in DMF (1 mL) was added. The solution was bubbled with nitrogen for another 15 minutes then Zn(CN)$_2$ and Pd(PPh$_3$)$_4$ were added. After bubbling in nitrogen for an additional 15 minutes, the mixture was heated to 80° C. and stirred overnight. The reaction mixture was diluted with ethyl acetate, washed with NH$_4$OH (2×), and concentrated in vacuo. The crude product was purified by preparative TLC (40/60 ethyl acetate/hexanes) to yield 13-E (52 mg, 47.3%). LC-MS: MW calculated 386.49, found 387.2.

Step F

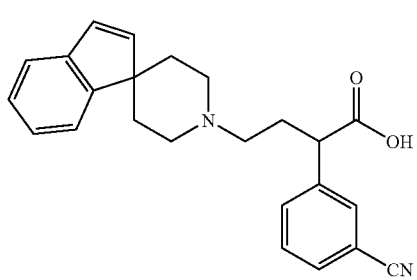
13-F

13-D (52 mg, 0.135 mmol) was first dissolved in a solution of THF (1 mL), MeOH (1 mL), and H₂O (1 mL). The mixture was cooled to 0° C. before LiOH (23 mg, 0.538 mmol) was added. The solution was stirred at 0° C. for 1 hour before raised to room temperature and stirred overnight. The reaction mixture was concentrated in vacuo and the residue was redissolved in a minimum amount of H₂O. After the pH was adjusted to 7.0 with 2N HCl, the aqueous layer was extracted with DCM (5×). The combined organic layers were concentrated in vacuo to yield the crude 13-F (38.7 mg, 77.4%), which was used on next step.

Step G

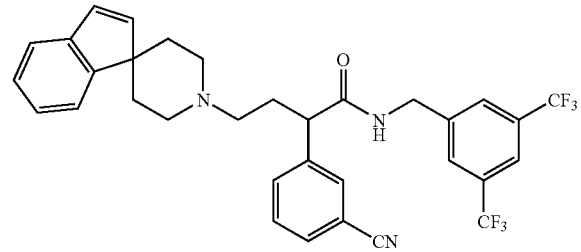

EXAMPLE 13

Intermediate 13-F (38.7 mg, 0.104 mmol), spiroindene-piperidine hydrochloride (29.1 mg, 0.104 mmol), Hunnig's base (72 µL, 0.416 mmol), HOAt (14.2 mg, 0.104 mmol), and EDC (30 mg, 0.156 mmol) in DCM were stirred overnight then washed with 1N NaOH solution and brine. The organic layer was dried over MgSO₄ and concentrated in vacuo. The crude product was purified by preparative TLC (60/40 ethyl acetate/hexanes) to yield Example 13 (747 mg, 53.7%). LC-MS: MW calculated 597.22, found 598.3.

EXAMPLE 14

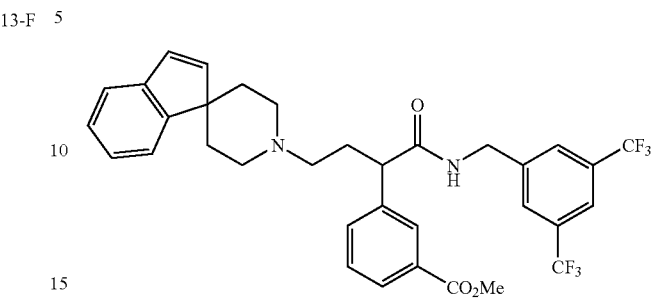

Step A

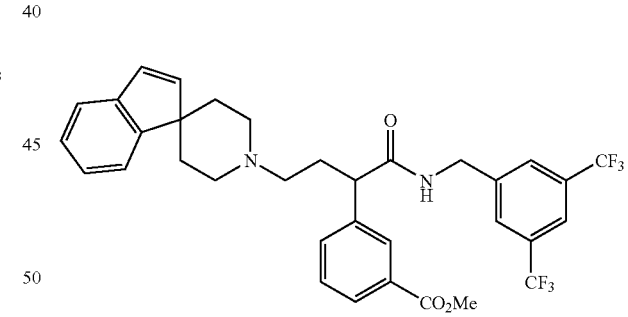
14-A

14-A was prepared as detailed in Example 13 (Steps F & G) using 13-D as the starting material.

Step B

EXAMPLE 14

A mixture of 14-A (444 mg, 0.682 mmol), Pd(dppf).DCM (56 mg, 0.068 mmol), Et₃N (190 µL, 1.36 mmol), DMF (7 mL), and MeOH (3 mL) was prepared under CO balloon. The mixture was stirred and heated at 95° C. overnight. The solid was filtered out and solvent was concentrated in vacuo. The concentrated was redissolved in H₂O, extracted with ethyl acetate, dried over MgSO₄, and concentrated in vacuo. The crude product was further purified by preparative TLC (60/40 ethyl acetate/hexanes) to yield Example 14 (187 mg, 43.5%). LC-MS: MW calculated 630.62, found 631.4.

EXAMPLE 15

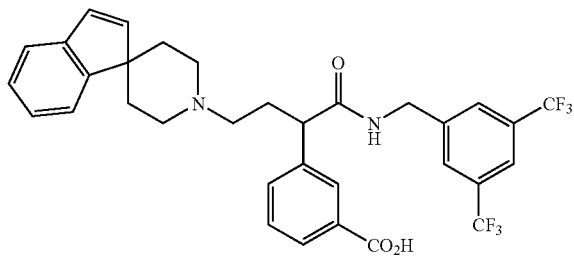

Example 14 (187 mg, 0.297 mmol) was first dissolved in a solution of THF (2 mL), MeOH (2 mL), and H$_2$O (2 mL). The mixture was cooled to 0° C. before LiOH (25 mg, 0.594 mmol) was added. The solution was stirred at 0° C. for 10 minutes before warming to room temperature and stirring for another 4 hours. TLC showed starting material so 1 eq of NaOH was added to push the reaction to completion. The reaction mixture was concentrated in vacuo and redissolved in DCM. A few drops of 4N HCl in dioxane was added and the mixture was concentrated and purified by preparative TLC (80/20 ethyl acetate/hexanes) to yield Example 15 (20 mg, 10.9%). LC-MS: MW calculated 616.59, found 617.4.

EXAMPLE 16

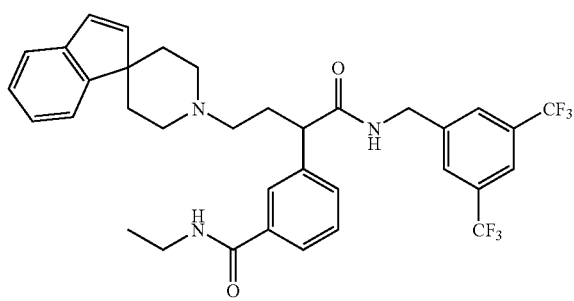

The product from Example 15 (18 mg, 0.029 mmol), ethylamine 2M (15 μL, 0.029 mmol), HOAt (4 mg, 0.029 mmol), EDC (9 mg, 0.044 mmol), and DCM were stirred overnight before washing with 1N NaOH. The organic layer was dried over MgSO$_4$ and concentrated in vacuo. The crude product was purified by preparative TLC (silica, 100% ethyl acetate) to yield Example 16. LC-MS: MW calculated 643.26, found 644.4.

Intermediate 14

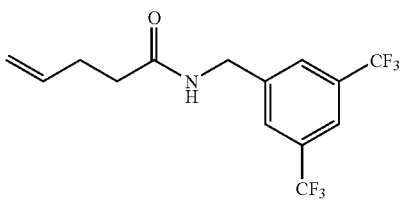

A solution of 4-pentenoic acid (100 mg, 1.0 mmol), 3,5-bis(trifluoromethyl)benzylamine hydrochloride (279 mg, 1.0 mmol), HOAt (136 mg, 1.0 mmol), and N,N-diisopropyl ethylamine (174 μl, 1.0 mmol) in dichloromethane (10 mL) was treated with 1-[3-(dimethylamino)propyl]-3-ethylcarbodiimide hydrochloride (EDC, 382 mg, 2.0 mmol) and stirred at room temperature overnight. The reaction mixture was diluted with dichloromethane (20 mL), washed with water (2×20 mL), brine (1×20 mL), dried over anhydrous sodium sulfate and the solvent was evaporated. Purification was accomplished by preparative TLC (eluant: 40% ethyl acetate/hexane) to yield 295 mg (90%) of the desired product.

EXAMPLE 17

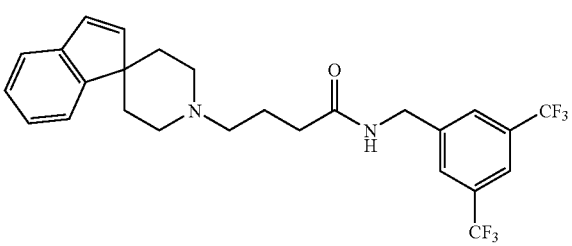

A solution of Intermediate 14 (100 mg, 0.307 mmol) in dichloromethane (5mL) was cooled to −78° C. and a stream of ozone was passed through until a permanent blue color indicated complete consumption of the olefin. The excess ozone was purged with a stream of nitrogen and the reaction mixture was allowed to warm up to ambient temperature. The solution was dried with magnesium sulfate, the drying agent was filtered off, and to the filtrate was added spiroindenylpiperidine hydrochloride (68 mg, 0.307 mmol), diisopropylethylamine (42 μL, 0.307 mmol), crushed 4 A molecular sieves (50 mg) and the resulting mixture was treated with sodium triacetoxyborohydride (325 g, 1.54 mmol). After stirring at ambient temperature for 24 hours, the sieves were filtered off, the filtrate was washed with a saturated solution of sodium bicarbonate (1×10 mL), water (3×5 mL) and brine (1×10 mL). After drying (anhydrous sodium sulfate) the solvent was evaporated to dryness under reduced pressure to leave 200 mg of crude product, which was further purified by preparative TLC (eluant: 5% methanol/95% ethyl acetate) to give 137 mg (68%) of the pure final product. $^1$H NMR (500 MHz, CDCl$_3$): 7.80 (s, 3H), 7.32 (d, J=7.3 Hz, 1H), 7.27–7.23 (m, 1H), 7.20–7.15 (m, 2H), 6.79 (d, J=5.7, 1H), 6.75 (d, J=5.7 Hz, 1H), 4.62 (d, J=6.0 Hz, 2H), 2.99 (br d, J=12.1 Hz, 2H), 2.58 (t, J=6.6 Hz, 2H), 2.48 (t, J=6.7 Hz, 2H), 2.37 (br t, J=12.0 Hz. 2H), 2.04 (br t, J=11.8 Hz, 2H), 1.96 (t, J=6.7 Hz, 2H), 1.34 (br d, 12.3 Hz, 2H). LC-MS: for C$_{26}$H$_{26}$N$_2$OF$_6$ [M+H] calculated 496.19, found 497.

Intermediate 15

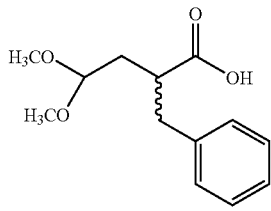

Step A

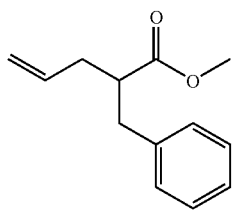

Lithium diisopropyl amide (LDA) was freshly prepared by treating a solution of diisopropylamine (3.75 ml, 26.8 mmol) in dry THF (10 ml) under nitrogen cooled to −78° C. with 2.5 M n-butyl lithium (10.72 ml, 26.79 mmol) added slowly via syringe. To this solution was added methyl hydrocinnamate (4.0 g, 24 mmol) in dry TB (50 ml) via syringe dropwise over a 30 minute period. The resulting solution was stirred at −78° C. for 1 hour; then allyl bromide (2.74 ml, 31.7 mmol) was added via syringe and the reaction mixture was stirred overnight allowing to warm to room temperature. The reaction was quenched with a saturated solution of ammonium chloride (100 ml) and the resulting mixture was poured into a separatory funnel. The organic layer was separated, washed with brine (1×100 mL), dried with anhydrous sodium sulfate and the solvent was evaporated. The crude residue was purified by MPLC (eluant 15% ethyl acetate/hexane) to yield 4.96 g (98%) of the racemic desired product.

Step B:

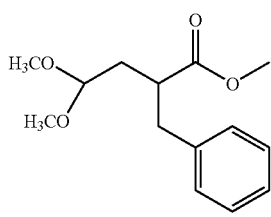

A solution of material from Step A, Intermediate 15 (2.86 g, 14.0 mmol) in dichloromethane (50 mL) was cooled to −78° C. and a stream of ozone was passed through until the permanent blue color indicated complete consumption of the olefin. The excess ozone was purged with a stream of nitrogen and allowed to warm up to ambient temperature. Methyl sulfide (10.3 ml, 140 mmol) was added to the solution to reduce the ozonide to the aldehyde. The solvent was evaporated under reduced pressure and then azeotroped with toluene to help remove most of the methyl sulfide.

The residue was then taken up into a solution of dichloromethane/methanol (1:1 solution, 80 ml) and treated with trimethyl orthoformate (7.66 ml, 70.0 mmol) and a catalytic amount of p-toluenesulfonic acid (266 mg, 1.40 mmol). After stirring overnight, the solvent was evaporated under reduced pressure and the residue was then dissolved in ethyl acetate (300 ml). The solution was washed with saturated sodium bicarbonate (2×100 ml), water (75 ml), brine (100 ml), dried over anhydrous sodium sulfate, filtered, and the solvent evaporated as before. Purification by MPLC (eluant: 15% ethyl acetate/hexane) afforded 2.16 g (62%) of the desired product.

$^1$H NMR (500 MHz, CDCl$_3$): 7.35–7.28 (m, 2H), 7.25–7.08 (m, 3H), 4.42 (t, J=6.6 Hz, 1H) 3.62 (s, 3H), 3.31 (s, 3H), 3.26 (s, 3H), 2.98 (app q, J=6.4 Hz, 1H), 2.85–2.73 (m, 2H), 2.09–1.99 (m, 1H), 1.80–1.72 (m, 1H).

Step C:

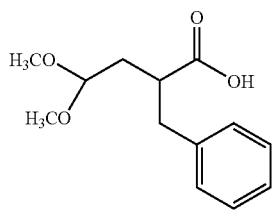

A solution of material from Step B, Intermediate 15 (2.16 g, 8.56 mmol) in THF/methanol/water (1:1:1 solution, 60 ml) was treated with lithium hydroxide monohydrate (1.80 g, 42.8 mmol) and the resulting solution was stirred at room temperature for 48 hours. The organic solvents were evaporated under reduced pressure to leave the aqueous layer containing the product. The aqueous layer was diluted with ethyl acetate (75 ml) and the pH adjusted to approximately 6 with 2N HCl solution. The organic layer was separated and the aqueous was extracted with ethyl acetate (3×75 ml). The organics were combined, washed with brine (1×100 ml), dried over anhydrous sodium sulfate, filtered, and the solvent evaporated under reduced pressure. The residue was azeotroped with toluene to remove any acetic acid, formed by the ethyl acetate extraction, and water to yield 1.77 g (87%) of the crude product which was used without further purification. $^1$H NMR (500 MHz, CDCl$_3$): 7.35–7.28 (m, 2H), 7.25–7.08 (m, 3H), 4.42 (t, J=6.6 Hz, 1H), 3.31 (s, 3H), 3.26 (s, 3H), 2.98 (dd, J=6.4, 10.6 Hz, 1H), 2.85–2.73 (m, 2H), 2.05–1.97 (m, 1H), 1.81–1.75 (m, 1H).

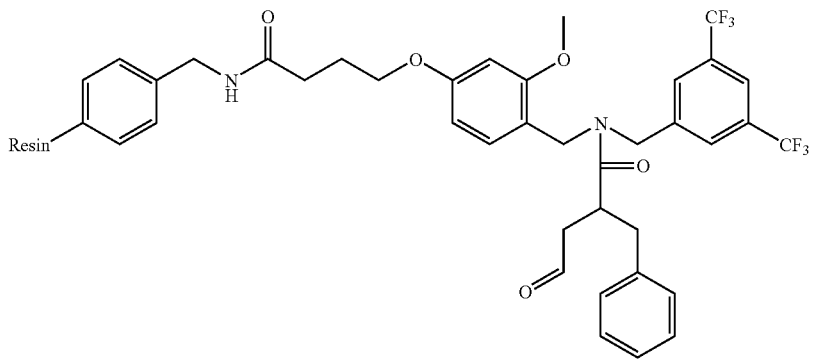

Step A:

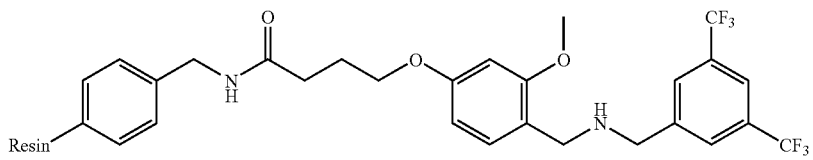

4-(4-Formyl-3-methoxyphenoxy)butyryl AM resin was swelled in dichloroethane (20 ml) for 30 minutes after which the solvent was drain. A fresh cocktail of 5% trimethyl orthoformate in dichloroethane (15 ml) was added to the resin. To this suspension was then added 3,5-bis(trifluoromethyl)benzyl amine (1.00 g, 4.05 mmol) and sodium triacetoxyborohydride (858 mg, 4.05 mmol) and the resulting mixture was spun on a mechanical rotary for 15 hours, releasing pressure every 15 minutes for the first 5 hours. The solvent was drained and the resin beads washed with methanol (2×10 ml), dichloroethane (3×10 ml), dimethyl formamide (5×10 ml), dichloromethane (3×10 ml) and ether (3×10 ml). The resin was first dried by flowing nitrogen through the container; then under high vacuum overnight.

Step B:

The prepared resin from Step A, Intermediate 16 (50 mg, 0.027 mmol) was swelled in dichloromethane (2 ml) for 15 minutes after which the solvent was drained. HOAt (19 mg, 0.14 mmol), Intermediate 15 (33 mg, 0.14 mmol), dry dichloromethane (2 ml) were added to the pre-swelled resin and was shaken for 2 minutes. To this mixture was then added DICI (22 µl, 0.14 mmol) and the resulting mixture was spun on the mechanical rotary overnight. The solvent was drained and the resin beads washed with methanol (2×10 ml), dichloroethane (3×10 ml), dimethyl formamide (5×10 ml), dichloromethane (3×10 ml) and ether (3×10 ml). The resin was first dried by flowing nitrogen through the container; then under high vacuum overnight.

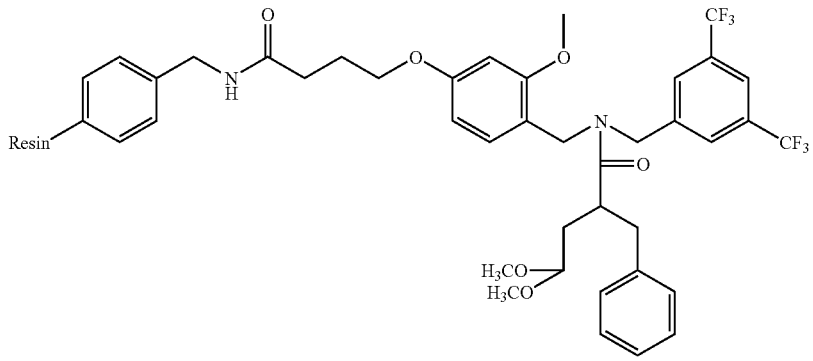

Step C

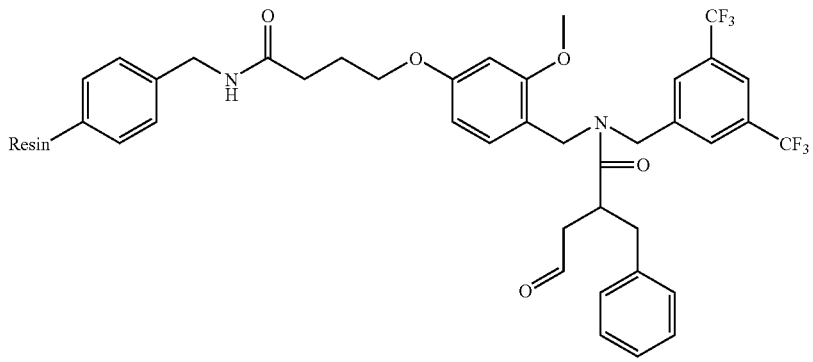

The prepared resin from Step B, Intermediate 16 (50 mg, 0.027 mmol) was treated with a pre-mixed cocktail of 1% trifluoroacetic acid in dichloromethane (2 ml) for 2 hours. The solvent was drained and the resin beads washed with dichloromethane (10×1 ml), 1% N,N-diisopropyl ethyl amine in dichloromethane (5×1 ml) and then again with dichloromethane (6×1 ml). The resin was then dried by flowing nitrogen through the container; followed by further drying under high vacuum.

EXAMPLE 18

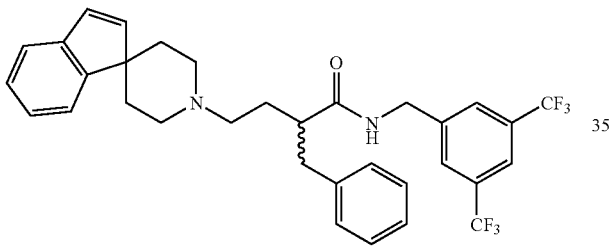

The prepared resin (Intermediate 16, 50 mg, 0.027 mmol) was swelled in dichloroethane (2 ml) for 15 minutes after which the solvent was drain. A fresh cocktail of 5% trimethyl orthoformate in dichloroethane (2 ml) was added to the resin. To this suspension was then added spiroindenylpiperidine hydrochloride (30 mg, 0.14 mmol), diisopropylethylamine (24 µL, 0.14 mmol), and sodium triacetoxyborohydride (57 g, 0.27 mmol) and the resulting mixture was spun on a mechanical rotary for 15 hours, releasing pressure every 15 minutes for the first 3 hours. The solvent was drained and the resin beads washed with methanol (3×2 ml), dichloroethane (5×2 ml), dimethyl formamide (5×2 ml), dichloromethane (10×2 ml). The resin was then immediately treated with a pre-mixed cocktail of 25% trifluoroacetic acid in dichloromethane (2 ml) for 2 hours. The beads became dark red after treatment with the acidic solution. The solvent was collected along with the dichloromethane washings (3×2 ml) and concentrated to dryness under reduced pressure to afford 2.5 mg (31%) of the desired final product with an HPLC purity analysis of 91%.

$^1$H NMR (500 MHz, CD$_3$OD): 7.87 (s, 1H), 7.78 (s, 2H), 7.36 (d, J=7.3 Hz, 1H), 7.28–7.22 (m, 1H), 7.18–7.10 (m, 2H), 6.99 (br s, 1H), 6.90 (br d, J=5.5 Hz, 1H), 4.55 (d, J=15.1 Hz, 1H), 4.28 (d, J=15.1 Hz, 1H), 3.74–3.66 (m, 1H), 3.30 (p, J=1.6 Hz, 1H), 3.36–3.26 (m, J=3H) 3.18–3.12 (m, 1H), 2.95 (dd, J=9.1, 13.3 Hz, 1H), 2.85 (dd, J=6.1, 13.2 Hz, 1H), 2.76–2.70 (m, 1H), 2.50–2.40 (m, 1H), 2.22–2.12 (m, 1H), 2.08–1.97 (m, 1H), 1.52 (br d, J=14.0 Hz, 2H). LC-MS: for C$_{33}$H$_{32}$N$_2$OF$_6$ [M+H] calculated 586.24, found 587.

Additional compounds were prepared in a similar fashion as Example 18, with the modification of replacing the benzyl intermediate with other aryl and alkyl groups.

TABLE 7

| Example | R | FW: formula/found (M + H) |
|---|---|---|
| 18-1 | 1-naphthyl | C$_{30}$H$_{32}$N$_2$OF$_6$ 623 |
| 18-2 | cyclohexylmethyl | C$_{30}$H$_{30}$N$_2$OF$_6$ 593 |
| 18-3 | phenyl | C$_{32}$H$_{30}$N$_2$OF$_6$ 573 |

Additional compounds were prepared in a similar fashion as Example 18 above, with the modification of replacing bis 3,5-(trifluoromethyl)benzyl amine with a varied array of substituted benzyl amines.

TABLE 8

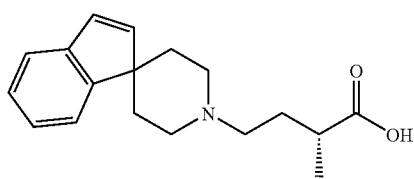

| Example | R | FW: formula/found (M + H) |
|---|---|---|
| 18-4 | ![benzyl NH] | C30H32N2O 437 |
| 18-5 | ![3,4-dichlorobenzyl NH] | C30H30N2OCl2 506, 508 |
| 18-6 | ![3,5-dichlorobenzyl NH] | C31H32N2OCl2 506, 508 |
| 18-7 | ![3-CF3 benzyl NH] | C31H31N2OF3 505 |
| 18-8 | ![2-OCH3 benzyl NH] | C31H34N2O2 467 |
| 18-9 | ![naphthylmethyl NH] | C34H34N2O 487 |

Intermediate 17

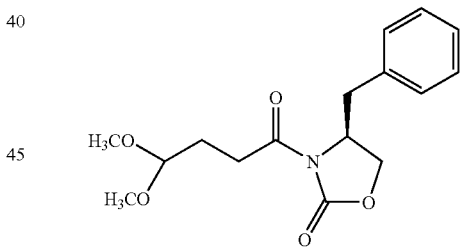

Step A:

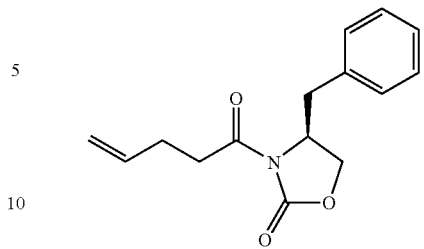

To a solution of 4-pentenoic acid (2.83 g, 28.2 mmol) and N,N-diisopropyl ethylamine (4.89 ml, 28.2 mmol) in dry THF (20 ml) under nitrogen cooled to 0° C. was added dropwise via syringe pivolylchloride (3.48 ml, 28.2 mmol) and the resulting solution stirred for 1 hour at the monitored temperature. A white precipitate forms quickly after the addition of the pivolylchloride.

In a second flask, a solution of (S)-(−)-4-benzyl-2-oxazolidine (Evan's auxiliary, 5.0 g, 28 mmol) in dry THF (20 ml) under nitrogen cooled to −78° C. was treated dropwise with 1.6M n-butyl lithium (18.51 ml, 29.63 mmol) and the resulting solution also stirred for 1 hour at the monitored temperature.

After one hour of stirring, the two solutions were combined by cannulating the 4-pentenoic acid solution into the Evan's auxiliary solution. The resulting mixture was stirred overnight allowing to warm to ambient temperature. The reaction was quenched with water (80 ml) and diluted with ethyl acetate (160 ml). The organic layer was extracted and washed with water (40 ml), brine (40 ml), dried over anhydrous sodium sulfate, filtered, and the solvent evaporated under reduced pressure. The residue was purified by MPLC (eluant: 30% ethyl acetate/hexane) to give 5.34 g (73%) of the desired product.

Step B:

A solution of material from Step A, Intermediate 17 (4.0 g, 15 mmol) in dichloromethane (50 mL) was cooled to −78° C. and a stream of ozone was passed through until the permanent blue color indicated complete consumption of the olefin. The excess ozone was purged with a stream of nitrogen and allowed to warm up to ambient temperature. Methyl sulfide (11.5 ml, 154 mmol) was added to the solution to reduce the ozonide to the aldehyde. The solvent was evaporated under reduced pressure and then azeotroped with toluene to help remove most of the methyl sulfide.

The residue was then taken up into a solution of dichloromethane/methanol (1:1 solution, 100 ml) and treated with trimethyl orthoformate (8.43 ml, 77.2 mmol) and a catalytic amount of p-toluenesulfonic acid (295 mg, 1.55 mmol). After stirring overnight, the solvent was evaporated under reduced pressure and the residue was then dissolved in ethyl acetate (300 ml). The solution was washed with saturated sodium bicarbonate (2×100 ml), water (75 ml), brine (100 ml), dried over anhydrous sodium sulfate, filtered, and the solvent evaporated as before. Purification by MPLC (eluant: 50% ethyl acetate/hexane) afforded 4.33 g (92%) of the desired product.

¹H NMR (400 MHz, CDCl₃): 7.40–7.24 (m, 3H), 7.22–7.18 (m, 2H), 4.76–4.62 (m, 1H), 4.51 (t, J=5.7 Hz, 1H), 4.24–4.08 (m, 3H) 3.32 (s, 3H), 3.29 (s, 3H), 3.27 (dd, J=3.4, 13.5 Hz, 1H), 3.05–2.90 (m, 2H), 2.78 (dd, J=9.6, 13.5 Hz, 1H), 2.06–2.00 (m, 2H).

Step C:

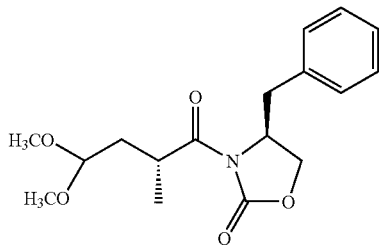

Lithium diisopropyl amide (LDA) was freshly prepared by treating a solution of diisopropylamine (280 µl, 2.0 mmol) in dry THF (4 ml) under nitrogen cooled to −78° C. with 2.5 M n-butyl lithium (791 µl, 2.00 mmol) added slowly via syringe. To this solution was added product from Step B, Intermediate 17 (520 mg, 2.00 mmol) in dry THF (16 ml) via syringe dropwise over a 15 minute period. The resulting solution was stirred at −78° C. for 1 hour, then methyl iodide (162 µl, 2.60 mmol) was added via syringe and the reaction mixture was stirred overnight allowing it to warm to room temperature. The reaction was quenched with a saturated solution of ammonium chloride (25 ml) and the resulting mixture was poured into a separatory funnel. The organic layer was separated, washed with brine (1×15 mL), dried with anhydrous sodium sulfate and the solvent was evaporated. The crude residue was purified by MPLC (eluant 40% ethyl acetate/hexane) to yield 422 mg (77%) of the desired isomerically pure 2-(R)-methyl substituted product.

¹H NMR (500 MHz, CDCl₃): 7.40–7.24 (m, 3H), 7.22–7.18 (m, 2H), 4.72–4.67 (m, 1H), 4.45 (t, J=5.7 Hz, 1H), 4.24–4.17 (m, 3H), 3.95–3.90 (m, 1H), 3.32 (s, 3H), 3.29 (s, 3H), 3.27 (dd, J=3.4, 13.5 Hz, 1H), 2.79 (dd, J=9.5, 13.4 Hz, 1H), 2.24–2.16 (m, 1H), 1.73 (dt, J=5.2, 13.8 Hz, 1H), 1.27 (d, J=7.1 Hz, 3H).

Step D:

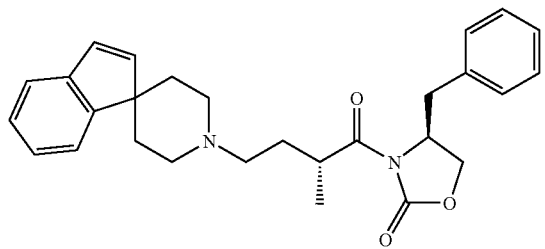

The product from Step C, Intermediate 17 (400 mg, 1.20 mmol) was treated with solution of 90% trifluoroacetic acid/water (8 ml) for 10 minutes. The reaction mixture was diluted with water (12 mL) and extracted with ether (3×10 ml). The organic layers were combined, washed with satu- rated sodium bicarbonate (3×10 mL), brine (1×10 mL), dried over anhydrous sodium sulfate and the solvent was evaporated in vacuo to yield 361 mg (100%) of the crude product.

A solution of the above crude product (361 mg, 1.20 mmol), spiroindenylpiperidine hydrochloride (266 mg, 1.20 mmol), diisopropylethylamine (205 µL, 1.20 mmol) and crushed molecular sieves (4A, 150 mg) in dichloroethane (20 mL) was treated with sodium triacetoxyborohydride (1.3 g, 6.0 mmol) and stirred at room temperature overnight. The sieves were filtered off (plug of Celite), washed with dichlo- romethane and the combined organic washings were extracted with a saturated solution of sodium bicarbonate (1×20 mL), brine (1×20 mL) and dried over anhydrous sodium sulfate. Solvent was evaporated to dryness and the residue was purified by preparative TLC (eluent: 5% metha- nol/95% ethyl acetate) to yield 245 mg (46%) of the desired product. ¹H NMR (500 MHz, CDCl₃): 7.38–7.14 (m, 9H), 6.84 (d, J=5.7 Hz, 1H), 6.75 (d, J=5.5 Hz, 1H), 4.81–4.75 (m, 1H), 4.30–4.21 (m, 2H) 3.93–3.86 (m, 1H), 3.35 (dd, J=3.4, 13.3 Hz, 1H), 3.00 (br d, J=11.2 Hz, 2H) 2.82 (dd, J=9.6, 13.3 Hz, 1H), 2.52 (br t, J=7.3 Hz, 2H), 2.38–2.26 (m, 2H), 2.17–2.08 (m, 3H), 1.73–1.64 (m, 2H), 1.36 (br d, J=13.3 Hz, 2H), 1.29 (d, J=7.1 Hz, 3H). LC-MS: for C₂₈H₃₂N₂O₃ [M+H] calculated 444.24, found 445.

Step E

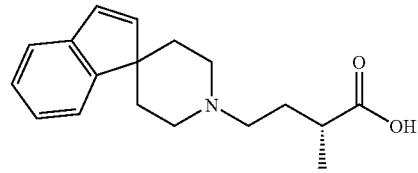

A solution of compound from Step D, Intermediate 17 (100 mg, 0.113 mmol) in THF (1 ml) was added via syringe to a prepared solution of hydrogen peroxide (94 µl, 0.90 mmol), lithium hydroxide monohydrate (18 mg, 0.45 mmol), water (0.667 ml) and THF (2 ml) cooled to 0° C. by ice/water bath. The resulting mixture turned cloudy after 10 minutes stirring at 0° C., then turned clear after an additional hour of stirring. The reaction was washed with ether (2×5 ml) and then the pH of the aqueous layer was adjusted to 7 by careful addition of 1N HCl. The product was extracted from the neutral aqueous layer with dichloromethane (6×5 ml). The organics were combined, dried over anhydrous sodium sulfate, filtered, and the solvent evaporated under reduced pressure to give 20 mg (32%) of the desired crude product as a clear oil.

EXAMPLE 19

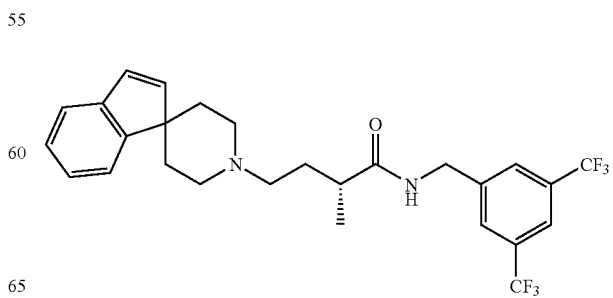

A mixture of the acid (Intermediate 17, 15 mg, 0.067 mmol), 3,5-bis(trifluoromethyl)benzylamine hydrochloride (15 mg, 0.067 mmol), HOAt (8 mg, 0.07 mmol), N,N-diisopropyl ethylamine (9 μl, 0.07 mmol) in dichloromethane (3 mL) was treated with 1-[3-(dimethylamino)propyl]-3-ethylcarbodiimide hydrochloride (EDC, 21 mg, 0.11 mmol) and stirred at room temperature overnight. The reaction mixture was diluted with dichloromethane (5 mL), washed with water (2×5 mL), brine (1×5 mL), dried over anhydrous sodium sulfate and the solvent was evaporated. Purification was done by preparative TLC (eluant: 5% methanol/95% ethyl acetate) to yield 14.1 mg (40%) of the desired final product. $^1$H NMR (500 MHz, CDCl$_3$): 7.80 (s, 2H), 7.59 (s, 1H), 7.34–7.18 (m, 4H), 6.79 (d, J=5.7 Hz, 1H), 6.75 (d, J=5.5 Hz, 1H), 4.68–4.56 (m, 2H), 3.15 (br d, J=13.5 Hz, 2H) 2.79 (br d, J=13.5 Hz, 1H), 2.52 (br t, J=7.3 Hz, 2H), 2.60–2.52 (m, 2H), 2.47–2.42 (m, 1H), 2.36 (dt, J=3.0, 13.4 Hz, 1H) 2.27 (dt, 3.1, 13.4 Hz, 1H), 2.08–2.02 (m, 1H), 1.96 (app br dt, J=2.8, 13.5 Hz, 1H), 1.90–1.75 (m, 2H), 1.40–1.29 (m, 2H) 1.29 (d, J=7.1 Hz, 3H). LC-MS: for C$_{27}$H$_{28}$N$_2$OF$_6$ [M+H] calculated 510.21, found 511.

Additional compounds were prepared in a similar fashion as Example 19 above, with the modification of replacing the methyl with different alkyl groups.

TABLE 9

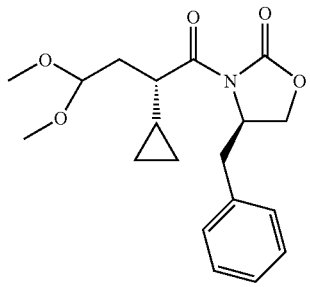

| Example | R | FW: formula/found (M + H) |
|---|---|---|
| 19-1 | (S) | C$_{29}$H$_{32}$N$_2$OF$_6$ 539 |
| 19-2 | (S) | C$_{29}$H$_{30}$N$_2$OF$_6$ 537 |

Intermediate 18

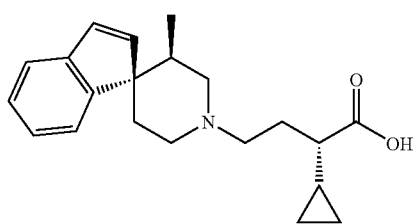

Step A

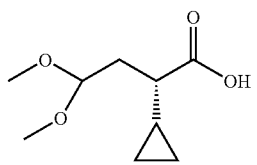

A solution containing cyclopropaneacetic acid (10.2 g, 102 mmol) and diisopropylethylamine (31.5 mL, 224 mmol) was cooled to −78° C. and butyl lithium (1.6M, 140 mL) was added drop-wise. The white suspension was allowed to warm up to app. +15° C., than it was heated to 50° C. for 30 minutes. The reaction mixture was cooled again to −10° C. and treated with 2,2-dimethyxy-1-bromoethane (24.1 mL, 204 mmol). The cooling bath was removed, and the reaction mixture was allowed to warm up to ambient temperature. The reaction was completed by heating to +50° C. for 30 minutes. It was standing at room temperature overnight. The reaction mixture was diluted with water, and the non-acidic components were extracted with diethyl ether. The pH of the aqueous solution was set to acidic (20 g of citric acid) and extracted with diethyl ether again. The combined (acidic) extracts were dried with anhydrous magnesium sulfate and evaporated to dryness. The crude product was further purified by distillation, which yielded 4.7447 g of recovered starting cyclopropanecacetic acid (b.p.: 75° C./0.3 mmHg) and 6.1538 g (32%) of the desired product, b.p.: 110° C./0.3 mmHg. $^1$H NMR (CDCl$_3$): 4.51 (t, J=5.72 Hz, 1H), 3.32 (s, 6H), 2.14 (ddd, J=14.7, 9.2, 6.0 Hz, 1H), 1.90 (dt, J=14.0, 5.5 Hz, 1H), 1.72 (ddd, J=9.6, 9.6, 5.3 Hz, 1H), 0.92 (m, 1H), 0.56 (m, 2H), 0.38 (m, 1H), 0.20 (m, 1H).

Step B

A solution of the acid from previous step (1.40 g, 7.44 mmol) in dry anhydrous tetrahydrofuran (30 mL), diisopropylethylamine (1.26 mL, 7.44 mmol) at 0° C. was treated with pivaloyl chloride (896 mg, 7.44 mmol) and stirred at this temperature for 1 hr. In a separate flask, a solution of 5-(5R)-benzyloxazolidin-2-one (1.32 g, 7.44 mmol) in dry tetrahydrofuran (30 mL) was treated at −78° C. with n-butyl lithium (3.12 mL, 1.6 M in hexanes, 7.81 mmol) and stirred at this temperature for 1 hr. The solution of the lithium salt was transferred into the flask containing the activated acid at 0° C., and the solution was stirred at room temperature overnight. The solvent was removed in vacuo, the residue was picked up into water (50 mL) and extracted with ethyl acetate (4×50 mL). The combined organic extracts were washed with brine, filtered and the solvent was distilled off on Rotavap. Flash chromatography (Lobar, Lichroprep Si60, 40–63 μm) using ethyl acetate/hexane (3:7) eluent gave 828 mg, (32%) of the higher eluting diastereoisomer and 277.6 mg (11%) of the lower eluting diastereoisomer. The absolute stereochemistry contained within the side-chain (C2) was optimal for maximum pharmacological activity.

Hi-$R_f$-Diastereoisomer: $^1$H NMR (CDCl$_3$): 7.34 (m, 2H), 7.26 (m, 3H), 4.68 (m, 1H), 4.55 (dd, J=7.1, 4.1 Hz, 1H), 4.15 (m, 2H), 3.44 (dd, J=12.7, 2.7 Hz, 1H), 3.34 (m, 1H), 3.31 (s, 3H), 3.29 (s, 3H), 2.64 (dd, J=13.3, 10.6 Hz, 1H), 2.35 (J=14.0, 9.6, 7.3 Hz, 1H), 1.97 (dt, J 14.0, 4.1 Hz,), 1.06 (m, 1H), 0.58 (m, 1H), 0.46 (m, 1H), 0.33 (m, 1H), 0.25 (m, 1H).

Lo-$R_f$-Diastereoisomer: $^1$H NMR (CDCl$_3$): 7.24 to 7.36 (bm, 5H), 4.75 (m, 1H), 4.47 (dd, J=7.1, 4.4 Hz, 1H), 4.18 (m, 2H), 3.37 (m, 1H), 3.29 (m, 1H), 3.28 (s, 3H), 3.26 (s, 3H), 2.85 (dd, J=13.5, 9.4 Hz, 1H), 2.33 (ddd, J=14.0, 9.9, 7.3 Hz, 1H), 1.94 (dt, J=14.0, 4.4 Hz, 1H), 1.08 (m, 1H), 0.61 (m, 1H), 0.50 (m, 2H), 0.29 (m, 1H).

Step C

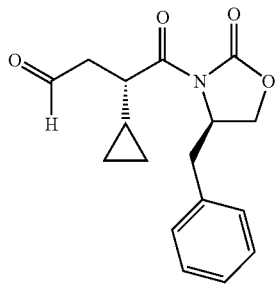

The more polar acetal from previous step (277.0 mg, 0.7973 mmol, Lo-$R_f$-Diastereoisomer) was briefly treated with 90% trifluoroacetic acid, diluted with diethyl ether and washed with saturated solution of sodium bicarbonate. The organic phase was dried with anhydrous magnesium sulfate and evaporated to dryness to yield 265 mg (96%) of the respective aldehyde.

$^1$H NMR (CDCl$_3$): 9.76 (s, 1H), 7.36 to 7.24 (bm, 5H), 4.76 (m, 1H), 4.31 (t, J=8.5 Hz, 1H), 4.20 (dd, J=8.9, 3.0 Hz, 1H), 3.75 (ddd, J=13.7, 9.8, 3.9 Hz, 1H), 3.26 (dd, J=13.5, 3.4 Hz, 1H), 3.19 (dd, J=18.5, 10.3 Hz, 1H), 2.87 (dd, J=13.5, 9.2 Hz, 1H), 2.83 (ddd, J=18.5, 4.1, 0.7 Hz, 1H), 1.02 (m, 1H), 0.68 (m, 1H), 0.62 (m, 1H), 0.54 (m, 1H), 0.27 (m, 1H).

Step D

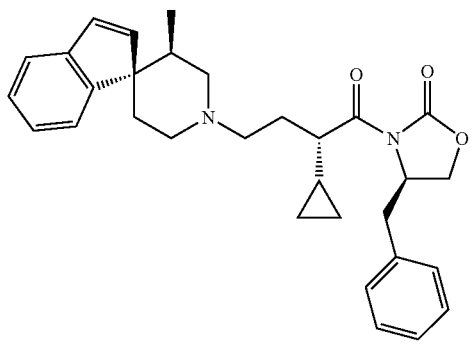

A solution of the aldehyde from previous step (265 mg, 0.763 mmol), methyspiroindene, hydrochloride (188 mg, 0.797 mmol), diisopropylethylamine (135 µL, 0.797 mmol) in dichloroethane (10 mL) was treated with sodium triacetoxyborohydride (500 mg, 2.359 mmol) and stirred at room temperature overnight. The reaction mixture was diluted with dichloromethane (50 mL), washed with saturated solution of sodium bicarbonate (1×30 mL), water (1×30 mL) and brine (1×30 mL). It was dried with anhydrous sodium sulfate, filtered and the solvent was removed in vacuo to leave 330.7 mg (86%) of product, pure enough to perform the subsequent step. $^1$H NMR (CDCl$_3$): 7.40 to 7.12 (bm, 9 H), 6.80 (d, J=m5.7 Hz, 1H), 6.65 (d, J=5.7 Hz, 1H), 4.84 (m, 1H), 4.27 (t, J=8.92 Hz, 1H), 4.22 (dd, J=8.9, 3.4 Hz, 1H), 3.36 (m, 2H), 2.86 (dd, J=13.5, 9.4 Hz, 1H), 2.24 (m, 4H), 1.30 (m, 1H), 1.1 (m, 1H), 0.64 (m, 1H), 0.54 (m, 1H), 0.47 (m, 1H), 0.32 (m, 4H).

Step E

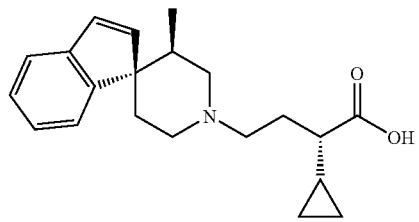

A solution of the imide from previous step (80 mg, 0.17 mmol) in THF (2.0 mL) was cooled to 0° C. and treated with 75 µL of hydrogen peroxide (30%, aqueous solution, app. 1.1 mmol) followed by a solution of lithium hydroxide (14 mg) in water (1.0 mL). This mixture was stirred at 0° C. for 10 minutes and the reaction was quenched with saturated solution of sodium sulfite (520 µL). Most of the THF was distilled off on Rotavap, the residue was diluted with water (2 mL) and extracted with dichloromethane (3×2 mL) to remove the non-acidic reaction components. pH was adjusted to 7.0 (1N HCl) and the product was extracted with chloroform (6×4 mL). The combined extracts were dried with anhydrous sodium sulfate and evaporated to dryness to leave 40.2 mg (75%) of the desired acid. $^1$H NMR (CDCl$_3$): 7.35 (bd, J=6.9 Hz, 1H), 7.31 (bd, J=6.9 Hz, 1H), 7.27 to 7.20 (bm, 2H), 6.88 (d, J=5.7 Hz, 1H), 6.61 (d, J=5.7 Hz, 1H), 3.44 (bd, J=11.7 Hz, 1H), 3.32 (dd, J=12.1 Hz, 2.3 Hz, 1H), 3.13 (m, 1H), 2.87 (m, 1H), 2.71 (dt, J=13.5, 2.5 Hz, 1H), 2.63 (m, 1H), 2.54 (dt, J=13.7, 3.9 Hz, 1H), 2.41 (t, J=12.1 Hz, 1H), 2.15 (m 1H), 2.00 (m, 1H), 1.84 (m, 1H), 1.41 (dt, J=14.0, 2.5 Hz, 1H), 1.05 (m, 1H), 0.68 (m 1H), 0.58 (m, 1H), 0.51 (m, 1H), 0.36 (d, J=6.63 Hz, 3H), 0.18 (m, 1H).

Intermediate 19

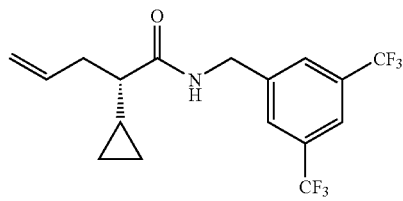

Was synthesized from the corresponding chiral acid (650 mg, 4.6368 mmol, obtained by allylation of N-cyclopropanylacetyl-5-(S)-benzyloxazolidin-2-one and cleavage of the auxiliary group as described for Intermediate 18) followed by amide formation with 3,5-bistrifluoromethylbenzylamine hydrochloride in a similar fashion as described under Intermediate 1, Step B. $^1$H NMR (CDCl$_3$): 7.79 (s, 1H), 7.74 (s, 2H), 6.20 (bs, 1H), 5.81 (m, 1H), 5.11 (bdd, J=17.2, 1.6 Hz, 1H), 5.04 (bd, J=10.1 Hz, 1H), 4.62 (m, 2H), 2.56 (m, 2H), 1.53 (ddd, J=9.8, 8.2, 5.5 Hz, 1H), 1.01 (m, 1H), 0.65 (m, 2H), 0.25 (m, 2H).

EXAMPLE 20

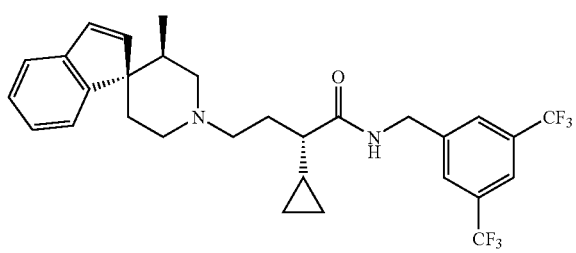

Procedure A

A solution of Intermediate 18 (145 mg, 0.446 mmol), 3,5-bistrifluoromethylbenzylamine hydrochloride (125 mg, 0.446 mmol), 1-hydroxy-7-azabenzotriazole (60 mg, 0.45 mmol), diisopropylethylamine (78 µL, 0.45 mmol) and 1-[3-(dimethylamino)propyl]-3-ethylcarbodiimide hydrochloride (EDC, 130 mg, 0.668 mmol) was stirred at room temperature overnight. Dichloromethane (30 mL) was added and the reaction mixture was extracted with saturated solution of sodium bicarbonate (1×30 mL). The aqueous phase was extracted with dichloromethane (2×20 mL), the organic phases were combined, dried and evaporated to dryness to leave 174.7 mg of crude product. This was further purified by preparative TLC (100% ethyl acetate) to give 115.1 mg (47%) of pure product.

Procedure B

A solution of the olefin Intermediate 19 (603 mg, 1.65 mmol) in dichloromethane (50 mL) was cooled to −78° C. and a stream of ozone was passed through until the permanent blue color indicated complete consumption of the olefin. The excess of ozone was purged with nitrogen, and the solution of the ozonide was allowed to warm up to room temperature. The solution was dried with anhydrous magnesium sulfate and filtered. 3-Methyl-4-spiroindenylpiperidine. hydrochloride (389 mg, 1.65 mmol) was added, followed by 4A molecular sieves, diisopropylethylamine (287 µL, 1.65 mmol) and finally sodium triacetoxyborohydride (1.75 g, 8.25 mmol). Stirring at room temperature was continued overnight. The reaction mixture was diluted with dichloromethane (100 mL) and the sieves were filtered off through a plug of Celite. The filtrate was extracted with saturated solution of sodium bicarbonate (1×50 mL), the aqueous extracts were back-washed with dichloromethane (1×50 mL). The combined organic phases were dried with anhydrous sodium sulfate and the solvent was removed in vacuo. The crude product was purified by flash chromatography (ethyl acetate methanol/95: 5) to yield 533 mg (58%) of pure product.

$^1$H NMR (Hydrochloride, CDCl$_3$): 11.9 (bs, 1H), 8.5 (bs, 1H), 7.86 (bs, 2H), 7.75 (s, 1H), 7.47 (m, 1H), 7.35 to 7.25 (bm, 3H), 6.94 (d, J=5.7 Hz, 1H), 6.48 (d, J=5.7 Hz, 1H), 4.64 (dd, J=15.6, 5.7 Hz, 1H), 4.54 (dd, 15.6, 6.0 Hz, 1H), 3.52 (bd, J=11.7 Hz, 1H), 3.14 (m, 2H), 2.98 (bs, 1H), 2.90 m (1H), 2.55 (m, 1H), 2.36 (m, 2H), 2.22 (m, 1H), 1.44 (d, J=14.7 Hz, 1H), 1.05 (m, 1H), 0.64 (m, 1H), 0.47 (m, 1H), 0.43 (d, J=6.9 Hz, 3H), 0.25 (m, 1H).

EXAMPLE 21

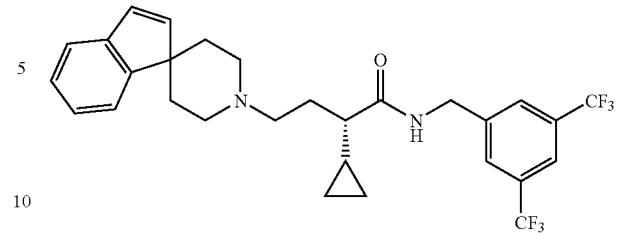

Example 21 was synthesized according to the procedure described for preparation of Example 20, except that 4-spiroindenylpiperidine was used instead of 3-methyl-4-spiroindenylpiperidine in Step D, Intermediate 18. $^1$H NMR (CDCl$_3$): 7.80 (bs, 3H), 7.33 (bd, J=7.3 Hz, 1H), 7.28 to 7.18 (bm, 3H), 7.07 (bs, 1H), 6.82 (d, J=5.7 Hz, 1H), 6.75 (d, J=5.7 Hz, 1H), 4.65 (m, 2H), 3.02 (bd, J=11.9 Hz, 1H), 2.85 (bd, J=11.9 Hz, 1H), 2.58 (m, 1H), 2.50 (m, 1H), 2.37 (dt, J=J=11.1, 2.5 Hz, 1H), 2.27 (dt, J=11.7, 2.1 Hz, 1H), 2.05 (m, 4H), 1.86 (m, 3H), 1.35 (m, 2H), 1.05 (m, 1H), 0.66 (m, 2H), 0.27 (m, 2H).

EXAMPLE 22

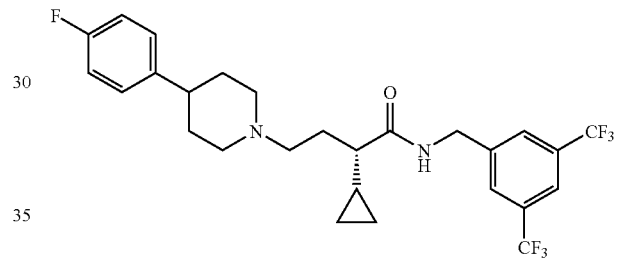

Example 22 was synthesized according to the procedure described for preparation of Example 20, except that 4-(4-fluorophenyl)piperidine was used instead of 3-methyl-4-spiroindenylpiperidine in Step D, Intermediate 18. $^1$H NMR (CDCl$_3$): 7.80 (bs, 1H), 7.77 (bs, 2H), 7.12 (m, 2H), 6.98 (m, 2H), 4.633 (m, 2H), 3.03 (bd, J=11.4 Hz, 2H), 2.85 (bd, J=11.4 Hz, 1H), 2.43 (m, 2H), 2.32 (m, 1H), 2.1 to 1.9 (bm, 4H), 1.86 to 1.50 (bm, 7H), 1.05 (m, 1H), 0.64 (m, 2H), 0.28 (m, 1H), 0.20 (m, 1H).

EXAMPLE 23

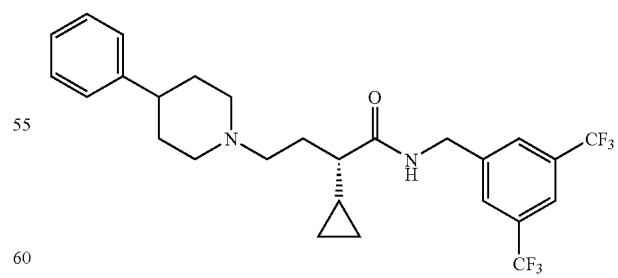

Example 23 was synthesized according to the procedure described for preparation of Example 20, except that 4-phenylpiperidine was used instead of 3-methyl-4-spiroindenylpiperidine in Step D, Intermediate 18. $^1$H NMR (CDCl$_3$): 7.79 (bs, 1H), 7.78 (bs, 2H), 7.32 to 7.15 (bm, 5H), 4.62 (m, 2H), 3.05 (bd, J=11.4 Hz, 1H), 2.85 (bd, J=11.4 Hz, 1H), 2.50 (m, 2H), 2.32 (m, 1H), 2.10 (dt, J=12.1, 2.5 Hz, 1H), 2.04 to 1.58 (bm, 10H), 1.05 (m, 1H), 0.64 (m, 2H), 0.32 to 0.18 (bm, 2H).

EXAMPLE 24

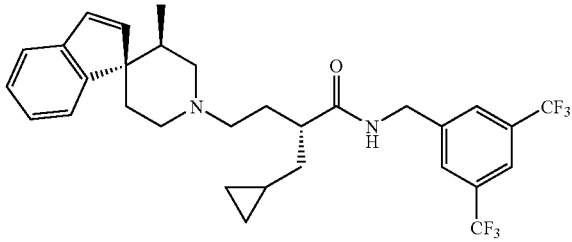

Example 24 was synthesized according to a procedure analogous to that described for preparation of Example 20. $^1$H NMR (CDCl$_3$): 7.82 (s, 2H), 7.80 (s, 1H), 7.32 to 7.18 (bm, 5H), 6.83 (d, J=5.7 Hz, 1H), 6.62 (d, J=5.7 Hz, 1H), 4.65 (dd, J=6.2, 15.6 Hz, 1H), 4.60 (dd, J=15.6, 6.0 Hz, 1H), 3.0 (bd, J=10.8 Hz, 1H), 2.88 (bd, J=11.0 Hz, 1H), 2.54 (bs, 2H), 2.45 (m, 1H), 2.32 (m, 2H), 2.22 (m, 1H), 2.02 (m, 3H), 1.89 (m, 2H), 1.75 (m, 1H), 1.37 (m, 1H), 1.28 (bd, J=13.5 Hz, 1H), 0.72 (m, 1H), 0.45 (m, 2H), 0.32 (d, J=6.6 Hz, 3H), 0.1 (m, 2H).

EXAMPLE 25

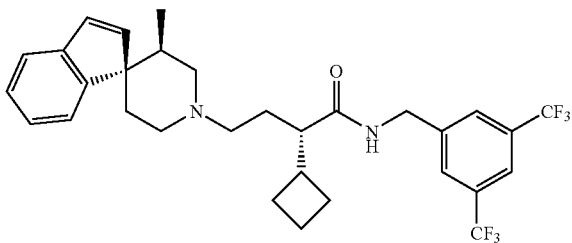

Example 25 was synthesized according to a procedure analogous to that described for preparation of Example 20. $^1$H NMR (CDCl$_3$): 7.78 (s, 3H), 7.32 to 7.18 (bm, 4H), 6.82 (d, J=5.7 Hz, 1H), 6.62 (d, J=5.7 Hz, 1H), 4.64 (dd, J=15.8, 6.2 Hz, 1H), 4.58 (dd, J=15.6, 6.2 Hz, 1H), 3.0 (bs, 1H), 2.88 (m, 1H), 2.7 to 1.6 (bm, 22H), 1.28 (m, 1H), 0.33 (d, J=6.9 Hz, 3H), 0.09, s 1H).

Intermediate 20

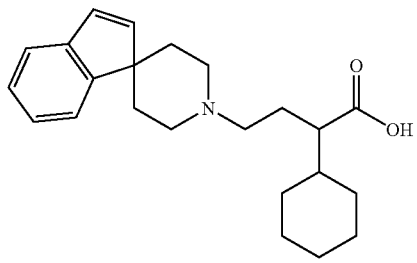

Step A

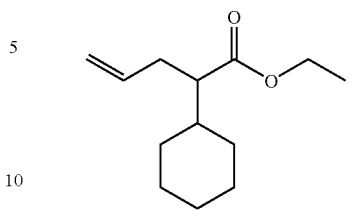

Lithium diisopropyl amide (LDA) was freshly prepared by treating a solution of diisopropylamine (3.24 ml, 23.1 mmol) in dry THF (40 ml) under nitrogen cooled to −78° C. with 2.5 M n-butyl lithium (9.244 ml, 23.11 mmol) added slowly via syringe. To this solution was added ethyl cyclohexylacetate (3.77 g, 21.0 mmol) in dry THF (60 ml) via syringe dropwise over a 30 minute period. The resulting solution was stirred at −78° C. for 1 hour; then allyl bromide (2.37 ml, 27.3 mmol) was added via syringe and the reaction mixture was stirred overnight allowing to warm to room temperature. The reaction was quenched with a saturated solution of ammonium chloride (100 ml) and the resulting mixture was poured into a separatory funnel. The organic layer was separated, washed with brine (1×100 mL), dried with anhydrous sodium sulfate and the solvent was evaporated. The crude residue was purified by MPLC (eluant 10% ethyl acetate/hexane) to yield 4.24 g (99%) of the racemic desired product Step B:

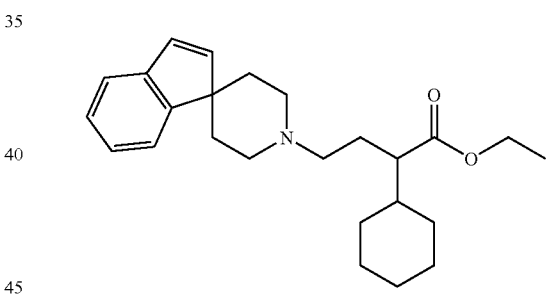

A solution of the compound synthesized in Step A, Intermediate 20 (500 mg, 1.68 mmol) in dichloromethane (20 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added spiroindenylpiperidine hydrochloride (419 mg, 1.80 mmol), diisopropylethylamine (328 μL, 1.80 mmol), crushed 4 A molecular sieves (250 mg) and the resulting mixture was treated with sodium triacetoxyborohydride (2.00 g, 9.46 mmol). After stirring at ambient temperature for 24 hours, the sieves were filtered off, the filtrate was washed with a saturated solution of sodium bicarbonate (1×100 mL), water (3×50 mL) and brine (1×100 mL). After drying (anhydrous sodium sulfate) the solvent was evaporated to dryness under reduced pressure to leave 620 mg of crude product, which was further purified by preparative TLC (eluant: 100% ethyl acetate) to give 456 mg (66%) of the pure desired product. LC-MS for $C_{25}H_{35}NO_2$ [M+H]$^+$ calculated 381.27, found 382.

Step C:

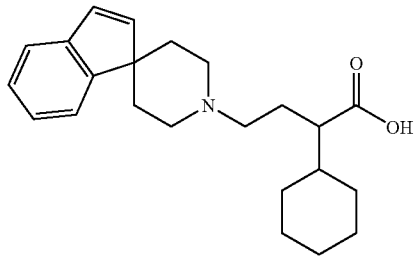

A solution of material from Step B, Intermediate 20 (450 mg, 1.12 mmol) in THF/methanol/water (1:1:1 solution, 30 ml) was treated with lithium hydroxide monohydrate (188 mg, 4.48 mmol) and the resulting solution was stirred at room temperature for 48 hours. The organic solvents were evaporated under reduced pressure to leave the aqueous layer containing the product. The aqueous layer was diluted with ethyl acetate (75 ml) and the pH adjusted to approximately 3 with 6N HCl solution. The organic layer was separated and the aqueous was extracted with ethyl acetate (3×50 ml). The organics were combined, washed with brine (1×50 ml), dried over anhydrous sodium sulfate, filtered, and the solvent evaporated under reduced pressure. The residue was azeotroped with toluene to remove any acetic acid, formed by the ethyl acetate extraction, and water to yield 397 mg (91%) of the crude product which was used without further purification.

EXAMPLE 26

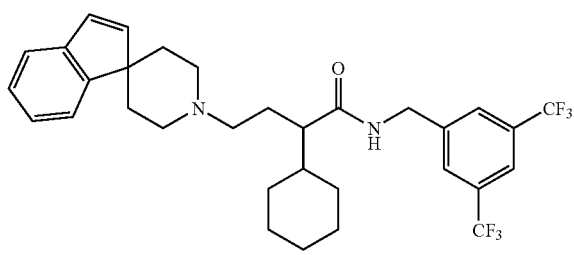

A mixture of the acid (Intermediate 20, 150 mg, 0.387 mmol), 3,5-bis(trifluoromethyl)benzylamine hydrochloride (109 mg, 0.387 mmol), HOAt (53 mg, 0.387 mmol), N,N-diisopropyl ethylamine (67 µl, 0.387 mmol) in dichloromethane (10 mL) was treated with 1-[3-(dimethylamino)propyl]-3-ethylcarbodiimide hydrochloride (EDC, 148 mg, 0.774 mmol) and stirred at room temperature overnight. The reaction mixture was diluted with dichloromethane (20 mL), washed with water (2×20 mL), brine (1×20 mL), dried over anhydrous sodium sulfate and the solvent was evaporated. Purification was done by preparative TLC (eluant: 60% ethyl acetate/hexane) to yield 173 mg (77%) of the desired final product. LC-MS for $C_{32}H_{36}N_2OF_6$ [M+H]$^+$ calculated 578.27, found 579.

Intermediate 21

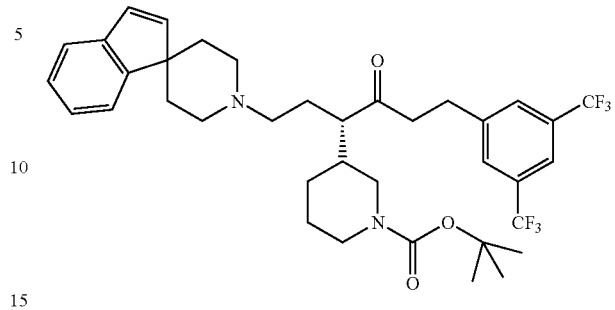

Step A

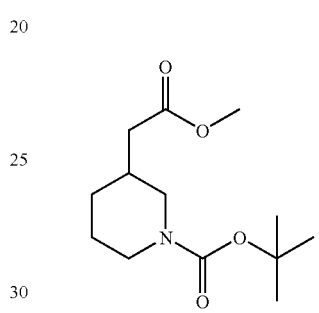

A suspension of ethyl-3-pyridylacetate (5.0 g, 30 mmol) and platinum oxide (500 mg), in acidic ethanol (200 ml of 1% HCl/EtOH) was placed on a parr shaker and treated with hydrogen at 50 psi for 15 hours. The reaction was then flushed with nitrogen, the catalyst filtered off (plug of Celite), and the solvent evaporated under reduced pressure to yield 5.86 g (100%) of a white solid.

The material was then dissolved in dichloromethane (200 ml) and treated with diisopropyl ethylamine (5.25 ml, 30.26 mmol) and di-tert-butyl-dicarbonate (7.00 g, 31.77 mmol). The resulting mixture was stirred at room temperature overnight. The solution was washed with 1N HCl (100 ml), saturated sodium bicarbonate (100 ml), brine (100 ml), dried over anhydrous sodium sulfate, and the solvent evaporated at reduced pressure to yield 7.5 g (97%) of the crude product as a yellow oil. Purification was done by MPLC (eluant: 10% ethyl acetate/hexane) to give 6.22 g (80%) of the pure desired product.

Step B

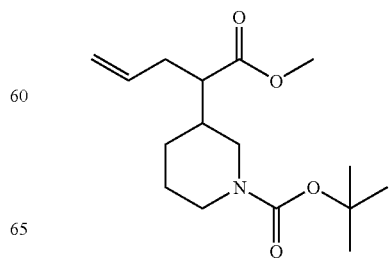

Lithium diisopropyl amide (LDA) was freshly prepared by treating a solution of diisopropylamine (1.80 ml, 12.8 mmol) in dry THF (20 ml) under nitrogen cooled to −78° C. with 2.5 M n-butyl lithium (5.13 ml, 12.8 mmol) added slowly via syringe. To this solution was added the product from Step A of Intermediate 21 (3.0 g, 12 mmol) in dry THF (80 ml) via syringe dropwise over a 30 minute period. The resulting solution was stirred at −78° C. for 1 hour; then allyl bromide(1.32 ml, 12.8 mmol) was added via syringe and the reaction mixture was stirred overnight allowing to warm to room temperature. The reaction was quenched with a saturated solution of ammonium chloride (100 ml) and the resulting mixture was poured into a separatory funnel. The organic layer was separated, washed with brine (1×100 mL), dried with anhydrous sodium sulfate and the solvent was evaporated. The crude residue was purified by MPLC (eluant 30% ethyl acetate/hexane) to yield 3.22 g (93%) of the racemic desired product Step C:

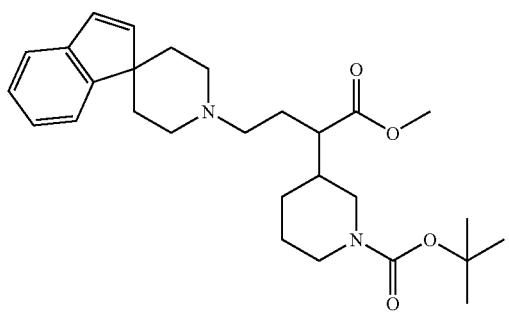

A solution of the compound synthesized in Step B, Intermediate 21 (1.00 g, 3.36 mmol) in dichloromethane (35 mL) was cooled to −78° C. and a stream of ozone was passed through until the permanent blue color indicated complete consumption of the olefin. The excess ozone was purged with a stream of nitrogen and allowed to warm up to ambient temperature. The solution was dried with magnesium sulfate, the drying agent was filtered off, and to the filtrate was added spiroindenylpiperidine hydrochloride (745 mg, 3.36 mmol), diisopropylethylamine (585 µL, 3.36 mmol), crushed 4 A molecular sieves (500 mg) and the resulting mixture was treated with sodium triacetoxyborohydride (3.56 g, 16.8 mmol). After stirring at ambient temperature for 24 hours, the sieves were filtered off, the filtrate was washed with a saturated solution of sodium bicarbonate (1×100 mL), water (3×50 mL) and brine (1×100 mL). After drying (anhydrous sodium sulfate) the solvent was evaporated to dryness under reduced pressure to leave 750 mg of crude product, which was further purified by preparative TLC (eluant: 100% ethyl acetate) to give 640 mg (51%) of the pure desired product. $^1$H NMR (500 MHz, CDCl$_3$): 7.37 (d, J=7.3 Hz, 1H), 7.32 (d, J=7.2 Hz, 1H), 7.26–7.18 (m, 2H), 6.84 (d, J=5.7, 1H), 6.75 (d, J=5.5 Hz, 1H), 4.26–4.17 (m, 1H), 4.06–3.86 (m, 1H), 3.04–2.96 (m, 2H), 2.68 (app t, J=12.4 Hz, 1H), 2.51–2.44 (m, 1H), 2.43–2.37 (m, 1H), 2.31 (br t, J=9.8 Hz, 2H), 2.24–2.12 (m, 2H), 2.00–1.88 (m, 2H), 1.82–1.64 (m, 4H), 1.47 (br s, 9H), 1.33 (t, J=7.1 Hz, 3H). LC-MS: for C28H40N2O4 [M+H] calculated 468.30, found 469.

Step D:

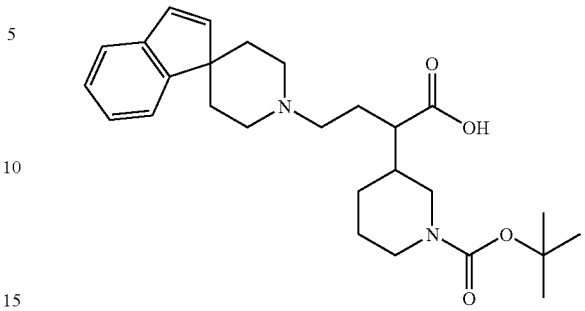

A solution of material from Step C, Intermediate 21 (640 mg, 1.28 mmol) in THF/methanol/water (1:1:1 solution, 30 ml) was treated with lithium hydroxide monohydrate (214 mg, 5.10 mmol) and the resulting solution was stirred at room temperature for 48 hours. The organic solvents were evaporated under reduced pressure to leave the aqueous layer containing the product. The aqueous layer was diluted with ethyl acetate (75 ml) and the pH adjusted to approximately 3 with 6N HCl solution. The organic layer was separated and the aqueous was extracted with ethyl acetate (3×50 ml). The organics were combined, washed with brine (1×50 ml), dried over anhydrous sodium sulfate, filtered, and the solvent evaporated under reduced pressure. The residue was azeotroped with toluene to remove any acetic acid, formed by the ethyl acetate extraction, and water to yield 510 mg (80%) of the crude product which was used without further purification.

Step E:

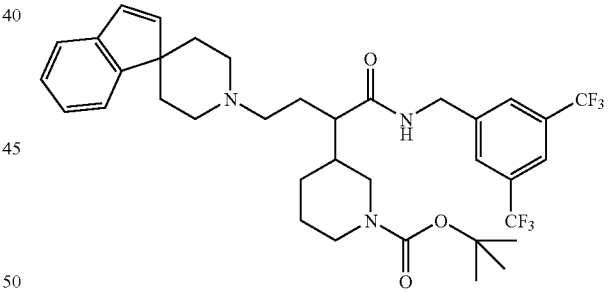

A mixture of the acid (Step D, Intermediate 21, 360 mg, 0.76 mmol), 3,5-bis(trifluoromethyl)benzylamine hydrochloride (212 mg, 0.76 mmol), HOAt (104 mg, 0.76 mmol), N,N-diisopropyl ethylamine (132 µl, 0.76 mmol) in dichloromethane (30 mL) was treated with 1-[3-(dimethylamino)propyl]-3-ethylcarbodiimide hydrochloride EDC, 292 mg, 1.52 mmol) and stirred at room temperature overnight. The reaction mixture was diluted with dichloromethane (30 mL), washed with water (2×20 mL), brine (1×30 mL), dried over anhydrous sodium sulfate and the solvent was evaporated. Purification was done by preparative TLC (eluant: 80% ethyl acetate/hexane) to yield 282 mg (53%) of the desired product. LC-MS: for $C_{36}H_{43}N_3O_3F_6$ [M+H] calculated 679.32, found 680 and 579 [M+H−Boc].

EXAMPLE 27

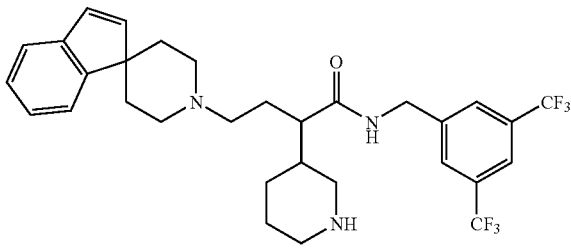

A solution of Intermediate 21 (200 mg, 0.317 mmol) in dichloromethane (2 ml) was treated with 4N HCl in dioxane (4 ml) and the resulting mixture stirred for 1 hour at room temperature. The solvent was evaporated under reduced pressure to give 197 mg, (99%) of the desired final product. LC-MS for $C_{31}H_{35}N_3OF_6$ [M+H]$^+$ calculated 579.27, found 580.

EXAMPLE 28

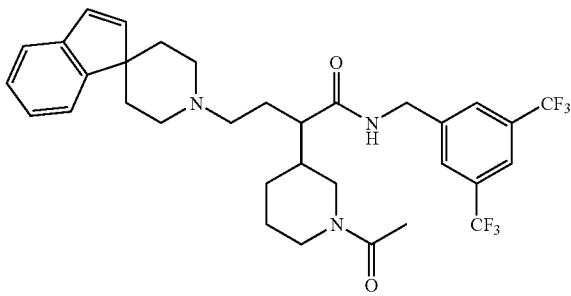

A solution of the above synthesized product (EXAMPLE 27, 97.5 mg, 0.162 mmol) and triethyl amine (90 μL, 0.65 mmol) in dichloromethane (6 ml) under nitrogen cooled to 0° C. was treated with acetyl chloride (13 μL, 0.18 mmol) and the resulting mixture was stirred for 2 hours at 0° C. The mixture was washed with saturated sodium bicarbonate (10 ml), dried over anhydrous sodium sulfate, filtered, and the solvent evaporated under reduced pressure. The residue was purified by preparative TLC (eluant: 5% methanol/95% ethyl acetate) to give 92 mg (92%) of the desired final product. LC-MS for $C_{33}H_{37}N_3O_2F_6$ [M+H]$^+$ calculated 621.28, found 622.

EXAMPLE 29

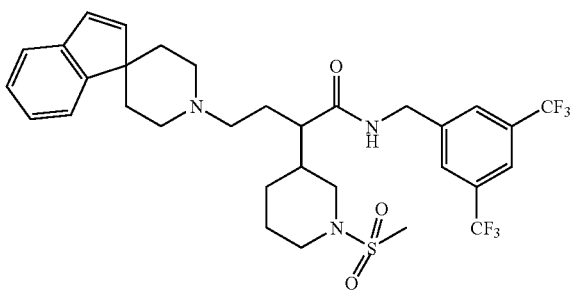

The title compound was prepared using a synthetic sequence analogous to that described in Example 28 except that methanesulfonylchloride was used instead of acetyl chloride. Purification by preparative TLC (eluant: 5% methanol/95% ethyl acetate) gave 94 mg (88%) of the desire final product. LC-MS for $C_{32}H_{37}N_3O_3F_6S$ [M+H]$^+$ calculated 657.25, found 658.

Intermediate 22

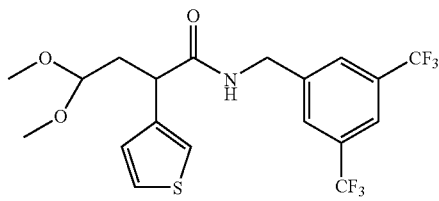

Step A

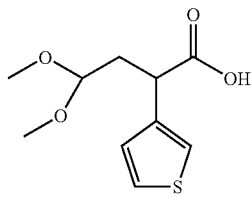

A solution of 3-thienylacetic acid (2.544 g, 17.89 mmol) in dry tetrahydrofuran (100 mL) was cooled with an ice/salt bath to −10° C. and the solution of lithium hexamethylsilazane (40 mL, 1M, in THF) was added drop-wise, over a period of 30 minutes. After additional stirring at cold for 30 minutes, the neat 2,2-dimethoxy-1-bromoethane was added via syringe. The cooling bath was removed and the stirring at room temperature was continued for another 3 hrs. The reaction mixture was poured onto water (100 mL), the non-acidic components were extracted with diethyl ether (2×50 mL). The pH of the aqueous solution was set to 3, (HCl, 2 N) and the crude acid was extracted into diethyl ether (3×50 mL). The combined organic extracts were dried with anhydrous sodium sulfate, and the solvent was evaporated to dryness to leave 1.12 g (27%) of the crude acid, used in the next step without additional purification.

This racemic acid could be resolved into its respective enantiomers using (R)- and/or (S)-α-phenylethylamine salts via crystallization from ethyl acetate. The acid, which ultimately led to the more active enantiomer of the racemate shown under Example 30, was obtained by crystallizations using the salts derived form the (S)-amine.

Step B

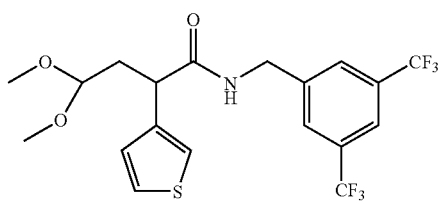

The solution of the crude acid from Step A (716 mg, 3.11 mmol) and 3,5-bistrifluoromethyl benzylamine hydrochloride (870 mg, 3.11 mmol) in dichloromethane (10 mL) was treated with 1-hydroxy-7-azabenzotriazole (423 mg, 3.11 mmol), diisopropylethylamine (600 µL, 3.20 mmol) and 1-[3-(dimethylamino)propyl]-3-ethylcarbodiimide hydrochloride (EDC, 895 mg, 4.664 mmol) and stirred at room temperature for 1 hr. The reaction mixture was poured onto water (30 mL), extracted with dichloromethane. The combined organic extracts were washed with brine (1×30 mL), dried with anhydrous magnesium sulfate and the solvent was evaporated to dryness under reduced pressure. Flash chromatography (Lobar, Lichroprep Si60, 40–63 µm) using ethyl acetate/hexane (4:6) eluent gave 644 mg, (45%, two steps) of pure product.

Either of the enantiomers of the starting acid could be transformed into the enantiomerically pure form of Intermediate 22 in a reaction similar to that performed with the racemic acid, as described under Intermediate 22, Step B.

$^1$H NMR (CDCl$_3$, 500 MHz): 7.76 (s, 1H), 7.62 (bs, 2H), 7.36 (dd, J=5.04, 2.98 Hz, 1H), 7.18 (bs, 1H), 7.06 (bd, J=5.03 Hz, 1H), 6.04 (t, J=5.5 Hz, 1H), 3.34 (s, 3H), 3.28 (s, 3H), 2.53 (ddd, J=14.2, 8.0, 6.2 Hz, 1H), 2.03 (ddd, J=14.0, 6.9, 5.5 Hz, 1H).

Intermediate 23

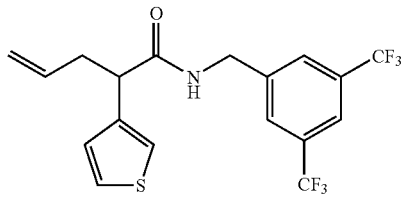

Step A

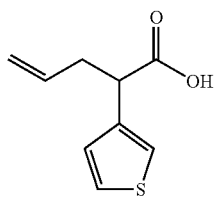

A solution of 3-thienylacetic acid (4.113 g, 28.92 mmol) in dry tetrahydrofurane (20 mL) and cooled to −10° C. with ice/salt bath. Allyl bromide (5.5 mL, 7.69 g, 63.6 mmol) was added via syringe and stirring was continued for another 1 hr at room temperature. The reaction was quenched with water (100 mL), the non-acidic components were extracted into diethyl ether. The pH of the aqueous phase was set to 3, and the crude product was extracted into diethyl ether. The combined organic extracts were washed with brine, dried with anhydrous magnesium sulfate, and evaporated to dryness. The remaining acid (4.08 g, 77%) was used in the next step without any further purification.

Step B

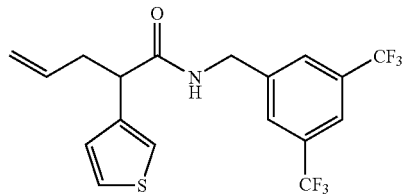

1.67 g, 9.16 mmol) and 3,5-bistrifluoromethyl benzylamine hydrochloride (2.562 g, 9.16 mmol) in dichloromethane (30 mL) was treated with 1-hydroxy-7-azabenzotriazole (423 mg, 3.109 mmol), diisopropylethylamine (1.60 mL, 9.18 mmol) and 1-[3-(dimethylamino)propyl]-3-ethylcarbodiimide hydrochloride (EDC, 2.64 g, 13.7 mmol) and stirred at room temperature overnight. The reaction mixture was poured onto water (50 mL), extracted with dichloromethane (3×50 mL). The combined organic extracts were washed with brine (1×30 mL), dried with anhydrous magnesium sulfate and the solvent was evaporated to dryness under reduced pressure. The crude product was crystallized from hexane to give 2.3962 g (64%) of pure Intermediate 23.

Intermediate 24

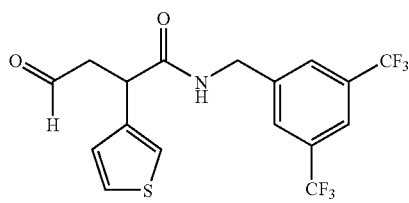

Procedure A

Intermediate 22 (177 mg, 0.389 mmol) was dissolved in trifluoroacetic acid (2.0 mL) and briefly stirred (about 5 minutes) at ambient temperature. The reaction mixture was diluted with diethyl ether and washed with water (5×30 mL). The organic layer was dried with anhydrous magnesium sulfate and evaporated to dryness. The crude product was co-distilled several times with benzene (to remove remaining trifluoroacetic acid) and used in the subsequent step immediately.

The respective chiral form Intermediate 24 was obtained in an analogous reaction, except that the respective chiral form of Intermediate 22 was used as starting material.

Procedure B

The solution of Intermediate 23 (472 mg, 1.16 mmol) and osmium tetroxide (36 mg, 0.14 mmol) in ethanol (10 mL) was treated with a solution of sodium periodate (620 mg, 2.90 mmol) in water (6 mL). The reaction mixture was stirred at room temperature for 30 minutes and the ethanol was distilled off under reduced pressure. The remaining aqueous suspension was extracted with ethyl acetate (3×30 mL), dried with anhydrous sodium sulfate, and evaporated to dryness to yield 362 mg of crude product, containing about 30% (HPLC, $^1$H NMR) of the desired aldehyde. This was used immediately in the next step.

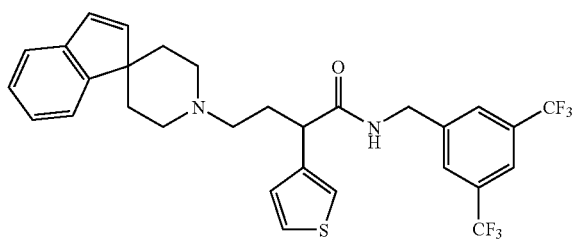

A solution of the Intermediate 24 (56 mg, 0.18 mmol) and 4-spiroindenylpiperidine hydrochloride (40.3 mg, 0.182 mmol) in dry dichloroethane (5 mL) was treated with diisopropylethylamine (40 μL, 0.22 mmol) and to this mixture, sodium triacetoxyborohydride (193 mg, 5.0 mmol) were added. The reaction was allowed to proceed overnight. It was quenched with saturated solution of sodium bicarbonate (20 mL), and the product was extracted with dichloromethane (3×30 mL). The combined organic layers were dried with anhydrous sodium sulfate and evaporated to dryness (78 mg). The crude product was further purified by preparative TLC using ethyl acetate/hexane (1:1) as eluent to obtain 28 mg, 27%) of pure product. $^1$H NMR (CDCl$_3$, 500 MHz): 7.77 (s, 1H), 7.67 (s, 2H), 7.38 (dd, J=5.0, 3.0 Hz, 1H), 7.34 (bt, J=7.8 Hz, 2H), 7.23 (m, 3H), 7.10 (dd, J=5.0, 1.4 Hz, 1H), 6.83, (d, J=5.5 Hz, 1H), 6.76 (d, J=5.7 Hz, 1H), 6.62 (bs, 1H), 4.60 (dd, J=15.6 Hz, 1H), 4.54 (dd, J=15.8, 6.2 Hz, 1H), 3.90 (t, J=7.55 Hz, 1H), 3.2 (bd, J=11.4 Hz, 1H), 2.96 (bd, J=11.4 Hz, 1H), 2.42 (m, 6H), 2,12 (m, 4H).

EXAMPLE 31

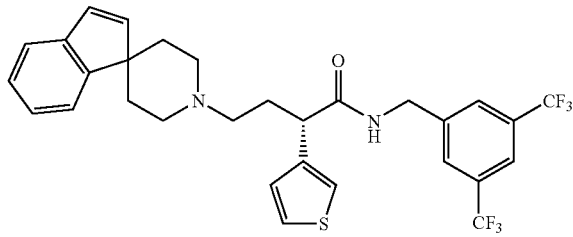

was synthesized starting from the chiral form of Intermediate 24 and 4-spiroindenylpiperidine according to the procedure described in Example 30.

EXAMPLE 32

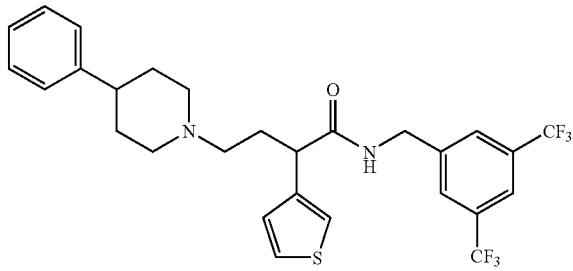

was synthesized starting from the chiral form of Intermediate 24 and 4-phenylpiperidine according to the procedure described in Example 30. $^1$H NMR (CDCl$_3$, 500 MHz): 7.78 (s, 1H), 7.66 (bs, 2H), 7.35 (m, 3H), 7.20 (m, 3H), 7.08 (d, J=5.0 Hz, 11), 6.78 (bs, 1H), 4.55 (m, 2H), 3.85 (m, 1H), 3.05 (d, J=11.2 Hz, 1H), 2.95 (d, J=11.2 Hz, 1H), 2.52 (m, 1H), 2.38 (m, 3H), 2.05 (m, 3H), 1.85, (m, 2H), 1.72 (m, 2H).

EXAMPLE 33

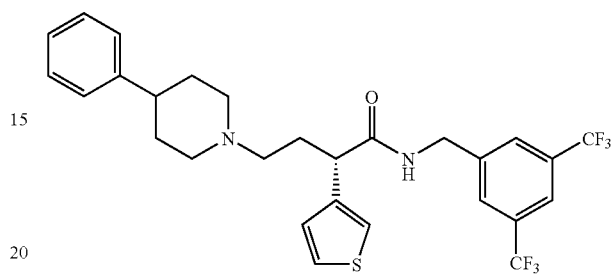

was synthesized starting from the chiral form of Intermediate 24 and 4-phenylpiperidine according to the procedure described in Example 30.

Intermediate 25

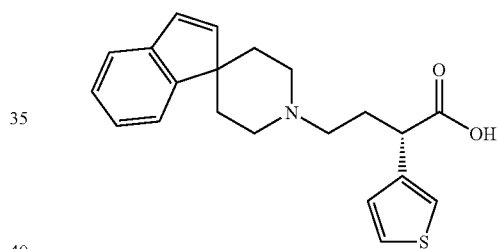

Step A

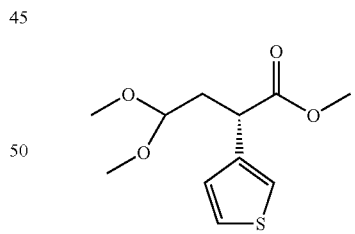

A solution of enantiomerically pure 4,4-dimethoxy-2-(thien-3-yl)butyric acid, synthesized according to the Procedure A, Intermediate 22 (640 mg, 2.6196 mmol) in diethyl ether was treated with an etheral solution of diazomethane, added in excess. As soon as effervescence subsided, the excess diazomethane was purged with a stream of nitrogen, and the solvent was evaporated under reduced pressure. $^1$H NMR (CDCl$_3$, 500 MHz): 7.28 (dd, J=5.0, 3.2, 1H), 7.15 (dd, J=2.8, 1.0 Hz, 1H), 7.06 (dd, J=5.0, 1.4 Hz, 1H), 4.28 (dd, J=6.4, 5.0 Hz, 1H), 3.88 (dd, J=8.5, 7.1 Hz, 1H), 3.69 (s, 3H), 3.33 (s, 1H), 3.0 (s, 3H), 2.41 (ddd, J=14.9, 8.5, 6.6 Hz, 1H), 2.03 (ddd, J=14.0, 6.9, 5.0 Hz, 1H), Step B

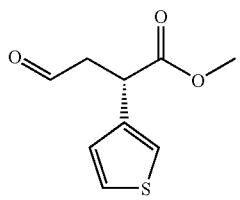

The acetal, synthesis of which was described under Step A (210 mg, 0.860 mmol), was dissolved in trifluoroacetic acid, and after 3 minutes diluted with ether. The organic solution was washed with water (1×30 mL), saturated aqueous solution of sodium bicarbonate (3×20 mL), water (1×30 mL) and brine (1×30 mL). The solvent was evaporated to dryness to leave behind 171.6 mg (100%) of the aldehyde, pure enough to be used in next reaction step. $^1$H NMR (CDCl$_3$, 500 MHz): 9.80 (s, 1H), 7.32 (dd, J=5.1, 3.2 Hz, 1H), 7.14 (m, 1H), 7.04 (dd, J=5.1, 1.1 Hz, 1H), 4.30 (dd, J=11.0, 6.2 Hz, 1H), 3.72 (s, 3H), 3.4 and 2.8 (Abq, J=5.5, 3 Hz, 2H), Step C

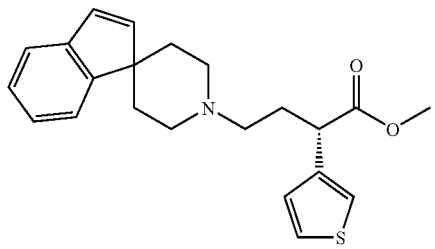

A dichloroethane (10 mL) solution containing the aldehyde from previous step (530 mg, 2.67 mmol), 4-spiroindenylpiperidine hydrochloride (475 mg, 2.14 mmol), diisopropylethylamine (390 µL, 2.20 mmol) was treated with sodium triacetoxyborohydride (2.27 g, 10.7 mmol) and stirred at room temperature overnight. The reaction was quenched by pouring onto saturated aqueous solution of sodium bicarbonate (20 mL), and extracted with dichloromethane (4×50 mL). The combined extracts were washed with brine (1×30 mL), and the solvent was evaporated under reduced pressure to leave 711 mg (90%) of the desired product. It was used in the subsequent step without any additional purification.

Step D

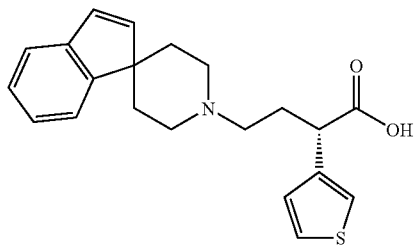

The amine-ester intermediate, synthesis of which was described in previous step (710 mg, 1.89 mmol) was dissolved in dioxane (6 mL), treated with HCl (2N, 2.0 mL) and heated to 80° C. until all starting material has disappeared, about 3 hrs. The reaction mixture was evaporated to dryness, the residual crude product was triturated with acetone/ether mixture to leave 705 mg (96%) in a form of an off white solid.

EXAMPLE 34

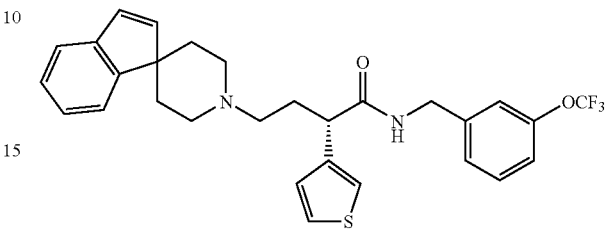

The solution of the acid Intermediate 25 (15.4 mg, 0.0395 mmol) and 3-trifluoromethoxybenzylamine (8.2 mg, 0.043 mmol) in dichloromethane (2 mL) was treated with 1-hydroxy-7-azabenzotriazole (5.4 mg, 0.040 mmol), diisopropylethylamine (7 µL, 0.04 mmol) and 1-[3-(dimethylamino)propyl]-3-ethylcarbodiimide hydrochloride (EDC, 15 mg, 0.08 mmol) and stirred at room temperature for 2 hr. The reaction mixture was poured onto water (5 mL), extracted with dichloromethane (3×2.5 mL). The combined organic extracts were washed with brine (1×2.5 mL), dried with anhydrous magnesium sulfate and the solvent was evaporated to dryness under reduced pressure. Preparative TLC using ethyl acetate gave 12 mg, 54%, two of pure product. MS: for C$_{29}$H$_{29}$F$_3$N$_2$O$_2$S [M+H]$^+$ calculated: 526.19, found 527.40.

EXAMPLE 35

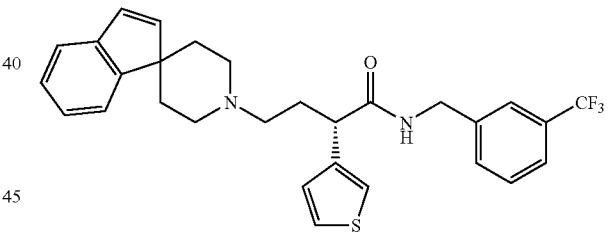

Example 35 was prepared in a similar manner to Example 34, substituting 3-trifluoromethylbenzylamine for 3-trifluoromethoxybenzylamine. MS: for C$_{29}$H$_{29}$F$_3$N$_2$OS [M+H]$^+$ calculated: 511.20, found 511.4.

EXAMPLE 36

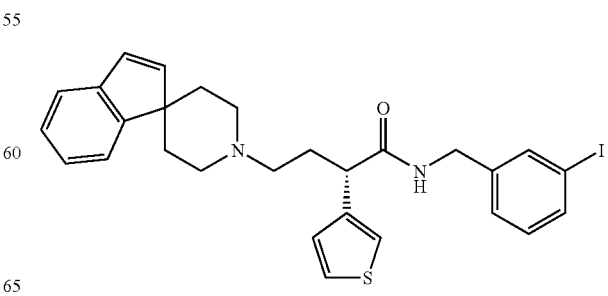

Example 36 was prepared in a similar manner to Example 34, substituting 3-iodobenzylamine for 3-trifluoromethoxybenzylamine. MS: for $C_{28}H_{29}IN_2S$ $[M+H]^+$ calculated: 569.10, found 569.3.

EXAMPLE 37

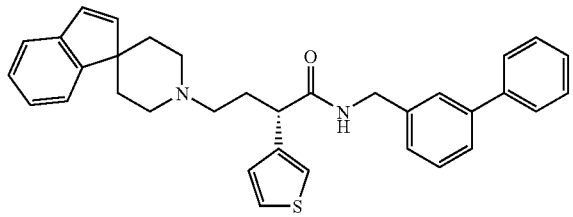

Example 37 was prepared in a similar manner to Example 34, substituting 3-phenylbenzylamine for 3-trifluoromethoxybenzylamine. MS: for $C_{34}H_{34}N_2OS$ $[M+H]^+$ calculated: 519.24, found 519.50.

EXAMPLE 38

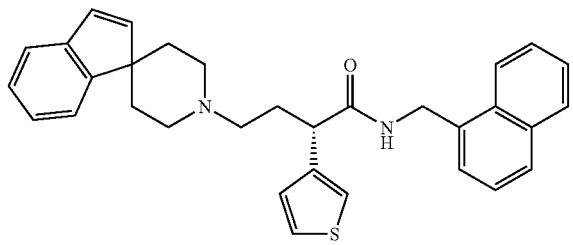

Example 38 was prepared in a similar manner to Example 34, substituting 1-aminomethylnaphthalene for 3-trifluoromethoxybenzylamine. MS: for $C_{32}H_{32}N_2OS$ $[M+H]^+$ calculated: 493.22, found 493.50.

EXAMPLE 39

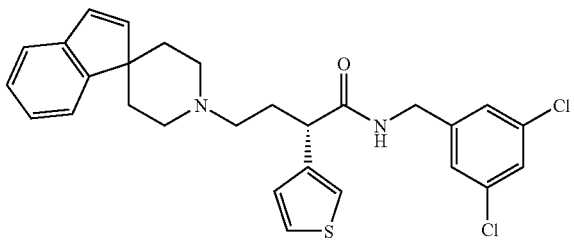

Example 39 was prepared in a similar manner to Example 34, substituting 3,5-dichlorobenzylamine for 3-trifluoromethoxybenzylamine. MS: for $C_{28}H_{28}Cl_2N_2OS$ $[M+H]^+$ calculated: 511.13, found 511.3.

EXAMPLE 40

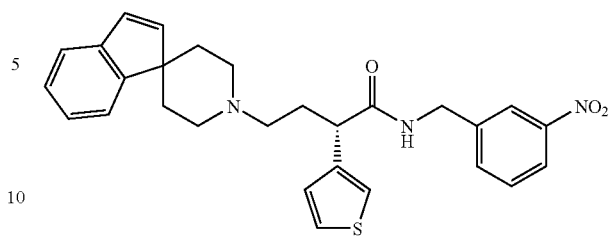

Example 40 was prepared in a similar manner to Example 34, substituting 3-nitrobenzylamine for 3-trifluoromethoxybenzylamine. MS: for $C_{29}H_{29}N_3O_3S$ $[M+H]^+$ calculated: 488.19, found 488.3.

EXAMPLE 41

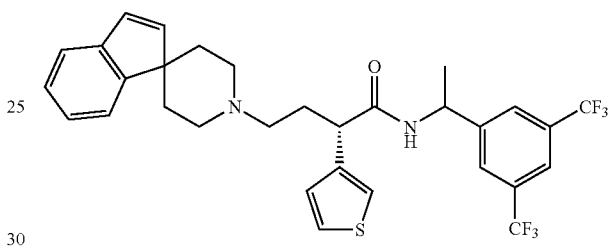

Example 41 was prepared in a similar manner to Example 34, substituting 3,5-bistrifluoromethyl-α-methylbenzylamine for 3-trifluoromethoxybenzylamine. MS: for $C_{31}H_{30}N_2OSF_6$ $[M+H]^+$ calculated: 593.20, found 593.4.

EXAMPLE 42

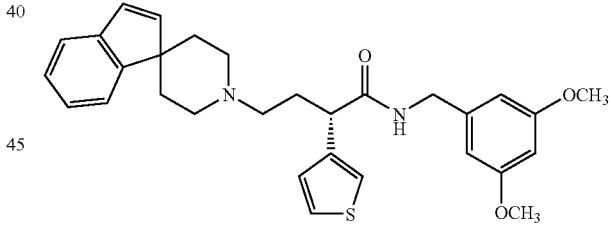

Example 42 was prepared in a similar manner to Example 34, substituting 3,5-dimethoxybenzylamine for 3-trifluoromethoxybenzylamine. MS: for $C_{30}H_{34}N_2O_3S$ $[M+H]^+$ calculated: 503.23, found 503.5.

EXAMPLE 43

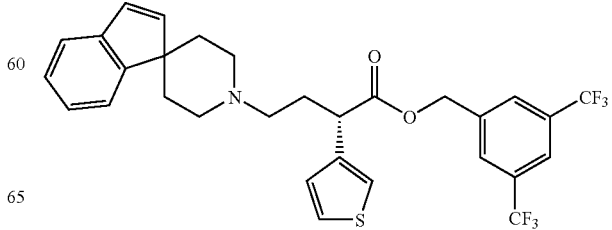

Example 43 was prepared in a similar manner to Example 34, substituting 3,5-bistrifluoromethylbenzylalcohol for 3-trifluoromethoxybenzylamine. MS: for $C_{30}H_{27}NO_2SF_6$ [M+H]$^+$ calculated: 580.17, found 580.4.

EXAMPLE 44

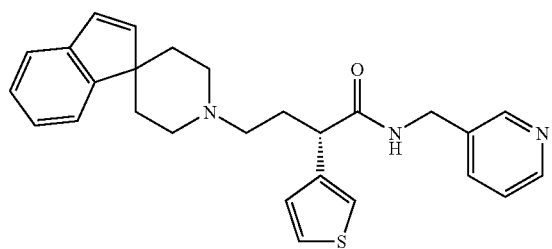

Example 44 was prepared in a similar manner to Example 34, substituting 3-aminomethylpyridine for 3-trifluoromethoxybenzylamine. MS: for $C_{27}H_{29}N_3OS$ [M+]$^+$ calculated: 444.20, found 444.40.

EXAMPLE 45

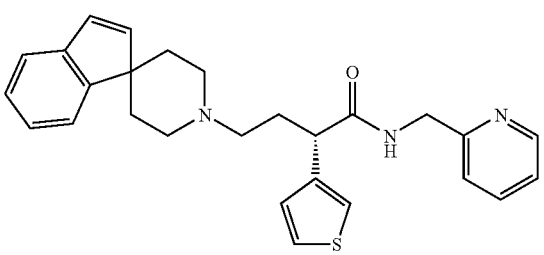

Example 45 was prepared in a similar manner to Example 34, substituting 2-aminomethylpyridine for 3-trifluoromethoxybenzylamine. MS: for $C_{27}H_{29}N_3OS$ [M+H]$^+$ calculated: 444.20, found 444.40.

Intermediate 26

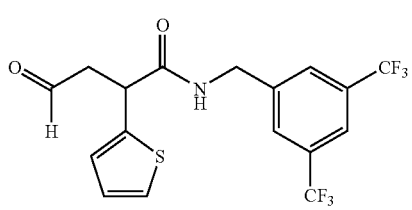

Step A

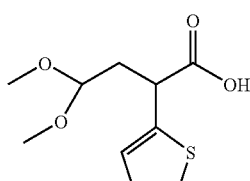

Starting form 2-thienylacetic acid (1.437 g, 10.1 mmol) and 3,3-dimethoxyethylbromide (2.63 mL, 22.2 mmol), the desired acid was synthesized under analogous conditions as described for Intermediate 22, Step A. The crude acid (2.0212 g, 87%) could be further purified by recrystallization from a mixture of diethyl ether and hexane (1:1).

Step B

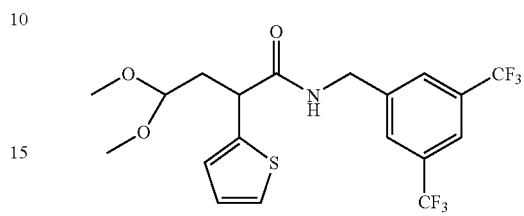

The desired amide was synthesized starting from 230 mg (1.00 mmol) of intermediate acid from Step A and 280 mg (1.00 mmol) of 3,5-bistrifluoromethylbenzylamine hydrochloride in a procedure analogous to that described for preparation of the corresponding isomeric amide under Intermediate 22, Step B in 74% yield. $^1$H NMR (CDCl$_3$, 500 MHz): 7.76 (s, 1H), 7.71 (s, 2H), 7.29 (dd, J=5.3, 1.1 Hz, 1H), 7.00 (m, 2H), 6.41 (t, J=6.0 Hz, 1H), 4.53 (d, J=6.0 Hz, 1H), 4.30 (t, J=5.0 Hz, 1H), 3.29 (s, 3H), 3.28 (s, 3H), 2.47 (m, 1H).

Step C

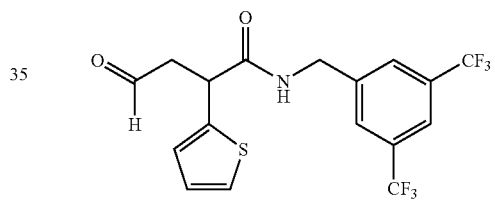

The acetal (160 mg, 0.3513 mmol), synthesis of which was described in previous step, was dissolved in trifluoroacetic acid (2 mL), and briefly stirred (<5 minutes) at room temperature. The reaction mixture was diluted with diethyl ether, washed with water, saturated solution of sodium bicarbonate, water, and brine. After drying with anhydrous magnesium sulfate, the solvent was evaporated to dryness, and the unstable aldehyde (112 mg) was used in the subsequent step immediately.

EXAMPLE 46

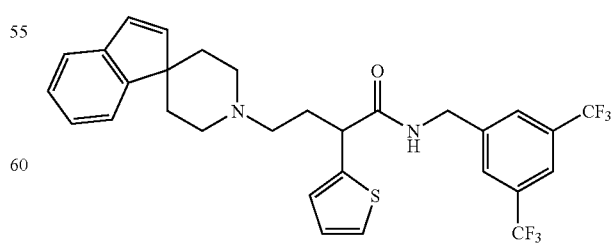

Starting from Intermediate 26 (110 mg, 0.268 mmol) and 4-spiroindenylpiperidine hydrochloride (78 mg, 0.351 mmol) the target compound was synthesized in a procedure similar to that described for the respective isomeric Example 30 in 13% yield. $^1$H NMR (CDCl$_3$, 500 MHz): 7.95 (s, 2H), 7.80 (s, 1H), 7.30 (m, 5H), 7.0 (m, 2H), 6.78 (m, 2H), 5.15 (d, J=7.32 Hz, 1H), 4.86 and 4.68 (ABq, J=14.9 Hz, 2H), 3.0 (dd, J=14.9 Hz, 7.6 Hz, 1H), 2.7–2.2 (m, 10H), 1.25 (m, 2H).

EXAMPLE 47

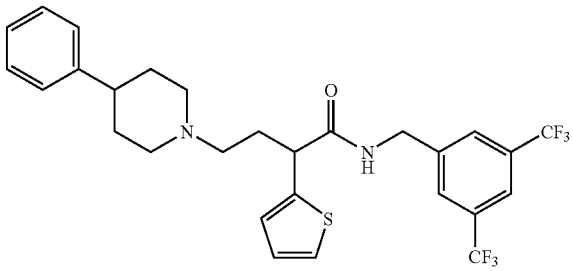

Example 47 was prepared in a similar manner to Example 46, substituting 4-phenylpiperidine hydrochloride for and 4-spiroindenylpiperidine hydrochloride. $^1$H NMR (CDCl$_3$): 7.95 (s, 2H), 7.80 (s, 1H), 7.32 (m, 2H), 7.23 (m, 3H), 6.98 (m, 2H), 5.12 (d, J=7.3 Hz, 1H), 4.82 and 4.64 (ABq, J=14.9 Hz, 2H), 3.36 (bd, J=10.5 Hz, 1H), 2.96 (dd, J=14.9, 7.8 Hz, 1H), 2.66–2.32 (bm, 7H), 2.05–1.68 (bm, 7H).

Intermediate 27

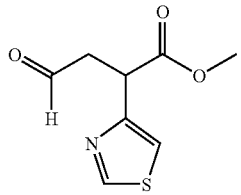

Step A

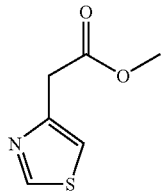

A solution of methyl 4-chloroacetoacetate (93 g, 0.62 mol) and thioformamide (25 g, 0.41 mol, prepared according to the published procedure of Erlenmeyer, Munzi, Hel.Chim.Acta, 31, 2071, (1948)) in ethyl alcohol (100 mL). Upon submerging the reaction vessel into a 90° C. preheated oil bath an exothermic reaction sets in at about 60° C. After the reaction subsided, a gentle reflux was maintained for another 20 minutes. The formed solid was filtered off, and the filtrate was evaporated to dryness. The residue was dissolved in 2N HCl (200 mL) and washed with diethyl ether (200 mL). The pH of the aqueous solution was set to basic (saturated solution of sodium bicarbonate), and the crude product was extracted into diethyl ether (4×100 mL). The combined organic extracts were dried (anhydrous sodium sulfate), and the solvent was removed in vacuo. The oily residue was purified by distillation, (b.p.: 84–88° C./0.5 mmHg) to yield 22.8 g (24%) of pure product. MS: for C$_6$H$_7$NO$_2$S [M+H]$^+$ calculated: 158.02, found 158.4.

Step B

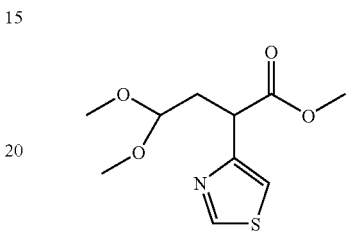

A suspension of sodium hydride (438 mg, 10.9 mmol, 60%) in DMF (10 mL) was cooled to 0° C. and with stirring, a solution of the methyl ester from previous step (1.563 g, 9.941 mmol) in DMF (10 mL) was added via syringe. The anion was allowed to form for 30 minutes at 0° C., whereupon the neat 2,2-dimethoxyethyl bromide was added, via syringe. The cooling bath was removed, and the reaction mixture was stirred at room temperature 24 hrs. It was the diluted with diethyl ether and washed with water. The organic phase was dried, and the solvent was removed in vacuo. The remaining oil was further purified by flash chromatography chromatography (Lobar, Lichroprep Si60, 40–63 μm) using ethyl acetate/hexane (6:4) eluent to give 670 mg (28%) of the desired product. $^1$H NMR (CDCl$_3$): 8.78 (d, J=2.0 Hz, 1H), 7.21 (d, J=1.8 Hz, 1H), 4.33 (dd, J=6.4, 5.3 Hz, 1H), 4.12 (dd, J=8.0, 6.6 Hz, 1H), 3.71 (s, 3H), 3.33 (s, 3H), 3.05 (s, 3H), 2.50 (ddd, J=14.2, 8.2, 6.4 Hz, 2H), 2.24 (ddd, 14.0, 7.0, 5.0 Hz, 2H).

Step C

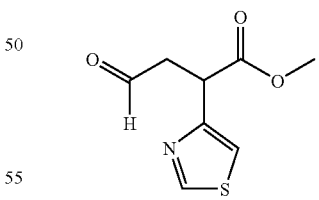

The acetal from the previous step (670 mg, 2.73 mmol) was dissolved in 90% trifluoroacetic acid (6.0 mL) and stirred briefly (<5 minutes) at room temperature. The reaction mixture was diluted with diethyl ether and washed with saturated solution of sodium bicarbonate. After drying (anhydrous magnesium sulfate) and evaporation of the solvent in vacuo 423 mg (78%) of the pure aldehyde was obtained. $^1$H NMR (CDCl$_3$): 9.80 (s, 1H), 8.78 (s, 1H), 7.22 (s, 1H), 4.48 (dd, J=8.5, 5.5 Hz, 1H), 3.73 (s, 3H), 3.43 (dd, J=18.5, 8.5 Hz, 1H), 3.03 (dd, J=18.5, 5.5, 1H).

Intermediate 28

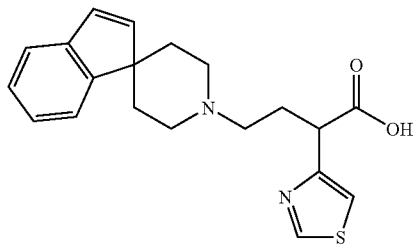

Step A

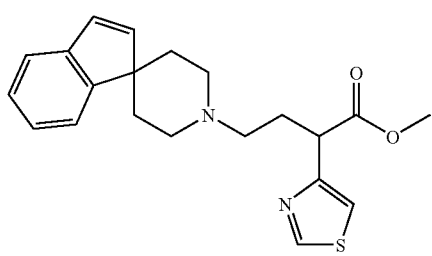

The solution of Intermediate 27 (210 mg, 1.05 mmol) and 4-spiroindenylpiperidine hydrochloride (222 mg, 1.00 mmol) in dichloroethane (15 mL) was treated with diisopropylethylamine (130 mg, 1 mmol) followed by sodium triacetoxyborohydride (1.06 g, 5.0 mmol) and stirred at ambient temperature for 2 hours. The reaction was quenched with saturated solution of sodium bicarbonate, back-washed with dichloromethane. The combined organic extracts were dried (anhydrous sodium sulfate) and evaporated to dryness. MS: for $C_{21}H_{24}N_2O_2S$ [M+H]$^+$ calculated: 369.16, found 369.0.

Step B

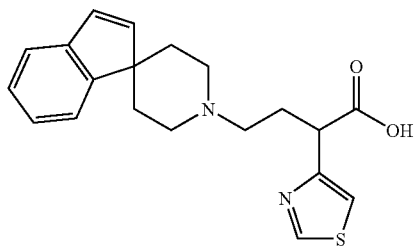

A solution of the ester from previous step (299 mg, 0.811 mmol) was dissolved in dioxane (4 mL) and aq. Solution of lithium hydroxide was added (1N, 2 mL). Stirring at room temperature was continued for 1 hr, the pH was adjusted to acidic (2N HCl) and the reaction mixture was evaporated to dryness. It was used in the next reaction step without any further purification. MS: for $C_{20}H_{22}N_2O_2S$ [M+H]$^+$ calculated: 355.14, found 355.2.

EXAMPLE 48

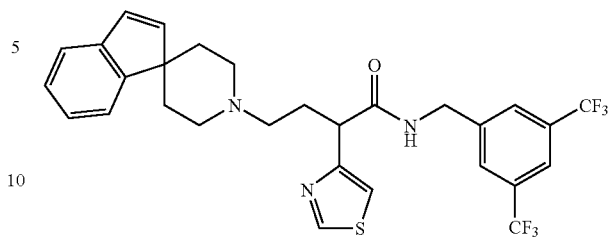

Example 48 was prepared in a similar manner to Example 34, substituting Intermediate 25 with Intermediate 28 and 3-trifluoromethoxybenzylamine with 3,5-bistrifluoromethylbenzylamine. $^1$H NMR (CDCl$_3$): 8.84 (d, J=1.8 Hz, 1H), 7.87 (t, 5.5 Hz, 1H), 7.76 (s, 1H), 7.70 (s, 2H), 7.30 (m, 5H), 6.82 (d, J=5.7 Hz, 1H), 6.76 (d, J=5.7 Hz, 1H), 4.60 (m, 3H), 4.10 (m, 1H), 3.50 (s, 1H), 3.0 (t, 2.12 Hz, 2H), 2.55 to 2.10 (bm, 8H), 1.35 (bs, 2H).

Intermediate 29

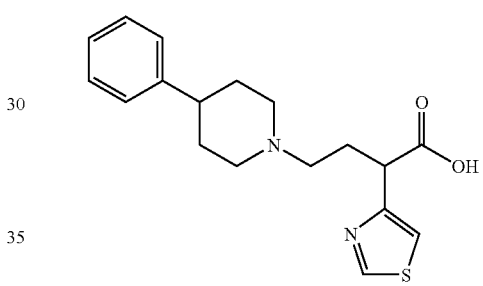

Intermediate 29 was prepared starting from 4-fluoropiperidine and Intermediate 27 as described for preparation of Intermediate 28. MS: for $C_{18}H_{22}N_2O_2S$ [M+H]$^+$ calculated: 331.14, found 331.2.

EXAMPLE 49

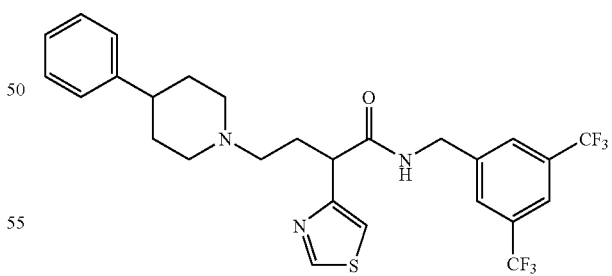

Example 49 was prepared in a similar manner to Example 34, substituting Intermediate 25 with Intermediate 29 and 3-trifluoromethoxybenzylamine with 3,5-bistrifluoromethylbenzylamine. $^1$H NMR (CDCl$_3$): 8.84 (8.82 (d, J=2.1 Hz, 1H), 7.94 (t, J=5.7 Hz, 1H), 7.76 (s, 1H), 7.70 (s, 2H), 7.32 to 7.18 (m, 6H), 4.60 (m, 2H), 3.05 (d, J=11.2 Hz, 1H), 3.00 (d, J=11.2 Hz, 1H), 2.55 to 2.35 (bm, 4H), 2.25 to 2.05 (bm, 4H), 1.88 to 1.70 (bm, 4H).

Intermediate 30

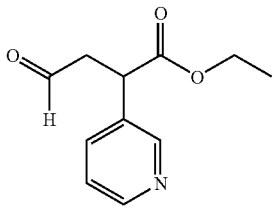

Step A

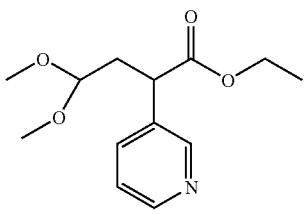

To a suspension of sodium hydride (1.446 g, 36.15 mmol, 60%) in DMF (30 mL) was added at 0° C. ethyl 3-pyridylacetate and stirred at this temperature for 1 hrs, and another 30 minutes at room temperature. The solution was re-cooled to 0° C. and neat 2,2-dimethoxy-bromoethane (5.05 mL, 47 mmol) was added via syringe. The cooling bath was removed and the reaction mixture was stirred at room temperature overnight. It was diluted with diethyl ether (200 mL) and washed with water (2×50 mL). The organic phase was dried (anhydrous magnesium sulfate), and the solvent was removed on Rotavap. The remaining oil was purified by vacuum distillation (b.p.: 138–140° C./0.1 mmHg) to yield 6.58 g (79%) of the desired product. $^1$H NMR (CDCl$_3$): 8.55 (bd, J=3.2 Hz, 1H), 7.68, (bd, J=8.0 Hz, 1H), 7.27 (m, 1H), 4.25 (bt, 5.5 Hz, 1H), 4,12 (m, 2H), 3.74 (t, J=7.3 Hz, 1H), 3.32 (s, 3H), 3.28 (s, 3H), 2.4 (m, 1H), 1.99 (ddd, J=14.0, 6.9, 5.3 Hz, 1H), 1.21 (t, J=7.1 Hz, 3H).

Step B

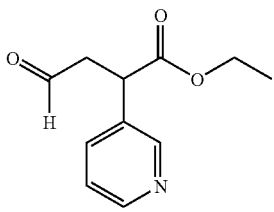

The acetal intermediate from previous step (518 mg, 2.045 mmol) was dissolved in TFA (5 mL) and stirred at room temperature briefly. The reaction mixture was diluted with diethyl ether and washed with saturated solution of sodium bicarbonate. The aqueous phases were combined and back washed with chloroform (3×50 mL). The combined organic extracts were dried with anhydrous magnesium sulfate and the solvent was removed in vacuo. The remaining oil was pure enough to perform the subsequent step without any additional purification. $^1$H NMR (CDCl$_3$): 9.74 (s, 1H), 8.51 (m, 2H), 7.59 (dt, J=8.0, 2.0 Hz, 1H), 7.24 (dd, J=8.0, 4.8 Hz, 1H), 4.11 (m, 3H), 3.38 (dd, J=18.8, 9.6 Hz, 1H), 2.80 (dd, J=18.5, 5.0 Hz, 1H), 1.16 (t, J=7.32 Hz, 3H).

Intermediate 31

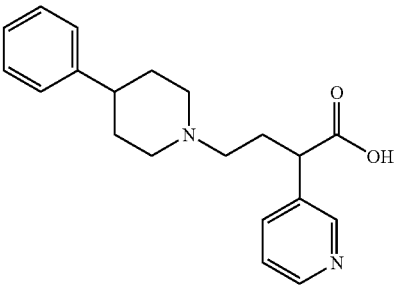

Step A

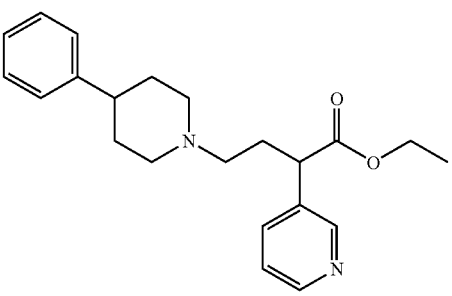

Intermediate 31 was prepared starting from Intermediate 30 and 4-phenylpiperidine using an analogous procedure as described for the preparation of Intermediate 28, Step A. MS: for $C_{22}H_{28}N_2O_2$ [M+H]$^+$ calculated: 353.22, found 353.0.

Step B

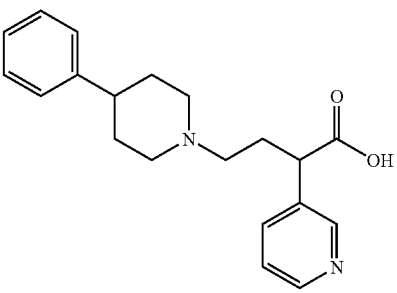

A solution of the ester from previous step (204 mg, 0.5992 mmol) was dissolved in 10 mL of dioxane and aqueous solution of lithium hydroxide (1.0 M, 2.0 mL) was added. The reaction mixture was stirred at room temperature until HPLC indicated complete hydrolysis (about 90 minutes). The pH was set acidic (2N HCl) and the entire reaction mixture was evaporated to dryness. It was used in the amide forming step without additional purification. MS: for $C_{20}H_{24}N_2O_2$ [M+H]$^+$ calculated: 325.18, found 325.2.

EXAMPLE 50

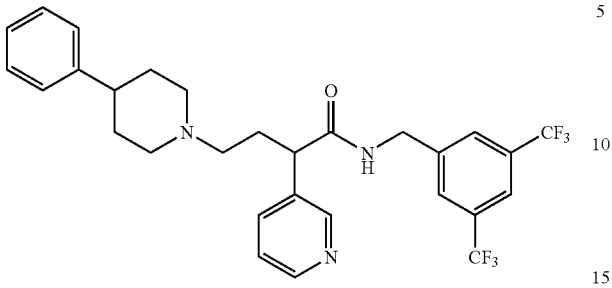

Example 50 was synthesized starting from acid Intermediate 31 and 3,5-bistrifluoromethylbenzylamine according to a procedure described for preparation of Example 34. MS: for $C_{29}H_{29}N_3OF_6$ [M+H]$^+$ calculated: 550.22, found 550.4.

Intermediate 32

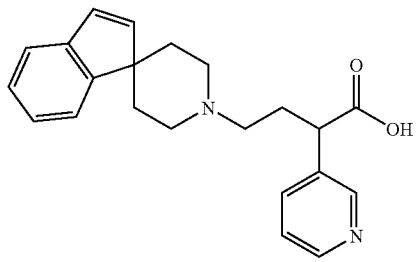

Intermediate 32 was prepared according to Step A and B described for Intermediate 31, except that 4-phenylpiperidine was replaced with 4-spiroindenylpiperidine in Step A. Both ester and the acid gave satisfactory MS results.

EXAMPLE 51

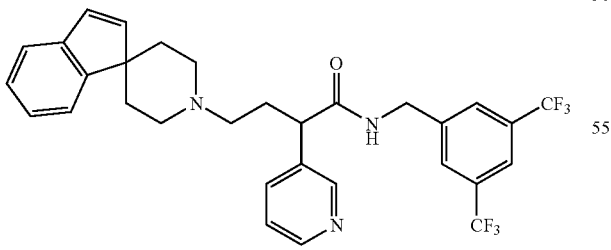

Example 51 was synthesized starting from acid Intermediate 32 and 3,5-bistrifluoromethylbenzylamine according to a procedure described for preparation of Example 34. MS: for $C_{31}H_{29}N_3OF_6$ [M+H]$^+$ calculated: 574.22, found 574.3.

Intermediate 33

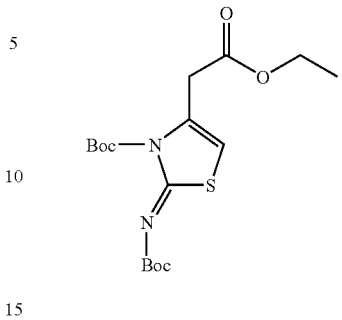

Ethyl(2-tert-butoxycarbonylimino-3-tert-butoxycarbonylthiazol-4-yl)acetate

A mixture of 186 g (1.00 mol) ethyl (2-aminothiazol-4-yl)acetate and 436 g (2.00 mol) di-tert-butyl dicarbonate in 500 mL of DMSO was stirred at RT until the entire mixture solidified (~5 days). The reaction mixture is transferred into a stirred mixture (1L) of ice-water in a 2 liter beak. The precipitate was filtered, washed with water (3 times), dissolved in 1500 mL of CH2Cl2. The organic layer was washed with water (3 times), dried over Na2SO4 and filtered. The filtrates were condensed to ~500 mL of volume. To the above mixture was added 1000 mL of hexane. The resulting crystals were collected by filtration and washing with hexane and drying in vacuo. The title compound was obtained as light-yellow solid (278 g, 72% yield). $^1$H NMR (300 MHz, CDCl$_3$): δ 1.23 (t, 3H), 1.50 (s, 9H), 1.58 (s, 9H), 3.70 (s, 2H), 4.13 (q, 2H), 6.23 (s, 1H). Mass Spectrum (NH$_3$—Cl): m/z 387 (M+1).

Intermediate 34

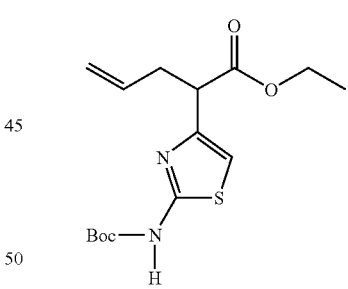

Ethyl 2-(2-tert-butoxycarbonylaminothiazol-yl)-4-pentenoate

A solution of 232 g (600 mmol) of Ethyl(2-tert-butoxycarbonylimino-3-tert-butoxycarbonylthiazol-4-yl) (Intermediate 33) in 1500 mL of THF at −78° C. was treated with 252 mL (630 mmol) of 2.5 M n-butyl lithium in hexane for 30 min. To the resulting red solution was added a neat solution of 57 mL (660 mmol) of allyl bromide. The reaction was stirred at −78° C. for 2 h and then warmed to 0° C. and stirred for 0.5 h. The reaction was quenched with 100 g of citric acid in 1000 mL of water. The mixture was stirred overnight, evaporated to remove THF and extracted with CH2Cl2 (2×1000 mL). The combined organic phases were washed with brine and dried over Na2SO4 and concentrtaed in vacuo. Flash chromatography on silica gel (2×500 g) using 1:9 v/v EtOAc/hexanes as the eluant afforded 184 g (94%) of the title compound as an oil. ¹H NMR (300 MHz, CDCl₃): δ 1.19 (m, 3H), 1.50 (s, 9H), 2.60 (m, 1H), 2.68 (m, 1H), 3.90 (t, 1H), 4.12 (m, 2H), 5.08 (m, 2H), 5.28 (m, 1H), 6.68 (s, 1H). Mass Spectrum (NH₃—CI): m/z 327 (M+1).

Intermediate 35

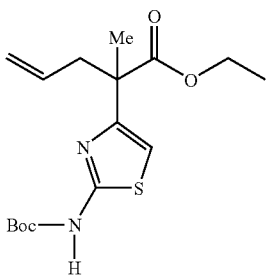

Ethyl 2-(2-tert-butoxycarbonylaminothiazol-yl)-2-methyl-4-pentenoate

A solution of 5.0 g (15 mmol) of Ethyl 2-(2-tert-butoxycarbonylaminothiazol-yl)-4-pentenoate (Intermediate 34) in 100 mL of THF at −78° C. was treated with 25 mL (43 mmol) of 1.7 M t-butyl lithium in hexane for 30 min. To the resulting red solution was added a neat solution of 2.82 g (20 mmol) of iodomethane. The reaction was stirred at −78° C. for 2 h and then warmed to 0° C. and stirred for 0.5 h. The reaction was quenched with 10 g of citric acid in 100 mL of water. The mixture was stirred overnight, evaporated to remove THF and extracted with CH2Cl2 (2×100 mL). The combined organic phases were washed with brine and dried over Na2SO4 and concentrtaed in vacuo. MPLC using 1:9 v/v EtOAc/hexanes as the eluant afforded 0.8 g of the title compound as an oil. ¹H NMR (300 MHz, CDCl₃): δ 1.15–1.22 (m, 3H), 1.42–1.67 (d, 12H), 2.67–2.76 (m, 2H), 4.09–4.17 (m, 2H), 5.00–5.10 (m, 2H), 5.50–5.65 (m, 1H), 6.63 (1, 1H), 7.91 (wide, 1H).

Intermediate 36

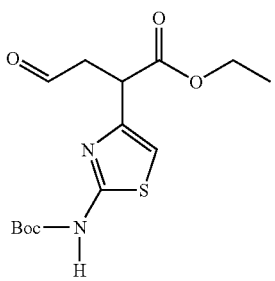

Ethyl 2-(2-tert-butoxycarbonylaminothiazol-4-yl)-3-formylpropanoate

A mixture of 150 g (460 mmol) of ethyl 2-(2-tert-butoxycarbonylaminothiazol-yl)-4-pentenoate (Intermediate 34), 57 g (470 mmol) of N-methyl morpholine oxide and 1.0 g of osmium tetroxide in 1250 mL of 4/1 v/v acetone/water was stirred at RT for 1.5 h. To the mixture was added 100 g of solid sodium bisulfate and continued to stir for 0.5 h. The solid was removed by filtration and washing with acetone. The filtrates were combined and evaporated. The residue was diluted with 1000 mL of water and 2000 mL of ethyl acetate. The organic phase was separated and washed with brine (3×1000 mL), dried over Na2SO4 and condensed in vacuo. The residue was redissolved in 1500 mL of methanol and 1000 mL of water. 148 g of sodium periodate was added. The mixture was stirred for one hour, The solid was discarded by filtration and washing with methanol. The filtrates were condensed in vacuo and the reside was dissolved in 1000 mL of ethyl acetate. The organic layer was washed with brine (2×1000 mL), dried over Na2SO4 and evaporated until the solid formed. 1000 mL of hexane was added and the flask was allowed to stand at RT to let crystallization proceed. The solid was collected by filtration and washing with hexane and drying in vacuo. 79 g of the title compound was obtained as white solid. The mother liquid was condensed and the residue was suspended in hexane. A second crop of solid (24 g) was obtained as a yellow solid. The mother liquid was condensed again to afford a brown solid (22 g) which contained impurity.

¹H NMR (300 MHz, CDCl₃): δ 1.21 (t, 3H), 1.53 (s, 9H), 2.95 (q, 2H), 3.12 (m, 1H), 4.16 (m, 3H), 4.26 (m, 1H), 6.66 (s, 1H), 8.78 (broad, 1H), 9.72 (s, 1H). Mass Spectrum (NH₃—CI): m/z 329 (M+1).

Intermediate 37

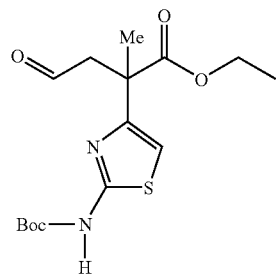

Ethyl 2-(2-tert-butoxycarbonylaminothiazol-4-yl)-2-methyl-4-formylpropanoate

A mixture of 0.60 g (2.0 mmol) of Ethyl 2-(2-tert-butoxycarbonylaminothiazol-yl)-2-methyl-4-pentenoate (Intermediate 35), 0.22 g (2.0 mmol) of N-methyl morpholine oxide and 20 mg of osmium tetroxide in 25 mL of 4/1 v/v acetone/water was stirred at RT for 1.5 h. To the mixture was added 1.0 g of solid sodium bisulfate and continued to stir for 0.5 h. The solid was removed by filtration and washing with acetone. The filtrates were combined and evaporated. The residue was diluted with 20 mL of water and 40 mL of ethyl acetate. The organic phase was separated and washed with brine (3×20 mL), dried over Na2SO4 and condensed in vacuo. The residue was redissolved in 20 mL of methanol and 20 mL of water. 0.64 g of sodium periodate was added. The mixture was stirred for one hour, The solid was discarded by filtration and washing with methanol. The filtrates were condensed in vacuo and the residue was dissolved in 100 mL of ethyl acetate. The organic layer was washed with brine (2×100 mL), dried over Na2SO4 and evaporated to afford the title compound as a light yellow oil. $^1$H NMR (300 MHz, CDCl$_3$): δ δ 1.15–1.22 (m, 3H), 1.42–1.46 (s, 9H), 1.60 (s, 3H), 2.45–2.52 (m, 2H), 4.10–4.20 (m, 2H), 6.50 (s, 1H), 9.65 (s, 1H).

Intermediate 38

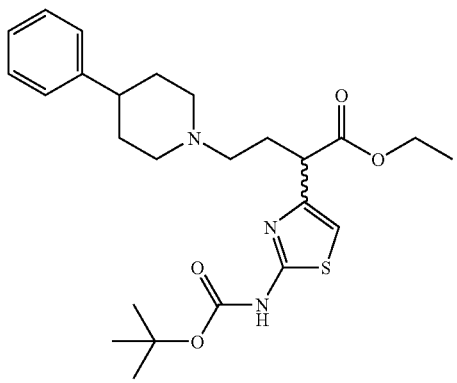

Ethyl 2-(2-tert-butoxycarbonylamino-thiazol-4-yl)-4-(phenyl-4'-piperidine)butanoate A mixture of 3.42 g (10 mmol) of ethyl 2-(2-tert-butoxycarbonylaminothiazolyl)-3-formylpropanoate (Intermediate 36), 1.61 g (10 mmol) of phenylpiperidine hydrochloride, 2.6 g (20 mmol) of DIEA and 4.22 g (20 mmol) of sodium triacetoxyborohydride in 20 mL of CH2Cl2 at RT was stirred for 0.5 h. The reaction mixture was diluted with 50 mL of CH2Cl2 and washed with water (3×100 mL). The organic phase was dried over Na2SO4 and concentrated in vacuo. 4.55 g (96%) of the title compound was obtained as a gummy material. $^1$H NMR (300 MHz, CDCl$_3$): δ 1.21 (t, 3H), 1.53 (s, 9H), 1.70–1.90 (m, 4H), 1.95–2.15 (m, 3H), 2.20–2.55 (m, 4H), 3.00–3.10 (m, 2H), 3.77 (t, 1H), 4.10–4.20 (m, 2H), 6.69 (s, 1H), 7.18–7.35 (m, 5H). Mass Spectrum (NH$_3$—CI): m/z 474 (M+1).

Intermediate 39

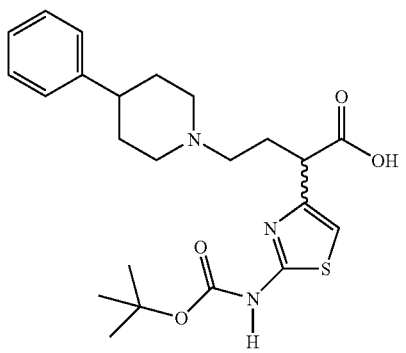

2-(2-tert-butoxycarbonylamino-thiazol-4-yl)-4-(phenyl-4'-piperidine)butanoic acid A mixture of 3.0 g (6.3 mmol) of ethyl 2-(2-tert-butoxycarbonylamino-thiazol-4-yl)-4-(phenyl-4'-piperidine)butanoate (Intermediate 38) and 0.53 g (12.6 mmol) of lithium hydroxide monohydrate in a solution of 60 mL of THF and 20 mL of water was heated at 60° C. for 2 h. The entire mixture was poured onto a silica gel column (50 g) and eluted out with 1/4 v/v MeOH/CH2Cl2. Evaporation in vacuo afforded a light yellow solid. The solid was further dissolved in 50 mL of toluene and evaporated in vacuo. 2.5 g of the title product was obtained as a fluffy solid. Mass Spectrum (NH$_3$—CI): m/z 446 (M+1).

Table 10 shows a number of Intermediates that were prepared in the same fashion as described for Intermediates 38 and 39.

TABLE 10

Intermediates 38a-k and 39a-k

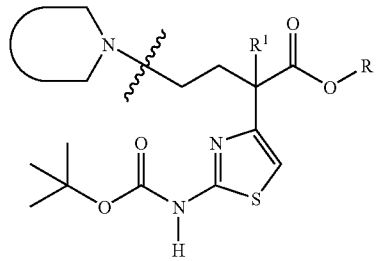

| Intermediate | Amine | R1 | 38 (M + 1) R = Et | 39 (M + 1) R = H |
|---|---|---|---|---|
| A | 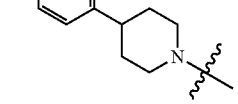 | H | 492 | 464 |
| B | 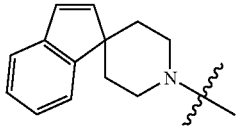 | H | 498 | 470 |
| C | 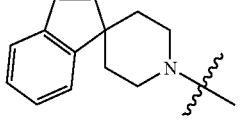 | Me | 512 | 484 |
| D | 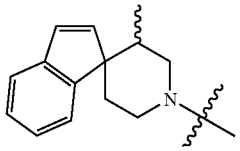 | H | 512 | 484 |
| E | 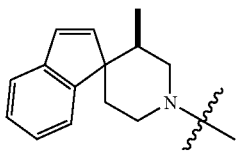 | H | 512 | 484 |

TABLE 10-continued

Intermediates 38a-k and 39a-k

| Intermediate | Amine | R1 | 38 (M + 1) R = Et | 39 (M + 1) R = H |
|---|---|---|---|---|
| F | (indane-spiro-piperidine) | H | 512 | 484 |
| G | (piperidine) | H | 398 | 370 |
| H | (morpholine) | H | 400 | 372 |
| I | (4-fluorophenyl-piperazine) | H | 493 | 465 |
| J | (phenyl-piperazine) | H | 489 | 462 |
| k | (o-tolyl-piperazine) | H | 489 | 462 |

Intermediate 40

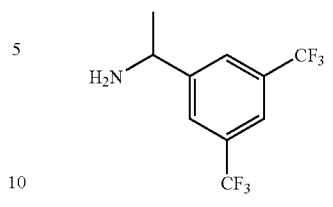

Step A: Bis-(trifluoromethyl)phenylethanol

To a solution of bis(trifluoromethyl)benzaldehyde (20 g, 0.0826 mol) in 200 mL of THF at −78° C. was added dropwise a solution of 84 mL of methylmagnesium bromide (1M, 0.084 mol) in butyl ether. The temperature was raised up to RT. The entire mixture was poured into a stirred mixture of ammonium chloride, ice and water (1000 mL), extracted with ethyl acetate (2×1000 mL). The organic phases were dried over NaSO4. Evaporation in vacuo afforded the title compound as a light yellow liquid (20.64 g, 98%).

Step B: N-(Bis[trifluoromethyl]phenylethyl)phthalimide

To a stirred solution of bis-(trifluoromethyl)phenylethanol (20.64 g, 0.08 mol), phthalimide (11.76 g, 0.08 mol) and triphenylphosphine (22.6 g, 0.1 mol) in 150 mL of THF at 0 C was added dropwise a solution of DEAD (17.4 g, 0.1 mol) in 100 mL of THF in 30 min. The mixture was then stirred at RT overnight, condensed in vacuo. Flash chromatography on silica gel (500 g) afforded the title compound as a light yellow solid.

Step C: Bis-(trifluoromethyl)phenylethylamine

A mixture of N-(bis-[trifluoromethyl]phenylethyl)phthalimide (all material, ~0.076 mol) and hydrazine (3.2 g, 0.1 mol) in 500 mL of ethanol was stirred at 80 C for 2 h. The flask was put into refrigerator overnight. The solid was removed by filtration and washing with ethanol. The filtrates were combined and evaporated in vacuo.

Step D: N-Butoxycarbonyl-bis-(trifluoromethyl)phenylethylamine

The above residue (Step C) was stirred with di-tert-butyl dicarbonate (17 g, 0.08 mol) in 200 mL of dioxane for 30 min, evaporated in vacuo. The residue was purified by flash chromatography on silica gel (400 g) using 30% EtOAc/hexanes. The title compound (20.7 g) was obtained as a white solid.

Step E: Bis-(trifluoromethyl)phenylethylamine hydrochloride

N-Butoxycarbonyl-bis-(trifluoromethyl)phenylethylamine (20.7 g) was stirred with a solution of 100 mL of 4M HCl dioxane for 2 h. The mixture was evaporated and dried in vacuo afford the title compound as a white solid (15.6 g).

Intermediate 41

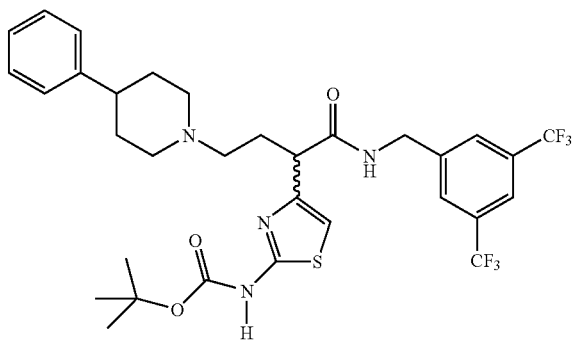

2-(2-tert-butoxycarbonylamino-thiazol-4-yl)-N-(3,5-bis-trifluoromethyl-benzyl)-4-(phenyl-4'-piperidine)-1'-butyramide A mixture of 2.5 g (5.6 mmol) of 2-(2-tert-butoxycarbonylamino-thiazol-4-yl)-4'-(phenyl-4'-piperidine)butanoic acid (intermediate 39) and 1.95 g (7 mmol) of bis-(trifluoromethyl)benzylamine hydrochloride in 50 mL of CH2Cl2 was stirred for 2 h. The reaction mixture was diluted with 100 mL of CH2Cl2 and washed with water (3×100 mL), dried over Na2SO4 and evaporated in vacuo. Flash chromatography on 50 g of silica gel using 1:9 v/v methanol/methylene chloride afforded 2.8 g (75%) of the title compound as a light-yellow solid. $^1$H NMR (300 MHz, CDCl$_3$): δ 1.52 (s, 9H), 1.60–1.80 (m, 4H), 1.90–2.10 (m, 3H), 2.22–2.50 (m, 4H), 2.90–3.10 (m, 2H), 3.75 (b, 1H), 4.50 (m, 2H), 6.70 (s, 1H), 7.14–7.30 (m, 5H), 7.60 (broad, 1H), 7.63 (s, 2H), 7.73 (s, 1H), 8.50 (broad, 1H). Mass Spectrum (NH$_3$—CI): m/z 671 (M+1).

Intermediate 42

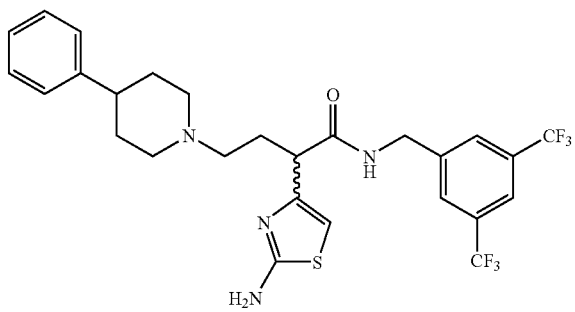

2-(2-Amino-thiazol-4-yl)-N-(3,5-bis-trifluoromethyl-benzyl)-4-(phenyl-4'-piperidine)-1'-butyramide 2.5 g (5.6 mmol) of 2-(2-tert-butoxycarbonylamino-thiazol-4-yl)-N-(3,5-bis-trifluoromethyl-benzyl)-4-(phenyl-4'-piperidine)-1'-butyramide (Intermediate 41) was stirred with 50 mL of 95:5 v/v TFA/H2O for 2 h. TFA was removed by vacuo and the residue was purified on preparative TLC using 1:9 [(1:9 aq. NH4OH/MeOH)/CH2Cl2). 1.70 g (81%) of the title compound was obtained as a yellow solid. $^1$H NMR (300 MHz, CDCl$_3$): δ 1.62–1.95 (m, 3H), 2.00–2.20 (m, 3H), 2.20–2.60 (m, 4H), 2.75–3.10 (m, 3H), 3.70 (t, 1H), 4.55 (m, 2H), 5.35 (s, 2H), 6.32 (s, 1H), 7.18–7.31 (m, 5H), 7.68–7.74 (m, 4H). Mass Spectrum (NH$_3$—CI): m/z 571 (M+1).

Table 11 shows other Intermediates prepared in the same fashion as Intermediates 41 and 42.

TABLE 11

Intermediates 41a–n and 42a–n

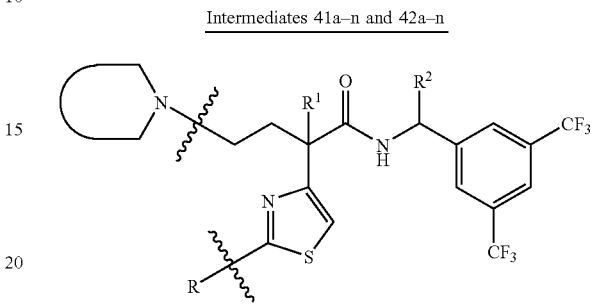

| Intermediate | Amine | R1 | R2 | 41 (M + 1) R = NHBoc | 42 (M + 1) R = NH2 |
|---|---|---|---|---|---|
| A | 4-fluorophenyl-piperidine | H | H | 689 | 589 |
| B | spiro-indene-piperidine | H | H | 695 | 595 |
| C | spiro-indene-piperidine | Me | H | 709 | 609 |
| D | spiro-indene-piperidine | H | Me | 709 | 609 |
| E | spiro-indene-piperidine | H | H | 697 | 597 |
| F | spiro-indene-piperidine | H | H | 709 | 609 |

TABLE 11-continued

Intermediates 41a–n and 42a–n

| Intermediate | Amine | R1 | R2 | 41 (M + 1) R = NHBoc | 42 (M + 1) R = NH2 |
|---|---|---|---|---|---|
| G | (spiro indane piperidine) | H | H | 711 | 611 |
| H | (methyl indane piperidine) | H | H | 709 | 609 |
| I | (methyl indane piperidine, other isomer) | H | H | 709 | 609 |
| J | (piperidine) | H | H | 595 | 495 |
| K | (morpholine) | H | H | 597 | 497 |
| L | (4-fluorophenyl piperazine) | H | H | 690 | 590 |
| M | (phenyl piperazine) | H | H | 686 | 586 |
| N | (2-tolyl piperazine) | H | H | 686 | 586 |

EXAMPLE 52

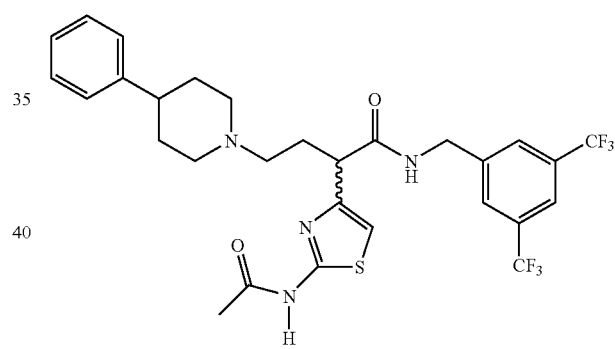

2-(2-Acetylamino-thiazol-4-yl)-N-(3,5-bis-trifluoromethyl-benzyl)-4-(phenyl-4'-piperidine)-1'-butyramide A mixture of 0.571 g (1 mmol) of 2-(2-Amino-thiazol-4-yl)-N-(3,5-bis-trifluoromethyl-benzyl)-4-(phenyl-4'-piperidine)-1'-butyramide (intermediate 42), 0.5 mL of acetic anhydride and 1.0 mL of pyridine in 5 mL of CH2Cl2 was stirred at RT overnight. Excess reagents were removed in vacuo. The residue was purified on preparative TLC using 1:9 [(1:9 aq. NH4OH/MeOH)/CH2Cl2). 0.53 g (87%) of the title compound was obtained as a yellow solid. $^1$H NMR (300 MHz, CDCl$_3$): δ 1.62–1.95 (m, 3H), 2.00–2.20 (m, 3H), 2.20–2.60 (m, 4H), 2.75–3.10 (m, 3H), 3.70 (t, 1H), 4.55 (m, 2H), 5.35 (s, 2H), 6.32 (s, 1H), 7.18–7.31 (m, 5H), 7.68–7.74 (m, 4H). Mass Spectrum (NH$_3$—CI): m/z 613 (M+1).

As shown in Table 12, a number of compounds were prepared in the same fashion as 52 starting from Intermediates 42a–n and the corresponding piperidines, piperazines and morphilines.

TABLE 12

EXAMPLES 52a–n

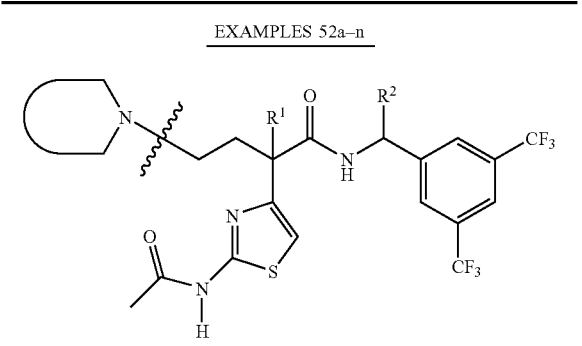

| Example | Amine | R1 | R2 | m/z (M + 1) |
|---|---|---|---|---|
| 52a | 4-F-phenyl-piperidine | H | H | 631 |
| 52b | spiro-indene-piperidine | H | H | 637 |
| 52c | spiro-indene-piperidine | H | Me | 651 |
| 52d | spiro-indene-piperidine | Me | H | 651 |
| 52e | spiro-indane-piperidine | H | H | 639 |
| 52f | spiro-indene-piperidine | H | H | 651 |
| 52g | spiro-indane-piperidine | H | H | 653 |

TABLE 12-continued

EXAMPLES 52a–n

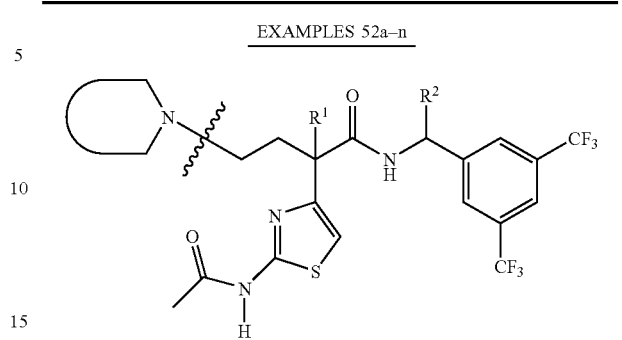

| Example | Amine | R1 | R2 | m/z (M + 1) |
|---|---|---|---|---|
| 52h | methyl-spiro-indene-piperidine | H | H | 651 |
| 52i | methyl-spiro-indene-piperidine | H | H | 651 |
| 52j | piperidine | H | H | 537 |
| 52k | morpholine | H | H | 539 |
| 52l | 4-F-phenyl-piperazine | H | H | 632 |
| 52m | phenyl-methyl-piperazine | H | H | 628 |
| 52n | 2-methyl-phenyl-piperazine | H | H | 628 |

EXAMPLE 52h-(S)

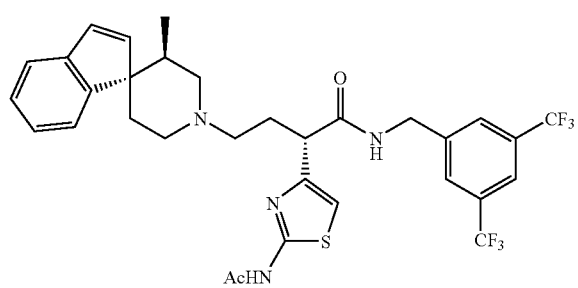

EXAMPLE 52h-(R)

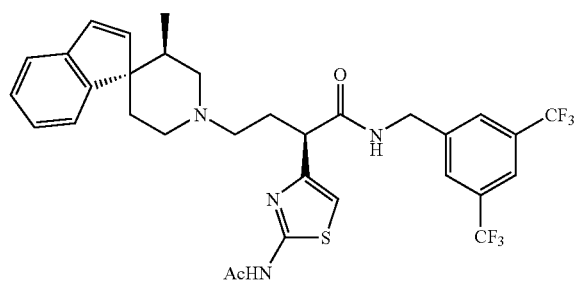

The two diastereomers of 52h which are epimeric α-to the amide carbonyl, could be separated into two pure single isomers using chiral HPLC (ChiralPak OD column, Hexane/Ethanol). Example 52h-(S): fast isomer, more active; Example 52h-(R): slow isomer, less active.

EXAMPLE 53

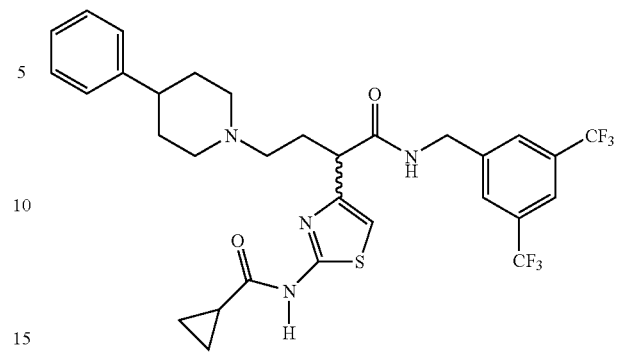

2-(2-cyclopropanecarbonylamino-thiazol-4-yl)-N-(3,5-bis-trifluoromethyl-benzyl)-4-(phenyl-4'piperidine)-1'-butyramide A mixture of 0.571 g (0.1 mmol) of 2-(2-Amino-thiazol-4-yl)-N-(3,5-bis-trifluoromethyl-benzyl)-4-(phenyl-4'-piperidine)-1'-butyramide (Intermediate 42), 0.27 g of cyclopropanecarboxylic acid, 0.57 g of EDAC hydrochloride, a granule of DMAP (cat.) in 5 mL of CH2Cl2 was stirred at RT overnight. Excess reagents were removed in vacuo. The residue was purified on preparative TLC using 1:9 [(1:9 aq. NH4OH/MeOH)/CH2Cl2]. 0.51 g (80%) of the title compound was obtained as a yellow solid. Mass Spectrum (NH3—CI): m/z 639 (M+1).

The examples 54–70 were prepared starting from the corresponding aminothiazole intermediates according to the same procedure as shown for the preparation of Example 53.

TABLE 13

EXAMPLES 54–70

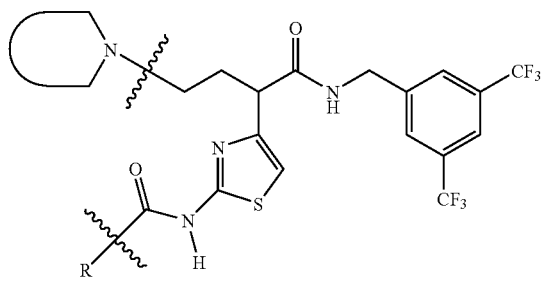

| Example | Amine | R | m/z (M + 1) | Note |
|---|---|---|---|---|
| 54 | ![4-phenylpiperidine] | ![tert-butyl] | 655 | |

TABLE 13-continued

EXAMPLES 54–70

| Example | Amine | R | m/z (M + 1) | Note |
|---------|-------|---|-------------|------|
| 55 | 4-phenylpiperidine | isopropyl | 641 | |
| 56 | 4-phenylpiperidine | ethyl | 627 | |
| 57 | 4-phenylpiperidine | methyl ester propyl | 685 | |
| 58 | 4-phenylpiperidine | carboxylic acid propyl | 671 | From Hydrolysis of Example 57 |
| 59 | 4-phenylpiperidine | 3-chloropropyl | 675/677 | |

TABLE 13-continued

EXAMPLES 54–70

| Example | Amine | R | m/z (M + 1) | Note |
|---|---|---|---|---|
| 60 | 4-phenylpiperidine | Boc-NH-CH(CH3)- | 728 | |
| 61 | 4-phenylpiperidine | H2N-CH(CH3)- | 628 | From TFA Treatment of Example 60 |
| 62 | 4-phenylpiperidine | phenyl | 675 | |
| 63 | methyl-indane-spiro-piperidine | adamantyl | 785 | |
| 64 | methyl-indane-spiro-piperidine | adamantyl-CH2- | 771 | |
| 65 | methyl-indane-spiro-piperidine | tert-butyl-CH(CH3)- | 693 (hold) | |
| 66 | methyl-indane-spiro-piperidine | Ph-(CH2)3- | 755 | |

TABLE 13-continued

EXAMPLES 54–70

| Example | Amine | R | m/z (M + 1) | Note |
|---------|-------|---|-------------|------|
| 67 | (4-methyl spiro[indene-piperidine]) | phenethyl | 741 | |
| 68 | (4-methyl spiro[indene-piperidine]) | benzyl | 727 | |
| 69 | (4-methyl spiro[indene-piperidine]) | phenyl | 713 | |
| 70 | (4-methyl spiro[indene-piperidine]) | cyclohexyl | 719 | |

EXAMPLE 71

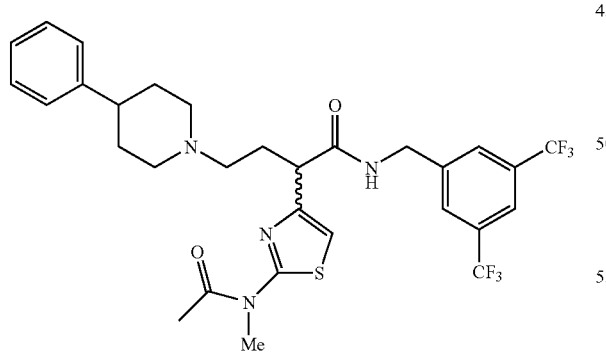

2-(2-Acetylmethylamino-thiazol-4-yl)-N-(3,5-bis-trifluoromethyl-benzyl)-4-(phenyl-4'-piperidine)-1'-butyramide A mixture of 0.061 g (1 mmol) of 2-(2-Acetylamino-thiazol-4-yl)-N-(3,5-bis-trifluoromethyl-benzyl)-4-(phenyl-4'-piperidine)-1'-butyramide (Example 52), 0.5 mL of methanol, 0.52 g of triphenylphosphine and 0.14 g of DEAD in 5 mL of THF was stirred at RT overnight. Excess reagents were removed in vacuo. The residue was purified on preparative TLC using 1:9 [(1:9 aq. NH4OH/MeOH)/CH2Cl2). 0.050 g (82%) of the title compound was obtained as a yellow solid. Mass Spectrum (NH$_3$—Cl): m/z 627 (M+1).

EXAMPLE 72

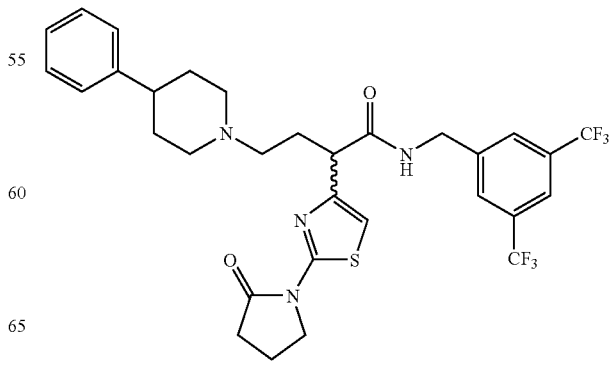

2-(2-[N-Butanoic acid]amino-thiazol-4-yl)-N-(3,5-bis-trifluoromethyl-benzyl)-4-(phenyl-4'-piperidine)-1'-butyramide A mixture of 0.0675 g (0.1 mmol) of 2-(2-[4-Chlorobutanoyl]amino-thiazolyl-4-yl)-N-(3,5-bis-trifluoromethyl-benzyl)-4-(phenyl-4'-piperidine)-1'-butyramide (Example 59), 0.03 g of sodium hydride in 2 mL of DMF was stirred at RT overnight. Excess reagents were removed in vacuo. The residue was purified on preparative TLC using 1:9 [(1:9 aq. NH4OH/MeOH)/CH2Cl2). 0.048 g (71%) of the title compound was obtained as a yellow solid. Mass Spectrum ($NH_3$—CI): m/z 639 (M+1).

EXAMPLE 73

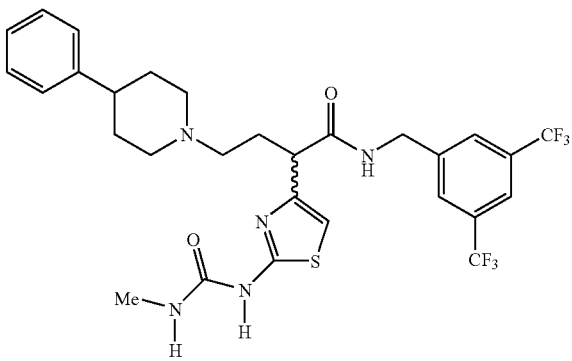

2-(2-methylaminocarbonyl]amino-thiazol-4-yl)-N-(3,5-bis-trifluoromethyl-benzyl)-4-(phenyl-4'-piperidine)-1'-butyramide A mixture of 0.115 g (0.2 mmol) of 2-(2-Amino-thiazol-4-yl)-N-(3,5-bis-trifluoromethyl-benzyl)-4-(phenyl-4'-piperidine)-1'-butyramide (Intermediate 42), 0.03 g of methylisocyanate in 5 mL of CH2Cl2 was heated in a capped vial at 60° C. overnight. Excess reagents were removed in vacuo. The residue was purified on preparative TLC using 1:9 [(1:9 aq. NH4OH/MeOH)/CH2Cl2). 0.082 g (65%) of the title compound was obtained as a white solid. Mass Spectrum ($NH_3$—CI): m/z 628 (M+1).

The Examples 74–79 in Table 14 were prepared according to the same procedure as described for Example 73 starting from the corresponding aminothiazole Intermediates described previously and methylisocyanate.

TABLE 14

EXAMPLES 74–79

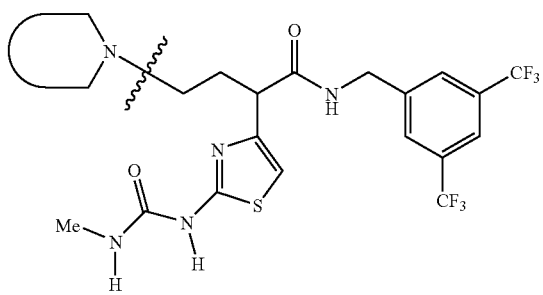

| Example | Amine | (M + 1) | Example | Amine | (M + 1) |
|---|---|---|---|---|---|
| 74 | 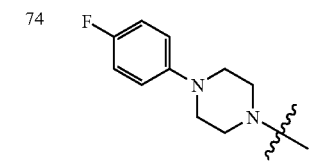 | 646 | 77 | 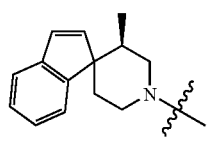 | 666 |
| 75 | 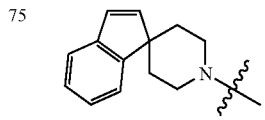 | 637 | 78 | 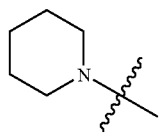 | 552 |

TABLE 14-continued

EXAMPLES 74–79

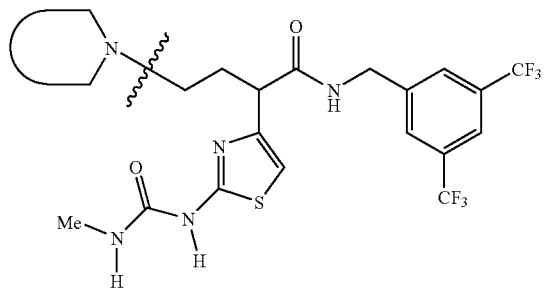

| Example | Amine | (M + 1) | Example | Amine | (M + 1) |
|---|---|---|---|---|---|
| 76 | 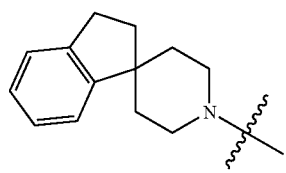 | 654 | 79 | 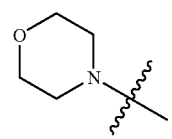 | 554 |

EXAMPLE 80

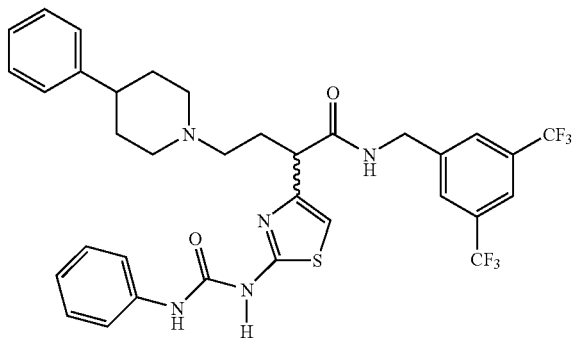

2-(2-[Phenylaminocarbonyl]amino-thiazol-4-yl)-N-(3,5-bis-trifluoromethyl-benzyl)-4-(phenyl-4'-piperidine)-1'-butyramide A mixture of 0.115 g (0.2 mmol) of 2-(2-Amino-thiazol-4-yl)-N-(3,5-bis-trifluoromethyl-benzyl)-4-(phenyl-4'-piperidine)-1'-butyramide (Intermediate 42), 0.036 g of phenyl-isocyanate in 5 mL of CH2Cl2 was heated in a capped vial at 60° C. overnight. Excess reagents were removed in vacuo. The residue was purified on preparative TLC using 1:9 [(1:9 aq. NH4OH/MeOH)/CH2Cl2). 0.10 g (72%) of the title compound was obtained as a white solid. Mass Spectrum (NH$_3$—Cl): m/z 690 (M+1).

EXAMPLE 81

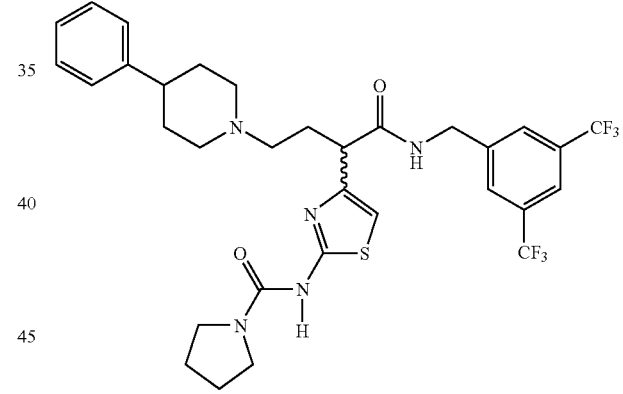

2-(2-[Pyrrolidinylcarbonyl]amino-thiazol-4-yl)-N-(3,5-bis-trifluoromethyl]-benzyl)-4-(phenyl-4'-piperidine)-1'-butyramide A mixture of 0.115 g (0.2 mmol) of 2-(2-Amino-thiazol-4-yl)-N-(3,5-bis-trifluoromethyl-benzyl)-4-(phenyl-4'-piperidine)-1'-butyramide (Intermediate 42) and 0.5 mL of phosgene (~20% in toluene) in 5 mL of CH2Cl2 was stirred in a capped vial for 1 h. Then 0.10 g of pyrrolidine was added and continued to be stirred for 2 h. Excess reagents were removed in vacuo. The residue was purified on preparative TLC using 1:9 [(1:9 aq. NH4OH/MeOH)/CH2Cl2). 0.072 g (54%) of the title compound was obtained as a white solid. Mass Spectrum (NH$_3$—Cl): m/z 668 (M+1).

EXAMPLE 82

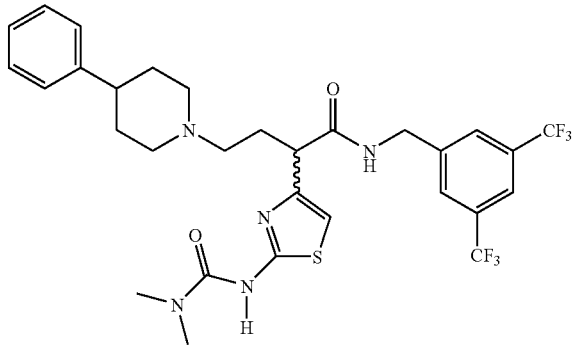

2-(2-[Dimethylaminocarbonyl]amino-thiazol-4-yl)-
N-(3,5-bis-trifluoromethyl-benzyl)-4-(phenyl-4'-
piperidine)-1'-butyramide A mixture of 0.115 g (1 mmol) of 2-(2-Amino-thiazol-4-yl)-N-(3,5-bis-trifluoromethyl-benzyl)-4-(phenyl-4'-piperidine)-1'-butyramide (Intermediate 42) and 0.032 g of dimethylaminocarbonyl chloride in 5 mL of CH2Cl2 was stirred in a capped vial overnight. Excess reagents were removed in vacuo. The residue was purified on preparative TLC using 1:9 [(1:9 aq. NH4OH/MeOH)/CH2Cl2). 0.073 g (57%) of the title compound was obtained as a yellow solid. Mass Spectrum (NH$_3$—CI): m/z 642 (M+1).

EXAMPLE 83

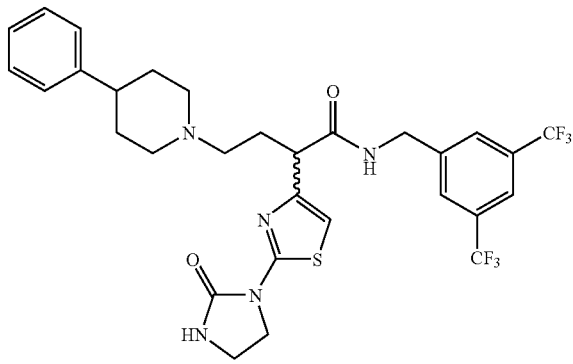

Step A: 2-(2-[N-Butoxyaminoethyl]butoxycarbonylamino-thiazol-4-yl)-N-(3,5-bis-trifluoromethylbenzyl)-4-(phenyl-4'-piperidine)-1'-butyramide A mixture of 0.134 g (0.2 mmol) of 2-(2-Butoxycarbonylamino-thiazol-4-yl)-N-(3,5-bis-trifluoromethyl-benzyl)-4-(phenyl-4'-piperidine)-1'-butyramide (Intermediate 41), 0.5 g of butoxycarbonylaminoethanol, 0.52 g of triphenylphosphine and 0.14 g of DEAD in 5 mL of THF was stirred at RT overnight. Excess reagents were removed in vacuo. The residue was purified on preparative TLC using 1:9 [(1:9 aq. NH4OH/MeOH)/CH2Cl2). 0.127 g (78%) of the title compound was obtained as a solid. Mass Spectrum (NH$_3$—CI): m/z 814 (M+1).

Step B: 2-(2-Aminoethylamino-thiazol-4-yl)-N-(3,5-bis-trifluoromethyl-benzyl)-4-(phenyl-4'-piperidine)-1'-butyramide A mixture of 0.127 g (0.15 mmol) of 2-(2-[N-Butoxyaminoethyl]butoxycarbonylamino-thiazol-4-yl)-N-(3,5-bis-trifluoromethyl-benzyl)-4-(phenyl-4'-piperidine)-1'-butyramide (from Example 83, Step A) and 1.0 mL of TFA was stirred at RT for 30 min. Excess reagents were removed in vacuo. The residue was purified on preparative TLC using 1:9 [(1:9 aq. NH4OH/MeOH)/CH2Cl2). 0.090 g (94%) of the title compound was obtained as a gummy solid. Mass Spectrum (NH$_3$—CI): m/z 614 (M+1).

Step C: 2-(2-N-[2-Imidazolidon]-thiazol-4-yl)-N-(3, 5-bis-trifluoromethyl-benzyl)-4-(phenyl-4'-piperidine)-1'-butyramide A mixture of 0.090 g (0.146 mmol) of 2-(2-Aminoethylamino-thiazol-4-yl)-N-(3,5-bis-trifluoromethyl-benzyl)-4-(phenyl-4'-piperidine)-1'-butyramide (from Example 83, Step B), 0.2 g of triphosgene, 0.2 mL of DIEA in 5 mL of CH2Cl2 was stirred at RT for 3 h. Excess reagents were removed in vacuo. The residue was purified on preparative TLC using 1:9 [(1:9 aq. NH4OH/MeOH)/CH2Cl2). 0.073 g (78%) of the title compound was obtained as a white solid. Mass Spectrum (NH$_3$—CI): m/z 640 (M+1).

EXAMPLE 84

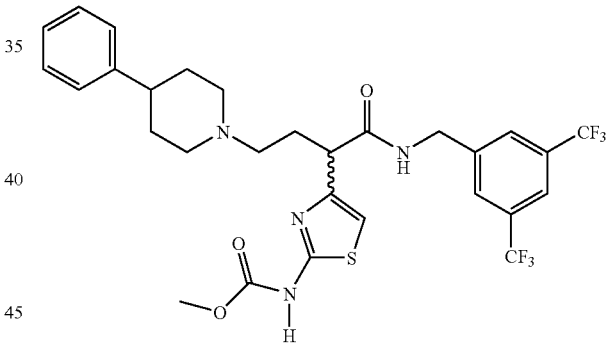

2-(2-[Methoxycarbonyl]amino-thiazol-4-yl)-N-(3,5-bis-trifluorothyl-benzyl)-4-(phenyl-4'-piperidine)-1'-butyramide A mixture of 0.115 g (0.2 mmol) of 2-(2-Amino-thiazol-4-yl)-N-(3,5-bis-trifluoromethyl-benzyl)-4-(phenyl-4'-piperidine)-1'-butyramide (Intermediate 42), 0.5 mL of methyoxycarbonyl chloride and 1.0 mL of pyridine in 5 mL of CH2Cl2 was stirred in a capped vial for overnight. Excess reagents were removed in vacuo. The residue was purified on preparative TLC using 1:9 [(1:9 aq. NH4OH/MeOH)/CH2Cl2). 0.117 g (93%) of the title compound was obtained as a yellow solid. Mass Spectrum (NH$_3$—CI): m/z 629 (M+1). The Examples 85–86 in Table 15 were synthesized according to the same procedure as that of Example 84 starting from the appropriate aminothiazole Intermediate (described previously).

TABLE 15

EXAMPLES 85-86

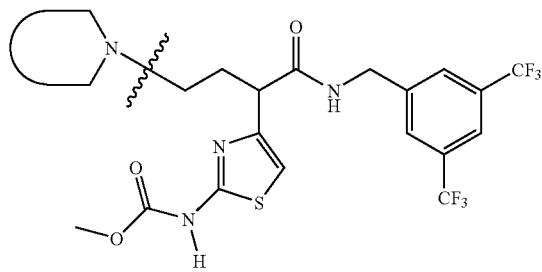

| Example | Amine | (M + 1) | Example | Amine | (M + 1) |
|---------|-------|---------|---------|-------|---------|
| 48 | F-⟨phenyl⟩-N(piperazine)N- | 647 | 49 | indene-spiro-piperidine-N- | 652 |

EXAMPLE 87

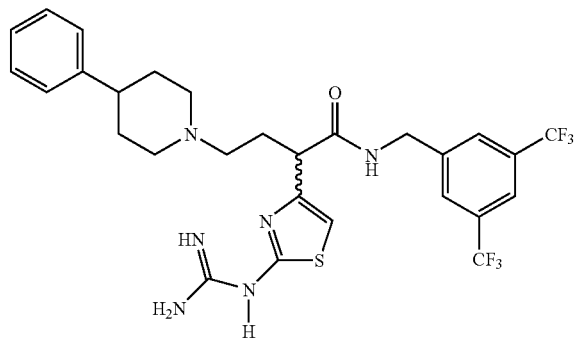

2-(2-guanidino-thiazol-4-yl)-N-(3,5-bis-trifluoromethyl-benzyl)-4-(phenyl-4'-piperidine)-1'-butyramide A mixture of 0.2 g (0.35 mmol) of 2-(2-Amino-thiazol-4-yl)-N-(3,5-bis-trifluoromethyl-benzyl)-4-(phenyl-4'-piperidine)-1'-butyramide (Intermediate 42) and 0.13 g of 1H-pyrazole-1-carboxamidine hydrochloride in 10 mL of nitrobenzene in a capped pressure tube was stirred at ~210° C. for 30 min Excess reagents were removed in vacuo. The residue was purified on preparative TLC using 1:9 [(1:9 aq. NH4OH/MeOH)/CH2Cl2). 0.08 g (37%) of the title compound was obtained as a yellow solid. Mass Spectrum (NH$_3$—Cl): m/z 613 (M+1).

The examples 88–92 in Table 16 were prepared according to similar procedures to Example 87 from Intermediates described previously.

TABLE 16

EXAMPLES 88–92

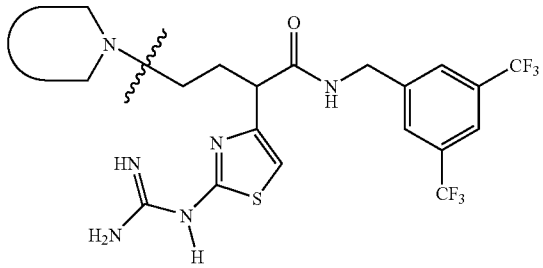

| Example | Amine | (M + 1) | Example | Amine | (M + 1) |
|---------|-------|---------|---------|-------|---------|
| 88 | F-⟨phenyl⟩-piperidine-N- | 631 | 91 | F-⟨phenyl⟩-N(piperazine)N- | 632 |

TABLE 16-continued

EXAMPLES 88–92

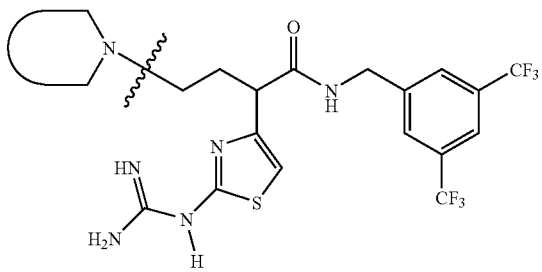

| Example | Amine | (M + 1) | Example | Amine | (M + 1) |
|---|---|---|---|---|---|
| 89 | 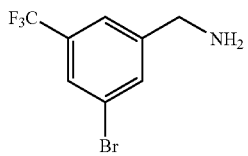 | 637 | 92 | 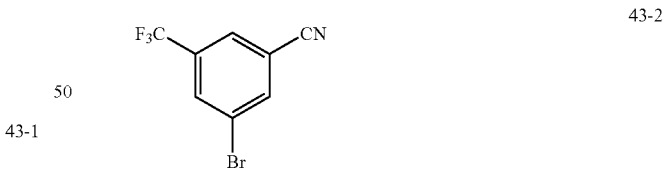 | 628 |
| 90 | 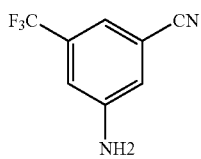 | 628 | | | |

Intermediate 43

![F3C-C6H3(Br)-CH2NH2]

Step 1

![F3C-C6H3(NH2)-CN] 43-1

DMF (10 mL) was deoxygenated by bubbling with nitrogen for 30 minutes before a solution of 3-amino-5-bromobenzotrifluoride (500 mg, 2.08 mmol) in DMF was added. The solution was bubbled with nitrogen for another 10 minutes fore zinc cyanide (147 mg, 1.25 mmol) and Tetrakis(triphenylphospine)-Pd (96 mg, 0.083 mmol) were added. The mixture was deoxygenated for another 15 minutes before heated to 80° C. in a sealed high pressure tube overnight. The reaction was diluted with ethyl acetate, washed with an ammonia hydroxide solution (2×), and concentrated in vacuo. The crude product was purified by preparation plates (30/70 ethyl acetate/hexanes) to yield 43-1 (289 mg, 74.5%). 1H NMR (400 MHz, CDCl3) δ 7.25 (d, J=0.6 Hz, 1H), 7.08 (s, 1H), 7.06 (d, J=0.9 Hz, 1H). LC-MS: MW calculated 186.13, found 227.8 (M+Acetonitrile+).

Step 2

![F3C-C6H3(Br)-CN] 43-2

A mixture of Copper(II) bromide (415 mg, 1.86 mmol), tert-butylnitrite (277 μL, 2.33 mmol), and anhydrous acetonitrile (7 mL), was cooled to 0° C. before a solution of 43-1 (289 mg, 1.55 mmol) in anhydrous acetonitrile (2 mL) was added slowly. After completion of addition, the reaction mixture was heated to 65° C. and monitored by TLC. The mixture was cooled to RT before poured into 20% aqueous HCl solution and extracted with ether. The organic layer was washed with 20% aqueous HCl solution, dried over anhydrous MgSO4, and concentrated in vacuo. The crude product was purified by a preparation plate (25/75, ethyl acetate/hexanes) to yield 43-2 (230 mg, 59.3%). LC-MS: MW calculated 248.94, found 249.02.

Step 3

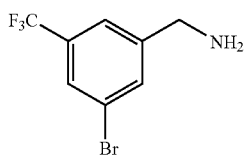
43-3

43-2 (50 mg, 0.200 mmol) was dissolved in THF (1 mL) before 1M Borane in THF (1 mL) was added. The mixture was stirred at RT overnight before concentrated in vacuo. The residue was redissolved in a solution of 1% HCl (4N in dioxane) in methanol and heated at 50° C. overnight. Solvent was stripped off and redissolved in 1% HCl in methanol. This process was repeated three times to get ride of excess borane and yield crude 43-3 (50 mg, 98.4%). LC-MS: MW calculated 252.97, found 253.8.

Intermediate 44

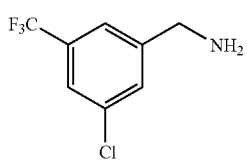

Intermediate 44 was prepared as detailed in Intermediate 43 using Cu(II)Cl$_2$ instead of Cu(II)Br$_2$ in Step 2. 1H NMR (400 MHz, CD3OD) δ 7.80 (m, 3H), 4.22 (s, 2H).

Intermediate 45

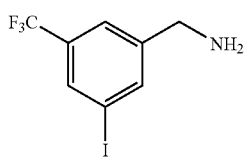

Step 1

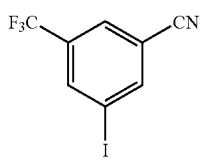
45-1

43-1 (500 mg, 2.69 mmol) was added to a mixture of concentrated HCl and water (5mL:5mL) (solution A). Sodium nitrite (342 mg, 4.95 mmol) was dissolved in water (5 mL) (solution B). The two solutions were cooled to 0° C. separately before solution B was added to solution A slowly. At end of addition, KI-starch paper was used to test presence of nitrous acid. A solution of KI (765 mg, 4.61 mmol) in water (5 mL) was added and stirred for 30 minutes before heated at 100° C. until no nitrogen gas evolution occurred. The mixture was cooled to RT and extracted with ether (2×), dried over anhydrous NaSO$_4$, and concentrated in vacuo. Crude product was purified by preparation plates (40/60, ethyl acetate/hexanes) to yield 45-1 (580 mg, 72.8%). 1H NMR (300 MHz, CDCl3) δ 8.18 (d, J=1.38 Hz, 2H), 7.89 (t, J=0.73 Hz, 1H).

Step 2

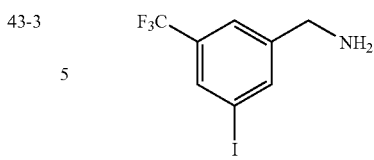

Intermediate 45

Intermediate 45 was prepared as detailed in Intermediate 43-Step 3. 1H NMR (400 MHz, CD3OD) δ 8.16 (s, 1H), 8.09 (s, 1H), 7.83 (s, 1H), 4.19 (s, 2H).

EXAMPLE 93

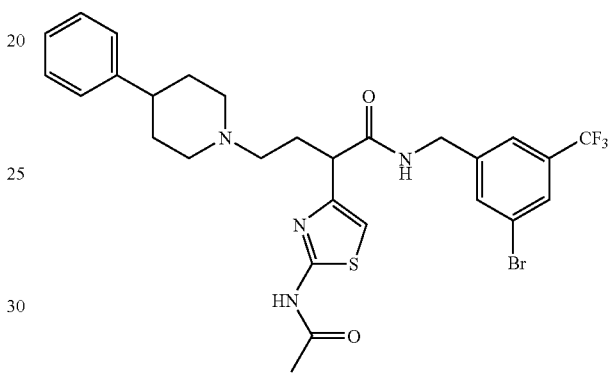

A mixture of Intermediate 43 (50 mg, 0.172 mmol), 2-(2-acetamido-thiazol-4-yl)-4-(phenyl-4'-piperidine)butanoic acid (prepared in an analogous fashion to Intermediate 39, 67 mg, 0.172 mmol), EDC (50 mg, 0.258 mmol), and DCM (5 mL) was stirred at room temperature overnight before concentrated in vacuo. The concentrate was purified by a preparation plate (5/95 MeOH/DCM) to yield Example 93 (90 mg, 65.7%). LC-MS: MW calculated 622.12, found 625.2.

EXAMPLE 94

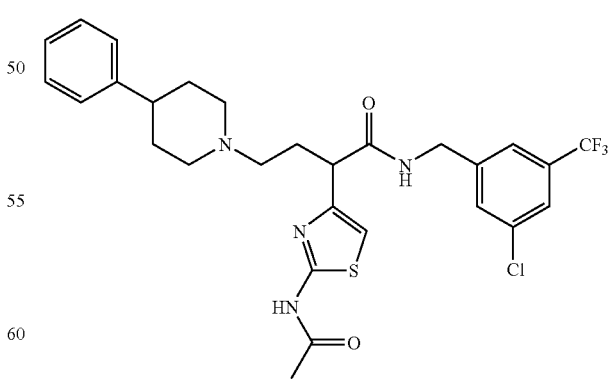

Example 94 was prepared as detailed in Example 93 using Intermediate 44 instead of Intermediate 43. LC-MS: MW calculated 578.17, found 579.2.

EXAMPLE 95

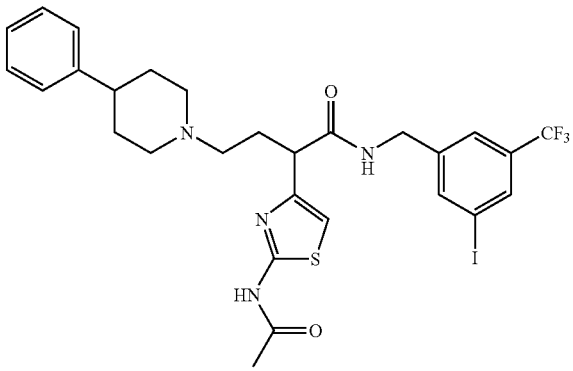

Example 95 was prepared as detailed in Example 93 using Intermediate 45 instead of Intermediate 43. The two enantiomers were further resolved by chiral columns. LC-MS: MW calculated 670.11, found 671.2.

EXAMPLE 96

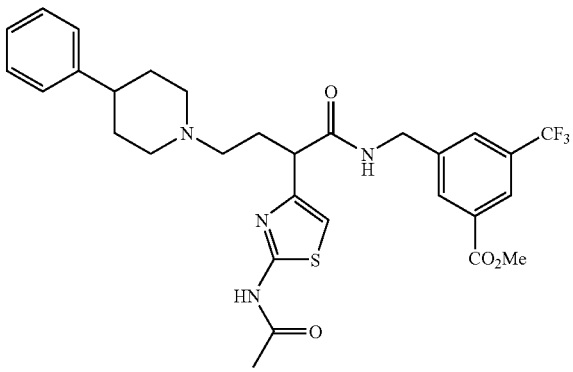

Example 96 was prepared as detailed in Example 14-Step B using Example 93 as starting material. LC-MS: MW calculated 602.22, found 603.3.

EXAMPLE 97

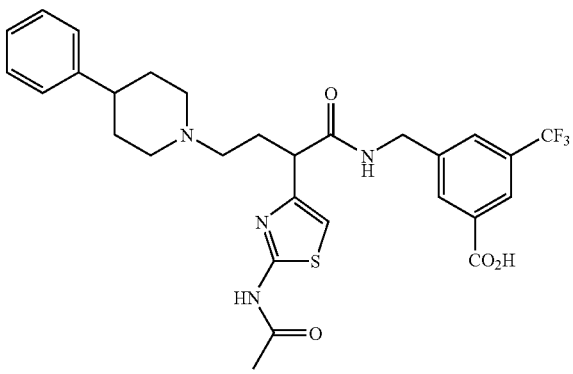

Example 97 was prepared as detailed in Example 15 using Example 96 as starting material. LC-MS: MW calculated 588.20, found 589.3.

Intermediate 46

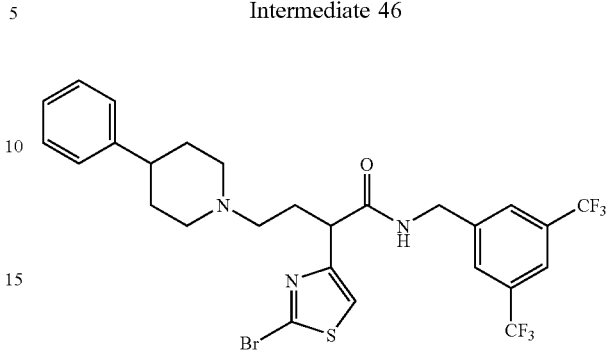

Step A:

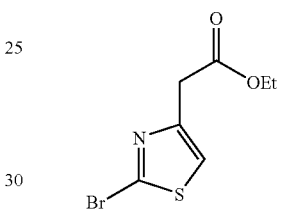

To a solution of CuBr$_2$ (14.4 g, 64.4 mmol) and t-butylnitrite (9.58 mL, 8.31 g, 80.5 mmol) in acetonitrile (200 mL) was aded in small portions ethyl 2-amino-4-thiazoleacetate (10.0 g, 53.7 mmol). The addition was accompanied by gas evolution. After 1 h no further gas evolution could be observed with an attached bubbler. The reaction mixture was poured into 2 N HCl (1 L) and washed twice with ether (500 mL ea.). The ethereal layers were combined and washed 2 N HCl (500 mL), saturated NaHCO$_3$ solution (500 mL), and brine (300 mL), then dried over MgSO$_4$, filtered and concentrated. Purification by MPLC, eluting with 35% ethyl actetate/hexane afforded 4.19 g (31%) of the desired product.

H NMR (CDCl$_3$, 500 MHz): δ 7.18 (t, J=1.0 Hz, 1H), 4.20 (q, J=7.0 Hz, 2H), 3.81 (d, J=1.0 Hz, 2H), 1.28 (t, J=7.0 Hz, 3H).

Step B:

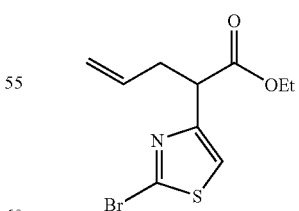

A solution of 2-bromo-4-thiazoleacetate (3.18 g, 12.7 mmol) in DMF (25 mL) at 0° C. was treated with sodium hydride (611 mg, 15.3 mmol), followed five min later with allyl bromide (1.10 mL, 1.54 g, 12.7 mmol). After 40 min at 0° C., the reaction mixture was poured into 5% citric acid solution (300 mL) and extracted twice with ether (300 mL).

The combined ethereal layers were washed twice with water and once with brine, dried over MgSO$_4$, filtered and concentrated. Purification by MPLC, eluting with 25% ethyl acetate/hexane gave 1.96 g (53%) of the desired product as a clear oil.

H NMR (CDCl$_3$, 500 MHz): δ 7.12 (br s, 1H), 5.73 (m, 1H), 5.01–5.11 (m, 2H), 4.12–4.22 (m, 2H), 3.93 (dd, J=7.5, 7.0 Hz, 1H), 2.73–2.80 (m, 1H), 2.64–2.71 (m, 1H), 1.24 (t, J=7.0 Hz, 3H).

Step C:

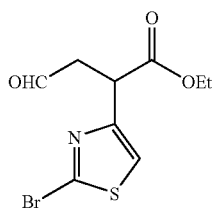

The olefin prepared in Step B above (1.96 g, 6.75 mmol) was dissolved in 65 mL of a 4:1 mixture by volume of acetone and water, cooled to 0° C., then treated with NMO (949 mg, 8.10 mmol), followed by 4% aqueous OsO$_4$ solution (2.1 mL, 0.34 mmol). After 0.5 h at 0° C. the reaction mixture was warmed to rt and stirred for an additional 2 h, whereupon solid NaHSO$_3$ (4.5 g) was added. This mixture was stirred for 5 min, then the acetone was removed at rt in vacuo. The residue was diluted with ether and washed with brine. The aqueous layer was extracted four more times with ether and the combined ethereal layers were dried over MgSO$_4$, filtered and concentrated. The crude diol was dissolved in 65 mL of a 1:1 mixture of MeOH/H$_2$O, cooled to 0° C., and treated with NaIO$_4$ (2.17 g, 10.1 mmol). The reaction mixture was permitted to warm to rt and stir for 45 min. The mixture was then filtered through celite, and partially concentrated to remove the MeOH. The resulting mixture was diluted with brine and extracted twice with ether. The combined ethereal layers were dried over MgSO$_4$, filtered, and concentrated to give 1.94 g of crude product which was used as is in the subsequent step.

H NMR (CDCl$_3$, 500 MHz): δ 9.79 (s, 1H), 7.11 (s, 1H), 4.34 (dd, J=8.0, 5.5 Hz, 1H), 4.15–4.20 (m, 2H), 3.36 (dd, J=18.5, 8.5 Hz, 1H), 3.07 (dd, J=19.0, 6.0 Hz, 1H), 1.24 (t, J=7.0 Hz, 3H).

Step D:

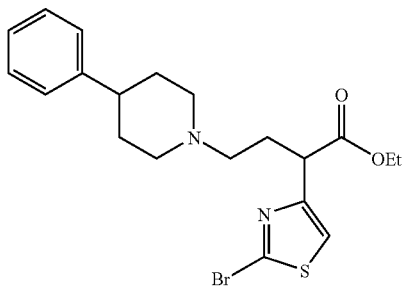

The aldehyde intermediate from the preceding step (1.94 g, 6.65 mmol) was combined with triethylamine (1.11 mL, 807 mg, 7.98 mmol) and phenylpiperidine hydrochloride (1.58 g, 7.98 mmol) in DCM (40 mL). Then NaB(OAc)$_3$H (4.23 g, 20.0 mmol) was added and the reaction mixture was stirred at rt for 2 h. The reaction mixture was then diluted with DCM (200 mL), and washed sequentially with saturated NaHCO$_3$ solution, and brine, dried over MgSO$_4$, filtered and concentrated to give 2.93 g of crude product which was used without further purification.

H NMR (CDCl$_3$, 500 MHz): δ 7.16–7.31 (m, 6H), 4.19 (m, 2H), 3.97 (t, J=7.0 Hz, 1H), 3.06 (app dd, J=25.5, 11.0 Hz, 2H), 2.43–2.52 (m, 3H), 2.34 (m, 1H), 2.09–2.17 (m, 3H), 1.83 (br s, 4H), 1.26 (t, J=7.0 Hz, 3H).

Step E:

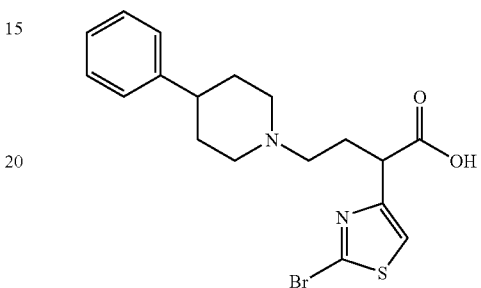

An aqueous solution of LiOH.H$_2$O (334 mg, 7.96 mmol) was added to a solution of ethyl ester prepared in the preceding step (2.90 g, 6.63 mmol) in 30 mL of 1:1 THF/MeOH. The reaction mixture was stirred at rt for 4 h, then neutralized with anhydrous HCl in ether (8.0 mL, 8.0 mmol) and concentrated to dryness, affording 3.43 g of crude amino acid (contaminated with LiCl). This material was used directly in the following step.

Step F:

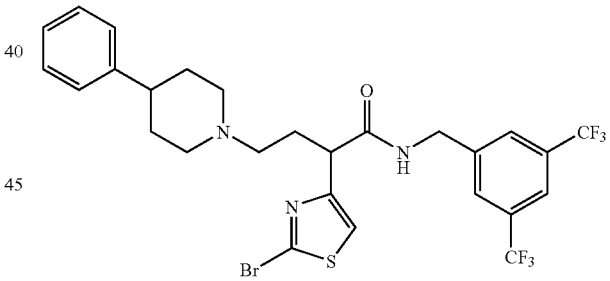

The acid prepared as described in the previous step ("6.63" mmol) was combined with Bis-(trifluoromethyl)-benzylamine hydrochloride (2.22 g, 7.96 mmol), EDC (2.54 g, 13.3 mmol), and DIEA (1.39 mL, 1.03 g, 7.96 mmol) in DCM (50 mL) and stirred at rt overnight. The reaction mixture was then diluted with DCM (200 mL) and washed with saturated NaHCO$_3$ solution (200 mL), water (200 mL), and brine (200 mL), then dried over MgSO$_4$, filtered, and concentrated. Purification by flash chromatography, eluting with 0.5/4.5/95 of concentrated NH$_4$OH solution, MeOH and DCM, gave 2.43 g (58% for three steps) of Intermediate 46 as a yellow oil.

H NMR (CDCl$_3$, 500 MHz): δ 7.77 (s, 1H), 7.68 (s, 2H), 7.56 (br s, 1H), 7.28 (m, 2H), 7.18 (m, 4H), 4.58 (d, J=6.0 Hz, 2H), 3.94 (t, J=7.50 Hz, 1H), 2.99 (d, J=11.5 Hz, 1H), 2.89 (d, J=11.0 Hz, 1H), 2.28–2.49 (m, 4H), 1.98–2.15 (m, 3H), 1.81 (m, 2H), 1.61–1.71 (m, 2H).

ESI-MS calc. for C27H26BrF6N3OS: 633, 635; Found: 634, 636 (M+H).

EXAMPLE 98

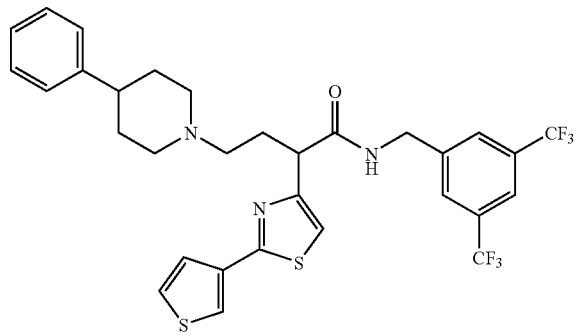

Thiophene-3-boronic acid (23 mg, 0.18 mmol), bromide Intermediate 46 (102 mg, 0.160 mmol) and 2M aqueous Na2CO3 (0.4 mL, 0.8 mmol) were combined in toluene (1 mL) and MeOH (0.4 mL). Pd(Ph3)2Cl2 (6 mg, 8 µmol) was added, after which the reaction mixture was purged with Argon and stirred at 80° C. overnight. The reaction mixture was concentrated. The residue was dissolved in ethyl acetate and washed with water, then brine, dried over MgSO4, filtered, and concentrated. Purification by preparative TLC, eluting with 0.5/4.5/95 of concentrated NH4OH solution, MeOH and DCM, gave 67.6 mg product which was converted to its hydrochloride salt by dissolving in DCM (1 mL), adding anhydrous 1N HCl in ether (112 µL, 0.112 mmol), and concentrating to afford 71 mg (66%) of Example 98 as a white solid. ESI-MS calc. for C31H29F6N3OS2: 637; Found: 638 (M+H).

EXAMPLE 99

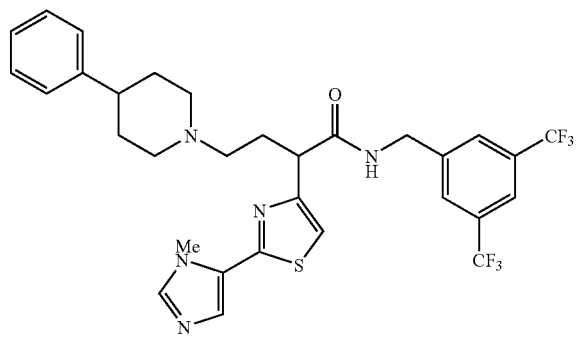

1-methyl-5-tributylstannyl-1H-imidazole (67 mg, 0.18 mmol), bromide Intermediate 46 (104 mg, 0.163 mmol), Ph3As (10 mg, 0.033 mmol), LiCl (21 mg, 0.49 mmol) and Pd2dba3 (7.5 mg, 8.2 µmol) were combined in NMP (2 mL) under argon and stirred at 80° C. for 48 h. Although the reaction was incomplete, it was worked up by diluting with ethyl acetate and washing with saturated NaHCO3 solution, water (3 times), and brine. The organic layer was dried over MgSO4, filtered, and concentrated. Purification by preparative TLC, eluting with 0.7/6.3/93 of concentrated NH4OH solution, MeOH and DCM, gave 12 mg of desired product. ESI-MS calc. for C31H31F6N5OS: 635; Found: 636 (M+H).

Some additional analogs prepared using the same experimental protocols as described in Examples 98 or 99 are displayed in Table 17.

TABLE 17

| Example | R | ESI-MS calc. MW | Found (M + H)+ |
|---|---|---|---|
| 100 | phenyl | 631 | 632 |
| 101 | 2-fluorophenyl | 649 | 650 |
| 102 | 2-methoxyphenyl | 661 | 662 |
| 103 | 3-methoxyphenyl | 661 | 662 |
| 104 | benzo[1,3]dioxol-5-yl | 675 | 676 |
| 105 | 2-(N-t-butylsulfamoyl)phenyl | 766 | 767 |
| 106 | 3-nitrophenyl | 676 | 677 |
| 107 | pyridin-4-yl | 632 | 633 |

TABLE 17-continued

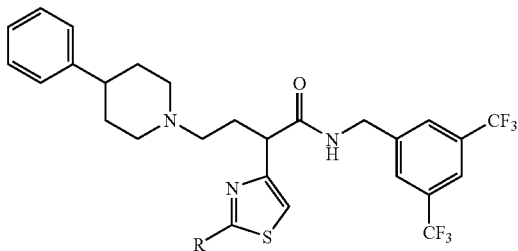

| Example | R | calc. MW | ESI-MS Found (M + H)+ |
|---|---|---|---|
| 108 | [3-pyridyl] | 632 | 633 |
| 109 | [3,4-dimethylisoxazol-5-yl] | 650 | 651 |
| 110 | [3-methylfuran-4-yl] | 621 | 622 |

EXAMPLE 111

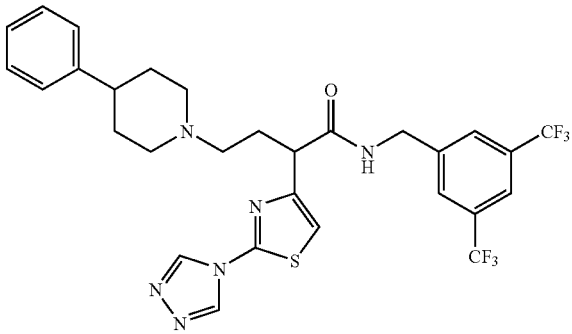

2-Aminothiazole Intermediate 42 (554 mg, 0.971 mmol) was combined with N,N'-dimethylformamide azine (276 mg, 1.94 mmol, ref. Bartlett, R. K.; Humprey, I. R. J. Chem. Soc. C 1967, 1664–1666.) and TsOH.H$_2$O (10 mg) in toluene (10 mL) and stirred at reflux for 12 h. Then the reaction mixture was stored at rt for 48 h. The reaction mixture was concentrated and the crude product purified by preparative TLC, eluting with 0.75/6.75/92.5 of concentrated NH$_4$OH solution, MeOH and DCM. The product was then converted to its hydrochloride salt by dissolving in DCM (1 mL), adding anhydrous 1 N HCl in ether solution (0.65 mL, 0.65 mmol), and concentrating to give 436 mg (68%) of a white solid.

ESI-MS calc. for C29H28F6N6OS: 622; Found: 623 (M+H).

EXAMPLE 112

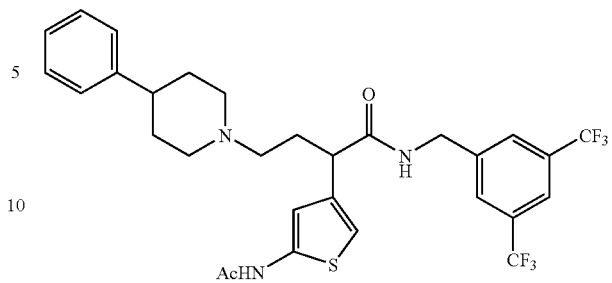

Step A:

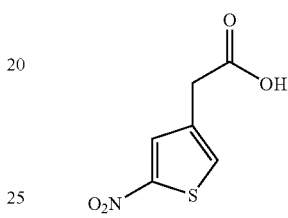

A suspension of sodium hydride (60% dispersion, 1.34 g, 33.4 mmol) in dioxane (25 mL) was treated at rt over 0.5 h with tetraethyldimethylaminomethylene diphosponate (10.5 g, 31.8 mmol). The addition was exothermic and was accompanied by foaming. The mixture was stirred at rt for 1.25 h, then 5-nitrothiophene-3-carboxylic aldehyde (5.0 g, 31.8 mmol) in dioxane (25 mL) was added. A thick oil precipitated from the reaction mixture. The reaction temperature was raised to 60° C. and heating was continued for 1.5 h, after which the reaction mixture was permitted to cool to rt and sit overnight. The solvent was removed in vacuo and the resulting residue was partitioned between ether and 1 N HCl solution (emulsion, insolubles). The aqueous layer was extracted two more times with ether. The ethereal layers were combined, washed with brine, dried over MgSO$_4$, filtered, and concentrated. The resulting residue was treated with 12N HCl solution (75 mL) and stirred at reflux for 20 min. The resulting mixture was extracted three times with ether, the ethereal layers were combined and they, in turn, were washed with water, then brine. The organic layer was dried over anhydrous MgSO$_4$, filtered and concentrated. Purification by MPLC, eluting with a 5–10% MeOH/ethyl actetate gradient provided 3.31 g (56%) of carboxylic acid.

H NMR (CD$_3$OD, 400 MHz): δ 7.96 (d, J=2.80 Hz, 1H), 7.62 (m, 1H), 3.68 (s, 2H).

Step B:

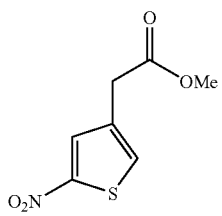

Iodomethane (1.04 mL, 2.36 g, 16.7 mmol) was added to solution of the carboxylic acid prepared as described in the preceding step (2.97 g, 15.9 mmol) and K₂CO₃ (5.49 g, 39.8 mmol) in DMF (30 mL) at 0° C. The resulting mixture was stirred at 0° C. for 45 min, then warmed to rt and stirred for an additional 1 h. The viscous reaction mixture was diluted with ether and washed with water. The aqueous layer was washed a second time with ether and the ethereal layers were combined and rinsed three times with water, and once with brine. The ethereal phase was then dried over MgSO₄, filtered, and concentrated. The resulting 2.79 g of ester (87%) was used without further purification.

H NMR (CDCl₃, 300 MHz): δ 7.89 (d, J=1.8 Hz, 1H), 7.39 (m, 1H), 3.74 (s, 3H), 3.65 (s, 2H).

Step C:

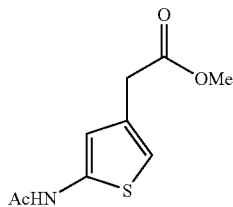

Iron powder (3.03 g, 54.3 nmol) was added to a mixture of the ester prepared as described in the previous step (2.02 g, 10.1 mmol) and acetic anhydride (10.0 mL, 10.8 g, 106 mmol) in acetic acid (40 mL). The temperature was raised to 60° C. and the reaction mixture was stirred for 1 h 10 min. The reaction mixture was filtered through celite, washing with ethyl acetate. A 3N NaOH solution was added (exotherm) and the layers were separated. It was determined that the ester had been inadvertantly hydrolyzed. The aqueous layer was therefore acidified with concentrated HCl solution, and extracted ten times with ethyl acetate. The combined organic layers were dried over MgSO₄, filtered, and concentrated to give 905 mg of acid. The acid was converted back to the methyl ester by stirring in anhydrous HCl in MeOH [prepared by adding thionyl chloride (1.33 mL, 2.16 g, 18.2 mmol) to MeOH (25 mL) at 0° C.] for 6 hrs at rt. The reaction mixture was then concentrated. Purification by MPLC (10% MeOH/DCM, then again with pure ethyl acetate, then a third time with 90% ethyl actetate/hexane) afforded 515 mg of desired product.

H NMR (CD₃OD, 500 MHz): δ 6.68 (m, 1H), 6.61 (d, J=1.5 Hz, 1H), 3.67 (s, 3H), 3.56 (s, 2H), 2.10 (s, 3H).

Step D:

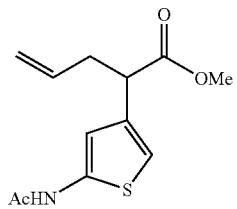

To a solution of the ester prepared in Step C above (352 mg, 1.65 mmol) in THF (20 mL) at −78° C. was added dropwise 1.5 M LDA in cyclohexane (2.75 mL, 4.13 mmol). After stirring for 50 min, allyl bromide (157 □L, 220 mg, 1.82 mmol) was added dropwise. Stirring was continued at −78° C. for 1.75 h, then the reaction mixture was poured into 10% aqueous citric acid solution, and extracted twice with ethyl acetate. The combined organic layers were washed with brine, dried over MgSO₄, filtered, and concentrated. Purification by MPLC, eluting with 95% ethyl actetate/hexane, provided 263 mg (63%) of the desired product.

H NMR (CDCl₃, 500 MHz): δ 7.97 (br s, 1H), 6.67 (s, 1H), 6.60 (d, J=1.5 Hz, 1H), 5.71 (m, 1H), 5.00–5.10 (m, 2H), 3.66 (m, 1H), 3.67 (s, 3H), 2.68–2.75 (m, 1H), 2.45–2.52 (m, 1H), 2.18 (s, 3H).

Step E:

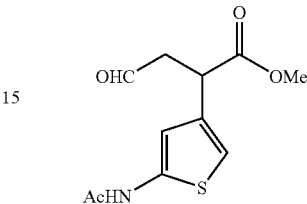

The olefin prepared in Step D above (209 mg, 0.825 mmol) was dissolved in 10 mL of a 4:1 mixture by volume of acetone and water, then treated with NMO (116 mg, 0.990 mmol), followed by 4% aqueous OsO₄ solution (0.26 mL, 0.041 mmol). The reaction mixture was stirred for 1.75 h, then NaIO₄ (265 mg, 1.24 mmol) was added. This mixture was stirred for 5 min, then the acetone was removed at rt in vacuo. The residue was diluted with DCM and washed with brine. The aqueous layer was extracted two more times with DCM and six times with ether and the combined organic layers were dried over Na₂SO₄, filtered and concentrated at rt. The crude diol was dissolved in 10 mL of a 1:1 mixture of MeOH/H₂O, and treated with NaIO₄ (2.17 g, 10.1 mmol). The reaction mixture was stirred for 30 min. The mixture was partially concentrated to remove the MeOH. The resulting solution was diluted with brine and extracted twice with DCM. The combined organic layers were dried over MgSO₄, filtered, and concentrated to give 66.3 mg of crude product which was used as is in the subsequent step.

Step F:

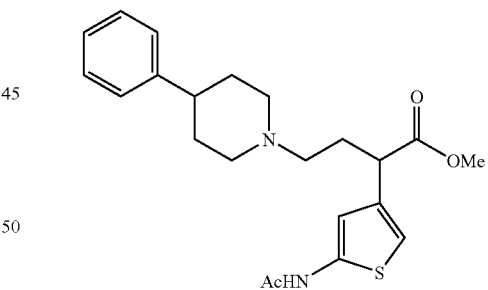

The aldehyde prepared as described in Step E immediately above (75 mg, 0.29 mmol) was combined with 4-phenylpiperidine hydrochloride (116 mg, 0.588 mmol), triethylamine (82 μL, 0.59 mmol), and sodium triacetoxyborohydride (312 mg, 1.47 mmol) in DCM (5 mL). The resulting mixture was stirred at room temperature overnight. The reaction mixture was then diluted with DCM and washed with saturated NaHCO₃ solution, followed by brine, dried over anhydrous MgSO₄, filtered, and concentrated. Purification by preparative TLC (silica, 0.35/3.15/96.5 of NH₄OH/methanol/DCM) provided 74.1 mg of the desired product.

ESI-MS calc. for C22H28N2O3S: 400; Found: 401 (M+H).

Step G:

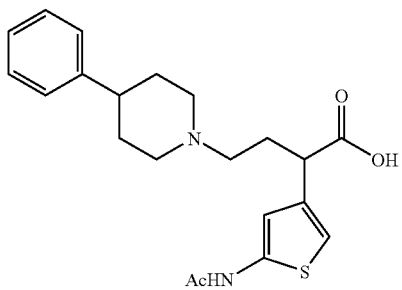

The aminoester product from Step F directly above (74 mg, 0.19 mmol) was dissolved in 1:1 methanol/THF (2 mL). To it was added a solution of LiOH.H$_2$O (15.5 mg, 0.370 mmol) in water (1 mL). The reaction mixture was stirred at room temperature for 4.5 h, then was neutralized with 1.0 N HCl in ether (370 μL, 0.370 mmol) and concentrated. Purification by preparative TLC (silica, 50% methanol/DCM) furnished 46.4 mg of aminoacid.

Step H:

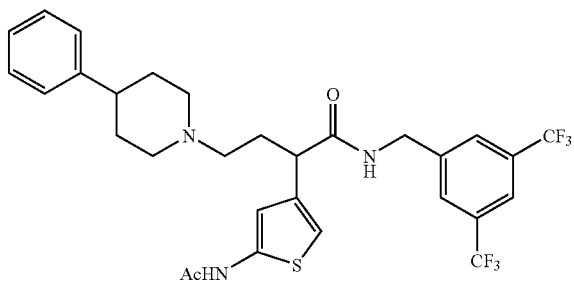

The aminoacid prepared as described in Step G above (46.4 mg, 0.120 mmol) was combined with 3,5-Bis(trifluoromethyl)benzylamine hydrochloride (67.1 mg, 0.240 mmol) and EDC (46.0 mg, 0.240 mmol) in DCM (2 mL). The reaction mixture was stirred at room temperature for 4 h, then was concentrated and applied directly to a preparative TLC plate (silica, 0.75/6.75/92.5 of NH$_4$OH/methanol/DCM). After purification, 63 mg of product were collected.

H NMR (CDCl$_3$, 500 MHz): δ 9.06 (s, 1H), 7.75 (s, 1H), 7.65 (s, 2H), 7.29 (m, 3H), 7.17 (m, 3H), 6.63 (d, J=1 Hz, 1H), 6.56 (d, J=1.5 Hz, 1H), 4.51 (d, J=6 Hz, 2H), 3.68 (t, J=7 Hz, 1H), 3.01 (d, J=11.5 Hz, 1H), 2.91 (d, J=11 Hz, 1H), 2.48 (m, 1H), 2.36 (m, 2H), 2.25 (m, 1H), 2.11 (s, 3H), 1.93–2.08 (m, 3H), 1.82 (m, 2H), 1.68 (m, 2H).

ESI-MS calc. for C30H31F6N3O2S: 611; Found: 612 (M+H).

EXAMPLE 113

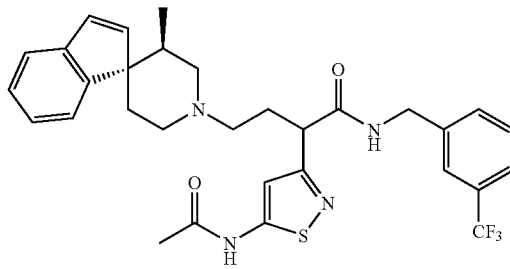

Step A:

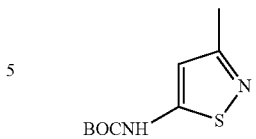

5-Amino-3-methylisothiazole hydrochloride (25.0 g, 166 mmol) was converted to its free base by partitioning between DCM and 2 N NaOH solution. The organic layer was dried over MgSO$_4$, filtered, and concentrated giving 13.8 g of free base. To the free base was added BOC$_2$O (70 g, 0.32 mol) and the mixture was warmed to 100° C. and stirred for 23 h. The reaction mixture was cooled to room temperature and the volatiles were removed under vacuum. The residue was purified by flash chromatography (silica, 20–40 gradient of ethyl acetate/hexane) to afford 21.3 g of product (82%). H NMR (CDCl$_3$, 500 MHz): δ 7.76 (br s, 1H), 6.43 (s, 1H), 2.37 (s, 3H), 1.53 (s, 9H).

ESI-MS calc. for C9H14N2O2S: 214; Found: 215 (M+H).

Step B:

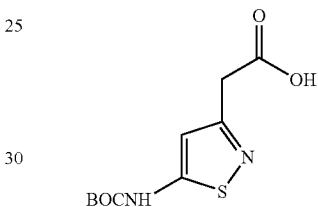

2.5 M n-butyl lithium (200 ml, 0.500 mol) was added to precooled (−78° C.) THF (100 mL) under N$_2$. By lowering bath attempted to control reaction temperature at −70° C. while adding dropwise a solution of N-t-butoxycarbonyl-5-amino-3-methylisothiazole hydrochloride (18.2 g, 90.9 mmol) in THF (100 mL). After stirring an additional 0.5 h at −70° C., the reaction mixture was warmed to −30° C. and crushed dry ice (then small pieces, ~50 g) was added (foaming-splashing). Then the reaction mixture was permitted to warm to room temperature and stir overnight. The reaction mixture was then partitioned between ethyl acetate and 2 N NaOH solution. The aqueous layer was made acidic (pH~3) by dropwise addition of concentrated HCl solution with swirling. The aqueous mixture was then extracted with ethyl acetate. The organic layer was dried over MgSO$_4$, filtered, and concentrated to give 6.37 g of product which was used without further purification.

ESI-MS calc. for C10H14N2O4S: 258; Found: 259 (M+H).

Step C:

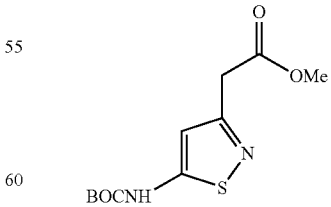

The crude acid from Step C above (6.15 g, 23.8 mmol) was combined with methanol (4.82 mL, 119 mmol), EDC (9.12 g, 47.6 mmol), and DMAP (145 mg, 1.19 mmol) in DCM (100 mL). The resulting mixture was stirred at room temperature for 4 h, then was diluted with DCM (400 mL) and washed with 1 N HCl solution (250 mL), water (250 mL), and brine (250 mL). The organic layer was dried over MgSO₄, filtered, and concentrated. Purification by MPLC (silica, 65% ethyl acetate/hexane) gave 1.27 g of pure product.

H NMR (CDCl₃, 500 MHz): δ 7.66 (br s, 1H), 6.63 (s, 1H), 3.76 (s, 2H), 3.72 (s, 3H), 1.53 (s, 9H).

Step D:

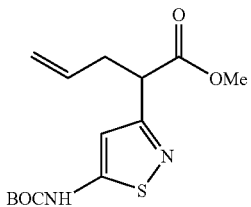

A solution of the ester from Step C (996 mg, 3.66 mmol) in THF (30 mL) at −78° C. under nitrogen was treated dropwise with a 1.5M solution of LDA.THF in cyclohexane (6.10 mL, 9.14 mmol). The mixture was stirred at −78° C. for 50 min, then was treated dropwise with allyl bromide (348 μL, 4.03 mmol). After stirring at −78° C. for 2 h, then reaction mixture was warmed to −10° C. (ice/salt bath) and stirred for 1 h. The reaction mixture was then warmed to room temperature, quenched by adding 10% citric acid solution, and partitioned between ethyl acetate and water. The organic layer was washed with brine, dried over MgSO₄, filtered, and concentrated. Purification by MPLC (silica, 35%–65% ethyl acetate/hexane in 10% increments) provided 47 mg of the desired product.

H NMR (CDCl₃, 500 MHz): δ 8.04 (s, 1H), 6.64 (s, 1H), 5.73 (m, 1H), 5.00–5.09 (m, 2H), 3.91 (t, J=7.5 Hz, 1H), 3.69 (s, 3H), 2.75–2.81 (m, 1H), 2.61–2.66 (m, 1H), 1.51 (s, 9H).

Step E:

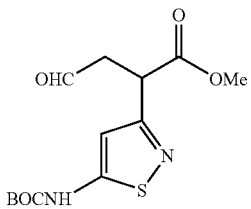

The olefin from Step D above (46 mg, 0.15 mmol) was dissolved in 4:1 acetone/water (2 mL) and treated with 1-methylmorpholine-N-oxide (21 mg, 0.18 mmol), followed by a 4% aqueous solution of OsO₄ (47 μL, 0.0074 mmol). The reaction mixture was stirred at room temperature for 2 h, then more 1-methylmorpholine-N-oxide (26 mg, 0.22 mmol) and 4% OsO₄ (50 μL) was added. After 2 more h, the reaction mixture was partially concentrated (at 16° C.) to remove the acetone. Ether was added and the mixture was washed with 1N NaHSO₃ solution. The aqueous layer was back extracted twice with more ether and the combined ether extracts were washed with brine, dried over MgSO₄, filtered, and concentrated. The resulting crude diol (51 mg) was dissolved in 1:1 methanol/water (2 mL) and treated with NaIO₄ (47 mg, 0.22 mmol). The reaction mixture was stirred for 0.5 h, then was partially concentrated to remove the methanol. The resulting aqueous mixture was partitioned between DCM and water. The organic layer was washed with brine, dried over MgSO₄, filtered, and concentrated to give 36.4 mg of the aldehyde, which was used in Step F without further purification.

Step F:

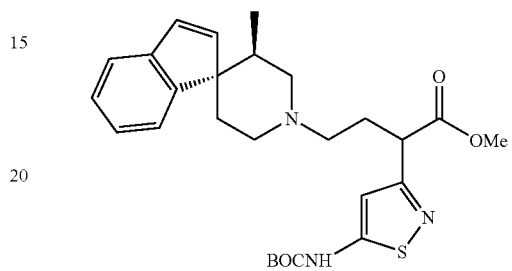

The aldehyde from Step E above (35 mg, 0.11 mmol) was combined with spiroindenepiperidine hydrochloride Intermediate 5 (52 mg, 0.22 mmol), triethylamine (31 μL, 0.22 mmol), and sodium triacetoxyborohydride (118 mg, 0.555 mmol) in DCM (3 mL). The reaction mixture was stirred at room temperature for 30 min, then was diluted with DCM and washed with saturated NaHCO₃ solution, followed by brine. The organic layer was dried over MgSO₄, filtered, and concentrated. Purification by preparative TLC (silica, 1/9/90 of NH₄OH/methanol/DCM) gave 45.2 mg of desired product.

ESI-MS calc. for C27H35N3O4S: 497; Found: 498 (M+H).

Step G:

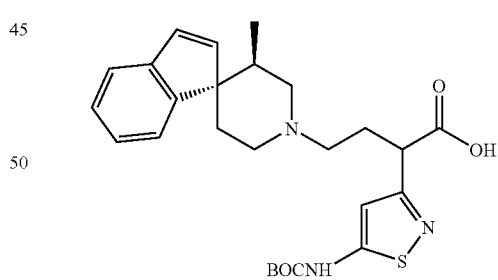

The aminoester from Step G above (43.5 mg, 0.0874 mmol) was dissolved in 1:1 methanol/THF (2 mL) and treated with a solution of LiOH.H₂O (9.2 mg, 0.22 mmol) in water (1 mL). The resulting mixture was stirred at room temperature for 16 h. The reaction mixture was quenched by addition of 1 N HCl in ether (219 μL, 0.219 mmol) and concentrated. This crude mixture was used as is in Step H below.

ESI-MS calc. for C26H33N3O4S: 483; Found: 484 (M+H).

Step H:

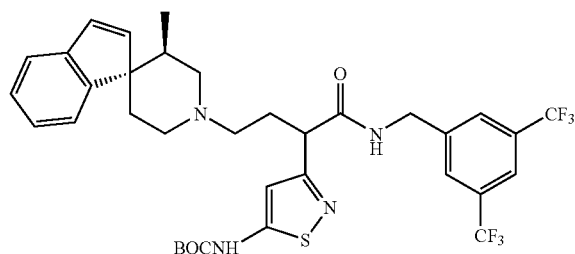

The crude acid from Step G (ca. 42 mg, 0.087 mmol) was combined with 3,5-Bis(trifluoromethyl)benzylamine hydrochloride (49 mg, 0.18 mmol), and EDC (34 mg, 0.18 mmol) in DCM (4 mL) and DMF (0.5 mL). The reaction mixture was stirred at room temperature for 5 h, then was concentrated to remove the DCM. The residue was diluted with ethyl acetate and washed with saturated $NaHCO_3$ solution, water, and brine. The organic layer was dried over anhydrous $MgSO_4$, filtered, and concentrated. Purification by preparative TLC (silica, 0.8/7.2/92 of $NH_4OH$/methanol/DCM) afforded 51.3 mg of the amide product.

ESI-MS calc. for C35H38F6N4O3S: 708; Found: 709 (M+H).

Step I:

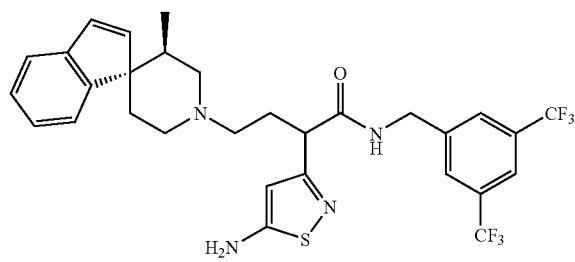

The Boc-aminoisothiazole from Step H (51 mg, 0.072 mmol) was dissolved in 95% TFA/water (1 mL), stirred at room temperature for 45 min, then concentrated. Purification of the residue by preparative TLC (silica, 0.8/7.2/92 of $NH_4OH$/methanol/DCM) gave 43.6 mg of product.

ESI-MS calc. for C30H30F6N4OS: 608; Found: 609 (M+H).

Step J:

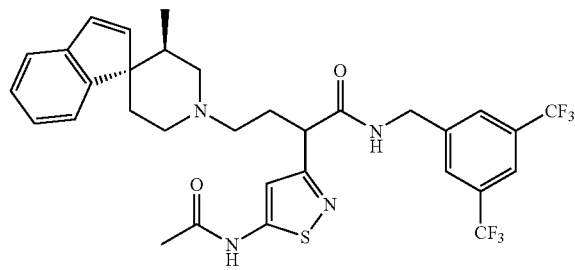

The aminoisothiazole from Step I above (37.5 mg, 0.0616 mmol) was dissolved in DCM (2 mL) and treated with pyridine (50 μL, 0.62 mmol), followed by acetic anhydride (58 μL, 0.62 mmol). The reaction mixture was stirred overnight at room temperature. The reaction mixture was concentrated and the resulting residue was purified by preparative TLC (silica, 0.8/7.2/92 of $NH_4OH$/methanol/DCM). The product was converted to its hydrochloride salt by dissolving in DCM (1 mL) and adding an excess of 1 M HCl in ether (~100 μL), then concentrating to give a white solid (25.5 mg).

ESI-MS calc. for C32H32F6N4O2S: 650; Found: 651 (M+H).

EXAMPLE 114

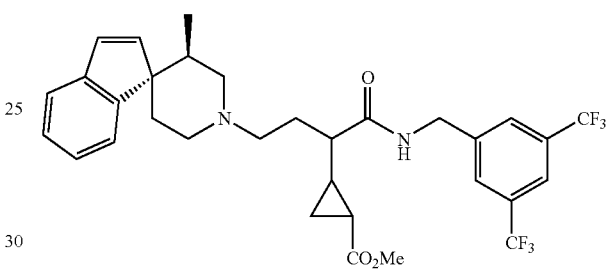

Step A:

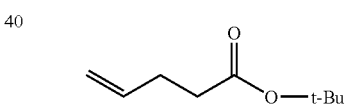

Concentrated $H_2SO_4$ (24.5 g, 0.250 mol) was added dropwise at a rapid rate to a suspension of $MgSO_4$ (120 g, 1.00 mol) in DCM (1l). The mixture was stirred magnetically overnight, however the next morning it was evident that solids prevented adequate stirring so a mechanical overhead stirring system was installed. 4-penteneoic acid (25 g, 0.25 mol) was added, followed by t-butanol (92.5 g, 1.25 mol). The mixture was stirred at rt for 4 days, upon which time TLC indicated that some starting material remained. None-the-less the reaction mixture was filtered through celite and washed with saturated $NaHCO_3$ solution (gas evolution). The aqueous layer was back extracted with DCM and the combined organic layers were then washed with saturated $NaHCO_3$ solution, twice with water, and with brine. The organic layer was dried over anhydrous $MgSO_4$, filtered, and concentrated. Flash chromatography (silica, 15% ether/pentane) afforded 19.6 g of pure ester (50% yield).

H NMR ($CDCl_3$, 500 MHz): δ 5.82 (m, 1H), 4.98–5.07 (m, 2H), 2.32 (m, 4H), 1.44 (s, 9H).

Step B:

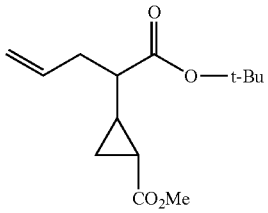

Threo product: t-Butyl-4-pentenoate prepared as described in the previous step (2.00 g, 12.8 mmol) was added in THF (10 mL) over 2–3 min to LDA (1.5 M in cyclohexane, 10.3 mL, 15.4 mmol) in THF (30 mL) precooled to −78° C. and under an $N_2$ atmosphere. The mixture was stirred at −78° C. for 0.5 h, then commercially available methyl 4-bromocrotonate (2.52 g, 14.1 mmol) in THF (10 mL) was added dropwise. The reaction mixure was allowed to slowly warm to rt and stir overnight. The reaction mixture was then poured into brine, and extracted twice with ether. The combined ethereal layers were dried over anhydrous $MgSO_4$, filtered, and concentrated. Purification by MPLC (silica, 15% ethyl acetate/hexane) provided 0.980 g of product, which by literature precedent was presumed to be threo, with trans substitution on the cyclopropyl ring.

H NMR (CDCl$_3$, 500 MHz): δ 5.77 (m, 1H), 5.01–5.10 (m, 2H), 3.66 (s, 3H), 2.45 (m, 1H), 2.33 (m, 1H), 1.75 (m, 1H), 1.63 (m, 1H), 1.53 (m, 1H), 1.43 (s, 9H), 1.25 (m, 1H), 0.77 (m, 1H).

Erythro product: To a solution of LDA (1.5 M in cyclohexane, 28.3 mL, 42.4 mmol) in a mixture of THF (60 mL) and HMPA (25 mL) under an $N_2$ atmosphere at −78° C. was added dropwise over 10 min t-Butyl-4-pentenoate prepared as described in step A (5.52 g, 35.3 mmol) in THF (20 mL). The reaction mixture was stirred at −78° C. for 30 min, then methyl 4-bromocrotonate (6.95 g, 38.8 mmol) in THF (20 mL) was added dropwise over 10 min. The resulting reaction mixture was stirred at −78° C. for 1 h, then was warmed to rt and stirred overnight. The reaction mixture was poured into water and extracted twice with ether. The combined ethereal layers were washed five times with water, and once with brine, dried over anhydrous $MgSO_4$, filtered, and concentrated. Purification by MPLC (silica, 15% ethyl acetate/hexane) afforded 2.39 g of product, which by literature precedent was assumed to be erythro, with trans substitution on the cyclopropyl ring.

H NMR (CDCl$_3$, 500 MHz): δ 5.75 (m, 1H), 5.00–5.08 (m, 2H), 3.67 (s, 3H), 2.46 (m, 1H), 2.33 (m, 1H), 1.75 (m, 1H), 1.56 (m, 1H), 1.47 (obscured m, 1H), 1.44 (s, 9H), 1.20 (m, 1H), 0.93 (m, 1H).

Step C:

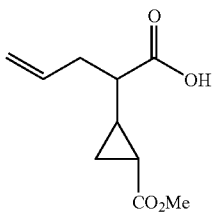

Threo isomer: The threo diester prepared as described in Step B (2.77 g, 10.9 mmol) was treated with TFA (20 mL), stirred at room temperature for one h, then concentrated to give 2.60 g of crude product, which was used as is in Step D.

Erythro isomer: The erythro diester was deprotected in an identical fashion to that described for the threo isomer immediately above.

Step D:

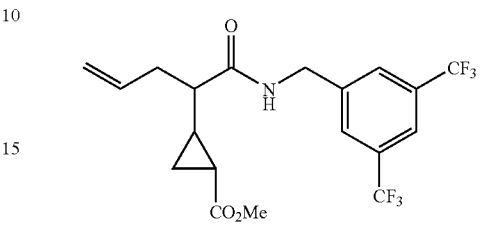

Threo isomers: The threo carboxylic acid prepared as described in Step C (10.4 mmol) was combined with 3,5-Bis(trifluoromethylbenzylamine hydrochloride (5.82 g, 20.8 mmol), HOAt (2.83 g, 20.8 mmol), and DIEA (4.63 mL, 26.0 mmol) in DCM (80 mL) and the resulting mixture was cooled to 0° C. EDC (3.99 g, 20.8 mmol) was added and the reaction mixture was permitted to warm to rt and stir for 2.5 h. The reaction mixture was diluted with DCM and washed with water, 1 N HCl solution, saturated NaHCO$_3$ solution, and brine. The organic layer was dried over anhydrous $MgSO_4$, filtered, and concentrated. The product was clean by H NMR and was used without further purification in Step E.

H NMR (CDCl$_3$, 500 MHz): δ 7.90 (s, 1H), 7.87 (s, 1H), 7.85 (s, 1H), 5.73 (m, 1H), 5.04 (app dq, J=1.5, 17 Hz, 1H), 4.96 (m, 1H), 4.56 (d, J=15.5 Hz, 1H), 4.45 (d, J=16 Hz, 1H), 3.59 (s, 3H), 2.48 (m, 1H), 2.35 (m, 1H), 1.80 (m, 1H), 1.58 (m, 2H), 1.19 (m, 1H), 0.86 (m, 1H).

Erythro isomers: The erythro amides were prepared in the same fashion as described for the synthesis of the threo amides immediately above.

H NMR (CDCl$_3$, 500 MHz): δ 7.90 (s, 1H), 7.87 (s, 1H), 7.85 (s, 1H), 5.73 (m, 1H), 5.03 (m, 1H), 4.96 (m, 1H), 4.55 (d, J=15.5 Hz, 1H), 4.48 (d, J=16 Hz, 1H), 3.65 (s, 3H), 2.48 (m, 1H), 2.34 (m, 1H), 1.81 (m, 1H), 1.56 (m, 2H), 1.11 (m, 1H), 0.93 (m, 1H).

Step E:

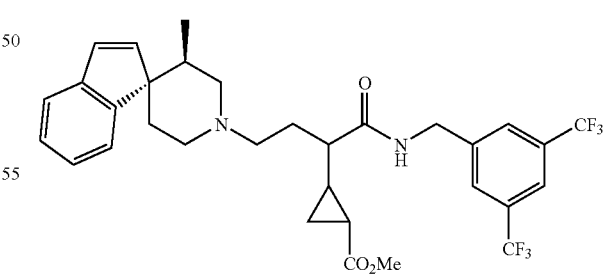

Threo diastereomers: Ozone gas was bubbled through a precooled solution of the threo amide prepared as described in Step D (10 mmol) in DCM (75 mL) at −78° C. until a blue color persisted. $N_2$ was then bubbled through the solution until the blue color has disappeared. The solution was dried over $MgSO_4$, filtered, and concentrated to a volume of approximately 40 mL. To the resulting aldehyde was added a solution of 3-methyl-4-spiroindenylpiperidine hydrochloride (Intermediate 5, 2.83 g, 12.0 mmol) and triethylamine (1.67 mL, 12.0 mmol) in DCM (15 mL). Approximately 5 g of 4° A molecular sieves (powder) was added. Then sodium triacetoxyborohydride (7.42 g, 35.0 mmol) was added and the reaction mixture was stirred at rt for 21.5 h. The reaction mixture was then diluted with DCM and filtered through a celite plug. The filtrate was washed with saturated NaHCO₃ solution, water, and brine, dried over anhydrous MgSO₄, filtered and concentrated. Two successive purifications by flash chromatography (silica, 5% of (10% NH₄OH/MeOH) in DCM) gave 1.90 g of product.

ESI-MS calc. for C32H34F6N2O3: 608; Found: 609 (M+H).

Erythro diastereomers: The erythro target compounds were prepared from the erythro olefin prepared as described in Step D (9.5 mmol) in exactly the same fashion as the threo compounds described immediately above to give 964 mg of desired product.

ESI-MS calc. for C32H34F6N2O3: 608; Found: 609 (M+H).

Single isomers of substituted cyclopropyl compounds can be prepared by resolution intermediate from Step B of Example 114 using a chiral oxazolidinone auxiliary. See for example resolution of the erythro isomers:

Step B1:

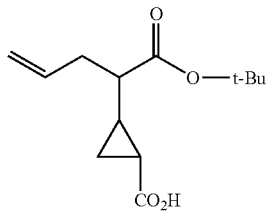

A solution of the diester from Step B above (erythro, 17.3 g, 68.0 mmol) in 200 mL of 1:1 THF/methanol was treated with a solution of LiOH.H₂O (14.3 g, 340 mmol) in 100 mL of water. The reaction mixture was stirred at room temperature for 3 h, then was quenched with excess 10% citric acid. The mixture was extracted with ethyl acetate and the organic layer was washed with 1 N HCl solution and brine, dried over anhydrous MgSO₄, filtered, and concentrated. Purification by flash chromatography (silica, 1–5% stepwise gradient methanol/DCM) afforded 13.0 g (80%) of acid.

H NMR (CDCl₃, 500 z): δ 5.78 (m, 1H), 5.08 (m, 2H), 2.48 (m, 1H), 2.37 (m, 1H), 1.78 (m, 1H), 1.65 (m, 1H), 1.47 (s, 9H), 1.46 (obsc m, 1H), 1.28 (m, 1H), 1.02 (m, 1H).

Step B2:

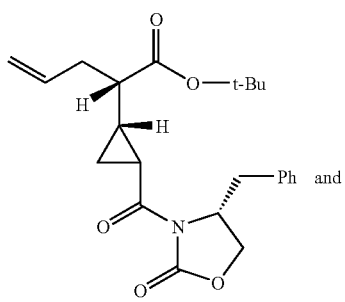

-continued

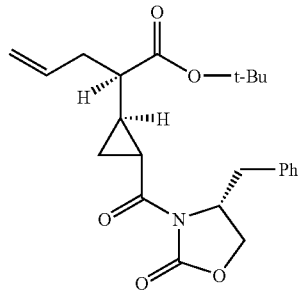

To a solution of the erythro carboxylic acid prepared as described in Step B1 (13.0 g, 54.2 mmol) in THP (50 mL) at 0° C. under an N₂ atmosphere was added dropwise DIEA (9.42 mL, 54.2 mmol), followed by pivaloyl chloride (6.64 mL, 54.2 mmol). In a separate vessel, a precooled (−78° C.) solution of (R)-(+)-4-benzyl-2-oxazolidinone (9.59 g, 54.2 mmol) in THF (50 mL) under an N₂ atmosphere was treated dropwise with n-butyl lithium in hexane (1.6 M, 33.9 mL, 54.2 mmol). Both solutions were stirred for approximately 30 min, at which time the solution of oxazolidinone anion was transferred by cannula to the preformed mixed anhydride. The resulting reaction mixture was permitted to warm to rt and stir overnight. The reaction mixture was diluted with ethyl acetate and washed with 1 N HCl solution, saturated NaHCO₃ solution, and brine (each time back extracting with more ethyl acetate). The organic layer was dried over anhydrous MgSO₄, filtered, and concentrated. The crude product was purified by MPLC (silica, 30% ethyl acetate/hexane) whereupon the two erythro diastereomers separated to give single diastereomers: 4.5 g of the higher band isomer and 6.0 g of the lower band isomer, as well as an additional 3.1 g of mixed isomers (total yield 63%).

Higher band: H NMR (CDCl₃, 400 MHz): δ 7.2–7.38 (m, 5H), 5.78 (m, 1H), 4.99–5.08 (m, 2H), 4.69 (m, 1H), 4.20 (m, 2H), 3.28 (dd, J=3.3, 13.5 Hz, 1H), 3.11 (m, 1H), 2.77 (dd, J=5.7, 13.3 Hz, 1H), 2.48 (m, 1H), 2.39 (m, 1H), 1.91 (m, 1H), 1.72 (m, 1H), 1.48 (s, 9H), 1.44 (obsc m, 1H), 1.14 (m, 1H).

Lower band: H NMR (CDCl₃, 400 MHz): δ 7.21–7.36 (m, 5H), 5.82 (m, 1H), 5.07 (m, 2H), 4.68 (m, 1H), 4.20 (m, 2H), 3.25 (dd, J=3.2, 13.2 Hz, 1H), 3.10 (m, 1H), 2.82 (dd, J=9.2, 13.2 Hz, 1H), 2.54 (m, 1H), 2.45 (m, 1H), 1.92 (m, 1H), 1.74 (m, 1H), 1.48 (s, 9H), 1.43 (m, 1H), 1.11 (m, 1H).

Step B3:

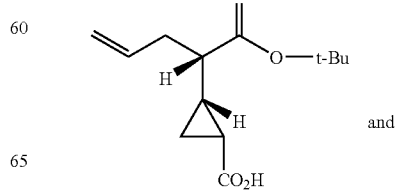

-continued

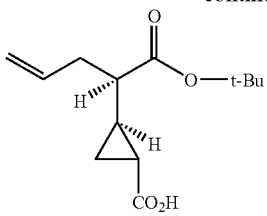

A solution LiOH.H₂O (1.04 g, 24.8 mmol) in water (60 mL) was added to a precooled (0° C.) mixture of 30% hydrogen peroxide solution (5.06 mL, 49.5 mmol) in THF (40 mL). Then a solution of the higher band erythro acyloxazolidinone prepared as described in Step B2 (4.95 g, 12.4 mmol) in THF (80 mL) was added dropwise. The reaction mixture was stirred at 0° C. for 40 min, then was quenched by addition of saturated Na₂SO₃ solution (40 mL), followed by saturated NaHCO₃ solution (40 mL). The resulting mixture was extracted three times with ethyl acetate to remove the chiral auxiliary. The aqueous layer was adjusted to pH~4 with 1 N HCl and then extracted six times with chloroform. The combined organic layers were dried over anhydrous MgSO₄, filtered, and concentrated to give 1.79 g (60%) of carboxylic acid as a single isomer. Note that the lower band erythro acyloxazolidinone could be hydrolyzed in an identical fashion (64% yield).

Higher band erythro acid: H NMR (CDCl₃, 500 MHz): δ 5.78 (m, 1H), 5.04–5.12 (m, 2H), 2.49 (m, 1H), 2.37 (m, 1H), 1.79 (m, 1H), 1.65 (m, 1H), 1.48 (obsc. M, 1H), 1.47 (s, 9H), 1.29 (m, 1H), 1.03 (m, 1H).

Lower band erythro acid: H NMR (CDCl₃, 500 MHz): δ 5.79 (m, 1H), 5.04–5.12 (m, 2H), 2.48 (m, 1H), 2.38 (m, 1H), 1.78 (m, 1H), 1.65 (m, 1H), 1.48 (obsc. M, 1H), 1.47 (s, 9H), 1.28 (m, 1H), 1.02 (m, 1H).

Note that acids resolved as described immediately above could be used to prepare a variety of isomerically pure CCR-2 antagonists by integrating them into syntheses such as shown in Example 114, as well as examples that follow.

EXAMPLE 115

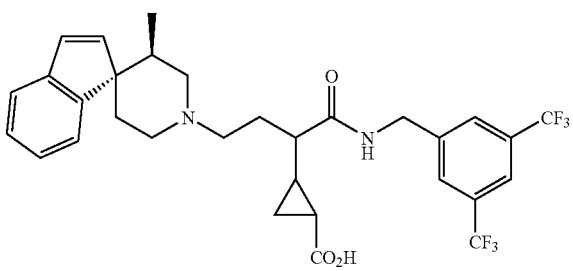

To a solution of the amino ester prepared as described in Example 114 (threo, 1.87 g, 3.06 mmol) in 12 mL of 1:1 THF/methanol was added a solution of LiOH.H₂O (385 mg, 9.17 mmol) in water (6 mL). The resulting mixture was stirred at rt for 5 h, then quenched by addition of 4 N HCl in dioxane (2.3 mL, 9.2 mmol). The reaction mixture was concentrated and purified by flash chromatography (silica, 25% methanol/DCM followed by 50% methanol/DCM) to give 1.90 g of product.

ESI-MS calc. for C31H32F6N2O3: 594; Found: 595 (M+H).

This same procedure was carried out on the erythro isomers.

EXAMPLE 116

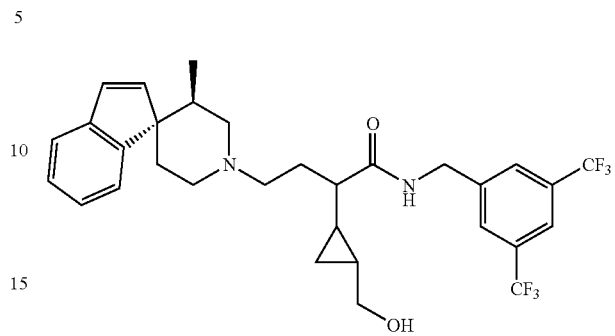

To a solution of the acid prepared as described in Example 115 (threo, 406 mg, 0.683 mmol) in, THF (6 mL) at 0° C. was added N-methylmorpholine (76 mg, 0.75 mmol) followed by i-butylchloroformate (103 mg, 0.751 mmol). The reaction mixture was stirred at 0° C. for 40 min, then was treated with a solution of sodium borohydride (41 mg, 1.09 mmol) in water (1 mL), whereupon gas evolution was observed. After 15 min at 0° C. the reaction mixture was diluted with ethyl acetate and washed with saturated NaHCO₃ solution and brine, dried over anhydrous MgSO₄, filtered, and concentrated. Purification by preparative TLC (silica, 7% of 1:9 NH₄—OH/methanol in DCM) gave 77 mg of alcohol.

ESI-MS calc. for C31H34F6N2O2: 580; Found: 581 (M+H).

EXAMPLE 117

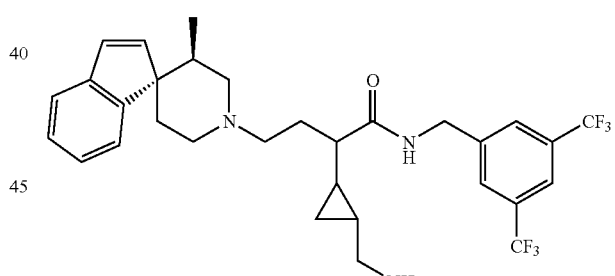

Step A:

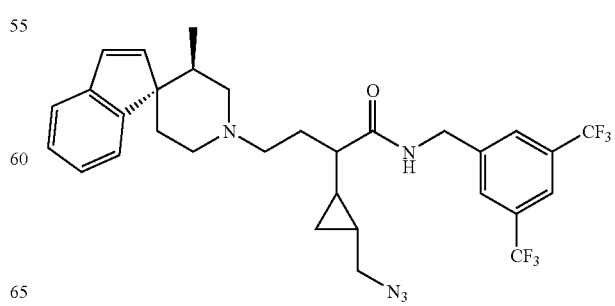

To a solution of the threo alcohol prepared as described in Example 116 (73.7 mg, 0.127 mmol) and N-methylmorpholine (19.3 mg, 0.191 mmol) in DCM (4 mL) at 0° C. was added methanesulfonyl chloride (17.5 mg, 0.152 mmol). The reaction mixture was placed in the freezer (~–20° C.) for overnight. The reaction mixture was diluted with DCM and washed with water twice, saturated NaHCO$_3$ solution, and brine, dried over anhydrous MgSO$_4$, filtered, and concentrated. The resulting crude mesylate was dissolved in DMF (4 mL) and treated with NaN$_3$ (25 mg, 0.38 mmol). The temperature was raised to 50° C., stirred for 3.5 h, then cooled to rt and left over the weekend. The reaction mixture was diluted with ethyl acetate and washed with water. The aqueous layer was back-washed with ethyl acetate. The combined organic layers were then washed with water and brine, dried over anhydrous MgSO$_4$, filtered, and concentrated. Purification by preparative TLC (silica, 5% of 1:9 NH4OH/methanol in DCM) gave 50 mg of azide product.

ESI-MS calc. for C31H33F6N5O: 605; Found: 606 (M+H).

Step B:

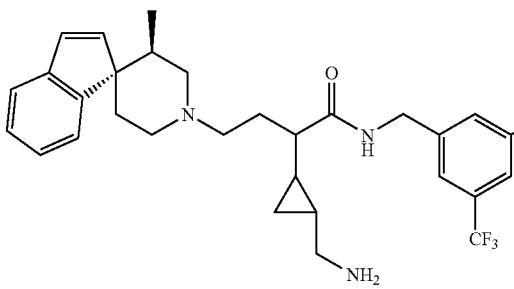

To a solution of the threo azide prepared as described in Step A (50 mg, 0.083 mmol) in THF (3 mL) was added triphenylphosphine (32 mg, 0.12 mmol). The mixture was stirred at rt for 30 min, then water was added (1 mL) and the mixture was stirred for overnight. The next day, the reaction had proceeded very little, so an additional amount of triphenylphosphine (217 mg, 0.826 mmol) was added, as well as 1 mL of water. After stirring overnight, the reaction mixture was concentrated and purified by preparative TLC (silica, 10% of 1:9 NH$_4$OH/methanol in DCM) to give 37 mg of amine. ESI-MS calc. for C31H35F6N3O: 579; Found: 580 (M+H).

EXAMPLE 118

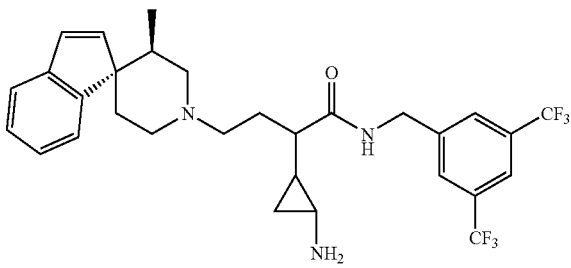

Step A:

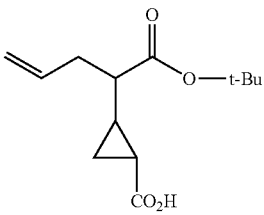

A solution of the diester from Step B Example 114 above (threo, 6.59 g, 25.9 mmol) in 50 mL of 1:1 THF/methanol was treated with a solution of LiOH.H$_2$O (5.44 g, 130 mmol) in 25 mL of water. The reaction mixture was stirred at room temperature for 5 h, then was partially concentrated to remove the organic solvents. The mixture was treated with excess 1 N HCl solution to make the pH acidic and was extracted twice with ethyl acetate. The combined organic layers were washed with brine, dried over anhydrous MgSO$_4$, filtered, and concentrated to give 5.94 g of acid.

Step B:

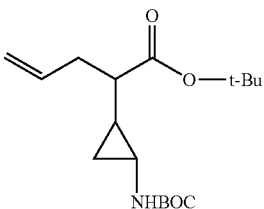

The threo acid prepared as described in Step A (4.92 g, 20.5 mmol) was combined with diphenylphosphoryl azide (4.86 mL, 22.6 mmol) and triethylamine (3.43 mL, 24.6 mmol) in toluene (30 mL) and stirred at 90° C. for 2 h. t-Butanol (40 mL) was then added and the reaction mixture was stirred at 90° C. for an additional 8 h. The reaction mixture was concentrated, redissolved in ether, and washed successively with 1 N HCl, saturated NaHCO$_3$ solution, and brine. The organic layer was dried over anhydrous MgSO$_4$, filtered, and concentrated. Purification by MPLC (silica, 25% ethyl acetate/hexane) provided 4.77 g of the t-butyl carbamate (75%).

H NMR (CDCl$_3$, 500 MHz): δ 5.76 (m, 1H), 5.00–5.09 (m, 2H), 4.66 (br s, 1H), 2.49 (m, 1H), 2.39 (m, 1H), 2.32 (m, 1H), 1.77 (m, 1H), 1.45 (s, 9H), 1.43 (2 overlapping s, 9H, rotameric BOC), 1.03 (m, 1H), 0.78 (m, 1H), 0.63 (m, 1H).

Step C:

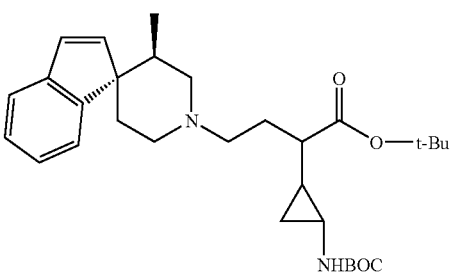

Ozone was bubbled through a cooled (–78° C.) solution of the t-butyl carbamate prepared as described in Step B (3.53 g, 11.3 mmol) until a blue color persisted. N$_2$ Gas was bubbled through the solution until the blue color had disappeared. Triphenylphosphine (3.26 g, 12.4 mmol) was added and the reaction mixture was allowed to warm to rt and stir for 2.5 h. The reaction mixture was concentrated. To the residue was added 55% ethyl acetate/hexane and the mixture was filtered to remove insoluble triphenylphosphine oxide. The filtrate was concentrated and purified by MPLC (silica, 55% ethyl acetate/hexane) to afford 1.84 g of aldehyde. The aldehyde (1.17 g, 3.73 mmol) was combined with 3-methyl-4-spiroindenylpiperidine hydrochloride (Intermediate 5, 880 mg, 3.73 mmol) and triethylamine (0.52 mL, 3.7 mmol) in DCM (15 mL). Then sodium triacetoxyborohydride (2.77 g, 13.1 mmol) was added and the reaction mixture was stirred at rt for 2 h. The reaction mixture was then diluted with DCM and washed with saturated NaHCO$_3$ solution, water, and brine, dried over anhydrous MgSO$_4$, filtered and concentrated. Purification by MPLC (silica, 80% ethyl acetate/hexane, then ethyl acetate) gave 1.53 g of threo amine product.

Step D:

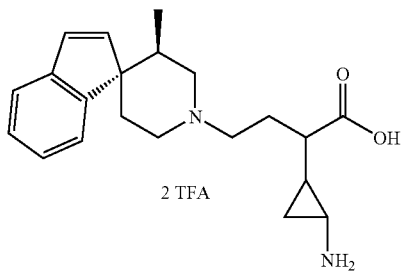

The aminoester prepared as described in Step C (1.46 g, 2.94 mmol) was dissolved in 1:1 TFA/DCM (20 mL) and stirred at room temperature for 3 h. The reaction mixture was concentrated, then redissolved in methanol/toluene and concentrated twice to remove some of the remaining TFA and providing 1.98 g of crude product (still contaminated with TFA).

ESI-MS calc. for C21H28N2O2: 340; Found: 341 (M+H).

Step E:

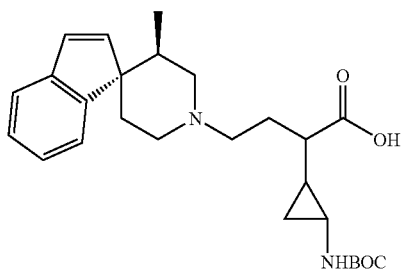

To a solution of the threo diaminoacid prepared as described in Step D (~2.9 mmol) in water (15 mL) was added a solution of NaOH (661 mg, 16.5 mmol) in water (10 mL) until the pH was 9. Then dioxane (10 mL) was added, followed by BOC$_2$O (1.27 g, 5.80 mmol) in dioxane (5 mL). The reaction mixture was stirred overnight, then neutralized with 1 N HCl, and concentrated. The residue was purified by flash chromatography (silica, 10–20% methanol/DCM stepwise gradient) to afford 1.47 g of product.

ESI-MS calc. for C26H36N2O4: 440; Found: 441 (M+H).

Step F:

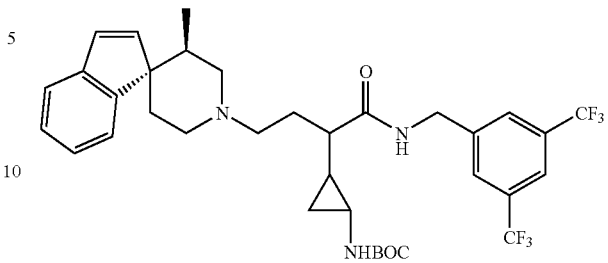

The BOC-aminoacid prepared as described in Step E (~2.6 mmol) was combined with 3,5-Bis(trifluoromethyl) benzylamine hydrochloride (1.47 g, 5.24 mmol) and HOAt (0.702 g, 5.24 mmol) in DCM (15 mL) and the resulting mixture was cooled to 0° C. EDC (1.01 g, 5.24 mmol) was added and the reaction mixture was stirred at 0° C. for 1.5 h, then warmed to rt and stirred for an additional 1.75 h. The reaction mixture was diluted with DCM and washed with water, 1 N HCl solution, saturated NaHCO$_3$ solution, and brine. The organic layer was dried over anhydrous MgSO$_4$, filtered, and concentrated. Purification by MPLC (silica, 10% methanol/ethyl acetate) gave 1.21 g of desired amide.

ESI-MS calc. for C35H41F6N3O3: 665; Found: 666 (M+H).

Step G:

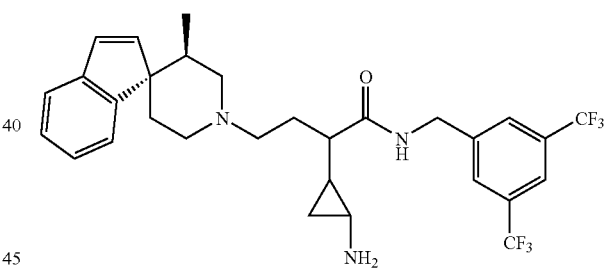

The threo BOC-amide prepared as described in Step F (1.15 g, 1.73 mmol) was dissolved in 4 N HCl in dioxane (25 mL), stirred for 3 h, and concentrated to give 1.25 g of crude product as its Bis-hydrochloride salt.

ESI-MS calc. for C30H33F6N3O: 565; Found: 566 (M+H).

The products from Examples 115–118 can themselves serve as intermediates for the synthesis of a variety of CCR-2 antagonists by forming amides, sulfonamides, carbamates, ureas, heterocycles, etc, using standard chemistry known to those skilled in the art. These compounds can be prepared as diastereomeric mixtures or as single diastereomers (by resolution of the final compounds by chiral HPLC or by use of optically pure building blocks for the synthesis-see Example 114). The following table lists some representative examples of compounds prepared using the title compounds from Examples 115–118 as intermediates.

TABLE

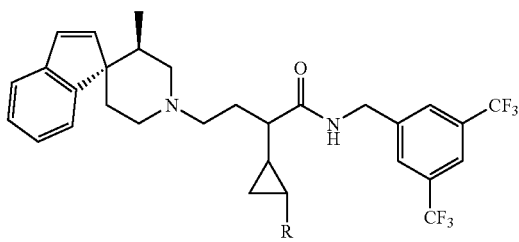

| Example | R group | Calc. MW | ESI-MS found (M + H)+ |
|---|---|---|---|
| 119 | CONHEt | 621 | 622 |
| 120 | NHCO2Me | 623 | 624 |
| 121 | NHAc | 607 | 608 |
| 122 | NHCOPh | 669 | 670 |
| 123 | NHCOCH2NH2 | 622 | 623 |
| 124 | 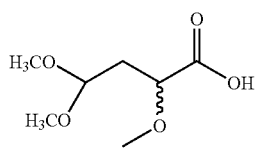 | 670 | 671 |
| 125 | NHSO2Me | 643 | 644 |
| 126 | NHSO2NMe2 | 672 | 673 |
| 127 | NHSO2NHCO2Et | 716 | 717 |
| 128 | NHSO2Ph | 705 | 706 |
| 129 | NHCONH2 | 608 | 609 |
| 130 | NHCONHMe | 622 | 623 |
| 131 | NHCONMe2 | 636 | 637 |
| 132 | (HN-C(O)-morpholine) | 678 | 679 |
| 133 | (triazole) | 617 | 618 |
| 134 | CH2—(triazole) | 631 | 632 |
| 135 | CH2NHAc | 621 | 622 |
| 136 | CH2NHCOPh | 683 | 684 |
| 137 | CH2NHCOCH2NH2 | 636 | 637 |
| 138 | CH2NMe2 | 607 | 608 |
| 139 | CH2NH-i-Pr | 621 | 622 |
| 140 | CH2NHSO2Me | 657 | 658 |
| 141 | CH2NHSO2CF3 | 711 | 712 |
| 142 | CH2NHSO2-i-Pr | 685 | 686 |
| 143 | CH2NHSO2Et | 671 | 672 |
| 144 | CH2NHSO2-n-Pr | 685 | 686 |
| 145 | CH2NHSO2-i-Bu | 699 | 700 |
| 146 | CH2NHSO2Ph | 719 | 720 |
| 147 | CH2NHSO2NMe2 | 686 | 687 |
| 148 | CH2NHCONH2 | 622 | 623 |
| 149 | CH2NHCONHMe | 636 | 637 |
| 150 | CH2NHCONMe2 | 650 | 651 |
| 151 | CH2NHCONHEt | 650 | 651 |
| 152 | CH2NHCONHPh | 698 | 699 |
| 153 | CH2NHCONH-t-Bu | 677 | 678 |
| 154 | CH2NHCONH-n-Bu | 677 | 678 |
| 155 | CH2NHCONH-cyclopropyl | 662 | 663 |
| 156 | CH2NHSO2NHCO2Et | 730 | 731 |
| 157 | CH2NHCO2Me | 637 | 638 |
| 158 | CH2OCONHEt | 651 | 652 |

TABLE-continued

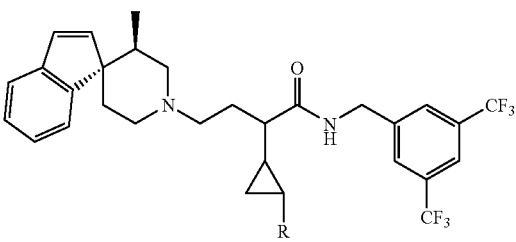

| Example | R group | Calc. MW | ESI-MS found (M + H)+ |
|---|---|---|---|
| 159 | CH2—NH—C(O)—morpholine | 692 | 693 |

Intermediate 47

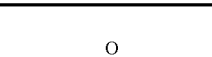

Step A

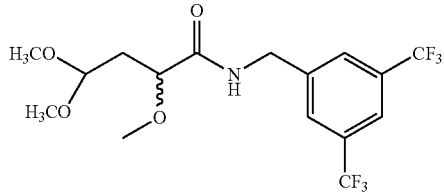

To a solution of lithium bis(trimethylsilyl)amide, LHMDS, (5.69 g, 34.0 mmol) in THF (50 ml) cooled to −78° C. by dry ice/acetone bath was added methoxyacetic acid (2.27 ml, 29.58 mmol) in 20 ml THF via syringe and the resulting mixture stirred for one hour. The mixture was treated with 2,2-dimethyoxy, 1-bromoethane (5 g, 29.58 mmol) and stirred overnight allowing to warm to room temperature. The reaction was quenched with a saturated solution of ammonium chloride (50 ml) and the resulting mixture was poured into a separatory funnel. The organic layer was separated, washed with brine (1×25 mL), dried with anhydrous sodium sulfate and the solvent was evaporated in vacuo to yield 2.16 g (41%) of the crude product. The crude residue was passed through a small plug of silica gel (eluant 60% ethyl acetate/hexane) to remove polar impurities to yield 1.69 g (32%) of the racemic desired product. $^1$H NMR (400 MHz, CDCl$_3$): 4.59 (dd, J=5.1, 6.6 Hz, 1H), 3.88 (dd, J=4.5, 6.7, 1H), 3.46 (s, 3H), 3.33 (s, 3H), 3.31 (s, 3H), 2.15–2.07 (m, 1H), 2.05–1.98 (m, 1H).

Step B

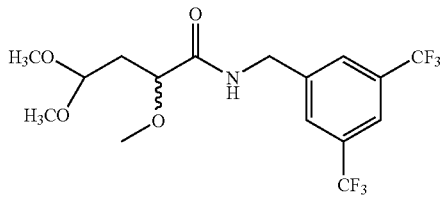

A mixture of the acid (described in step A, 64 mg, 0.54 mmol), 3,5-bis(trifluoromethyl)benzylamine hydrochloride (151 mg, 0.54 mmol), HOBt (73 mg, 0.54 mmol), N,N-diisopropyl ethylamine (94 µl, 0.54 mmol) in dichloromethane (3 mL) was treated with 1-[3-(dimethylamino)propyl]-3-ethylcarbodiimide hydrochloride (EDC, 208 mg, 1.08 mmol) and stirred at room temperature overnight. The reaction mixture was diluted with dichloromethane (7 mL), washed with water (2×5 mL), brine (1×5 mL), dried over anhydrous sodium sulfate and the solvent was evaporated. Purification was done by preparative TLC (eluent: 30% ethyl acetate/hexane) to yield 157 mg (72%) of the desired product. LC-MS for $C_{16}H_{19}NO_4F_6$ $[M+H]^+$ calculated 403.16, found 404.

EXAMPLE 160

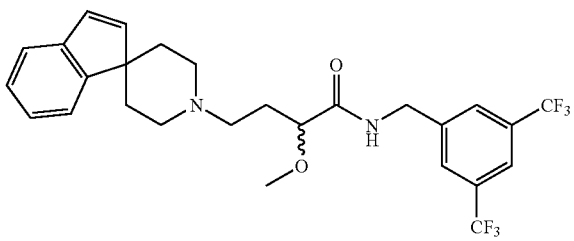

Intermediate 47 (50 mg, 0.134 mmol) was treated with a solution of 90% trifluoroacetic acid/water (1 ml) for 10 minutes. The reaction mixture was diluted with water (2 mL) and extracted with ether (3×10 ml). The organic layers were combined, washed with saturated sodium bicarbonate (3×3 mL), brine (1×5 mL), dried over anhydrous sodium sulfate and the solvent was evaporated in vacuo to yield 45 mg (96%) of the crude product.

A solution of the above crude product (45 mg, 0.129 mmol), spiroindenylpiperidine hydrochloride (30 mg, 0.134 mmol), diisopropylethylamine (24 µL, 0.134 mmol) and crushed molecular sieves (4A, 25 mg) in dichloroethane (2 mL) was treated with sodium triacetoxyborohydride (143 mg, 0.134 mmol) and stirred at room temperature overnight. The sieves were filtered off (plug of Celite), washed with dichloromethane and the combined organic washings were extracted with a saturated solution of sodium bicarbonate (1×5 mL), brine (1×5 mL) and dried over anhydrous sodium sulfate. Solvent was evaporated to dryness and the residue was purified by preparative TLC (eluent: 5% methanol/95% ethyl acetate) to yield 30.1 mg (41%) of the final pure desired product. $^1$H NMR (400 MHz, $CD_3OD$): 7.94 (s, 2H), 7.83 (s, 1H), 7.36–7.34 (m, 2H), 7.27–7.23 (m, 2H), 7.00 (d, J=5.7 Hz, 1H), 6.90 (d, J=5.5 Hz, 1H), 4.58 (ABq, J=4.6 Hz, 2), 3.94 (dd, J=4.8, 6.6 Hz, 1H), 3.74–3.65 (m, 2H), 3.47 (s, 3H), 3.37–3.29 (m, 41), 2.43 (br t, J=4.6 Hz, 1H), 2.36–2.25 (m, 1H), 2.23–2.14 (m, 1H). 1.50 (br d, J=4.6 Hz, 1H), 1.37–1.28 (m, 2H). LC-MS for $C_{27}H_{28}N_2OF_6[M+H]^+$ calculated 526.21, found 527.

EXAMPLE 161

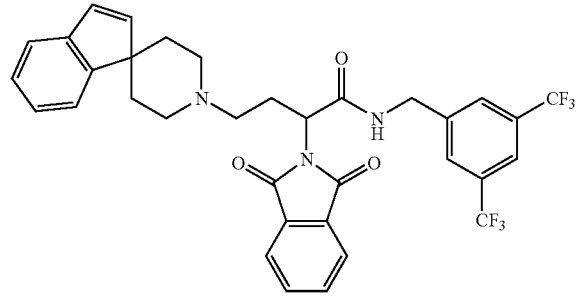

Step A

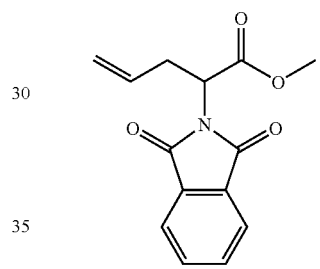

A solution of methyl 2-amino-4-butenoate (2.32 g, 17.96 mmol) and phthalic anhydride (2.96 g, 20 mmol) in toluene (60 mL) was heated with stirring to reflux for 6 hrs. The reaction solvent was evaporated, and the residue was recrystallized from diethyl ether hexane (1:1) mixture to yield 4.20 g (90%) of the pure product. $^1$H NMR ($CDCl_3$): 7.87 (m, 2H), 7.75 (m, 2H), 5.74 (m, 1H), 5.08 (ddd, J=17.2, 3.0, 1.4 Hz, 1H), 5.00 (dd, J=10.3, 0.9 Hz, 1H), 4.96 (dd, J=9.2, 6.6 Hz, 1H), 3.77 (s, 3H), 3.00 (m, 2H).

Step B

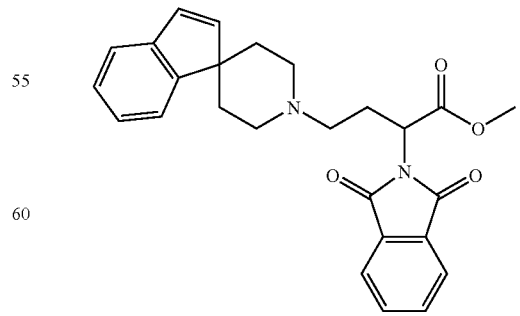

A solution of the olefin from previous step (910 mg, 3.4264 mmol) in dichloromethane (30 mL) was cooled to −78° C. and ozone was passed through until a permanent blue color indicated consumption of the olefin. Excess ozone was purged with nitrogen, and 3 mL of dimethyl sulfide was added. Cooling bath was removed, and the reaction mixture was allowed to warm up to room temperature. The solvent was removed in vacuo and the crude aldehyde was dissolved in dichloroethane (20 mL). 4-Spiroindenyl piperidine hydrochloride (772 mg, 3.4822 mmol), diisopropylethylamine (600 μL, 3.4822 mmol) and finally sodium triacetoxyborohydride (3.70 g, 17.4 mmol) were added and the reaction mixture was stirred at room temperature overnight. It was diluted with dichloromethane (100 mL) and extracted with water (2×50 mL), dried with anhydrous sodium sulfate and evaporated to dryness. The crude product (1.60 g, 100%) was taken into the next step without additional purification. MS: for $C_{26}H_{26}N_2O_4$ [M+H]$^+$ calculated: 431.19, found 431.0.

Step C

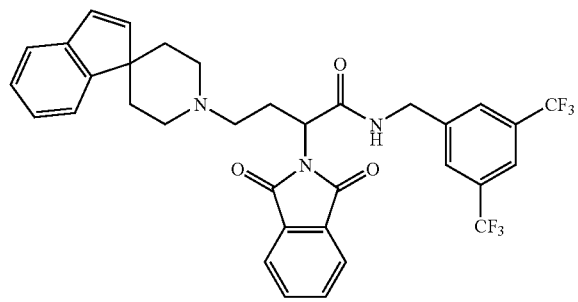

A solution of the crude product from previous step (1.60 g, 3.4264 mmol) in dioxane (30 mL) was treated with aqueous solution of lithium hydroxide (1N, 12.0 mL) and stirred at room temperature for 1 hr. 6.0 mL of 2N HCl was added to neutralize the lithium hydroxide, and the reaction mixture was evaporated to dryness.

The crude product (containing lithium chloride) was suspended in dichloromethane, 3,5-bistrifluoromethylbenzylamine hydrochloride (958 mg, 3.4264 mmol), diisopropylethylamine (1.19 mL, 6.8528 mmol), 1-hydroxy-7-azabenzotriazole (466 mg, 3.4264 mmol), and 1-[3-(dimethylamino)propyl]-3-ethylcarbodiimide hydrochloride (EDC, 985 mg, 5.1396 mmol) were added and the reaction mixture was stirred at room temperature overnight. It was diluted with dichloromethane, washed with water. After drying with anhydrous sodium sulfate the solvent was evaporated to dryness, and the residue was purified by flash chromatography (ethyl acetate hexanes/7:3) to yield 244 mg (10%) of the pure product. MS: for $C_{34}H_{29}N_2O_4F_6$ [M+H]$^+$ calculated: 642.21, found 642.4.

EXAMPLE 162

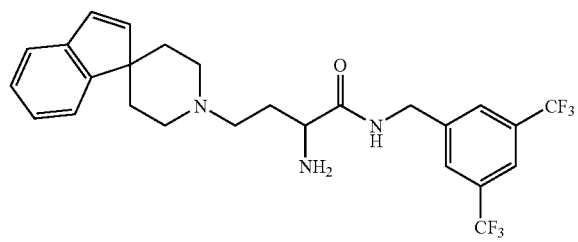

A solution of the phthalimide, preparation of which was described in Example 161(216 mg, 0.3367 mmol) in ethyl alcohol (15 mL) was treated with hydrazine (100 μL) and heated to reflux for 60 minutes. The reaction mixture was allowed to cool down to ambient temperature and the precipitate of the phthalic hydrazide was filtered off. The filtrate was evaporated to dryness, the remaining solid was boiled briefly with diethyl ether and filtered again. The filtrate was evaporated to dryness to leave after its conversion to the respective dihydrochloride 204 mg of the pure product. MS: for $C_{26}H_{27}N_3OF_6$ [M+H]$^+$ calculated: 512.21, found 512.30.

EXAMPLE 163

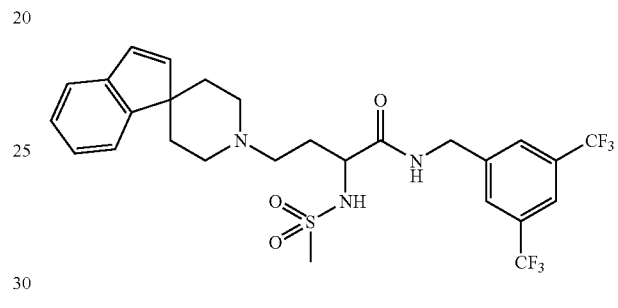

A solution of the primary amine hydrochloride described in Example 162 (12 mg, 0.0219 mmol), diisopropylethylamine (12 μL, 0.0657 mmol) in dichloromethane (2 mL) was treated with methanesulfonyl chloride (2 μL, 0.026 mmol) and stirred at room temperature for 1 hr. Water (2 mL) was added and the organic layer was separated. It was washed with water 2 more times, finally with brine. After drying with anhydrous sodium sulfate the solvent was evaporated to leave 9.0 mg (66%) of pure product. MS: for $C_{27}H_{29}N_3O_3SF_6$ [M+H]$^+$ calculated: 5.90.18, found 590.30.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula Ib:
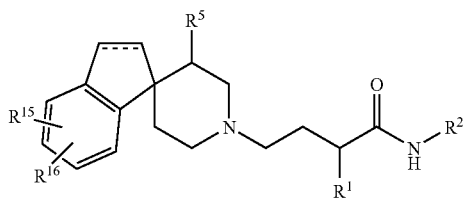
wherein the dashed line represents a single or a double bond and wherein
R¹ is selected from:
(1) —CH(CH₃)₂,
(2) —CH₂CH₂CH₃,
(3) —CH₂CH(CH₃)₂,
(4) —cyclopropyl,
(5) —cyclobutyl,
(6) —cyclopentyl,
(7) —CH₂—cyclopropyl,
(8) —CH₂—cyclobutyl,
(9) —C(CH₃)₂(OH),
(10) —(OH)cyclobutyl,
(11) —(OH)cyclopentyl,
(12) —C(CH₃)₂(NHCOCH₃),
(13) —O—CH₃,
(14) —O—CH(CH₃)₂,
(15) —S—CH₃,
(16) —S—CF₃,
(17) —SO₂—CH₃,
(18) —S—CH(CH₃)₂,
(19) —SO₂—CH(CH₃)₂,
(20) —NH—SO₂—CH₃,
(21) —phenyl,
(22)–(38)
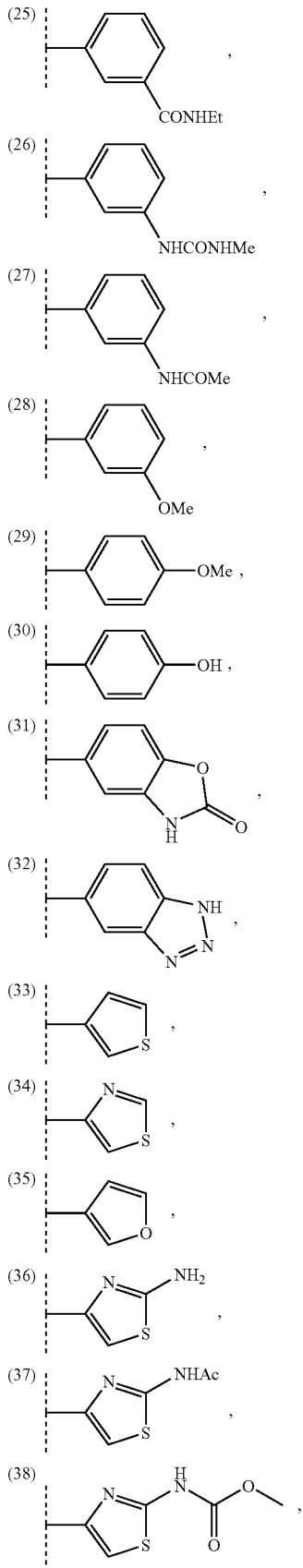

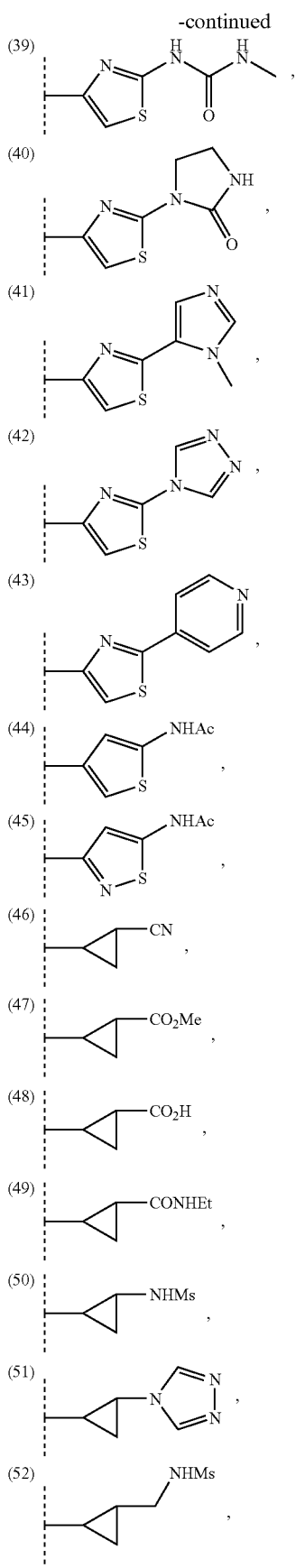
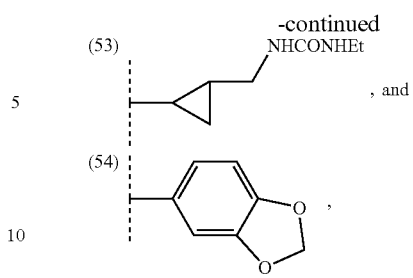

and positional and stereo isomers thereof;
R[2] is selected from: ($C_{0-6}$alkyl)-phenyl and ($C_{0-6}$alkyl)-heterocycle, where the alkyl is unsubstituted or substituted with 1–7 substituents where the substituents are independently selected from:
(a) halo,
(b) hydroxy,
(c) —O—$C_{1-3}$alkyl,
(d) trifluoromethyl,
(e) —$C_{1-3}$alkyl,
(f) —$CO_2R^9$, and
(g) oxo;
and where the phenyl and the heterocycle may be unsubstituted or substituted with 1–5 substituents where the substituents are independently selected from:
(a) halo,
(b) trifluoromethyl
(c) trifluoromethoxy,
(d) hydroxy,
(e) $C_{1-6}$alkyl,
(f) $C_{3-7}$cycloalkyl,
(g) —O—$C_{1-6}$alkyl,
(h) —O—$C_{3-7}$cycloalkyl,
(i) —$SCF_3$,
(j) —S—$C_{1-6}$alkyl,
(k) —$SO_2$—$C_{1-6}$alkyl,
(l) phenyl,
(m) hetreocycle,
(n) —$CO_2R^9$,
(o) —CN,
(p) —$NR^9R^{10}$,
(q) —$NR^9$—$SO_2$—$R^{10}$,
(r) —$SO_2$—$NR^9R^{10}$,
(s) —$ONR^9R^{10}$, and
(t) —O -phenyl;
$R^5$ is selected from:
(a) hydrogen,
(b) hydroxy,
(c) $C_{1-6}$alkyl,
(d) $C_{1-6}$alkyl-hydroxy,
(e) —O—$C_{1-3}$alkyl,
(f) oxo, and
(g) halo,
(h) $C_{0-4}CO_2R^9$, and
(i) $CF_3$,
$R^{15}$ and $R^{16}$ are independently selected from:
(a) hydrogen,
(b) halo,
(c) trifluoromethyl,
(d) hydroxy,
(e) $C_{1-3}$alkyl,
(f) —O—$C_{1-3}$alkyl,
(g) —$CO_2H$,
(h) –$CO_2C_{1-3}$alkyl, (i) —CN, and
(j) heterocycle;
and pharmaceutically acceptable salts and individual diastereomers thereof.

2. The compound of claim 1 wherein $R^2$ is selected from:
(1) —CH$_2$-(phenyl),
(2) —CH$_2$-(4-bromophenyl),
(3) —CH$_2$-(3-chlorophenyl),
(4) —CH$_2$-(3,5-difluorophenyl),
(5) —CH$_2$-((2-trifluoromethyl)phenyl),
(6) —CH$_2$-((3-trifluoromethyl)phenyl),
(7) —CH$_2$-((4-trifluoromethyl)phenyl),
(8) —CH$_2$-((3-trifluoromethoxy)phenyl),
(9) —CH$_2$-((3-trifluoromethylthio)phenyl),
(10) —CH$_2$-((3-trifluoromethoxy-5-thiomethyl)phenyl),
(11) —CH$_2$-((3-trifluoromethoxy-5-methoxy)phenyl),
(12) —CH$_2$-((3-trifluoromethoxy-5-methanesulfonyl)phenyl),
(13) —CH$_2$-((3-trifluoromethoxy-5-amino)phenyl),
(14) —CH$_2$-((3-trifluoromethoxy-5-aminomethanesulfonyl)phenyl),
(15) —CH$_2$-((3-trifluoromethoxy-5-sulfonylamino)phenyl),
(16) —CH$_2$-((3,5-bis-trifluoromethyl)phenyl),
(17) —CH$_2$-((3-fluoro-5-trifluoromethyl)phenyl),
(18) —CH(CH$_3$)-((3,5-bis-trifluoromethyl)phenyl),
(19) —C(CH$_3$)$_2$-((3,5-bis-trifluoromethyl)phenyl),
(20) —CH$_2$-(4-(2-trifluoromethyl)pyridyl),
(21) —CH$_2$-(5-(3-trifluoromethyl)pyridyl),
(22) —CH$_2$-(5-(3-trifluoromethyl)pyridazinyl),
(23) —CH$_2$-(4-(2-trifluoromethyl)pyridyl-N-oxide), and
(24) —CH$_2$-(5-(3-trifluoromethyl)pyridyl-N-oxide).

3. The compound of claim 1 of the formula:

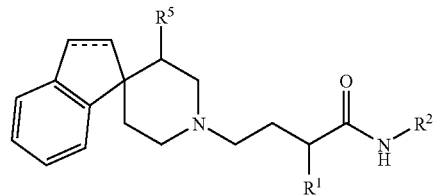

wherein the dashed line represents a single or a double bond,
$R^5$ is hydrogen or methyl;
and pharmaceutically acceptable salts and individual diastereomers thereof.

* * * * *